US008404244B2

(12) United States Patent
Schiller et al.

(10) Patent No.: US 8,404,244 B2
(45) Date of Patent: Mar. 26, 2013

(54) PAPILLOMAVIRUS L2 N-TERMINAL PEPTIDES FOR THE INDUCTION OF BROADLY CROSS-NEUTRALIZING ANTIBODIES

(75) Inventors: John T. Schiller, Kensington, MD (US); Diana V. Pastrana, McLean, VA (US); Richard B. S. Roden, Severna Park, MD (US); Ratish Gambhira, Mandeville, LA (US); Douglas R. Lowy, Bethesda, MD (US)

(73) Assignees: The United States of America, as represented by the Secretary, Department of Health and Human Services, Washington, DC (US); The Johns Hopkins University, Baltimore, MD (US)

( * ) Notice: Subject to any disclaimer, the term of this patent is extended or adjusted under 35 U.S.C. 154(b) by 781 days.

(21) Appl. No.: 11/883,495

(22) PCT Filed: Feb. 1, 2006

(86) PCT No.: PCT/US2006/003601
§ 371 (c)(1),
(2), (4) Date: May 13, 2008

(87) PCT Pub. No.: WO2006/083984
PCT Pub. Date: Aug. 10, 2006

(65) Prior Publication Data
US 2009/0047301 A1    Feb. 19, 2009

Related U.S. Application Data

(60) Provisional application No. 60/649,249, filed on Feb. 1, 2005, provisional application No. 60/697,655, filed on Jul. 7, 2005, provisional application No. 60/752,268, filed on Dec. 21, 2005.

(51) Int. Cl.
*A61K 39/12* (2006.01)
*C07K 5/00* (2006.01)

(52) U.S. Cl. .................. 424/186.1; 424/184.1; 530/300

(58) Field of Classification Search ..................... None
See application file for complete search history.

(56) References Cited

U.S. PATENT DOCUMENTS

| 5,618,536 | A | 4/1997 | Lowy et al. |
| 5,866,553 | A | 2/1999 | Donnelly et al. |
| 6,020,309 | A | 2/2000 | Campo et al. |
| 6,174,532 | B1 * | 1/2001 | Campo et al. ............... 424/204.1 |
| 6,344,314 | B2 * | 2/2002 | Cole et al. ......................... 435/5 |
| 7,217,419 | B2 * | 5/2007 | Wettendorff ............... 424/204.1 |

FOREIGN PATENT DOCUMENTS

| JP | H10506796 A | 7/1998 |
| JP | 2002-053597 A | 2/2002 |
| WO | WO 96/11274 A1 | 4/1996 |
| WO | WO 2005/108564 A | 11/2005 |

OTHER PUBLICATIONS

Embers (Journal of Virology, 2002, vol. 79, p. 9788-9805).*
de Jong et al. (Vaccine, 2002, vol. 20 p. 3456-3464).*
HPV L2 protein seach performed on Jun. 17, 2010.*
HPV16 L2 protein search performed on Jun. 18, 2010.*
Bosch, F.X. et al. (1995) "Prevalence of human papillomavirus in cervical cancer; a worldwide prospective." *J. Natl. Cancer Inst.* 87:796-802.
Bosch, F.X. et al. (2003) "Chapter 1; human papillomavirus and cervical cancer-burden and assessment of causality." *J. Natl. Cancer Inst. Monogr.* 31:3-13.
Breitburd, F. et al. (1995) "Immunization with virus-like particles from cottontail rabbit papillomavirus (CRPV) can protect against experimental CRPV infection." *J. Virol.* 69:3959-3963.
Buck, C.B. et al. (2004) "Efficient intracellular assembly of papillomaviral vectors." *J. Virol.* 78:751-757.
Buck, C.B. et al. (2005) "Maturation of papillomavirus capsids." *J. VIrol.* 79:2839-2846.
Campo, M.S. et al. (1997) "A peptide encoding a B-cell epitope from the N-terminus of the capsid protein L2 of bovine papillomavirus-4 prevents disease." *Virology* 234:261-266.
Chandrachud, L.M. et al. (1995) "Vaccination of cattle with the N-terminus of L2 is necessary and sufficient for preventing infection by bovine papillomavirus-4." *Virology* 211:204-208.
Christensen, N.D. et al. (1990) "Monoclonal antibody mediated neutralization of infectious human papillomavirus type 11." *J. Virol.* 64:5678-5681.
Christensen, N.D. et al. (1990) "Antibody-mediated neutralization in vivo of infectious papillomaviruses." *J. Virol.* 64:3151-3156.
Christensen, N.D. et al. (1991) "Neutralization of CRPV infectivity by monoclonal antibodies that identify conformational epitopes on intact virions." *Virus Res.* 2:169-179.

(Continued)

*Primary Examiner* — Agnieszka Boesen
(74) *Attorney, Agent, or Firm* — Woodcock Washburn LLP

(57) ABSTRACT

The invention comprises a method for inducing broadly cross-neutralizing antibodies against cutaneous and mucosal papillomavirus types or against heterologous papillomavirus types in humans comprising administering to a human in need thereof an immunogenic peptide or protein (or polynucleotide encoding therefor), where the immunogenic peptide or protein is: (a) a peptide or protein of at least 10 amino acid residues in length having a sequence corresponding to either a sequence from the N terminal amino acids 1-200 of papillomavirus L2 protein (for cross-neutralizing antibodies against cutaneous and mucosal papillomavirus types) or a sequence from the N terminal amino acids 1-88 of papillomavirus L2 protein (for cross-neutralizing antibodies against heterologous papillomavirus types), (b) a peptide or protein of at least 10 amino acid residues in length with at least 55% identity with the sequence from (a), or (c) a peptide or protein as defined in either (a) or (b) which is conjugated or fused to a protein or peptide other than a papillomavirus L2 protein or peptide.

4 Claims, 15 Drawing Sheets

OTHER PUBLICATIONS

Christensen, N.D. et al. (1991) "The open reading frame L2 of cottontail rabbit papillomavirus contains antibody-inducing neutralizing epitopes." *Virology* 181:572-579.

Christensen, N.D. et al. (1996) "Immunization with virus-like particles induces long-term protection of rabbits against challenge with cottontail rabbit papillomaviruses." *J. Virol.* 70:960-965.

Christensen, N.D. et al. (1996) "Surface conformational and linear epitopes on HPV-16 and HPV-18 L1 virus-like particles as defined by monoclonal antibodies." *Virology* 223:174-184.

Christensen, N.D. et al. (1994) "Human papillomavirus types 6 and 11 have antigenically distinct strongly immunogenic conformationally dependent neutralizing epitopes." *Virology* 205:329-335.

Clifford, G.M. et al. (2003) "Human papillomavirus types in invasive cervical cancer worldwide: a meta-analysis." *Br. J. Cancer* 88: 63-73.

Combita, A.L. et al. (2002) "Identification of two cross-neutralizing linear epitopes within the L I major capsid protein of human papillomaviruses." *J. Virol.* 76:6480-6486.

Culp, T.D. et al. (2003) "Quantitative RT-PCR assay for HPV infection in cultured cells." *J. Virol. Methods* 111:135-144.

Culp, T.D. et al. (2004) "Kinetics of in vitro adsorption and entry of papilloma virus virions." *Virology* 319 :152-161.

Donello, I.E. et al. (1998) "Woodchuck hepatitis virus contains a tripartite posttranscriptional regulatory element." *J. Virol.* 72:5085-5092.

Embers, M.E. et al. (2002) "Protective immunity to rabbit oral and cutaneous papillomaviruses by immunization with short pep tides of L2, the minor capsid protein." *J. Virol.* 76:9798-9805.

Gambhira, R. et al. (2007) "A protective and broadly cross-neutralizing epitope of human papillomavirus L2." *J. Virol.* 81:13927-31.

Ghim, S. et al. (1991) "Comparison of neutralization of BPV-1 infection of CI27 cells and bovine fetal skin xenografts." *Int. J. Cancer* 49:285-289.

Giroglou, T. et al. (2001) "Immunological analyses of human papillomavirus capsids." *Vaccine* 9:1783-1793.

International Preliminary Report on Patentability dated Aug. 7, 2007, from PCT/US2006/003601 filed Feb. 1, 2006.

Jarrett, W.F.H. et al. (1990) "Studies on vaccination against papilloma viruses: the immunity after infection and vaccination with bovine papillomaviruses of different types." *Vet. Res.* 126:473-475.

Kawana, K. et al. (1999) "Common neutralization epitope in minor capsid protein L2 of human papillomavirus types 16 and 6." *J. Virol.* 73:6188-6190.

Kawana, K. et al. (2001) "Nasal immunization of mice with peptide having a cross-neutralization epitope on minor capsid protein L2 of human papillomavirus type 16 elicit systemic and mucosal antibodies." *Vaccine* 19:1496-1502.

Kawana, K. et al. (2003) "Safety and immunogenicity of a peptide containing the cross-neutralization epitope of HPV 16 L2 administered nasally in healthy volunteers." *Vaccine* 2:4256-4260.

Kirnbauer, R. et al. (1994) "A virus-like particle enzyme-linked immunosorbent assay detects serum antibodies in a majority of women infected with human papillomavirus type 16." *J. Natl. Cancer Inst.* 86:494-499.

Kirnbauer, R. et al. (1996) "Virus-like particles of bovine papillomavirus type 4 in prophylactic and therapeutic immunization." *Virology* 219:37-44.

Koutsky, L.A. et al. (2002) "A controlled trial of a human papillomavirus type 16 vaccine." *N. Engl. J. Med.* 347:1645-1651.

Leder, C. et al. (2001) "Enhancement of capsid gene expression: preparing the human papillomavirus type 16 major structural gene L1 for DNA vaccination purposes." *J. Virol.* 75:9201-9209.

Liu, w.J. et al. (1997) "Sequence close to the N-terminus of L2 protein is displayed on the surface of bovine papillomavirus type I virions." *Virology* 227:474-483.

Munoz, N. et al. (2004) "Against which human papillomavirus types shall we vaccinate and screen? The international perspective." *Int. J. Cancer* 111:278-285.

Notredame, C. et al. (2000) "T-Coffee: a novel method for fast and accurate multiple sequence alignment." *J. Mol. Biol.* 302:205-217.

Palmer, K.E et al. (2006) "Protection of rabbits against cutaneous papillomavirus infection using recombinant tobacco mosaic virus containing L2 capsid epitopes." *Vaccine* 24:5516-5525.

Pastrana, D.V. et al. (2004) "Reactivity of human sera in a sensitive, high throughput pseudovirus-based papillomavirus neutralization assay for HPV16 and HPV18." *Virology* 321:205-216.

Pastrana, D.V. et al. (2005) "Cross-neutralization of cutaneous and mucosal Papillomavirus types with anti-sera to the amino terminus of L2" *Virology* 337:365-372.

Roden, R. B.S. et al. (2000) "Minor Capsid Protein of Human Genital Papillomaviruses Contains Subdominant, Cross-Neutralizing Epitopes" *Virology* 270: 254-257.

Roden, R.B. et al. (1995) "Papilloma virus L1 capsids agglutinate mouse erythrocytes through a proteinaceous receptor." *J. Virol.* 69:5147-5151.

Roden, R.B. et al. (2001) "Positively charged termini of the L2 minor capsid protein are necessary for papillomavirus infection." *J. Virol.* 75:10493-10497.

Roden, R.B.S. et al. (1996) "Assessment of the serological relatedness of genital human papillomaviruses by hemagglutination inhibition." *J. Virol.* 70:3298-3301.

Roden, R.KS. et al. (1994) "Neutralization of bovine papillomavirus by antibodies to L1 and L2 capsid proteins." *J. Virol.* 68:7570-7574.

Suzich, J.A. et al. (1995) "Systemic immunization with papillomavirus L1 protein completely prevents the development of viral mucosal papillomas." *PNAS USA* 92:11553-11557.

Walboomers, J.M. et al. (1999) "Human papillomavirus is a necessary cause of invasive cervical cancer worldwide." *J. Pathol.* 189:12-19.

White, W.I. et al. (1998) "In vitro infection and type-restricted antibody-mediated neutralization of authentic human papillomavirus type 16." *J. Virol.* 72: 959-964.

Yang, R. et al. (2003) "Cell surface-binding motifs of L2 that facilitate papillomavirus infection." *J. Virol.* 77:3531-3541.

Zhou, J. et al. (1994) "Interaction of human papillomavirus (HPV) type 16 capsid proteins with HPV DNA requires an intact L2 N-terminal sequence." *J. Virol.* 68:619-625.

Zhou, J. et al. (1999) "Papillomavirus capsid protein expression level depends on the match between codon usage and tRNA availability." *J. Virol.* 73:4972-4982.

C. Siegrist, Vaccine Immunology, in Vaccines (Stanley A. Plotkin, Walter A. Orenstein, and Paul A. Offit eds., 2008).

* cited by examiner

```
BPV      ---MSARKRVKRASAYDLYRTCKQAGTCPPDVIPKVEGDTIADKILKFGG
HP16     MRHKRSAKRTKRASATQLYKTCKQAGTCPPDIIPKVEGKTIADQILQYGS
HPV18    -MVSHRAARRKRASVTDLYKTCKQSGTCPPDVVPKVEGTTLADKILQWSS
HPV31    MRSKRSTKRTKRASATQLYQTCKAAGTCPSDVIPKIEHTTIADQILRYGS
HPV6B    -MAHSRARRRKRASATQLYQTCKLTGTCPPDVIPKVEHNTIADQILKWGS
CRPV     ---MVARSRKRRAAPQDIYPTCKIAGNCPADIQNKFENKTIADKILQYGS
              *  :**: :* *** :*.**.*:  *.:* *:***:::..

BPV      LAIYLGGLGIGTWSTGRVAAGGSPRYTPLRTAGSTSSLASI    (SEQ ID NO: 22)
HPV16    MGVFFGGLGIGTGS----GTGGRTGYIPLGTRPPTATDTLA    (SEQ ID NO: 23)
HPV18    LGIFLGGLGIGTGS----GTGGRTGYIPLGGRSNTVVDVGP    (SEQ ID NO: 24)
HPV31    MGVFFGGLGIGSGS----GTGGRTGYVPLSTRPSTVSEASI    (SEQ ID NO: 25)
HPV6B    LGVFFGGLGIGTGS----GTGGRTGYVPLQTSAKPSITSGP    (SEQ ID NO: 26)
CRPV     LGVFFGGLGISSAG----GSGGRLGYTPLSGGGGRVIAAAP    (SEQ ID NO: 27)
          .:** ****:*  .     :** * ** .          * **
```

"*" denotes identical residues in that column in all sequences in the alignment.
":" denotes conserved substitutions
"." denotes semi-conserved substitutions.

FIG. 3

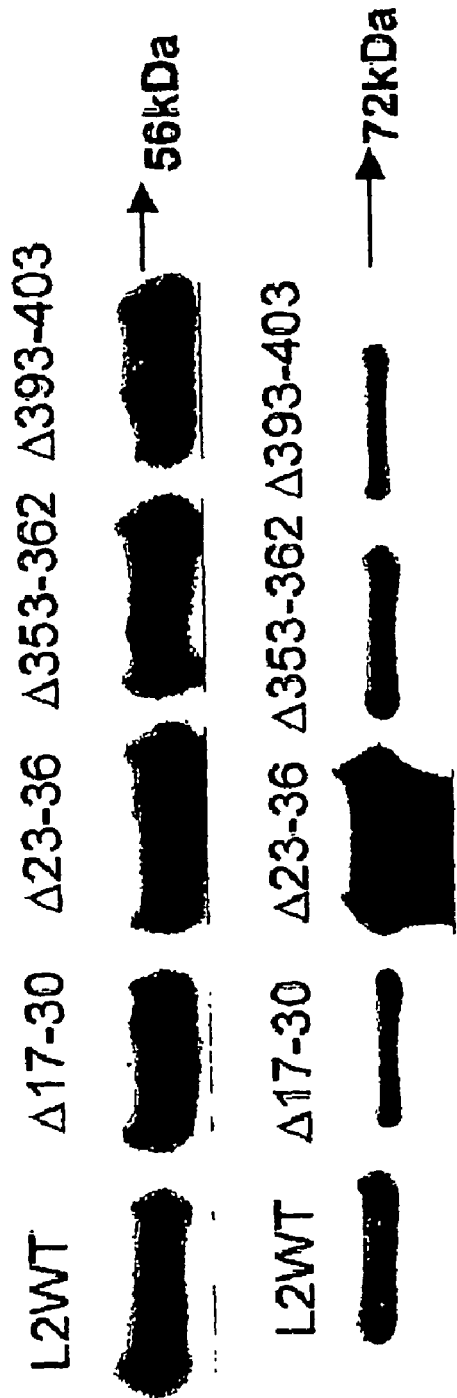
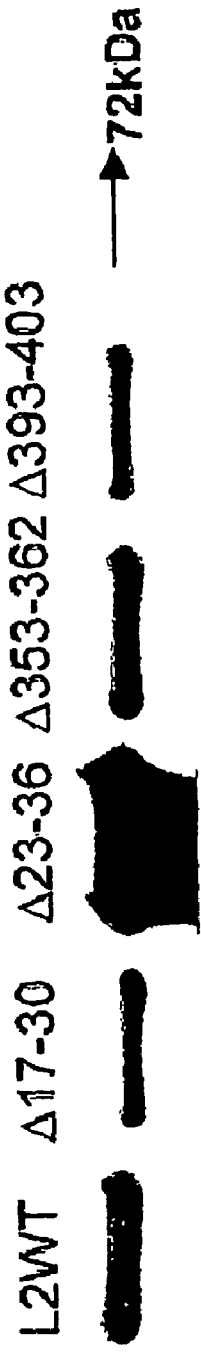
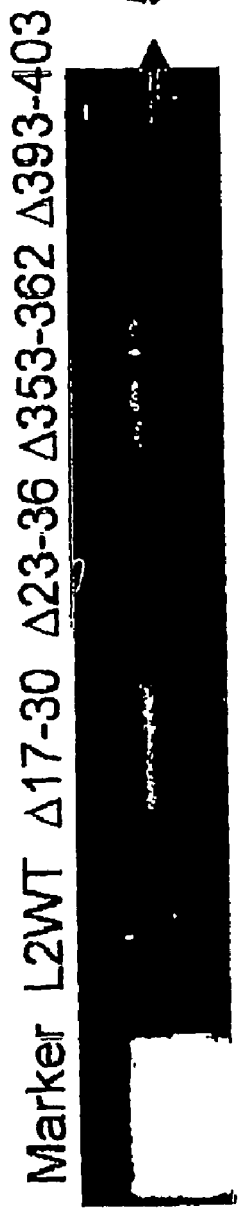
FIG. 6A
FIG. 6B
FIG. 6C

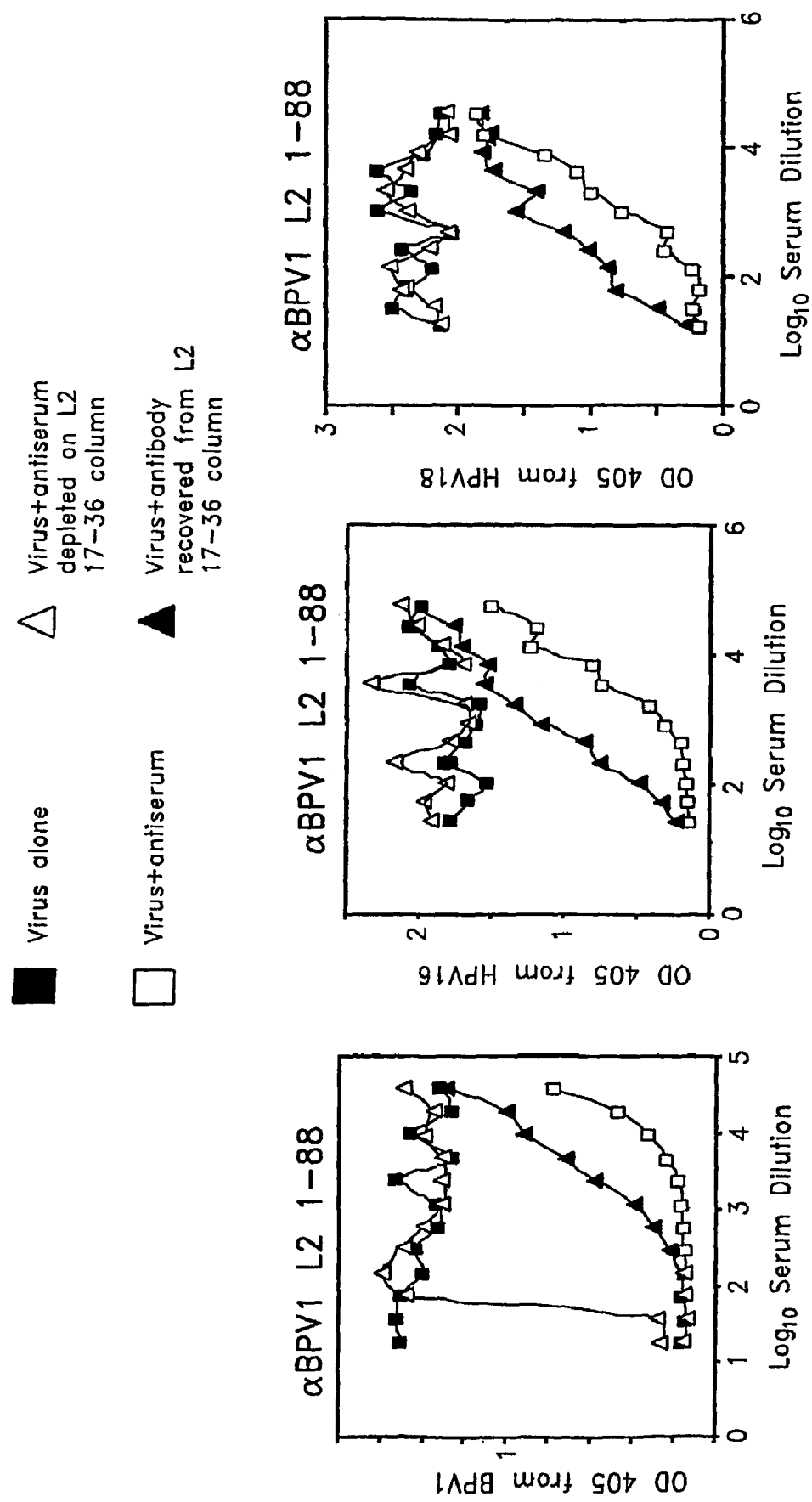

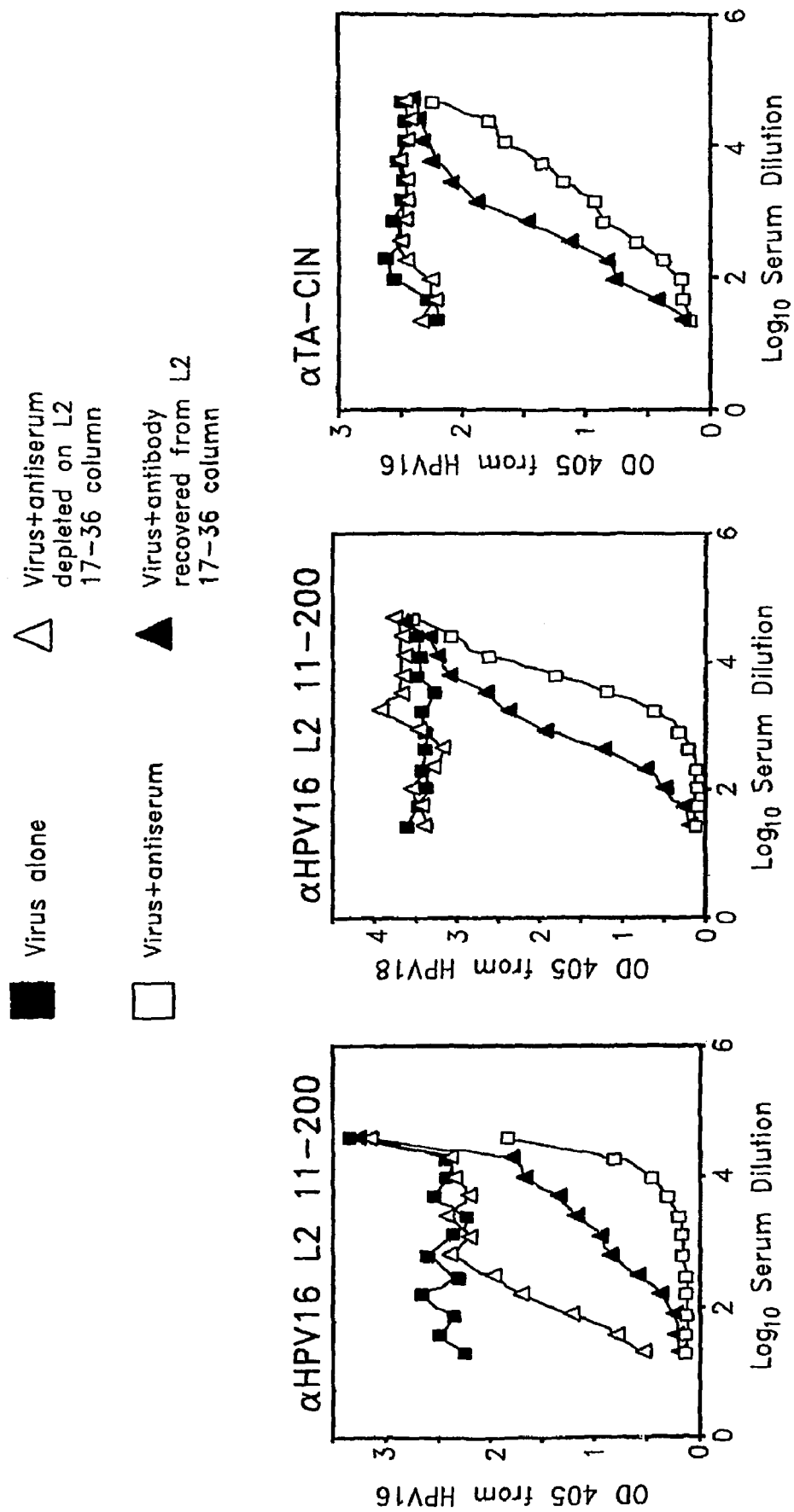

US 8,404,244 B2

PAPILLOMAVIRUS L2 N-TERMINAL PEPTIDES FOR THE INDUCTION OF BROADLY CROSS-NEUTRALIZING ANTIBODIES

RELATED APPLICATIONS

This application is a U.S. National Phase of International Application No. PCT/US2006/003601, filed Feb. 1, 2006, which claims the benefit of U.S. Provisional Application No. 60/649,249, filed Feb. 1, 2005, U.S. Provisional Application No. 60/697,655, filed Jul. 7, 2005, and U.S. Provisional Application No. 60/752,268, filed Dec. 21, 2005, which are hereby incorporated by reference in their entireties.

FIELD OF THE INVENTION

The present invention relates to the use of papillomavirus L2 protein fragments in medicine. In particular, the invention relates to vaccine preparations for immunization against papillomavirus and papillomavirus related diseases in mammals, particularly in humans.

DESCRIPTION OF THE RELATED ART

Human papillomaviruses (HPVs) can be classified into those that infect non-genital cutaneous sites and those that infect ano-genital and oral mucosal sites (reviewed in Lowy, D. R. and Howley, P. M. in *Fields Virology: Papillomaviruses*, Knipe, D. M., Howley, P. M. (Eds.), 4th ed., vol. 2, 2001, Lippincott Williams & Wilkins, Philadelphia, pp. 2231-2264). Non-genital skin warts are a prevalent disease of childhood, while most ano-genital and oral infections affect adult populations. Among the genital-mucosal genotypes, persistent infection with "high-risk" or "oncogenic" HPV genotypes is a necessary but not sufficient cause of cervical cancer (Bosch, F. X., et al. 1995 *J Natl Cancer Inst* 87:796-802; Clifford, G. M. et al. 2003 *Br J Cancer* 88:63-73; Walboomers, J. M. et al. 1999 *J Pathol* 189:12-19). Infection with "low-risk" HPV genotypes (especially HPV6 and HPV11) accounts for most cases of genital warts. Elimination of cervical cancer will require effective vaccination against more than 15 known genital HPV types (Bosch, F. X. and de Sanjose, S. 2003 *J Natl Cancer Inst Monogr* 31:3-13; Munoz, N. et al. 2004 *Int J Cancer* 111:278-285). Protection from infection by immunization with virus-like particles (VLPs) and by passive transfer of antibodies in animal models (Breitburd, F. et al. 1995 *J Virol* 69:3959-3963; Christensen, N. D. et al. 1996 *J Virol* 70:960-965; Kirnbauer, R. et al. 1996 *Virology* 219:37-44; Suzich, J. A. et al. 1995 *Proc Natl Acad Sci USA* 92:11553-11557) have provided the rationale for initiating vaccine trials in humans in an effort to curb the morbidity and mortality associated with these viruses. Immunization with VLPs composed of the Papillomavirus (PV) major capsid protein, L1, generates neutralizing antibodies that are primarily type specific (Christensen, N. D. and Kreider, J. W. 1990 *J Virol* 64:3151-3156; Christensen, N. D. and Kreider, J. W. 1991 *Virus Res* 21:169-179; Christensen, N. D. et al. 1990 *J Virol* 64:5678-5681; Ghim, S. et al. 1991 *Int J Cancer* 49:285-289; Kimbauer, R. et al. 1994 *J Natl Cancer Inst* 86:494-499; Koutsky, L. A. et al. 2002 *N Engl J Med* 347:1645-1651; Roden, R. B. et al. 1995 *J Virol* 69:5147-5151). Limited cross-reactivity has been observed among closely related types such as HPV18 and 45, and HPV6 and 11 (Christensen, N. D. et al. 1994 *Virology* 205:329-335; Combita, A. L. et al. 2002 *J Virol* 76:6480-6486; Giroglou, T. et al. 2001 *Vaccine* 19:1783-1793; Roden, R. B. S. et al. 1996 *J Virol* 70:3298-3301; White, W. I. et al. 1998 *J Virol* 72:959-964) when L1 or L1/L2 VLPs were the immunogen. Furthermore, both animal challenge (Breitburd, F. et al. 1995 *J Virol* 69:3959-3963; Jarret, W. F. H. et al. 1990 *Vet Res* 126:473-475) and clinical studies (Koutsky, L. A. et al. 2002 *N Engl J Med* 347:1645-1651) have suggested that protection will be largely type-specific. The plethora of oncogenic types (notably HPV16, HPV18, HPV45, HPV31, HPV33, HPV52 and HPV58, which together are responsible for 87% of cervical cancer cases (Munoz, N. et al. 2004 *Int J Cancer* 111:278-285), indicate that broad protection will require a multivalent vaccine directed against as many of the >15 oncogenic HPV types as possible. Alternative vaccination protocols yielding cross-protective antibodies against a single antigen would greatly reduce the complexity and expense of generating and analyzing multi-type vaccines if they achieved similar protection levels.

Vaccination with L2 can provide immunity from homologous PV challenge in animal model systems. This protection appears to be mediated by a relatively low-titer neutralizing antibody response in vaccinated animals (Chandrachud, L. M. et al. 1995 *Virology* 211:204-208; Christensen, N. D. et al. 1991 *Virology* 181:572-579; Embers, M. E. et al. 2002 *J Virol* 76:9798-9805). In contrast to the predominantly type-specific antibodies directed against L1 neutralization epitopes, cross-neutralization has been observed among divergent genital HPV types, that is, HPV6, 16 and 18 (Roden, R. B. et al. 2000 *Virology* 270:254-257), or HPV6 and 16 (Kawana, K. et al. 1999 *J Virol* 73:6188-6190) with antibodies generated against HPV L2 proteins or peptides. Although they provide protection, neutralizing antibody titers elicited by L2 vaccination are typically 2-3 orders of magnitude lower than those found in L1 VLP vaccinated animals. Furthermore, it is unclear how effective anti-L2 antibodies would be at neutralizing even more distantly related papillomaviruses.

SEGUE TO THE INVENTION

Here, we study the cross-neutralizing activity of antibodies generated against recombinant L2 proteins and peptides from different animal and human papillomavirus types that represent both genital and cutaneous groups.

SUMMARY OF THE INVENTION

The invention comprises a method for inducing broadly cross-neutralizing antibodies against cutaneous and mucosal papillomavirus types in humans comprising administering to a human in need thereof an immunogenic peptide or protein (or polynucleotide encoding therefor), where the immunogenic peptide or protein is: (a) a peptide or protein of at least 10 amino acid residues in length having a sequence corresponding to a sequence from the N terminal amino acids 1-200 of papillomavirus L2 protein, (b) a peptide or protein of at least 10 amino acid residues in length with at least 55% identity with the sequence from (a), or (c) a peptide or protein as defined in either (a) or (b) which is conjugated or fused to a protein or peptide other than a papillomavirus L2 protein or peptide.

In another embodiment, the invention comprises a method for inducing broadly cross-neutralizing antibodies against heterologous papillomavirus types in humans comprising administering to a human in need thereof an immunogenic peptide or protein (or polynucleotide encoding therefor), where the immunogenic peptide or protein is: (a) a peptide or protein of at least 10 amino acid residues in length having a sequence corresponding to a sequence from the N terminal amino acids 1-88 of papillomavirus L2 protein, (b) a peptide or protein of at least 10 amino acid residues in length with at least 55% identity with the sequence from (a), or (c) a peptide or protein as defined in either (a) or (b) which is conjugated or fused to a protein or peptide other than a papillomavirus L2 protein or peptide.

BRIEF DESCRIPTION OF THE DRAWINGS

FIG. 3. Homology of amino termini of papillomavirus L2 protein.

FIG. 6A-F. HPV16 L2 17-36 motif is evolutionarily conserved, critical for infection and induces broadly neutralizing antibodies.

FIG. 7A-F. Depletion of HPV16 L2 17-36aa anti-peptide antibodies from L2 immune serum abolishes cross neutralization.

DETAILED DESCRIPTION OF THE PREFERRED EMBODIMENT

Figure 1A:
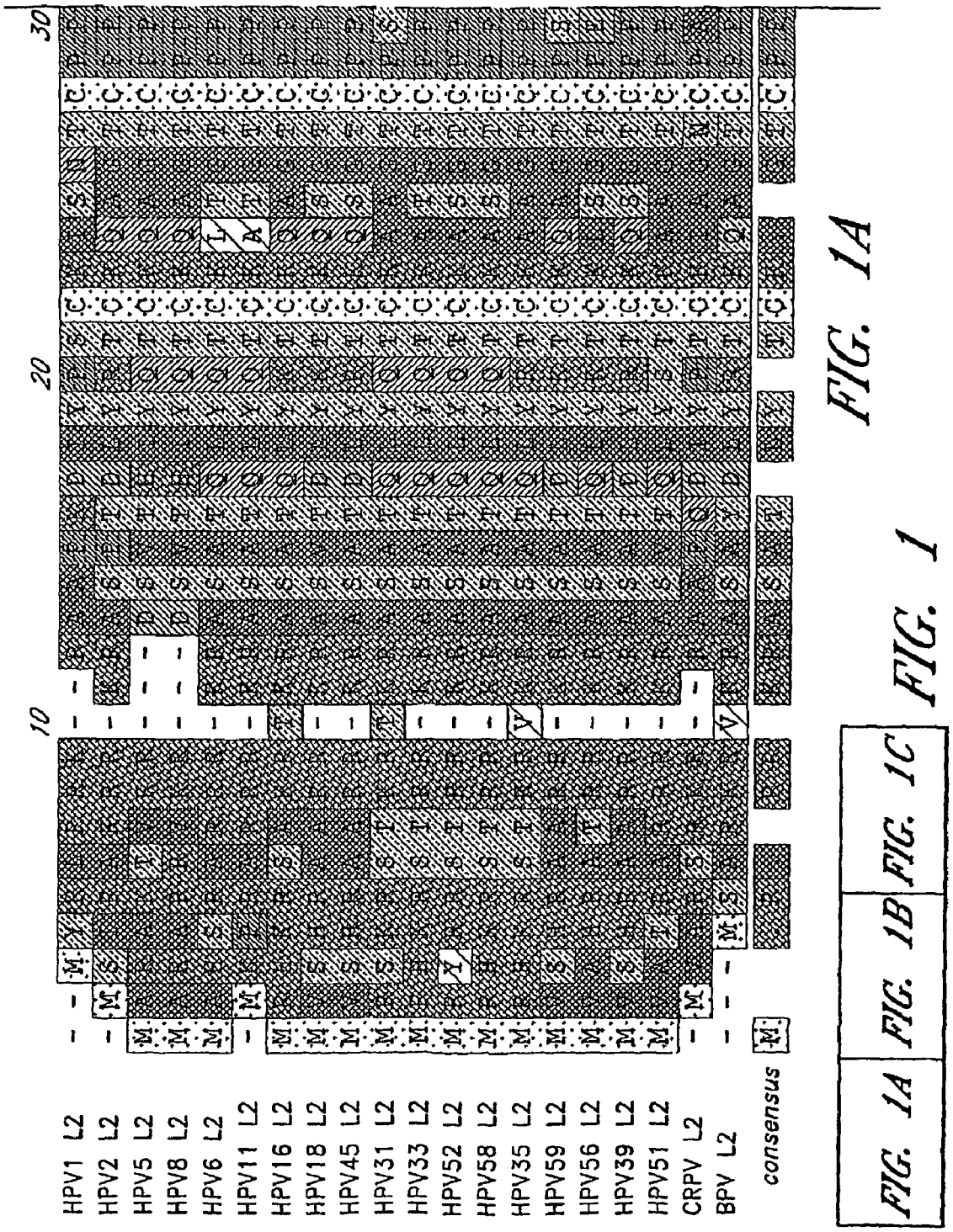
FIG. 1. Conservation of L2's N-terminus.
Figure 1B:
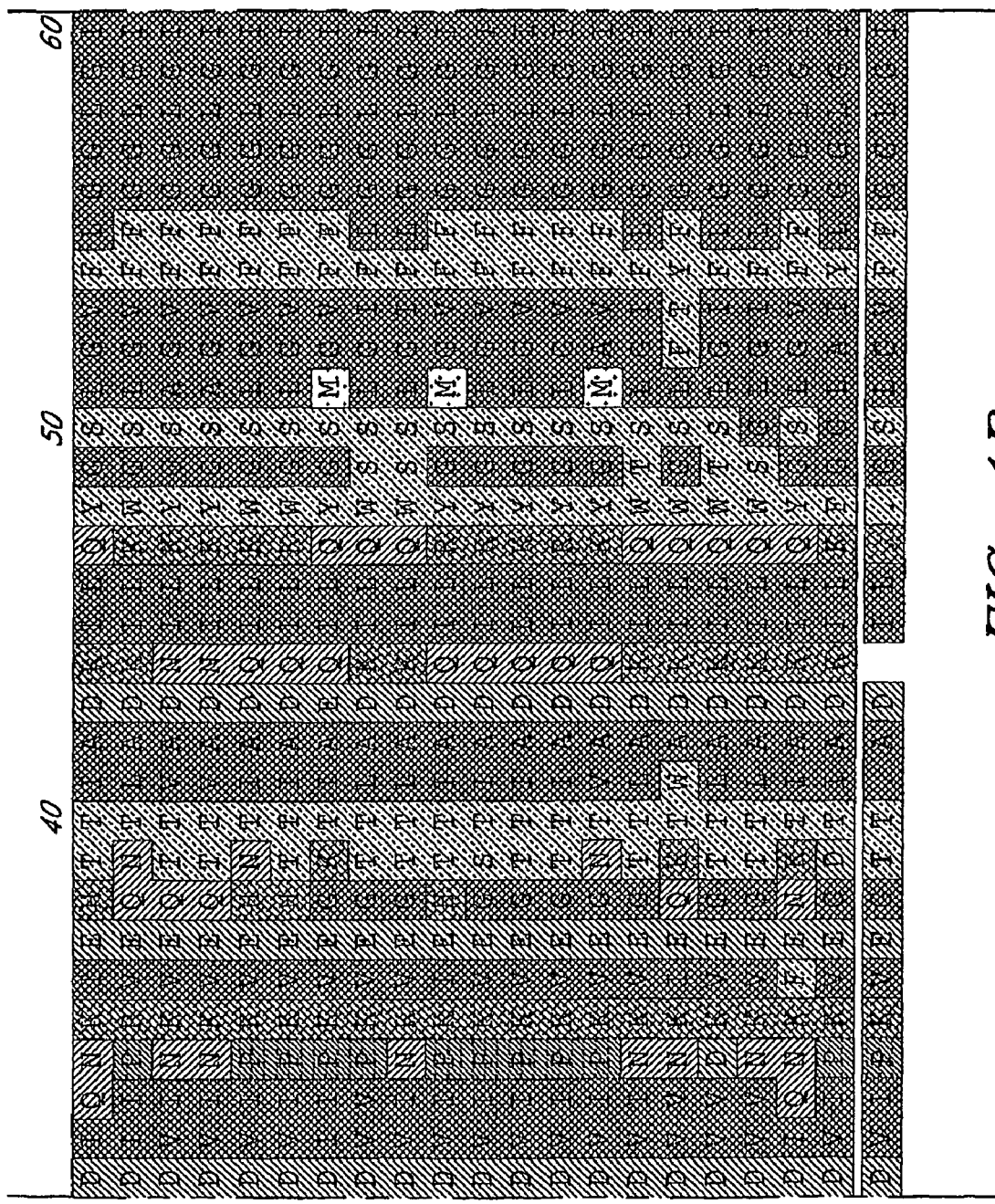
Figure 1C:
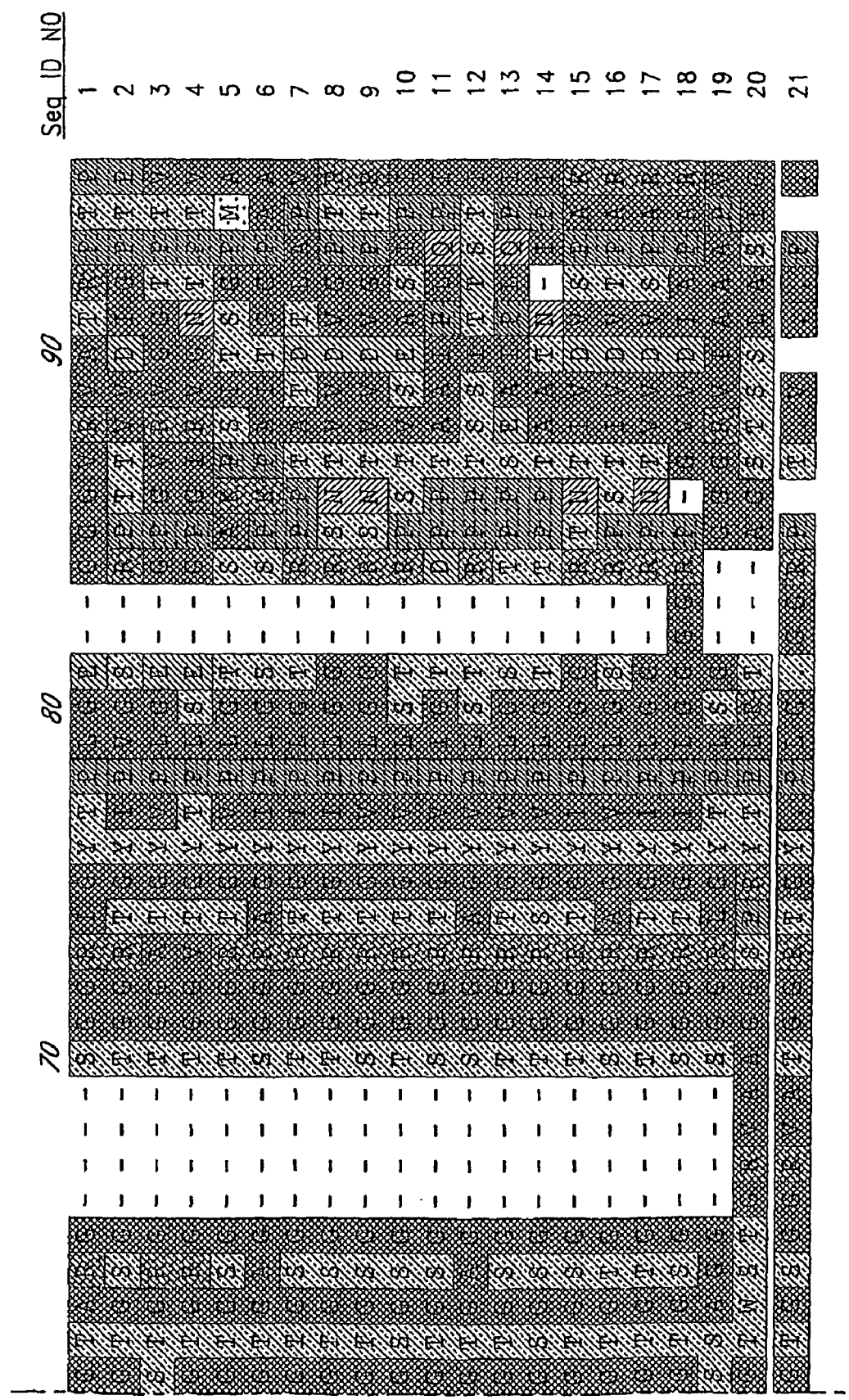
Figure 2:
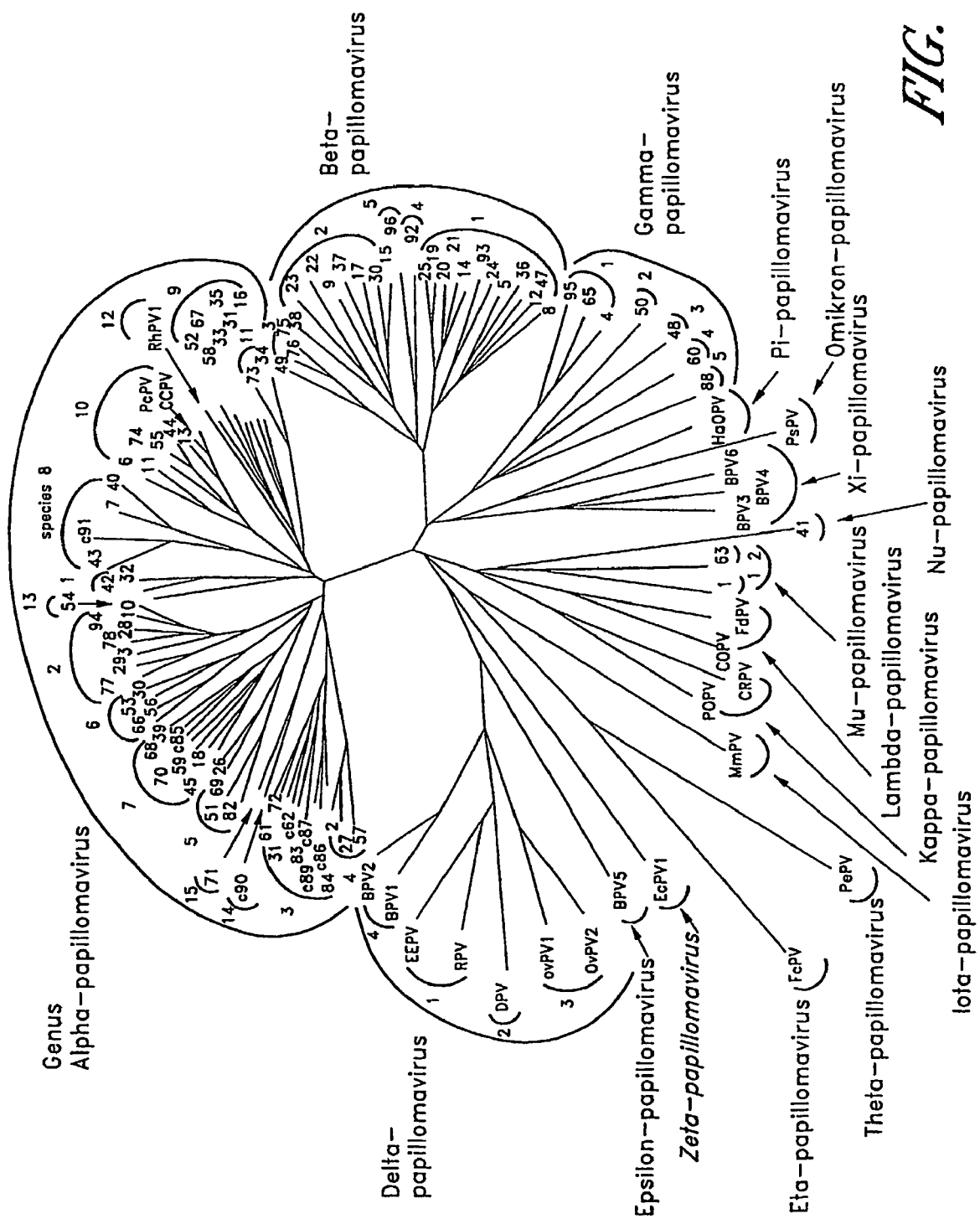
FIG. 2. Phylogenetic tree containing the sequences of 118 papillomavirus types.

Vaccination with papillomavirus L2 has been shown to induce neutralizing antibodies that protect against homologous type infection and cross-neutralize a limited number of genital HPVs. Surprisingly, we found that antibodies to bovine papillomavirus (BPV1) L2 amino acids 1-88 induced similar titers of neutralizing antibodies against Human papillomavirus (HPV) 16 and 18 and BPV1 pseudoviruses and also neutralized HPV11 native virions. These antibodies also neutralized each of the other pseudovirus types tested, HPV31, HPV6 and Cottontail rabbit papillomavirus (CRPV) pseudoviruses. HPV16, HPV18, HPV31, HPV6 and CRPV L2 antisera also displayed cross-neutralization. This study demonstrates the presence of broadly cross-neutralizing epitopes at the N-terminus of L2 that are shared by cutaneous and mucosal types and by types that infect divergent species. BPV1 L2 was exceptionally effective at inducing cross-neutralizing antibodies to these shared epitopes.

Immunogenic papillomavirus L2 peptides and proteins and methods of use are provided. The peptides and proteins include one or more neutralizing antigenic epitopes. Preferably, a peptide or protein is an isolated, recombinant, or synthetic peptide or protein containing at least about 10 amino acid residues between amino acid residues 1 and 200 from the N-terminal of the papillomavirus L2 protein, substantially in isolation from sequences naturally occurring adjacent thereto in the papillomavirus L2 protein, including at least one neutralizing epitope. Alternatively, a peptide or protein includes at least about 10 amino acid residues between amino acid residues 1 and 88 from the N-terminal of a papillomavirus L2 protein, substantially in isolation from sequences naturally occurring adjacent thereto in the papillomavirus L2 protein, including at least one neutralizing epitope. Optionally, a peptide or protein includes amino acid residues 17 through 36 of the N-terminal of the papillomavirus L2 protein.

The amino acids of particular importance to the peptides and proteins of the invention are by no means limited to the exact position as defined for the, e.g., BPV1 L2 of papillomavirus but are simply used in an exemplary manner to point out the preferred amino acids being at that position or corresponding to that position in other types such as found in L2 protein of HPV16 etc. and papillomaviruses in general since they are highly conserved. For papillomaviruses other than BPV1 L2 the numbering of the positions of the preferred amino acids is often different but an expert in the field of the molecular biology of papillomaviruses will easily identify these preferred amino acids by their position relative to the highly conserved amino acids of the papillomavirus L2.

In one embodiment, peptides and proteins of the invention are located within the first 88 amino acids of the N-terminal region of HPV16 L2 and are 10-88 amino acids in length, substantially in isolation from sequences naturally occurring adjacent thereto in the papillomavirus L2 protein.

Peptides and Proteins that Begin with Amino Acid 1 of HPV16 L2

1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87 and 1-88.

Peptides and Proteins that Begin with Amino Acid 2 of HPV16 L2

2-11, 2-12, 2-13, 2-14, 2-15, 2-16, 2-17, 2-18, 2-19, 2-20, 2-21, 2-22, 2-23, 2-24, 2-25, 2-26, 2-27, 2-28, 2-29, 2-30, 2-31, 2-32, 2-33, 2-34, 2-35, 2-36, 2-37, 2-38, 2-39, 2-40, 2-41, 2-42, 2-43, 2-44, 2-45, 2-46, 2-47, 2-48, 2-49, 2-50, 2-51, 2-52, 2-53, 2-54, 2-55, 2-56, 2-57, 2-58, 2-59, 2-60, 2-61, 2-62, 2-63, 2-64, 2-65, 2-66, 2-67, 2-68, 2-69, 2-70, 2-71, 2-72, 2-73, 2-74, 2-75, 2-76, 2-77, 2-78, 2-79, 2-80, 2-81, 2-82, 2-83, 2-84, 2-85, 2-86, 2-87 and 2-88.

Peptides and Proteins that Begin with Amino Acid 3 of HPV16 L2

3-12, 3-13, 3-14, 3-15, 3-16, 3-17, 3-18, 3-19, 3-20, 3-21, 3-22, 3-23, 3-24, 3-25, 3-26, 3-27, 3-28, 3-29, 3-30, 3-31, 3-32, 3-33, 3-34, 3-35, 3-36, 3-37, 3-38, 3-39, 3-40, 3-41, 3-42, 3-43, 3-44, 3-45, 3-46, 3-47, 3-48, 3-49, 3-50, 3-51, 3-52, 3-53, 3-54, 3-55, 3-56, 3-57, 3-58, 3-59, 3-60, 3-61, 3-62, 3-63, 3-64, 3-65, 3-66, 3-67, 3-68, 3-69, 3-70, 3-71, 3-72, 3-73, 3-74, 3-75, 3-76, 3-77, 3-78, 3-79, 3-80, 3-81, 3-82, 3-83, 3-84, 3-85, 3-86, 3-87 and 3-88.

Peptides and Proteins that Begin with Amino Acid 4 of HPV16 L2

4-13, 4-14, 4-15, 4-16, 4-17, 4-18, 4-19, 4-20, 4-21, 4-22, 4-23, 4-24, 4-25, 4-26, 4-27, 4-28, 4-29, 4-30, 4-31, 4-32, 4-33, 4-34, 4-35, 4-36, 4-37, 4-38, 4-39, 4-40, 4-41, 4-42, 4-43, 4-44, 4-45, 4-46, 4-47, 4-48, 4-49, 4-50, 4-51, 4-52, 4-53, 4-54, 4-55, 4-56, 4-57, 4-58, 4-59, 4-60, 4-61, 4-62, 4-63, 4-64, 4-65, 4-66, 4-67, 4-68, 4-69, 4-70, 4-71, 4-72, 4-73, 4-74, 4-75, 4-76, 4-77, 4-78, 4-79, 4-80, 4-81, 4-82, 4-83, 4-84, 4-85, 4-86, 4-87 and 4-88.

Peptides and Proteins that Begin with Amino Acid 5 of HPV16 L2

5-14, 5-15, 5-16, 5-17, 5-18, 5-19, 5-20, 5-21, 5-22, 5-23, 5-24, 5-25, 5-26, 5-27, 5-28, 5-29, 5-30, 5-31, 5-32, 5-33, 5-34, 5-35, 5-36, 5-37, 5-38, 5-39, 5-40, 5-41, 5-42, 5-43, 5-44, 5-45, 546, 5-47, 5-48, 5-49, 5-50, 5-51, 5-52, 5-53, 5-54, 5-55, 5-56, 5-57, 5-58, 5-59, 5-60, 5-61, 5-62, 5-63, 5-64, 5-65, 5-66, 5-67, 5-68, 5-69, 5-70, 5-71, 5-72, 5-73, 5-74, 5-75, 5-76, 5-77, 5-78, 5-79, 5-80, 5-81, 5-82, 5-83, 5-84, 5-85, 5-86, 5-87 and 5-88.

Peptides and Proteins that Begin with Amino Acid 6 of HPV16 L2

6-15, 6-16, 6-17, 6-18, 6-19, 6-20, 6-21, 6-22, 6-23, 6-24, 6-25, 6-26, 6-27, 6-28, 6-29, 6-30, 6-31, 6-32, 6-33, 6-34, 6-35, 6-36, 6-37, 6-38, 6-39, 6-40, 6-41, 6-42, 6-43, 6-44, 6-45, 6-46, 6-47, 6-48, 6-49, 6-50, 6-51, 6-52, 6-53, 6-54, 6-55, 6-56, 6-57, 6-58, 6-59, 6-60, 6-61, 6-62, 6-63, 6-64, 6-65, 6-66, 6-67, 6-68, 6-69, 6-70, 6-71, 6-72, 6-73, 6-74, 6-75, 6-76, 6-77, 6-78, 6-79, 6-80, 6-81, 6-82, 6-83, 6-84, 6-85, 6-86, 6-87 and 6-88.

Peptides and Proteins that Begin with Amino Acid 7 of HPV16 L2

7-16, 7-17, 7-18, 7-19, 7-20, 7-21, 7-22, 7-23, 7-24, 7-25, 7-26, 7-27, 7-28, 7-29, 7-30, 7-31, 7-32, 7-33, 7-34, 7-35, 7-36, 7-37, 7-38, 7-39, 7-40, 7-41, 7-42, 7-43, 7-44, 7-45, 7-46, 7-47, 7-48, 7-49, 7-50, 7-51, 7-52, 7-53, 7-54, 7-55, 7-56, 7-57, 7-58, 7-59, 7-60, 7-61, 7-62, 7-63, 7-64, 7-65, 7-66, 7-67, 7-68, 7-69, 7-70, 7-71, 7-72, 7-73, 7-74, 7-75, 7-76, 7-77, 7-78, 7-79, 7-80, 7-81, 7-82, 7-83, 7-84, 7-85, 7-86, 7-87 and 7-88.

Peptides and Proteins that Begin with Amino Acid 8 of HPV16 L2

8-17, 8-18, 8-19, 8-20, 8-21, 8-22, 8-23, 8-24, 8-25, 8-26, 8-27, 8-28, 8-29, 8-30, 8-31, 8-32, 8-33, 8-34, 8-35, 8-36, 8-37, 8-38, 8-39, 8-40, 8-41, 8-42, 8-43, 8-44, 8-45, 8-46, 8-47, 8-48, 8-49, 8-50, 8-51, 8-52, 8-53, 8-54, 8-55, 8-56, 8-57, 8-58, 8-59, 8-60, 8-61, 8-62, 8-63, 8-64, 8-65, 8-66, 8-67, 8-68, 8-69, 8-70, 8-71, 8-72, 8-73, 8-74, 8-75, 8-76, 8-77, 8-78, 8-79, 8-80, 8-81, 8-82, 8-83, 8-84, 8-85, 8-86, 8-87 and 8-88.

Peptides and Proteins that Begin with Amino Acid 9 of HPV16 L2

9-18, 9-19, 9-20, 9-21, 9-22, 9-23, 9-24, 9-25, 9-26, 9-27, 9-28, 9-29, 9-30, 9-31, 9-32, 9-33, 9-34, 9-35, 9-36, 9-37, 9-38, 9-39, 9-40, 9-41, 9-42, 9-43, 9-44, 9-45, 9-46, 9-47, 9-48, 9-49, 9-50, 9-51, 9-52, 9-53, 9-54, 9-55, 9-56, 9-57, 9-58, 9-59, 9-60, 9-61, 9-62, 9-63, 9-64, 9-65, 9-66, 9-67, 9-68, 9-69, 9-70, 9-71, 9-72, 9-73, 9-74, 9-75, 9-76, 9-77, 9-78, 9-79, 9-80, 9-81, 9-82, 9-83, 9-84, 9-85, 9-86, 9-87 and 9-88.

Peptides and Proteins that Begin with Amino Acid 10 of HPV16 L2

10-19, 10-20, 10-21, 10-22, 10-23, 10-24, 10-25, 10-26, 10-27, 10-28, 10-29, 10-30, 10-31, 10-32, 10-33, 10-34, 10-35, 10-36, 10-37, 10-38, 10-39, 10-40, 1041, 10-42, 10-43, 10-44, 10-45, 10-46, 10-47, 10-48, 10-49, 10-50, 10-51, 10-52, 10-53, 10-54, 10-55, 10-56, 10-57, 10-58, 10-59, 10-60, 10-61, 10-62, 10-63, 10-64, 10-65, 10-66, 10-67, 10-68, 10-69, 10-70, 10-71, 10-72, 10-73, 10-74, 10-75, 10-76, 10-77, 10-78, 10-79, 10-80, 10-81, 10-82, 10-83, 10-84, 10-85, 10-86, 10-87 and 10-88.

Peptides and Proteins that Begin with Amino Acid 11 of HPV16 L2

11-20, 11-21, 11-22, 11-23, 11-24, 11-25, 11-26, 11-27, 11-28, 11-29, 11-30, 11-31, 11-32, 11-33, 11-34, 11-35, 11-36, 11-37, 11-38, 11-39, 11-40, 11-41, 11-42, 11-43, 11-44, 11-45, 11-46, 11-47, 11-48, 11-49, 11-50, 11-51, 11-52, 11-53, 11-54, 11-55, 11-56, 11-57, 11-58, 11-59, 11-60, 11-61, 11-62, 11-63, 11-64, 11-65, 11-66, 11-67, 11-68, 11-69, 11-70, 11-71, 11-72, 11-73, 11-74, 11-75, 11-76, 11-77, 11-78, 11-79, 11-80, 11-81, 11-82, 11-83, 11-84, 11-85, 11-86, 11-87 and 11-88.

Peptides and Proteins that Begin with Amino Acid 12 of HPV16 L2

12-21, 12-22, 12-23, 12-24, 12-25, 12-26, 12-27, 12-28, 12-29, 12-30, 12-31, 12-32, 12-33, 12-34, 12-35, 12-36, 12-37, 12-38, 12-39, 12-40, 12-41, 12-42, 12-43, 12-44, 12-45, 12-46, 12-47, 12-48, 12-49, 12-50, 12-51, 12-52, 12-53, 12-54, 12-55, 12-56, 12-57, 12-58, 12-59, 12-60, 12-61, 12-62, 12-63, 12-64, 12-65, 12-66, 12-67, 12-68, 12-69, 12-70, 12-71, 12-72, 12-73, 12-74, 12-75, 12-76, 12-77, 12-78, 12-79, 12-80, 12-81, 12-82, 12-83, 12-84, 12-85, 12-86, 12-87 and 12-88.

Peptides and Proteins that Begin with Amino Acid 13 of HPV16 L2

13-22, 13-23, 13-24, 13-25, 13-26, 13-27, 13-28, 13-29, 13-30, 13-31, 13-32, 13-33, 13-34, 13-35, 13-36, 13-37, 13-38, 13-39, 13-40, 13-41, 13-42, 13-43, 13-44, 13-45, 13-46, 13-47, 13-48, 13-49, 13-50, 13-51, 13-52, 13-53, 13-54, 13-55, 13-56, 13-57, 13-58, 13-59, 13-60, 13-61, 13-62, 13-63, 13-64, 13-65, 13-66, 13-67, 13-68, 13-69, 13-70, 13-71, 13-72, 13-73, 13-74, 13-75, 13-76, 13-77, 13-78, 13-79, 13-80, 13-81, 13-82, 13-83, 13-84, 13-85, 13-86, 13-87 and 13-88.

Peptides and Proteins that Begin with Amino Acid 14 of HPV16 L2

14-23, 14-24, 14-25, 14-26, 14-27, 14-28, 14-29, 14-30, 14-31, 14-32, 14-33, 14-34, 14-35, 14-36, 14-37, 14-38, 14-39, 14-40, 14-41, 14-42, 14-43, 14-44, 14-45, 14-46, 14-47, 14-48, 14-49, 14-50, 14-51, 14-52, 14-53, 14-54, 14-55, 14-56, 14-57, 14-58, 14-59, 14-60, 14-61, 14-62, 14-63, 14-64, 14-65, 14-66, 14-67, 14-68, 14-69, 14-70, 14-71, 14-72, 14-73, 14-74, 14-75, 14-76, 14-77, 14-78, 14-79, 14-80, 14-81, 14-82, 14-83, 14-84, 14-85, 14-86, 14-87 and 14-88.

Peptides and Proteins that Begin with Amino Acid 15 of HPV16 L2

15-24, 15-25, 15-26, 15-27, 15-28, 15-29, 15-30, 15-31, 15-32, 15-33, 15-34, 15-35, 15-36, 15-37, 15-38, 15-39, 15-40, 15-41, 15-42, 15-43, 1544, 15-45, 15-46, 15-47, 15-48, 15-49, 15-50, 15-51, 15-52, 15-53, 15-54, 15-55, 15-56, 15-57, 15-58, 15-59, 15-60, 15-61, 15-62, 15-63, 15-64, 15-65, 15-66, 15-67, 15-68, 15-69, 15-70, 15-71, 15-72, 15-73, 15-74, 15-75, 15-76, 15-77, 15-78, 15-79, 15-80, 15-81, 15-82, 15-83, 15-84, 15-85, 15-86, 15-87 and 15-88.

Peptides and Proteins that Begin with Amino Acid 16 of HPV16 L2

16-25, 16-26, 16-27, 16-28, 16-29, 16-30, 16-31, 16-32, 16-33, 16-34, 16-35, 16-36, 16-37, 16-38, 16-39, 16-40, 16-41, 16-42, 16-43, 16-44, 16-45, 16-46, 16-47, 16-48, 16-49, 16-50, 16-51, 16-52, 16-53, 16-54, 16-55, 16-56, 16-57, 16-58, 16-59, 16-60, 16-61, 16-62, 16-63, 16-64, 16-65, 16-66, 16-67, 16-68, 16-69, 16-70, 16-71, 16-72, 16-73, 16-74, 16-75, 16-76, 16-77, 16-78, 16-79, 16-80, 16-81, 16-82, 16-83, 16-84, 16-85, 16-86, 16-87 and 16-88.

Peptides and Proteins that Begin with Amino Acid 17 of HPV16 L2

17-26, 17-27, 17-28, 17-29, 17-30, 17-31, 17-32, 17-33, 17-34, 17-35, 17-36, 17-37, 17-38, 17-39, 17-40, 17-41, 17-42, 17-43, 17-44, 17-45, 17-46, 1747, 17-48, 17-49, 17-50, 17-51, 17-52, 17-53, 17-54, 17-55, 17-56, 17-57, 17-58, 17-59, 17-60, 17-61, 17-62, 17-63, 17-64, 17-65, 17-66, 17-67, 17-68, 17-69, 17-70, 17-71, 17-72, 17-73, 17-74, 17-75, 17-76, 17-77, 17-78, 17-79, 17-80, 17-81, 17-82, 17-83, 17-84, 17-85, 17-86, 17-87 and 17-88.

Peptides and Proteins that Begin with Amino Acid 18 of HPV16 L2
18-27, 18-28, 18-29, 18-30, 18-31, 18-32, 18-33, 18-34, 18-35, 18-36, 18-37, 18-38, 18-39, 18-40, 18-41, 18-42, 18-43, 18-44, 18-45, 18-46, 18-47, 18-48, 1849, 18-50, 18-51, 18-52, 18-53, 18-54, 18-55, 18-56, 18-57, 18-58, 18-59, 18-60, 18-61, 18-62, 18-63, 18-64, 18-65, 18-66, 18-67, 18-68, 18-69, 18-70, 18-71, 18-72, 18-73, 18-74, 18-75, 18-76, 18-77, 18-78, 18-79, 18-80, 18-81, 18-82, 18-83, 18-84, 18-85, 18-86, 18-87 and 18-88.

Peptides and Proteins that Begin with Amino Acid 19 of HPV16 L2
19-28, 19-29, 19-30, 19-31, 19-32, 19-33, 19-34, 19-35, 19-36, 19-37, 19-38, 19-39, 19-40, 19-41, 19-42, 19-43, 19-44, 19-45, 19-46, 19-47, 19-48, 19-49, 19-50, 19-51, 19-52, 19-53, 19-54, 19-55, 19-56, 19-57, 19-58, 19-59, 19-60, 19-61, 19-62, 19-63, 19-64, 19-65, 19-66, 19-67, 19-68, 19-69, 19-70, 19-71, 19-72, 19-73, 19-74, 19-75, 19-76, 19-77, 19-78, 19-79, 19-80, 19-81, 19-82, 19-83, 19-84, 19-85, 19-86, 19-87 and 19-88.

Peptides and Proteins that Begin with Amino Acid 20 of HPV16 L2
20-29, 20-30, 20-31, 20-32, 20-33, 20-34, 20-35, 20-36, 20-37, 20-38, 20-39, 20-40, 20-41, 20-42, 20-43, 20-44, 20-45, 20-46, 20-47, 20-48, 20-49, 20-50, 20-51, 20-52, 20-53, 20-54, 20-55, 20-56, 20-57, 20-58, 20-59, 20-60, 20-61, 20-62, 20-63, 20-64, 20-65, 20-66, 20-67, 20-68, 20-69, 20-70, 20-71, 20-72, 20-73, 20-74, 20-75, 20-76, 20-77, 20-78, 20-79, 20-80, 20-81, 20-82, 20-83, 20-84, 20-85, 20-86, 20-87 and 20-88.

Peptides and Proteins that Begin with Amino Acid 21 of HPV16 L2
21-30, 21-31, 21-32, 21-33, 21-34, 21-35, 21-36, 21-37, 21-38, 21-39, 21-40, 21-41, 21-42, 21-43, 21-44, 21-45, 21-46, 21-47, 21-48, 2149, 21-50, 21-51, 21-52, 21-53, 21-54, 21-55, 21-56, 21-57, 21-58, 21-59, 21-60, 21-61, 21-62, 21-63, 21-64, 21-65, 21-66, 21-67, 21-68, 21-69, 21-70, 21-71, 21-72, 21-73, 21-74, 21-75, 21-76, 21-77, 21-78, 21-79, 21-80, 21-81, 21-82, 21-83, 21-84, 21-85, 21-86, 21-87 and 21-88.

Peptides and Proteins that Begin with Amino Acid 22 of HPV16 L2
22-31, 22-32, 22-33, 22-34, 22-35, 22-36, 22-37, 22-38, 22-39, 22-40, 2241, 22-42, 22-43, 22-44, 22-45, 22-46, 22-47, 22-48, 22-49, 22-50, 22-51, 22-52, 22-53, 22-54, 22-55, 22-56, 22-57, 22-58, 22-59, 22-60, 22-61, 22-62, 22-63, 22-64, 22-65, 22-66, 22-67, 22-68, 22-69, 22-70, 22-71, 22-72, 22-73, 22-74, 22-75, 22-76, 22-77, 22-78, 22-79, 22-80, 22-81, 22-82, 22-83, 22-84, 22-85, 22-86, 22-87 and 22-88.

Peptides and Proteins that Begin with Amino Acid 23 of HPV16 L2
23-32, 23-33, 23-34, 23-35, 23-36, 23-37, 23-38, 23-39, 23-40, 23-41, 23-42, 23-43, 23-44, 23-45, 23-46, 23-47, 23-48, 23-49, 23-50, 23-51, 23-52, 23-53, 23-54, 23-55, 23-56, 23-57, 23-58, 23-59, 23-60, 23-61, 23-62, 23-63, 23-64, 23-65, 23-66, 23-67, 23-68, 23-69, 23-70, 23-71, 23-72, 23-73, 23-74, 23-75, 23-76, 23-77, 23-78, 23-79, 23-80, 23-81, 23-82, 23-83, 23-84, 23-85, 23-86, 23-87 and 23-88.

Peptides and Proteins that Begin with Amino Acid 24 of HPV16 L2
24-33, 24-34, 24-35, 24-36, 24-37, 24-38, 24-39, 24-40, 24-41, 24-42, 24-43, 24-44, 24-45, 24-46, 24-47, 24-48, 24-49, 24-50, 24-51, 24-52, 24-53, 24-54, 24-55, 24-56, 24-57, 24-58, 24-59, 24-60, 24-61, 24-62, 24-63, 24-64, 24-65, 24-66, 24-67, 24-68, 24-69, 24-70, 24-71, 24-72, 24-73, 24-74, 24-75, 24-76, 24-77, 24-78, 24-79, 24-80, 24-81, 24-82, 24-83, 24-84, 24-85, 24-86, 24-87 and 24-88.

Peptides and Proteins that Begin with Amino Acid 25 of HPV16 L2
25-34, 25-35, 25-36, 25-37, 25-38, 25-39, 25-40, 25-41, 25-42, 25-43, 25-44, 2545, 25-46, 25-47, 25-48, 25-49, 25-50, 25-51, 25-52, 25-53, 25-54, 25-55, 25-56, 25-57, 25-58, 25-59, 25-60, 25-61, 25-62, 25-63, 25-64, 25-65, 25-66, 25-67, 25-68, 25-69, 25-70, 25-71, 25-72, 25-73, 25-74, 25-75, 25-76, 25-77, 25-78, 25-79, 25-80, 25-81, 25-82, 25-83, 25-84, 25-85, 25-86, 25-87 and 25-88.

Peptides and Proteins that Begin with Amino Acid 26 of HPV16 L2
26-35, 26-36, 26-37, 26-38, 26-39, 26-40, 26-41, 26-42, 26-43, 2644, 26-45, 26-46, 26-47, 26-48, 26-49, 26-50, 26-51, 26-52, 26-53, 26-54, 26-55, 26-56, 26-57, 26-58, 26-59, 26-60, 26-61, 26-62, 26-63, 26-64, 26-65, 26-66, 26-67, 26-68, 26-69, 26-70, 26-71, 26-72, 26-73, 26-74, 26-75, 26-76, 26-77, 26-78, 26-79, 26-80, 26-81, 26-82, 26-83, 26-84, 26-85, 26-86, 26-87 and 26-88.

Peptides and Proteins that Begin with Amino Acid 27 of HPV16 L2
27-36, 27-37, 27-38, 27-39, 27-40, 27-41, 27-42, 27-43, 27-44, 27-45, 27-46, 27-47, 27-48, 27-49, 27-50, 27-51, 27-52, 27-53, 27-54, 27-55, 27-56, 27-57, 27-58, 27-59, 27-60, 27-61, 27-62, 27-63, 27-64, 27-65, 27-66, 27-67, 27-68, 27-69, 27-70, 27-71, 27-72, 27-73, 27-74, 27-75, 27-76, 27-77, 27-78, 27-79, 27-80, 27-81, 27-82, 27-83, 27-84, 27-85, 27-86, 27-87 and 27-88.

Peptides and Proteins that Begin with Amino Acid 28 of HPV16 L2
28-37, 28-38, 28-39, 28-40, 28-41, 28-42, 28-43, 28-44, 28-45, 28-46, 28-47, 28-48, 28-49, 28-50, 28-51, 28-52, 28-53, 28-54, 28-55, 28-56, 28-57, 28-58, 28-59, 28-60, 28-61, 28-62, 28-63, 28-64, 28-65, 28-66, 28-67, 28-68, 28-69, 28-70, 28-71, 28-72, 28-73, 28-74, 28-75, 28-76, 28-77, 28-78, 28-79, 28-80, 28-81, 28-82, 28-83, 28-84, 28-85, 28-86, 28-87 and 28-88.

Peptides and Proteins that Begin with Amino Acid 29 of HPV16 L2
29-38, 29-39, 29-40, 29-41, 29-42, 29-43, 29-44, 29-45, 29-46, 29-47, 29-48, 29-49, 29-50, 29-51, 29-52, 29-53, 29-54, 29-55, 29-56, 29-57, 29-58, 29-59, 29-60, 29-61, 29-62, 29-63, 29-64, 29-65, 29-66, 29-67, 29-68, 29-69, 29-70, 29-71, 29-72, 29-73, 29-74, 29-75, 29-76, 29-77, 29-78, 29-79, 29-80, 29-81, 29-82, 29-83, 29-84, 29-85, 29-86, 29-87 and 29-88.

Peptides and Proteins that Begin with Amino Acid 30 of HPV16 L2
30-39, 30-40, 30-41, 30-42, 30-43, 30-44, 30-45, 30-46, 3047, 30-48, 30-49, 30-50, 30-51, 30-52, 30-53, 30-54, 30-55, 30-56, 30-57, 30-58, 30-59, 30-60, 30-61, 30-62, 30-63, 30-64, 30-65, 30-66, 30-67, 30-68, 30-69, 30-70, 30-71, 30-72, 30-73, 30-74, 30-75, 30-76, 30-77, 30-78, 30-79, 30-80, 30-81, 30-82, 30-83, 30-84, 30-85, 30-86, 30-87 and 30-88.

Peptides and Proteins that Begin with Amino Acid 31 of HPV16 L2
31-40, 31-41, 31-42, 31-43, 31-44, 31-45, 31-46, 3147, 31-48, 31-49, 31-50, 31-51, 31-52, 31-53, 31-54, 31-55, 31-56, 31-57, 31-58, 31-59, 31-60, 31-61, 31-62, 31-63, 31-64, 31-65, 31-66, 31-67, 31-68, 31-69, 31-70, 31-71, 31-72, 31-73, 31-74, 31-75, 31-76, 31-77, 31-78, 31-79, 31-80, 31-81, 31-82, 31-83, 31-84, 31-85, 31-86, 31-87 and 31-88.

Peptides and Proteins that Begin with Amino Acid 32 of HPV16 L2
32-41, 32-42, 32-43, 32-44, 32-45, 32-46, 32-47, 3248, 32-49, 32-50, 32-51, 32-52, 32-53, 32-54, 32-55, 32-56, 32-57, 32-58, 32-59, 32-60, 32-61, 32-62, 32-63, 32-64, 32-65, 32-66, 32-67, 32-68, 32-69, 32-70, 32-71, 32-72, 32-73, 32-74, 32-75, 32-76, 32-77, 32-78, 32-79, 32-80, 32-81, 32-82, 32-83, 32-84, 32-85, 32-86, 32-87 and 32-88.

Peptides and Proteins that Begin with Amino Acid 33 of HPV16 L2
3342, 33-43, 33-44, 33-45, 3346, 33-47, 33-48, 33-49, 33-50, 33-51, 33-52, 33-53, 33-54, 33-55, 33-56, 33-57, 33-58, 33-59, 33-60, 33-61, 33-62, 33-63, 33-64, 33-65, 33-66, 33-67, 33-68, 33-69, 33-70, 33-71, 33-72, 33-73, 33-74, 33-75, 33-76, 33-77, 33-78, 33-79, 33-80, 33-81, 33-82, 33-83, 33-84, 33-85, 33-86, 33-87 and 33-88.

Peptides and Proteins that Begin with Amino Acid 34 of HPV16 L2
34-43, 34-44, 34-45, 34-46, 34-47, 3448, 34-49, 34-50, 34-51, 34-52, 34-53, 34-54, 34-55, 34-56, 34-57, 34-58, 34-59, 34-60, 34-61, 34-62, 34-63, 34-64, 34-65, 34-66, 34-67, 34-68, 34-69, 34-70, 34-71, 34-72, 34-73, 34-74, 34-75, 34-76, 34-77, 34-78, 34-79, 34-80, 34-81, 34-82, 34-83, 34-84, 34-85, 34-86, 34-87 and 34-88.

Peptides and Proteins that Begin with Amino Acid 35 of HPV16 L2
35-44, 35-45, 3546, 35-47, 35-48, 35-49, 35-50, 35-51, 35-52, 35-53, 35-54, 35-55, 35-56, 35-57, 35-58, 35-59, 35-60, 35-61, 35-62, 35-63, 35-64, 35-65, 35-66, 35-67, 35-68, 35-69, 35-70, 35-71, 35-72, 35-73, 35-74, 35-75, 35-76, 35-77, 35-78, 35-79, 35-80, 35-81, 35-82, 35-83, 35-84, 35-85, 35-86, 35-87 and 35-88.

Peptides and Proteins that Begin with Amino Acid 36 of HPV16 L2
36-45, 3646, 36-47, 36-48, 36-49, 36-50, 36-51, 36-52, 36-53, 36-54, 36-55, 36-56, 36-57, 36-58, 36-59, 36-60, 36-61, 36-62, 36-63, 36-64, 36-65, 36-66, 36-67, 36-68, 36-69, 36-70, 36-71, 36-72, 36-73, 36-74, 36-75, 36-76, 36-77, 36-78, 36-79, 36-80, 36-81, 36-82, 36-83, 36-84, 36-85, 36-86, 36-87 and 36-88.

Peptides and Proteins that Begin with Amino Acid 37 of HPV16 L2
37-46, 37-47, 37-48, 37-49, 37-50, 37-51, 37-52, 37-53, 37-54, 37-55, 37-56, 37-57, 37-58, 37-59, 37-60, 37-61, 37-62, 37-63, 37-64, 37-65, 37-66, 37-67, 37-68, 37-69, 37-70, 37-71, 37-72, 37-73, 37-74, 37-75, 37-76, 37-77, 37-78, 37-79, 37-80, 37-81, 37-82, 37-83, 37-84, 37-85, 37-86, 37-87 and 37-88.

Peptides and Proteins that Begin with Amino Acid 38 of HPV16 L2
38-47, 38-48, 38-49, 38-50, 38-51, 38-52, 38-53, 38-54, 38-55, 38-56, 38-57, 38-58, 38-59, 38-60, 38-61, 38-62, 38-63, 38-64, 38-65, 38-66, 38-67, 38-68, 38-69, 38-70, 38-71, 38-72, 38-73, 38-74, 38-75, 38-76, 38-77, 38-78, 38-79, 38-80, 38-81, 38-82, 38-83, 38-84, 38-85, 38-86, 38-87 and 38-88.

Peptides and Proteins that Begin with Amino Acid 39 of HPV16 L2
39-48, 39-49, 39-50, 39-51, 39-52, 39-53, 39-54, 39-55, 39-56, 39-57, 39-58, 39-59, 39-60, 39-61, 39-62, 39-63, 39-64, 39-65, 39-66, 39-67, 39-68, 39-69, 39-70, 39-71, 39-72, 39-73, 39-74, 39-75, 39-76, 39-77, 39-78, 39-79, 39-80, 39-81, 39-82, 39-83, 39-84, 39-85, 39-86, 39-87 and 39-88.

Peptides and Proteins that Begin with Amino Acid 40 of HPV16 L2
40-49, 40-50, 40-51, 40-52, 40-53, 40-54, 40-55, 40-56, 40-57, 40-58, 40-59, 40-60, 40-61, 40-62, 40-63, 40-64, 40-65, 40-66, 40-67, 40-68, 40-69, 40-70, 40-71, 40-72, 40-73, 40-74, 40-75, 40-76, 40-77, 40-78, 40-79, 40-80, 40-81, 40-82, 40-83, 40-84, 40-85, 40-86, 40-87 and 40-88.

Peptides and Proteins that Begin with Amino Acid 41 of HPV16 L2
41-50, 41-51, 41-52, 41-53, 41-54, 41-55, 41-56, 41-57, 41-58, 41-59, 41-60, 41-61, 41-62, 41-63, 41-64, 41-65, 41-66, 41-67, 41-68, 41-69, 41-70, 41-71, 41-72, 41-73, 41-74, 41-75, 41-76, 41-77, 41-78, 41-79, 41-80, 41-81, 41-82, 41-83, 41-84, 41-85, 41-86, 41-87 and 41-88.

Peptides and Proteins that Begin with Amino Acid 42 of HPV16 L2
42-51, 42-52, 42-53, 42-54, 42-55, 42-56, 42-57, 42-58, 42-59, 42-60, 42-61, 42-62, 42-63, 42-64, 42-65, 42-66, 42-67, 42-68, 42-69, 42-70, 42-71, 42-72, 42-73, 42-74, 42-75, 42-76, 42-77, 42-78, 42-79, 42-80, 42-81, 42-82, 42-83, 42-84, 42-85, 42-86, 42-87 and 42-88.

Peptides and Proteins that Begin with Amino Acid 43 of HPV16 L2
43-52, 43-53, 43-54, 43-55, 43-56, 43-57, 43-58, 43-59, 43-60, 43-61, 43-62, 43-63, 43-64, 43-65, 43-66, 43-67, 43-68, 43-69, 43-70, 43-71, 43-72, 43-73, 43-74, 43-75, 43-76, 43-77, 43-78, 43-79, 43-80, 43-81, 43-82, 43-83, 43-84, 43-85, 43-86, 43-87 and 43-88.

Peptides and Proteins that Begin with Amino Acid 44 of HPV16 L2
44-53, 44-54, 44-55, 44-56, 44-57, 44-58, 44-59, 44-60, 44-61, 44-62, 44-63, 44-64, 44-65, 44-66, 44-67, 44-68, 44-69, 44-70, 44-71, 44-72, 44-73, 44-74, 44-75, 44-76, 44-77, 44-78, 44-79, 44-80, 44-81, 44-82, 44-83, 44-84, 44-85, 44-86, 44-87 and 44-88.

Peptides and Proteins that Begin with Amino Acid 45 of HPV16 L2
45-54, 45-55, 45-56, 45-57, 45-58, 45-59, 45-60, 45-61, 45-62, 45-63, 45-64, 45-65, 45-66, 45-67, 45-68, 45-69, 45-70, 45-71, 45-72, 45-73, 45-74, 45-75, 45-76, 45-77, 45-78, 45-79, 45-80, 45-81, 45-82, 45-83, 45-84, 45-85, 45-86, 45-87 and 45-88.

Peptides and Proteins that Begin with Amino Acid 46 of HPV16 L2
46-55, 46-56, 46-57, 46-58, 46-59, 46-60, 46-61, 46-62, 46-63, 46-64, 46-65, 46-66, 46-67, 46-68, 46-69, 46-70, 46-71, 46-72, 46-73, 46-74, 46-75, 46-76, 46-77, 46-78, 46-79, 46-80, 46-81, 46-82, 46-83, 46-84, 46-85, 46-86, 46-87 and 46-88.

Peptides and Proteins that Begin with Amino Acid 47 of HPV16 L2
47-56, 47-57, 47-58, 47-59, 47-60, 47-61, 47-62, 47-63, 47-64, 47-65, 47-66, 47-67, 47-68, 47-69, 47-70, 47-71, 47-72, 47-73, 47-74, 47-75, 47-76, 47-77, 47-78, 47-79, 47-80, 47-81, 47-82, 47-83, 47-84, 47-85, 47-86, 47-87 and 47-88.

Peptides and Proteins that Begin with Amino Acid 48 of HPV16 L2
48-57, 48-58, 48-59, 48-60, 48-61, 48-62, 48-63, 48-64, 48-65, 48-66, 48-67, 48-68, 48-69, 48-70, 48-71, 48-72, 48-73, 48-74, 48-75, 48-76, 48-77, 48-78, 48-79, 48-80, 48-81, 48-82, 48-83, 48-84, 48-85, 48-86, 48-87 and 48-88.

Peptides and Proteins that Begin with Amino Acid 49 of HPV16 L2
49-58, 49-59, 49-60, 49-61, 49-62, 49-63, 49-64, 49-65, 49-66, 49-67, 49-68, 49-69, 49-70, 49-71, 49-72, 49-73, 49-74, 49-75, 49-76, 49-77, 49-78, 49-79, 49-80, 49-81, 49-82, 49-83, 49-84, 49-85, 49-86, 49-87 and 49-88.

Peptides and Proteins that Begin with Amino Acid 50 of HPV16 L2
50-59, 50-60, 50-61, 50-62, 50-63, 50-64, 50-65, 50-66, 50-67, 50-68, 50-69, 50-70, 50-71, 50-72, 50-73, 50-74, 50-75, 50-76, 50-77, 50-78, 50-79, 50-80, 50-81, 50-82, 50-83, 50-84, 50-85, 50-86, 50-87 and 50-88.

Peptides and Proteins that Begin with Amino Acid 51 of HPV16 L2
51-60, 51-61, 51-62, 51-63, 51-64, 51-65, 51-66, 51-67, 51-68, 51-69, 51-70, 51-71, 51-72, 51-73, 51-74, 51-75, 51-76, 51-77, 51-78, 51-79, 51-80, 51-81, 51-82, 51-83, 51-84, 51-85, 51-86, 51-87 and 51-88.

Peptides and Proteins that Begin with Amino Acid 52 of HPV16 L2
52-61, 52-62, 52-63, 52-64, 52-65, 52-66, 52-67, 52-68, 52-69, 52-70, 52-71, 52-72, 52-73, 52-74, 52-75, 52-76, 52-77, 52-78, 52-79, 52-80, 52-81, 52-82, 52-83, 52-84, 52-85, 52-86, 52-87 and 52-88.

Peptides and Proteins that Begin with Amino Acid 53 of HPV16 L2
53-62, 53-63, 53-64, 53-65, 53-66, 53-67, 53-68, 53-69, 53-70, 53-71, 53-72, 53-73, 53-74, 53-75, 53-76, 53-77, 53-78, 53-79, 53-80, 53-81, 53-82, 53-83, 53-84, 53-85, 53-86, 53-87 and 53-88.

Peptides and Proteins that Begin with Amino Acid 54 of HPV16 L2
54-63, 54-64, 54-65, 54-66, 54-67, 54-68, 54-69, 54-70, 54-71, 54-72, 54-73, 54-74, 54-75, 54-76, 54-77, 54-78, 54-79, 54-80, 54-81, 54-82, 54-83, 54-84, 54-85, 54-86, 54-87 and 54-88.

Peptides and Proteins that Begin with Amino Acid 55 of HPV16 L2
55-64, 55-65, 55-66, 55-67, 55-68, 55-69, 55-70, 55-71, 55-72, 55-73, 55-74, 55-75, 55-76, 55-77, 55-78, 55-79, 55-80, 55-81, 55-82, 55-83, 55-84, 55-85, 55-86, 55-87 and 55-88.

Peptides and Proteins that Begin with Amino Acid 56 of HPV16 L2
56-65, 56-66, 56-67, 56-68, 56-69, 56-70, 56-71, 56-72, 56-73, 56-74, 56-75, 56-76, 56-77, 56-78, 56-79, 56-80, 56-81, 56-82, 56-83, 56-84, 56-85, 56-86, 56-87 and 56-88.

Peptides and Proteins that Begin with Amino Acid 57 of HPV16 L2
57-66, 57-67, 57-68, 57-69, 57-70, 57-71, 57-72, 57-73, 57-74, 57-75, 57-76, 57-77, 57-78, 57-79, 57-80, 57-81, 57-82, 57-83, 57-84, 57-85, 57-86, 57-87 and 57-88.

Peptides and Proteins that Begin with Amino Acid 58 of HPV16 L2
58-67, 58-68, 58-69, 58-70, 58-71, 58-72, 58-73, 58-74, 58-75, 58-76, 58-77, 58-78, 58-79, 58-80, 58-81, 58-82, 58-83, 58-84, 58-85, 58-86, 58-87 and 58-88.

Peptides and Proteins that Begin with Amino Acid 59 of HPV16 L2
59-68, 59-69, 59-70, 59-71, 59-72, 59-73, 59-74, 59-75, 59-76, 59-77, 59-78, 59-79, 59-80, 59-81, 59-82, 59-83, 59-84, 59-85, 59-86, 59-87 and 59-88.

Peptides and Proteins that Begin with Amino Acid 60 of HPV16 L2
60-69, 60-70, 60-71, 60-72, 60-73, 60-74, 60-75, 60-76, 60-77, 60-78, 60-79, 60-80, 60-81, 60-82, 60-83, 60-84, 60-85, 60-86, 60-87 and 60-88.

Peptides and Proteins that Begin with Amino Acid 61 of HPV16 L2
61-70, 61-71, 61-72, 61-73, 61-74, 61-75, 61-76, 61-77, 61-78, 61-79, 61-80, 61-81, 61-82, 61-83, 61-84, 61-85, 61-86, 61-87 and 61-88.

Peptides and Proteins that Begin with Amino Acid 62 of HPV16 L2
62-71, 62-72, 62-73, 62-74, 62-75, 62-76, 62-77, 62-78, 62-79, 62-80, 62-81, 62-82, 62-83, 62-84, 62-85, 62-86, 62-87 and 62-88.

Peptides and Proteins that Begin with Amino Acid 63 of HPV16 L2
63-72, 63-73, 63-74, 63-75, 63-76, 63-77, 63-78, 63-79, 63-80, 63-81, 63-82, 63-83, 63-84, 63-85, 63-86, 63-87 and 63-88.

Peptides and Proteins that Begin with Amino Acid 64 of HPV16 L2
64-73, 64-74, 64-75, 64-76, 64-77, 64-78, 64-79, 64-80, 64-81, 64-82, 64-83, 64-84, 64-85, 64-86, 64-87 and 64-88.

Peptides and Proteins that Begin with Amino Acid 65 of HPV16 L2
65-74, 65-75, 65-76, 65-77, 65-78, 65-79, 65-80, 65-81, 65-82, 65-83, 65-84, 65-85, 65-86, 65-87 and 65-88.

Peptides and Proteins that Begin with Amino Acid 66 of HPV16 L2
66-75, 66-76, 66-77, 66-78, 66-79, 66-80, 66-81, 66-82, 66-83, 66-84, 66-85, 66-86, 66-87 and 66-88.

Peptides and Proteins that Begin with Amino Acid 67 of HPV16 L2

67-76, 67-77, 67-78, 67-79, 67-80, 67-81, 67-82, 67-83, 67-84, 67-85, 67-86, 67-87 and 67-88.

Peptides and Proteins that Begin with Amino Acid 68 of HPV16 L2

68-77, 68-78, 68-79, 68-80, 68-81, 68-82, 68-83, 68-84, 68-85, 68-86, 68-87 and 68-88.

Peptides and Proteins that Begin with Amino Acid 69 of HPV16 L2

69-78, 69-79, 69-80, 69-81, 69-82, 69-83, 69-84, 69-85, 69-86, 69-87 and 69-88.

Peptides and Proteins that Begin with Amino Acid 70 of HPV16 L2

70-79, 70-80, 70-81, 70-82, 70-83, 70-84, 70-85, 70-86, 70-87 and 70-88.

Peptides and Proteins that Begin with Amino Acid 71 of HPV16 L2

71-80, 71-81, 71-82, 71-83, 71-84, 71-85, 71-86, 71-87 and 71-88.

Peptides and Proteins that Begin with Amino Acid 72 of HPV16 L2

72-81, 72-82, 72-83, 72-84, 72-85, 72-86, 72-87 and 72-88.

Peptides and Proteins that Begin with Amino Acid 73 of BPV16 L2

73-82, 73-83, 73-84, 73-85, 73-86, 73-87 and 73-88.

Peptides and Proteins that Begin with Amino Acid 74 of HPV16 L2

74-83, 74-84, 74-85, 74-86, 74-87 and 74-88.

Peptides and Proteins that Begin with Amino Acid 75 of HPV16 L2

75-84, 75-85, 75-86, 75-87 and 75-88.

Peptides and Proteins that Begin with Amino Acid 76 of HPV16 L2
76-85, 76-86, 76-87 and 76-88.
Peptides and Proteins that Begin with Amino Acid 77 of HPV16 L2
77-86, 77-87 and 77-88.
Peptides and Proteins that Begin with Amino Acid 78 of HPV16 L2
78-87 and 78-88.
Peptides and Proteins that Begins with Amino Acid 79 of HPV16 L2
79-88.

In other embodiments, peptides and proteins of the invention are located within the first 200 amino acids of the N-terminal region of HPV16 L2 and are 10-200 amino acids in length, substantially in isolation from sequences naturally occurring adjacent thereto in the papillomavirus L2 protein.

Peptides and Proteins that Begin with Amino Acid 1 of HPV16 L2
1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, and 1-200.

Peptides and Proteins that Begin with Amino Acid 2 of HPV16 L2
2-89, 2-90, 2-91, 2-92, 2-93, 2-94, 2-95, 2-96, 2-97, 2-98, 2-99, 2-100, 2-101, 2-102, 2-103, 2-104, 2-105, 2-106, 2-107, 2-108, 2-109, 2-110, 2-111, 2-112, 2-113, 2-114, 2-115, 2-116, 2-117, 2-118, 2-119, 2-120, 2-121, 2-122, 2-123, 2-124, 2-125, 2-126, 2-127, 2-128, 2-129, 2-130, 2-131, 2-132, 2-133, 2-134, 2-135, 2-136, 2-137, 2-138, 2-139, 2-140, 2-141, 2-142, 2-143, 2-144, 2-145, 2-146, 2-147, 2-148, 2-149, 2-150, 2-151, 2-152, 2-153, 2-154, 2-155, 2-156, 2-157, 2-158, 2-159, 2-160, 2-161, 2-162, 2-163, 2-164, 2-165, 2-166, 2-167, 2-168, 2-169, 2-170, 2-171, 2-172, 2-173, 2-174, 2-175, 2-176, 2-177, 2-178, 2-179, 2-180, 2-181, 2-182, 2-183, 2-184, 2-185, 2-186, 2-187, 2-188, 2-189, 2-190, 2-191, 2-192, 2-193, 2-194, 2-195, 2-196, 2-197, 2-198, 2-199, and 2-200.

Peptides and Proteins that Begin with Amino Acid 3 of HPV16 L2
3-89, 3-90, 3-91, 3-92, 3-93, 3-94, 3-95, 3-96, 3-97, 3-98, 3-99, 3-100, 3-101, 3-102, 3-103, 3-104, 3-105, 3-106, 3-107, 3-108, 3-109, 3-110, 3-111, 3-112, 3-113, 3-114, 3-115, 3-116, 3-117, 3-118, 3-119, 3-120, 3-121, 3-122, 3-123, 3-124, 3-125, 3-126, 3-127, 3-128, 3-129, 3-130, 3-131, 3-132, 3-133, 3-134, 3-135, 3-136, 3-137, 3-138, 3-139, 3-140, 3-141, 3-142, 3-143, 3-144, 3-145, 3-146, 3-147, 3-148, 3-149, 3-150, 3-151, 3-152, 3-153, 3-154, 3-155, 3-156, 3-157, 3-158, 3-159, 3-160, 3-161, 3-162, 3-163, 3-164, 3-165, 3-166, 3-167, 3-168, 3-169, 3-170, 3-171, 3-172, 3-173, 3-174, 3-175, 3-176, 3-177, 3-178, 3-179, 3-180, 3-181, 3-182, 3-183, 3-184, 3-185, 3-186, 3-187, 3-188, 3-189, 3-190, 3-191, 3-192, 3-193, 3-194, 3-195, 3-196, 3-197, 3-198, 3-199, and 3-200.

Peptides and Proteins that Begin with Amino Acid 4 of HPV16 L2
4-89, 4-90, 4-91, 4-92, 4-93, 4-94, 4-95, 4-96, 4-97, 4-98, 4-99, 4-100, 4-101, 4-102, 4-103, 4-104, 4-105, 4-106, 4-107, 4-108, 4-109, 4-110, 4-111, 4-112, 4-113, 4-114, 4-115, 4-116, 4-117, 4-118, 4-119, 4-120, 4-121, 4-122, 4-123, 4-124, 4-125, 4-126, 4-127, 4-128, 4-129, 4-130, 4-131, 4-132, 4-133, 4-134, 4-135, 4-136, 4-137, 4-138, 4-139, 4-140, 4-141, 4-142, 4-143, 4-144, 4-145, 4-146, 4-147, 4-148, 4-149, 4-150, 4-151, 4-152, 4-153, 4-154, 4-155, 4-156, 4-157, 4-158, 4-159, 4-160, 4-161, 4-162, 4-163, 4-164, 4-165, 4-166, 4-167, 4-168, 4-169, 4-170, 4-171, 4-172, 4-173, 4-174, 4-175, 4-176, 4-177, 4-178, 4-179, 4-180, 4-181, 4-182, 4-183, 4-184, 4-185, 4-186, 4-187, 4-188, 4-189, 4-190, 4-191, 4-192, 4-193, 4-194, 4-195, 4-196, 4-197, 4-198, 4-199, and 4-200.

Peptides and Proteins that Begin with Amino Acid 5 of HPV16 L2
5-89, 5-90, 5-91, 5-92, 5-93, 5-94, 5-95, 5-96, 5-97, 5-98, 5-99, 5-100, 5-101, 5-102, 5-103, 5-104, 5-105, 5-106, 5-107, 5-108, 5-109, 5-110, 5-111, 5-112, 5-113, 5-114, 5-115, 5-116, 5-117, 5-118, 5-119, 5-120, 5-121, 5-122, 5-123, 5-124, 5-125, 5-126, 5-127, 5-128, 5-129, 5-130, 5-131, 5-132, 5-133, 5-134, 5-135, 5-136, 5-137, 5-138, 5-139, 5-140, 5-141, 5-142, 5-143, 5-144, 5-145, 5-146, 5-147, 5-148, 5-149, 5-150, 5-151, 5-152, 5-153, 5-154, 5-155, 5-156, 5-157, 5-158, 5-159, 5-160, 5-161, 5-162, 5-163, 5-164, 5-165, 5-166, 5-167, 5-168, 5-169, 5-170, 5-171, 5-172, 5-173, 5-174, 5-175, 5-176, 5-177, 5-178, 5-179, 5-180, 5-181, 5-182, 5-183, 5-184, 5-185, 5-186, 5-187, 5-188, 5-189, 5-190, 5-191, 5-192, 5-193, 5-194, 5-195, 5-196, 5-197, 5-198, 5-199, and 5-200.

Peptides and Proteins that Begin with Amino Acid 6 of HPV16 L2
6-89, 6-90, 6-91, 6-92, 6-93, 6-94, 6-95, 6-96, 6-97, 6-98, 6-99, 6-100, 6-101, 6-102, 6-103, 6-104, 6-105, 6-106, 6-107, 6-108, 6-109, 6-110, 6-111, 6-112, 6-113, 6-114, 6-115, 6-116, 6-117, 6-118, 6-119, 6-120, 6-121, 6-122, 6-123, 6-124, 6-125, 6-126, 6-127, 6-128, 6-129, 6-130, 6-131, 6-132, 6-133, 6-134, 6-135, 6-136, 6-137, 6-138, 6-139, 6-140, 6-141, 6-142, 6-143, 6-144, 6-145, 6-146, 6-147, 6-148, 6-149, 6-150, 6-151, 6-152, 6-153, 6-154, 6-155, 6-156, 6-157, 6-158, 6-159, 6-160, 6-161, 6-162, 6-163, 6-164, 6-165, 6-166, 6-167, 6-168, 6-169, 6-170, 6-171, 6-172, 6-173, 6-174, 6-175, 6-176, 6-177, 6-178, 6-179, 6-180, 6-181, 6-182, 6-183, 6-184, 6-185, 6-186, 6-187, 6-188, 6-189, 6-190, 6-191, 6-192, 6-193, 6-194, 6-195, 6-196, 6-197, 6-198, 6-199, and 6-200.

Peptides and Proteins that Begin with Amino Acid 7 of HPV16 L2
7-89, 7-90, 7-91, 7-92, 7-93, 7-94, 7-95, 7-96, 7-97, 7-98, 7-99, 7-100, 7-101, 7-102, 7-103, 7-104, 7-105, 7-106, 7-107, 7-108, 7-109, 7-110, 7-111, 7-112, 7-113, 7-114, 7-115, 7-116, 7-117, 7-118, 7-119, 7-120, 7-121, 7-122, 7-123, 7-124, 7-125, 7-126, 7-127, 7-128, 7-129, 7-130, 7-131, 7-132, 7-133, 7-134, 7-135, 7-136, 7-137, 7-138, 7-139, 7-140, 7-141, 7-142, 7-143, 7-144, 7-145, 7-146, 7-147, 7-148, 7-149, 7-150, 7-151, 7-152, 7-153, 7-154, 7-155, 7-156, 7-157, 7-158, 7-159, 7-160, 7-161, 7-162, 7-163, 7-164, 7-165, 7-166, 7-167, 7-168, 7-169, 7-170, 7-171, 7-172, 7-173, 7-174, 7-175, 7-176, 7-177, 7-178, 7-179, 7-180, 7-181, 7-182, 7-183, 7-184, 7-185, 7-186, 7-187, 7-188, 7-189, 7-190, 7-191, 7-192, 7-193, 7-194, 7-195, 7-196, 7-197, 7-198, 7-199, and 7-200.

Peptides and Proteins that Begin with Amino Acid 8 of HPV16 L2
8-89, 8-90, 8-91, 8-92, 8-93, 8-94, 8-95, 8-96, 8-97, 8-98, 8-99, 8-100, 8-101, 8-102, 8-103, 8-104, 8-105, 8-106, 8-107, 8-108, 8-109, 8-110, 8-111, 8-112, 8-113, 8-114, 8-115, 8-116, 8-117, 8-118, 8-119, 8-120, 8-121, 8-122, 8-123, 8-124, 8-125, 8-126, 8-127, 8-128, 8-129, 8-130, 8-131, 8-132, 8-133, 8-134, 8-135, 8-136, 8-137, 8-138, 8-139, 8-140, 8-141, 8-142, 8-143, 8-144, 8-145, 8-146, 8-147, 8-148, 8-149, 8-150, 8-151, 8-152, 8-153, 8-154, 8-155, 8-156, 8-157, 8-158, 8-159, 8-160, 8-161, 8-162, 8-163, 8-164, 8-165, 8-166, 8-167, 8-168, 8-169, 8-170, 8-171, 8-172, 8-173, 8-174, 8-175, 8-176, 8-177, 8-178, 8-179, 8-180, 8-181, 8-182, 8-183, 8-184, 8-185, 8-186, 8-187, 8-188, 8-189, 8-190, 8-191, 8-192, 8-193, 8-194, 8-195, 8-196, 8-197, 8-198, 8-199, and 8-200.

Peptides and Proteins that Begin with Amino Acid 9 of HPV16 L2

9-89, 9-90, 9-91, 9-92, 9-93, 9-94, 9-95, 9-96, 9-97, 9-98, 9-99, 9-100, 9-101, 9-102, 9-103, 9-104, 9-105, 9-106, 9-107, 9-108, 9-109, 9-110, 9-111, 9-112, 9-113, 9-114, 9-115, 9-116, 9-117, 9-118, 9-119, 9-120, 9-121, 9-122, 9-123, 9-124, 9-125, 9-126, 9-127, 9-128, 9-129, 9-130, 9-131, 9-132, 9-133, 9-134, 9-135, 9-136, 9-137, 9-138, 9-139, 9-140, 9-141, 9-142, 9-143, 9-144, 9-145, 9-146, 9-147, 9-148, 9-149, 9-150, 9-151, 9-152, 9-153, 9-154, 9-155, 9-156, 9-157, 9-158, 9-159, 9-160, 9-161, 9-162, 9-163, 9-164, 9-165, 9-166, 9-167, 9-168, 9-169, 9-170, 9-171, 9-172, 9-173, 9-174, 9-175, 9-176, 9-177, 9-178, 9-179, 9-180, 9-181, 9-182, 9-183, 9-184, 9-185, 9-186, 9-187, 9-188, 9-189, 9-190, 9-191, 9-192, 9-193, 9-194, 9-195, 9-196, 9-197, 9-198, 9-199, and 9-200.

Peptides and Proteins that Begin with Amino Acid 10 of HPV16 L2

10-89, 10-90, 10-91, 10-92, 10-93, 10-94, 10-95, 10-96, 10-97, 10-98, 10-99, 10-100, 10-101, 10-102, 10-103, 10-104, 10-105, 10-106, 10-107, 10-108, 10-109, 10-110, 10-111, 10-112, 10-113, 10-114, 10-115, 10-116, 10-117, 10-118, 10-119, 10-120, 10-121, 10-122, 10-123, 10-124, 10-125, 10-126, 10-127, 10-128, 10-129, 10-130, 10-131, 10-132, 10-133, 10-134, 10-135, 10-136, 10-137, 10-138, 10-139, 10-140, 10-141, 10-142, 10-143, 10-144, 10-145, 10-146, 10-147, 10-148, 10-149, 10-150, 10-151, 10-152, 10-153, 10-154, 10-155, 10-156, 10-157, 10-158, 10-159, 10-160, 10-161, 10-162, 10-163, 10-164, 10-165, 10-166, 10-167, 10-168, 10-169, 10-170, 10-171, 10-172, 10-173, 10-174, 10-175, 10-176, 10-177, 10-178, 10-179, 10-180, 10-181, 10-182, 10-183, 10-184, 10-185, 10-186, 10-187, 10-188, 10-189, 10-190, 10-191, 10-192, 10-193, 10-194, 10-195, 10-196, 10-197, 10-198, 10-199, and 10-200.

Peptides and Proteins that Begin with Amino Acid 11 of HPV16 L2

11-89, 11-90, 11-91, 11-92, 11-93, 11-94, 11-95, 11-96, 11-97, 11-98, 11-99, 11-100, 11-101, 11-102, 11-103, 11-104, 11-105, 11-106, 11-107, 11-108, 11-109, 11-110, 11-111, 11-112, 11-113, 11-114, 11-115, 11-116, 11-117, 11-118, 11-119, 11-120, 11-121, 11-122, 11-123, 11-124, 11-125, 11-126, 11-127, 11-128, 11-129, 11-130, 11-131, 11-132, 11-133, 11-134, 11-135, 11-136, 11-137, 11-138, 11-139, 11-140, 11-141, 11-142, 11-143, 11-144, 11-145, 11-146, 11-147, 11-148, 11-149, 11-150, 11-151, 11-152, 11-153, 11-154, 11-155, 11-156, 11-157, 11-158, 11-159, 11-160, 11-161, 11-162, 11-163, 11-164, 11-165, 11-166, 11-167, 11-168, 11-169, 11-170, 11-171, 11-172, 11-173, 11-174, 11-175, 11-176, 11-177, 11-178, 11-179, 11-180, 11-181, 11-182, 11-183, 11-184, 11-185, 11-186, 11-187, 11-188, 11-189, 11-190, 11-191, 11-192, 11-193, 11-194, 11-195, 11-196, 11-197, 11-198, 11-199, and 11-200.

Peptides and Proteins that Begin with Amino Acid 12 of HPV16 L2

12-89, 12-90, 12-91, 12-92, 12-93, 12-94, 12-95, 12-96, 12-97, 12-98, 12-99, 12-100, 12-101, 12-102, 12-103, 12-104, 12-105, 12-106, 12-107, 12-108, 12-109, 12-110, 12-111, 12-112, 12-113, 12-114, 12-115, 12-116, 12-117, 12-118, 12-119, 12-120, 12-121, 12-122, 12-123, 12-124, 12-125, 12-126, 12-127, 12-128, 12-129, 12-130, 12-131, 12-132, 12-133, 12-134, 12-135, 12-136, 12-137, 12-138, 12-139, 12-140, 12-141, 12-142, 12-143, 12-144, 12-145, 12-146, 12-147, 12-148, 12-149, 12-150, 12-151, 12-152, 12-153, 12-154, 12-155, 12-156, 12-157, 12-158, 12-159, 12-160, 12-161, 12-162, 12-163, 12-164, 12-165, 12-166, 12-167, 12-168, 12-169, 12-170, 12-171, 12-172, 12-173, 12-174, 12-175, 12-176, 12-177, 12-178, 12-179, 12-180, 12-181, 12-182, 12-183, 12-184, 12-185, 12-186, 12-187, 12-188, 12-189, 12-190, 12-191, 12-192, 12-193, 12-194, 12-195, 12-196, 12-197, 12-198, 12-199, and 12-200.

Peptides and Proteins that Begin with Amino Acid 13 of HPV16 L2

13-89, 13-90, 13-91, 13-92, 13-93, 13-94, 13-95, 13-96, 13-97, 13-98, 13-99, 13-100, 13-101, 13-102, 13-103, 13-104, 13-105, 13-106, 13-107, 13-108, 13-109, 13-110, 13-111, 13-112, 13-113, 13-114, 13-115, 13-116, 13-117, 13-118, 13-119, 13-120, 13-121, 13-122, 13-123, 13-124, 13-125, 13-126, 13-127, 13-128, 13-129, 13-130, 13-131, 13-132, 13-133, 13-134, 13-135, 13-136, 13-137, 13-138, 13-139, 13-140, 13-141, 13-142, 13-143, 13-144, 13-145, 13-146, 13-147, 13-148, 13-149, 13-150, 13-151, 13-152, 13-153, 13-154, 13-155, 13-156, 13-157, 13-158, 13-159, 13-160, 13-161, 13-162, 13-163, 13-164, 13-165, 13-166, 13-167, 13-168, 13-169, 13-170, 13-171, 13-172, 13-173, 13-174, 13-175, 13-176, 13-177, 13-178, 13-179, 13-180, 13-181, 13-182, 13-183, 13-184, 13-185, 13-186, 13-187, 13-188, 13-189, 13-190, 13-191, 13-192, 13-193, 13-194, 13-195, 13-196, 13-197, 13-198, 13-199, and 13-200.

Peptides and Proteins that Begin with Amino Acid 14 of HPV16 L2

14-89, 14-90, 14-91, 14-92, 14-93, 14-94, 14-95, 14-96, 14-97, 14-98, 14-99, 14-100, 14-101, 14-102, 14-103, 14-104, 14-105, 14-106, 14-107, 14-108, 14-109, 14-110, 14-111, 14-112, 14-113, 14-114, 14-115, 14-116, 14-117, 14-118, 14-119, 14-120, 14-121, 14-122, 14-123, 14-124, 14-125, 14-126, 14-127, 14-128, 14-129, 14-130, 14-131, 14-132, 14-133, 14-134, 14-135, 14-136, 14-137, 14-138, 14-139, 14-140, 14-141, 14-142, 14-143, 14-144, 14-145, 14-146, 14-147, 14-148, 14-149, 14-150, 14-151, 14-152, 14-153, 14-154, 14-155, 14-156, 14-157, 14-158, 14-159, 14-160, 14-161, 14-162, 14-163, 14-164, 14-165, 14-166, 14-167, 14-168, 14-169, 14-170, 14-171, 14-172, 14-173, 14-174, 14-175, 14-176, 14-177, 14-178, 14-179, 14-180, 14-181, 14-182, 14-183, 14-184, 14-185, 14-186, 14-187, 14-188, 14-189, 14-190, 14-191, 14-192, 14-193, 14-194, 14-195, 14-196, 14-197, 14-198, 14-199, and 14-200.

Peptides and Proteins that Begin with Amino Acid 15 of HPV16 L2

15-89, 15-90, 15-91, 15-92, 15-93, 15-94, 15-95, 15-96, 15-97, 15-98, 15-99, 15-100, 15-101, 15-102, 15-103, 15-104, 15-105, 15-106, 15-107, 15-108, 15-109, 15-110, 15-111, 15-112, 15-113, 15-114, 15-115, 15-116, 15-117, 15-118, 15-119, 15-120, 15-121, 15-122, 15-123, 15-124, 15-125, 15-126, 15-127, 15-128, 15-129, 15-130, 15-131, 15-132, 15-133, 15-134, 15-135, 15-136, 15-137, 15-138, 15-139, 15-140, 15-141, 15-142, 15-143, 15-144, 15-145, 15-146, 15-147, 15-148, 15-149, 15-150, 15-151, 15-152, 15-153, 15-154, 15-155, 15-156, 15-157, 15-158, 15-159, 15-160, 15-161, 15-162, 15-163, 15-164, 15-165, 15-166, 15-167, 15-168, 15-169, 15-170, 15-171, 15-172, 15-173, 15-174, 15-175, 15-176, 15-177, 15-178, 15-179, 15-180, 15-181, 15-182, 15-183, 15-184, 15-185, 15-186, 15-187, 15-188, 15-189, 15-190, 15-191, 15-192, 15-193, 15-194, 15-195, 15-196, 15-197, 15-198, 15-199, and 15-200.

Peptides and Proteins that Begin with Amino Acid 16 of HPV16 L2

16-89, 16-90, 16-91, 16-92, 16-93, 16-94, 16-95, 16-96, 16-97, 16-98, 16-99, 16-100, 16-101, 16-102, 16-103, 16-104, 16-105, 16-106, 16-107, 16-108, 16-109, 16-110, 16-111, 16-112, 16-113, 16-114, 16-115, 16-116, 16-117, 16-118, 16-119, 16-120, 16-121, 16-122, 16-123, 16-124, 16-125, 16-126, 16-127, 16-128, 16-129, 16-130, 16-131, 16-132, 16-133, 16-134, 16-135, 16-136, 16-137, 16-138, 16-139, 16-140, 16-141, 16-142, 16-143, 16-144, 16-145, 16-146, 16-147, 16-148, 16-149, 16-150, 16-151, 16-152, 16-153, 16-154, 16-155, 16-156, 16-157, 16-158, 16-159, 16-160, 16-161, 16-162, 16-163, 16-164, 16-165, 16-166, 16-167, 16-168, 16-169, 16-170, 16-171, 16-172, 16-173, 16-174, 16-175, 16-176, 16-177, 16-178, 16-179, 16-180, 16-181, 16-182, 16-183, 16-184, 16-185, 16-186, 16-187, 16-188, 16-189, 16-190, 16-191, 16-192, 16-193, 16-194, 16-195, 16-196, 16-197, 16-198, 16-199, and 16-200.

Peptides and Proteins that Begin with Amino Acid 17 of HPV16 L2

17-89, 17-90, 17-91, 17-92, 17-93, 17-94, 17-95, 17-96, 17-97, 17-98, 17-99, 17-100, 17-101, 17-102, 17-103, 17-104, 17-105, 17-106, 17-107, 17-108, 17-109, 17-110, 17-111, 17-112, 17-113, 17-114, 17-115, 17-116, 17-117, 17-118, 17-119, 17-120, 17-121, 17-122, 17-123, 17-124, 17-125, 17-126, 17-127, 17-128, 17-129, 17-130, 17-131, 17-132, 17-133, 17-134, 17-135, 17-136, 17-137, 17-138, 17-139, 17-140, 17-141, 17-142, 17-143, 17-144, 17-145, 17-146, 17-147, 17-148, 17-149, 17-150, 17-151, 17-152, 17-153, 17-154, 17-155, 17-156, 17-157, 17-158, 17-159, 17-160, 17-161, 17-162, 17-163, 17-164, 17-165, 17-166, 17-167, 17-168, 17-169, 17-170, 17-171, 17-172, 17-173, 17-174, 17-175, 17-176, 17-177, 17-178, 17-179, 17-180, 17-181, 17-182, 17-183, 17-184, 17-185, 17-186, 17-187, 17-188, 17-189, 17-190, 17-191, 17-192, 17-193, 17-194, 17-195, 17-196, 17-197, 17-198, 17-199, and 17-200.

Peptides and Proteins that Begin with Amino Acid 18 of HPV16 L2

18-89, 18-90, 18-91, 18-92, 18-93, 18-94, 18-95, 18-96, 18-97, 18-98, 18-99, 18-100, 18-101, 18-102, 18-103, 18-104, 18-105, 18-106, 18-107, 18-108, 18-109, 18-110, 18-111, 18-112, 18-113, 18-114, 18-115, 18-116, 18-117, 18-118, 18-119, 18-120, 18-121, 18-122, 18-123, 18-124, 18-125, 18-126, 18-127, 18-128, 18-129, 18-130, 18-131, 18-132, 18-133, 18-134, 18-135, 18-136, 18-137, 18-138, 18-139, 18-140, 18-141, 18-142, 18-143, 18-144, 18-145, 18-146, 18-147, 18-148, 18-149, 18-150, 18-151, 18-152, 18-153, 18-154, 18-155, 18-156, 18-157, 18-158, 18-159, 18-160, 18-161, 18-162, 18-163, 18-164, 18-165, 18-166, 18-167, 18-168, 18-169, 18-170, 18-171, 18-172, 18-173, 18-174, 18-175, 18-176, 18-177, 18-178, 18-179, 18-180, 18-181, 18-182, 18-183, 18-184, 18-185, 18-186, 18-187, 18-188, 18-189, 18-190, 18-191, 18-192, 18-193, 18-194, 18-195, 18-196, 18-197, 18-198, 18-199, and 18-200.

Peptides and Proteins that Begin with Amino Acid 19 of HPV16 L2

19-89, 19-90, 19-91, 19-92, 19-93, 19-94, 19-95, 19-96, 19-97, 19-98, 19-99, 19-100, 19-101, 19-102, 19-103, 19-104, 19-105, 19-106, 19-107, 19-108, 19-109, 19-110, 19-111, 19-112, 19-113, 19-114, 19-115, 19-116, 19-117, 19-118, 19-119, 19-120, 19-121, 19-122, 19-123, 19-124, 19-125, 19-126, 19-127, 19-128, 19-129, 19-130, 19-131, 19-132, 19-133, 19-134, 19-135, 19-136, 19-137, 19-138, 19-139, 19-140, 19-141, 19-142, 19-143, 19-144, 19-145, 19-146, 19-147, 19-148, 19-149, 19-150, 19-151, 19-152, 19-153, 19-154, 19-155, 19-156, 19-157, 19-158, 19-159, 19-160, 19-161, 19-162, 19-163, 19-164, 19-165, 19-166, 19-167, 19-168, 19-169, 19-170, 19-171, 19-172, 19-173, 19-174, 19-175, 19-176, 19-177, 19-178, 19-179, 19-180, 19-181, 19-182, 19-183, 19-184, 19-185, 19-186, 19-187, 19-188, 19-189, 19-190, 19-191, 19-192, 19-193, 19-194, 19-195, 19-196, 19-197, 19-198, 19-199, and 19-200.

Peptides and Proteins that Begin with Amino Acid 20 of HPV16 L2

20-89, 20-90, 20-91, 20-92, 20-93, 20-94, 20-95, 20-96, 20-97, 20-98, 20-99, 20-100, 20-101, 20-102, 20-103, 20-104, 20-105, 20-106, 20-107, 20-108, 20-109, 20-110, 20-111, 20-112, 20-113, 20-114, 20-115, 20-116, 20-117, 20-118, 20-119, 20-120, 20-121, 20-122, 20-123, 20-124, 20-125, 20-126, 20-127, 20-128, 20-129, 20-130, 20-131, 20-132, 20-133, 20-134, 20-135, 20-136, 20-137, 20-138, 20-139, 20-140, 20-141, 20-142, 20-143, 20-144, 20-145, 20-146, 20-147, 20-148, 20-149, 20-150, 20-151, 20-152, 20-153, 20-154, 20-155, 20-156, 20-157, 20-158, 20-159, 20-160, 20-161, 20-162, 20-163, 20-164, 20-165, 20-166, 20-167, 20-168, 20-169, 20-170, 20-171, 20-172, 20-173, 20-174, 20-175, 20-176, 20-177, 20-178, 20-179, 20-180, 20-181, 20-182, 20-183, 20-184, 20-185, 20-186, 20-187, 20-188, 20-189, 20-190, 20-191, 20-192, 20-193, 20-194, 20-195, 20-196, 20-197, 20-198, 20-199, and 20-200.

Peptides and Proteins that Begin with Amino Acid 21 of HPV16 L2

21-89, 21-90, 21-91, 21-92, 21-93, 21-94, 21-95, 21-96, 21-97, 21-98, 21-99, 21-100, 21-101, 21-102, 21-103, 21-104, 21-105, 21-106, 21-107, 21-108, 21-109, 21-110, 21-111, 21-112, 21-113, 21-114, 21-115, 21-116, 21-117, 21-118, 21-119, 21-120, 21-121, 21-122, 21-123, 21-124, 21-125, 21-126, 21-127, 21-128, 21-129, 21-130, 21-131, 21-132, 21-133, 21-134, 21-135, 21-136, 21-137, 21-138, 21-139, 21-140, 21-141, 21-142, 21-143, 21-144, 21-145, 21-146, 21-147, 21-148, 21-149, 21-150, 21-151, 21-152, 21-153, 21-154, 21-155, 21-156, 21-157, 21-158, 21-159, 21-160, 21-161, 21-162, 21-163, 21-164, 21-165, 21-166, 21-167, 21-168, 21-169, 21-170, 21-171, 21-172, 21-173, 21-174, 21-175, 21-176, 21-177, 21-178, 21-179, 21-180, 21-181, 21-182, 21-183, 21-184, 21-185, 21-186, 21-187, 21-188, 21-189, 21-190, 21-191, 21-192, 21-193, 21-194, 21-195, 21-196, 21-197, 21-198, 21-199, and 21-200.

Peptides and Proteins that Begin with Amino Acid 22 of HPV16 L2

22-89, 22-90, 22-91, 22-92, 22-93, 22-94, 22-95, 22-96, 22-97, 22-98, 22-99, 22-100, 22-101, 22-102, 22-103, 22-104, 22-105, 22-106, 22-107, 22-108, 22-109, 22-110, 22-111, 22-112, 22-113, 22-114, 22-115, 22-116, 22-117, 22-118, 22-119, 22-120, 22-121, 22-122, 22-123, 22-124, 22-125, 22-126, 22-127, 22-128, 22-129, 22-130, 22-131, 22-132, 22-133, 22-134, 22-135, 22-136, 22-137, 22-138, 22-139, 22-140, 22-141, 22-142, 22-143, 22-144, 22-145, 22-146, 22-147, 22-148, 22-149, 22-150, 22-151, 22-152, 22-153, 22-154, 22-155, 22-156, 22-157, 22-158, 22-159, 22-160, 22-161, 22-162, 22-163, 22-164, 22-165, 22-166, 22-167, 22-168, 22-169, 22-170, 22-171, 22-172, 22-173, 22-174, 22-175, 22-176, 22-177, 22-178, 22-179, 22-180, 22-181, 22-182, 22-183, 22-184, 22-185, 22-186, 22-187, 22-188, 22-189, 22-190, 22-191, 22-192, 22-193, 22-194, 22-195, 22-196, 22-197, 22-198, 22-199, and 22-200.

Peptides and Proteins that Begin with Amino Acid 23 of HPV16 L2

23-89, 23-90, 23-91, 23-92, 23-93, 23-94, 23-95, 23-96, 23-97, 23-98, 23-99, 23-100, 23-101, 23-102, 23-103, 23-104, 23-105, 23-106, 23-107, 23-108, 23-109, 23-110, 23-111, 23-112, 23-113, 23-114, 23-115, 23-116, 23-117, 23-118, 23-119, 23-120, 23-121, 23-122, 23-123, 23-124, 23-125, 23-126, 23-127, 23-128, 23-129, 23-130, 23-131, 23-132, 23-133, 23-134, 23-135, 23-136, 23-137, 23-138, 23-139, 23-140, 23-141, 23-142, 23-143, 23-144, 23-145, 23-146, 23-147, 23-148, 23-149, 23-150, 23-151, 23-152, 23-153, 23-154, 23-155, 23-156, 23-157, 23-158, 23-159, 23-160, 23-161, 23-162, 23-163, 23-164, 23-165, 23-166, 23-167, 23-168, 23-169, 23-170, 23-171, 23-172, 23-173, 23-174, 23-175, 23-176, 23-177, 23-178, 23-179, 23-180, 23-181, 23-182, 23-183, 23-184, 23-185, 23-186, 23-187, 23-188, 23-189, 23-190, 23-191, 23-192, 23-193, 23-194, 23-195, 23-196, 23-197, 23-198, 23-199, and 23-200.

Peptides and Proteins that Begin with Amino Acid 24 of HPV16 L2

24-89, 24-90, 24-91, 24-92, 24-93, 24-94, 24-95, 24-96, 24-97, 24-98, 24-99, 24-100, 24-101, 24-102, 24-103, 24-104, 24-105, 24-106, 24-107, 24-108, 24-109, 24-110, 24-111, 24-112, 24-113, 24-114, 24-115, 24-116, 24-117, 24-118, 24-119, 24-120, 24-121, 24-122, 24-123, 24-124, 24-125, 24-126, 24-127, 24-128, 24-129, 24-130, 24-131, 24-132, 24-133, 24-134, 24-135, 24-136, 24-137, 24-138, 24-139, 24-140, 24-141, 24-142, 24-143, 24-144, 24-145, 24-146, 24-147, 24-148, 24-149, 24-150, 24-151, 24-152, 24-153, 24-154, 24-155, 24-156, 24-157, 24-158, 24-159, 24-160, 24-161, 24-162, 24-163, 24-164, 24-165, 24-166, 24-167, 24-168, 24-169, 24-170, 24-171, 24-172, 24-173, 24-174, 24-175, 24-176, 24-177, 24-178, 24-179, 24-180, 24-181, 24-182, 24-183, 24-184, 24-185, 24-186, 24-187, 24-188, 24-189, 24-190, 24-191, 24-192, 24-193, 24-194, 24-195, 24-196, 24-197, 24-198, 24-199, and 24-200.

Peptides and Proteins that Begin with Amino Acid 25 of HPV16 L2

25-89, 25-90, 25-91, 25-92, 25-93, 25-94, 25-95, 25-96, 25-97, 25-98, 25-99, 25-100, 25-101, 25-102, 25-103, 25-104, 25-105, 25-106, 25-107, 25-108, 25-109, 25-110, 25-111, 25-112, 25-113, 25-114, 25-115, 25-116, 25-117, 25-118, 25-119, 25-120, 25-121, 25-122, 25-123, 25-124, 25-125, 25-126, 25-127, 25-128, 25-129, 25-130, 25-131, 25-132, 25-133, 25-134, 25-135, 25-136, 25-137, 25-138, 25-139, 25-140, 25-141, 25-142, 25-143, 25-144, 25-145, 25-146, 25-147, 25-148, 25-149, 25-150, 25-151, 25-152, 25-153, 25-154, 25-155, 25-156, 25-157, 25-158, 25-159, 25-160, 25-161, 25-162, 25-163, 25-164, 25-165, 25-166, 25-167, 25-168, 25-169, 25-170, 25-171, 25-172, 25-173, 25-174, 25-175, 25-176, 25-177, 25-178, 25-179, 25-180, 25-181, 25-182, 25-183, 25-184, 25-185, 25-186, 25-187, 25-188, 25-189, 25-190, 25-191, 25-192, 25-193, 25-194, 25-195, 25-196, 25-197, 25-198, 25-199, and 25-200.

Peptides and Proteins that Begin with Amino Acid 26 of HPV16 L2

26-89, 26-90, 26-91, 26-92, 26-93, 26-94, 26-95, 26-96, 26-97, 26-98, 26-99, 26-100, 26-101, 26-102, 26-103, 26-104, 26-105, 26-106, 26-107, 26-108, 26-109, 26-110, 26-111, 26-112, 26-113, 26-114, 26-115, 26-116, 26-117, 26-118, 26-119, 26-120, 26-121, 26-122, 26-123, 26-124, 26-125, 26-126, 26-127, 26-128, 26-129, 26-130, 26-131, 26-132, 26-133, 26-134, 26-135, 26-136, 26-137, 26-138, 26-139, 26-140, 26-141, 26-142, 26-143, 26-144, 26-145, 26-146, 26-147, 26-148, 26-149, 26-150, 26-151, 26-152, 26-153, 26-154, 26-155, 26-156, 26-157, 26-158, 26-159, 26-160, 26-161, 26-162, 26-163, 26-164, 26-165, 26-166, 26-167, 26-168, 26-169, 26-170, 26-171, 26-172, 26-173, 26-174, 26-175, 26-176, 26-177, 26-178, 26-179, 26-180, 26-181, 26-182, 26-183, 26-184, 26-185, 26-186, 26-187, 26-188, 26-189, 26-190, 26-191, 26-192, 26-193, 26-194, 26-195, 26-196, 26-197, 26-198, 26-199, and 26-200.

Peptides and Proteins that Begin with Amino Acid 27 of HPV16 L2

27-89, 27-90, 27-91, 27-92, 27-93, 27-94, 27-95, 27-96, 27-97, 27-98, 27-99, 27-100, 27-101, 27-102, 27-103, 27-104, 27-105, 27-106, 27-107, 27-108, 27-109, 27-110, 27-111, 27-112, 27-113, 27-114, 27-115, 27-116, 27-117, 27-118, 27-119, 27-120, 27-121, 27-122, 27-123, 27-124, 27-125, 27-126, 27-127, 27-128, 27-129, 27-130, 27-131, 27-132, 27-133, 27-134, 27-135, 27-136, 27-137, 27-138, 27-139, 27-140, 27-141, 27-142, 27-143, 27-144, 27-145, 27-146, 27-147, 27-148, 27-149, 27-150, 27-151, 27-152, 27-153, 27-154, 27-155, 27-156, 27-157, 27-158, 27-159, 27-160, 27-161, 27-162, 27-163, 27-164, 27-165, 27-166, 27-167, 27-168, 27-169, 27-170, 27-171, 27-172, 27-173, 27-174, 27-175, 27-176, 27-177, 27-178, 27-179, 27-180, 27-181, 27-182, 27-183, 27-184, 27-185, 27-186, 27-187, 27-188, 27-189, 27-190, 27-191, 27-192, 27-193, 27-194, 27-195, 27-196, 27-197, 27-198, 27-199, and 27-200.

Peptides and Proteins that Begin with Amino Acid 28 of HPV16 L2

28-89, 28-90, 28-91, 28-92, 28-93, 28-94, 28-95, 28-96, 28-97, 28-98, 28-99, 28-100, 28-101, 28-102, 28-103, 28-104, 28-105, 28-106, 28-107, 28-108, 28-109, 28-110, 28-111, 28-112, 28-113, 28-114, 28-115, 28-116, 28-117, 28-118, 28-119, 28-120, 28-121, 28-122, 28-123, 28-124, 28-125, 28-126, 28-127, 28-128, 28-129, 28-130, 28-131, 28-132, 28-133, 28-134, 28-135, 28-136, 28-137, 28-138, 28-139, 28-140, 28-141, 28-142, 28-143, 28-144, 28-145, 28-146, 28-147, 28-148, 28-149, 28-150, 28-151, 28-152, 28-153, 28-154, 28-155, 28-156, 28-157, 28-158, 28-159, 28-160, 28-161, 28-162, 28-163, 28-164, 28-165, 28-166, 28-167, 28-168, 28-169, 28-170, 28-171, 28-172, 28-173, 28-174, 28-175, 28-176, 28-177, 28-178, 28-179, 28-180, 28-181, 28-182, 28-183, 28-184, 28-185, 28-186, 28-187, 28-188, 28-189, 28-190, 28-191, 28-192, 28-193, 28-194, 28-195, 28-196, 28-197, 28-198, 28-199, and 28-200.

Peptides and Proteins that Begin with Amino Acid 29 of HPV16 L2

29-89, 29-90, 29-91, 29-92, 29-93, 29-94, 29-95, 29-96, 29-97, 29-98, 29-99, 29-100, 29-101, 29-102, 29-103, 29-104, 29-105, 29-106, 29-107, 29-108, 29-109, 29-110, 29-111, 29-112, 29-113, 29-114, 29-115, 29-116, 29-117, 29-118, 29-119, 29-120, 29-121, 29-122, 29-123, 29-124, 29-125, 29-126, 29-127, 29-128, 29-129, 29-130, 29-131, 29-132, 29-133, 29-134, 29-135, 29-136, 29-137, 29-138, 29-139, 29-140, 29-141, 29-142, 29-143, 29-144, 29-145, 29-146, 29-147, 29-148, 29-149, 29-150, 29-151, 29-152, 29-153, 29-154, 29-155, 29-156, 29-157, 29-158, 29-159, 29-160, 29-161, 29-162, 29-163, 29-164, 29-165, 29-166, 29-167, 29-168, 29-169, 29-170, 29-171, 29-172, 29-173, 29-174, 29-175, 29-176, 29-177, 29-178, 29-179, 29-180, 29-181, 29-182, 29-183, 29-184, 29-185, 29-186, 29-187, 29-188, 29-189, 29-190, 29-191, 29-192, 29-193, 29-194, 29-195, 29-196, 29-197, 29-198, 29-199, and 29-200.

Peptides and Proteins that Begin with Amino Acid 30 of HPV16 L2

30-89, 30-90, 30-91, 30-92, 30-93, 30-94, 30-95, 30-96, 30-97, 30-98, 30-99, 30-100, 30-101, 30-102, 30-103, 30-104, 30-105, 30-106, 30-107, 30-108, 30-109, 30-110, 30-111, 30-112, 30-113, 30-114, 30-115, 30-116, 30-117, 30-118, 30-119, 30-120, 30-121, 30-122, 30-123, 30-124, 30-125, 30-126, 30-127, 30-128, 30-129, 30-130, 30-131, 30-132, 30-133, 30-134, 30-135, 30-136, 30-137, 30-138, 30-139, 30-140, 30-141, 30-142, 30-143, 30-144, 30-145, 30-146, 30-147, 30-148, 30-149, 30-150, 30-151, 30-152, 30-153, 30-154, 30-155, 30-156, 30-157, 30-158, 30-159, 30-160, 30-161, 30-162, 30-163, 30-164, 30-165, 30-166, 30-167, 30-168, 30-169, 30-170, 30-171, 30-172, 30-173, 30-174, 30-175, 30-176, 30-177, 30-178, 30-179, 30-180, 30-181, 30-182, 30-183, 30-184, 30-185, 30-186, 30-187, 30-188, 30-189, 30-190, 30-191, 30-192, 30-193, 30-194, 30-195, 30-196, 30-197, 30-198, 30-199, and 30-200.

Peptides and Proteins that Begin with Amino Acid 31 of HPV16 L2

31-89, 31-90, 31-91, 31-92, 31-93, 31-94, 31-95, 31-96, 31-97, 31-98, 31-99, 31-100, 31-101, 31-102, 31-103, 31-104, 31-105, 31-106, 31-107, 31-108, 31-109, 31-110, 31-111, 31-112, 31-113, 31-114, 31-115, 31-116, 31-117, 31-118, 31-119, 31-120, 31-121, 31-122, 31-123, 31-124, 31-125, 31-126, 31-127, 31-128, 31-129, 31-130, 31-131, 31-132, 31-133, 31-134, 31-135, 31-136, 31-137, 31-138, 31-139, 31-140, 31-141, 31-142, 31-143, 31-144, 31-145, 31-146, 31-147, 31-148, 31-149, 31-150, 31-151, 31-152, 31-153, 31-154, 31-155, 31-156, 31-157, 31-158, 31-159, 31-160, 31-161, 31-162, 31-163, 31-164, 31-165, 31-166, 31-167, 31-168, 31-169, 31-170, 31-171, 31-172, 31-173, 31-174, 31-175, 31-176, 31-177, 31-178, 31-179, 31-180, 31-181, 31-182, 31-183, 31-184, 31-185, 31-186, 31-187, 31-188, 31-189, 31-190, 31-191, 31-192, 31-193, 31-194, 31-195, 31-196, 31-197, 31-198, 31-199, and 31-200.

Peptides and Proteins that Begin with Amino Acid 32 of HPV16 L2

32-89, 32-90, 32-91, 32-92, 32-93, 32-94, 32-95, 32-96, 32-97, 32-98, 32-99, 32-100, 32-101, 32-102, 32-103, 32-104, 32-105, 32-106, 32-107, 32-108, 32-109, 32-110, 32-111, 32-112, 32-113, 32-114, 32-115, 32-116, 32-117, 32-118, 32-119, 32-120, 32-121, 32-122, 32-123, 32-124, 32-125, 32-126, 32-127, 32-128, 32-129, 32-130, 32-131, 32-132, 32-133, 32-134, 32-135, 32-136, 32-137, 32-138, 32-139, 32-140, 32-141, 32-142, 32-143, 32-144, 32-145, 32-146, 32-147, 32-148, 32-149, 32-150, 32-151, 32-152, 32-153, 32-154, 32-155, 32-156, 32-157, 32-158, 32-159, 32-160, 32-161, 32-162, 32-163, 32-164, 32-165, 32-166, 32-167, 32-168, 32-169, 32-170, 32-171, 32-172, 32-173, 32-174, 32-175, 32-176, 32-177, 32-178, 32-179, 32-180, 32-181, 32-182, 32-183, 32-184, 32-185, 32-186, 32-187, 32-188, 32-189, 32-190, 32-191, 32-192, 32-193, 32-194, 32-195, 32-196, 32-197, 32-198, 32-199, and 32-200.

Peptides and Proteins that Begin with Amino Acid 33 of HPV16 L2

33-89, 33-90, 33-91, 33-92, 33-93, 33-94, 33-95, 33-96, 33-97, 33-98, 33-99, 33-100, 33-101, 33-102, 33-103, 33-104, 33-105, 33-106, 33-107, 33-108, 33-109, 33-110, 33-111, 33-112, 33-113, 33-114, 33-115, 33-116, 33-117, 33-118, 33-119, 33-120, 33-121, 33-122, 33-123, 33-124, 33-125, 33-126, 33-127, 33-128, 33-129, 33-130, 33-131, 33-132, 33-133, 33-134, 33-135, 33-136, 33-137, 33-138, 33-139, 33-140, 33-141, 33-142, 33-143, 33-144, 33-145, 33-146, 33-147, 33-148, 33-149, 33-150, 33-151, 33-152, 33-153, 33-154, 33-155, 33-156, 33-157, 33-158, 33-159, 33-160, 33-161, 33-162, 33-163, 33-164, 33-165, 33-166, 33-167, 33-168, 33-169, 33-170, 33-171, 33-172, 33-173, 33-174, 33-175, 33-176, 33-177, 33-178, 33-179, 33-180, 33-181, 33-182, 33-183, 33-184, 33-185, 33-186, 33-187, 33-188, 33-189, 33-190, 33-191, 33-192, 33-193, 33-194, 33-195, 33-196, 33-197, 33-198, 33-199, and 33-200.

Peptides and Proteins that Begin with Amino Acid 34 of HPV16 L2

34-89, 34-90, 34-91, 34-92, 34-93, 34-94, 34-95, 34-96, 34-97, 34-98, 34-99, 34-100, 34-101, 34-102, 34-103, 34-104, 34-105, 34-106, 34-107, 34-108, 34-109, 34-110, 34-111, 34-112, 34-113, 34-114, 34-115, 34-116, 34-117, 34-118, 34-119, 34-120, 34-121, 34-122, 34-123, 34-124, 34-125, 34-126, 34-127, 34-128, 34-129, 34-130, 34-131, 34-132, 34-133, 34-134, 34-135, 34-136, 34-137, 34-138, 34-139, 34-140, 34-141, 34-142, 34-143, 34-144, 34-145, 34-146, 34-147, 34-148, 34-149, 34-150, 34-151, 34-152, 34-153, 34-154, 34-155, 34-156, 34-157, 34-158, 34-159, 34-160, 34-161, 34-162, 34-163, 34-164, 34-165, 34-166, 34-167, 34-168, 34-169, 34-170, 34-171, 34-172, 34-173, 34-174, 34-175, 34-176, 34-177, 34-178, 34-179, 34-180, 34-181, 34-182, 34-183, 34-184, 34-185, 34-186, 34-187, 34-188, 34-189, 34-190, 34-191, 34-192, 34-193, 34-194, 34-195, 34-196, 34-197, 34-198, 34-199, and 34-200.

Peptides and Proteins that Begin with Amino Acid 35 of HPV16 L2

35-89, 35-90, 35-91, 35-92, 35-93, 35-94, 35-95, 35-96, 35-97, 35-98, 35-99, 35-100, 35-101, 35-102, 35-103, 35-104, 35-105, 35-106, 35-107, 35-108, 35-109, 35-110, 35-111, 35-112, 35-113, 35-114, 35-115, 35-116, 35-117, 35-118, 35-119, 35-120, 35-121, 35-122, 35-123, 35-124, 35-125, 35-126, 35-127, 35-128, 35-129, 35-130, 35-131, 35-132, 35-133, 35-134, 35-135, 35-136, 35-137, 35-138, 35-139, 35-140, 35-141, 35-142, 35-143, 35-144, 35-145, 35-146, 35-147, 35-148, 35-149, 35-150, 35-151, 35-152, 35-153, 35-154, 35-155, 35-156, 35-157, 35-158, 35-159, 35-160, 35-161, 35-162, 35-163, 35-164, 35-165, 35-166, 35-167, 35-168, 35-169, 35-170, 35-171, 35-172, 35-173, 35-174, 35-175, 35-176, 35-177, 35-178, 35-179, 35-180, 35-181, 35-182, 35-183, 35-184, 35-185, 35-186, 35-187, 35-188, 35-189, 35-190, 35-191, 35-192, 35-193, 35-194, 35-195, 35-196, 35-197, 35-198, 35-199, and 35-200.

Peptides and Proteins that Begin with Amino Acid 36 of HPV16 L2

36-89, 36-90, 36-91, 36-92, 36-93, 36-94, 36-95, 36-96, 36-97, 36-98, 36-99, 36-100, 36-101, 36-102, 36-103, 36-104, 36-105, 36-106, 36-107, 36-108, 36-109, 36-110, 36-111, 36-112, 36-113, 36-114, 36-115, 36-116, 36-117, 36-118, 36-119, 36-120, 36-121, 36-122, 36-123, 36-124, 36-125, 36-126, 36-127, 36-128, 36-129, 36-130, 36-131, 36-132, 36-133, 36-134, 36-135, 36-136, 36-137, 36-138, 36-139, 36-140, 36-141, 36-142, 36-143, 36-144, 36-145, 36-146, 36-147, 36-148, 36-149, 36-150, 36-151, 36-152, 36-153, 36-154, 36-155, 36-156, 36-157, 36-158, 36-159, 36-160, 36-161, 36-162, 36-163, 36-164, 36-165, 36-166, 36-167, 36-168, 36-169, 36-170, 36-171, 36-172, 36-173, 36-174, 36-175, 36-176, 36-177, 36-178, 36-179, 36-180, 36-181, 36-182, 36-183, 36-184, 36-185, 36-186, 36-187, 36-188, 36-189, 36-190, 36-191, 36-192, 36-193, 36-194, 36-195, 36-196, 36-197, 36-198, 36-199, and 36-200.

Peptides and Proteins that Begin with Amino Acid 37 of HPV16 L2

37-89, 37-90, 37-91, 37-92, 37-93, 37-94, 37-95, 37-96, 37-97, 37-98, 37-99, 37-100, 37-101, 37-102, 37-103, 37-104, 37-105, 37-106, 37-107, 37-108, 37-109, 37-110, 37-111, 37-112, 37-113, 37-114, 37-115, 37-116, 37-117, 37-118, 37-119, 37-120, 37-121, 37-122, 37-123, 37-124, 37-125, 37-126, 37-127, 37-128, 37-129, 37-130, 37-131, 37-132, 37-133, 37-134, 37-135, 37-136, 37-137, 37-138, 37-139, 37-140, 37-141, 37-142, 37-143, 37-144, 37-145, 37-146, 37-147, 37-148, 37-149, 37-150, 37-151, 37-152, 37-153, 37-154, 37-155, 37-156, 37-157, 37-158, 37-159, 37-160, 37-161, 37-162, 37-163, 37-164, 37-165, 37-166, 37-167, 37-168, 37-169, 37-170, 37-171, 37-172, 37-173, 37-174, 37-175, 37-176, 37-177, 37-178, 37-179, 37-180, 37-181, 37-182, 37-183, 37-184, 37-185, 37-186, 37-187, 37-188, 37-189, 37-190, 37-191, 37-192, 37-193, 37-194, 37-195, 37-196, 37-197, 37-198, 37-199, and 37-200.

Peptides and Proteins that Begin with Amino Acid 38 of HPV16 L2
38-89, 38-90, 38-91, 38-92, 38-93, 38-94, 38-95, 38-96, 38-97, 38-98, 38-99, 38-100, 38-101, 38-102, 38-103, 38-104, 38-105, 38-106, 38-107, 38-108, 38-109, 38-110, 38-111, 38-112, 38-113, 38-114, 38-115, 38-116, 38-117, 38-118, 38-119, 38-120, 38-121, 38-122, 38-123, 38-124, 38-125, 38-126, 38-127, 38-128, 38-129, 38-130, 38-131, 38-132, 38-133, 38-134, 38-135, 38-136, 38-137, 38-138, 38-139, 38-140, 38-141, 38-142, 38-143, 38-144, 38-145, 38-146, 38-147, 38-148, 38-149, 38-150, 38-151, 38-152, 38-153, 38-154, 38-155, 38-156, 38-157, 38-158, 38-159, 38-160, 38-161, 38-162, 38-163, 38-164, 38-165, 38-166, 38-167, 38-168, 38-169, 38-170, 38-171, 38-172, 38-173, 38-174, 38-175, 38-176, 38-177, 38-178, 38-179, 38-180, 38-181, 38-182, 38-183, 38-184, 38-185, 38-186, 38-187, 38-188, 38-189, 38-190, 38-191, 38-192, 38-193, 38-194, 38-195, 38-196, 38-197, 38-198, 38-199, and 38-200.

Peptides and Proteins that Begin with Amino Acid 39 of HPV16 L2
39-89, 39-90, 39-91, 39-92, 39-93, 39-94, 39-95, 39-96, 39-97, 39-98, 39-99, 39-100, 39-101, 39-102, 39-103, 39-104, 39-105, 39-106, 39-107, 39-108, 39-109, 39-110, 39-111, 39-112, 39-113, 39-114, 39-115, 39-116, 39-117, 39-118, 39-119, 39-120, 39-121, 39-122, 39-123, 39-124, 39-125, 39-126, 39-127, 39-128, 39-129, 39-130, 39-131, 39-132, 39-133, 39-134, 39-135, 39-136, 39-137, 39-138, 39-139, 39-140, 39-141, 39-142, 39-143, 39-144, 39-145, 39-146, 39-147, 39-148, 39-149, 39-150, 39-151, 39-152, 39-153, 39-154, 39-155, 39-156, 39-157, 39-158, 39-159, 39-160, 39-161, 39-162, 39-163, 39-164, 39-165, 39-166, 39-167, 39-168, 39-169, 39-170, 39-171, 39-172, 39-173, 39-174, 39-175, 39-176, 39-177, 39-178, 39-179, 39-180, 39-181, 39-182, 39-183, 39-184, 39-185, 39-186, 39-187, 39-188, 39-189, 39-190, 39-191, 39-192, 39-193, 39-194, 39-195, 39-196, 39-197, 39-198, 39-199, and 39-200.

Peptides and Proteins that Begin with Amino Acid 40 of HPV16 L2
40-89, 40-90, 40-91, 40-92, 40-93, 40-94, 40-95, 40-96, 40-97, 40-98, 40-99, 40-100, 40-101, 40-102, 40-103, 40-104, 40-105, 40-106, 40-107, 40-108, 40-109, 40-110, 40-111, 40-112, 40-113, 40-114, 40-115, 40-116, 40-117, 40-118, 40-119, 40-120, 40-121, 40-122, 40-123, 40-124, 40-125, 40-126, 40-127, 40-128, 40-129, 40-130, 40-131, 40-132, 40-133, 40-134, 40-135, 40-136, 40-137, 40-138, 40-139, 40-140, 40-141, 40-142, 40-143, 40-144, 40-145, 40-146, 40-147, 40-148, 40-149, 40-150, 40-151, 40-152, 40-153, 40-154, 40-155, 40-156, 40-157, 40-158, 40-159, 40-160, 40-161, 40-162, 40-163, 40-164, 40-165, 40-166, 40-167, 40-168, 40-169, 40-170, 40-171, 40-172, 40-173, 40-174, 40-175, 40-176, 40-177, 40-178, 40-179, 40-180, 40-181, 40-182, 40-183, 40-184, 40-185, 40-186, 40-187, 40-188, 40-189, 40-190, 40-191, 40-192, 40-193, 40-194, 40-195, 40-196, 40-197, 40-198, 40-199, and 40-200.

Peptides and Proteins that Begin with Amino Acid 41 of HPV16 L2
41-89, 41-90, 41-91, 41-92, 41-93, 41-94, 41-95, 41-96, 41-97, 41-98, 41-99, 41-100, 41-101, 41-102, 41-103, 41-104, 41-105, 41-106, 41-107, 41-108, 41-109, 41-110, 41-111, 41-112, 41-113, 41-114, 41-115, 41-116, 41-117, 41-118, 41-119, 41-120, 41-121, 41-122, 41-123, 41-124, 41-125, 41-126, 41-127, 41-128, 41-129, 41-130, 41-131, 41-132, 41-133, 41-134, 41-135, 41-136, 41-137, 41-138, 41-139, 41-140, 41-141, 41-142, 41-143, 41-144, 41-145, 41-146, 41-147, 41-148, 41-149, 41-150, 41-151, 41-152, 41-153, 41-154, 41-155, 41-156, 41-157, 41-158, 41-159, 41-160, 41-161, 41-162, 41-163, 41-164, 41-165, 41-166, 41-167, 41-168, 41-169, 41-170, 41-171, 41-172, 41-173, 41-174, 41-175, 41-176, 41-177, 41-178, 41-179, 41-180, 41-181, 41-182, 41-183, 41-184, 41-185, 41-186, 41-187, 41-188, 41-189, 41-190, 41-191, 41-192, 41-193, 41-194, 41-195, 41-196, 41-197, 41-198, 41-199, and 41-200.

Peptides and Proteins that Begin with Amino Acid 42 of HPV16 L2
42-89, 42-90, 42-91, 42-92, 42-93, 42-94, 42-95, 42-96, 42-97, 42-98, 42-99, 42-100, 42-101, 42-102, 42-103, 42-104, 42-105, 42-106, 42-107, 42-108, 42-109, 42-110, 42-111, 42-112, 42-113, 42-114, 42-115, 42-116, 42-117, 42-118, 42-119, 42-120, 42-121, 42-122, 42-123, 42-124, 42-125, 42-126, 42-127, 42-128, 42-129, 42-130, 42-131, 42-132, 42-133, 42-134, 42-135, 42-136, 42-137, 42-138, 42-139, 42-140, 42-141, 42-142, 42-143, 42-144, 42-145, 42-146, 42-147, 42-148, 42-149, 42-150, 42-151, 42-152, 42-153, 42-154, 42-155, 42-156, 42-157, 42-158, 42-159, 42-160, 42-161, 42-162, 42-163, 42-164, 42-165, 42-166, 42-167, 42-168, 42-169, 42-170, 42-171, 42-172, 42-173, 42-174, 42-175, 42-176, 42-177, 42-178, 42-179, 42-180, 42-181, 42-182, 42-183, 42-184, 42-185, 42-186, 42-187, 42-188, 42-189, 42-190, 42-191, 42-192, 42-193, 42-194, 42-195, 42-196, 42-197, 42-198, 42-199, and 42-200.

Peptides and Proteins that Begin with Amino Acid 43 of HPV16 L2
43-89, 43-90, 43-91, 43-92, 43-93, 43-94, 43-95, 43-96, 43-97, 43-98, 43-99, 43-100, 43-101, 43-102, 43-103, 43-104, 43-105, 43-106, 43-107, 43-108, 43-109, 43-110, 43-111, 43-112, 43-113, 43-114, 43-115, 43-116, 43-117, 43-118, 43-119, 43-120, 43-121, 43-122, 43-123, 43-124, 43-125, 43-126, 43-127, 43-128, 43-129, 43-130, 43-131, 43-132, 43-133, 43-134, 43-135, 43-136, 43-137, 43-138, 43-139, 43-140, 43-141, 43-142, 43-143, 43-144, 43-145, 43-146, 43-147, 43-148, 43-149, 43-150, 43-151, 43-152, 43-153, 43-154, 43-155, 43-156, 43-157, 43-158, 43-159, 43-160, 43-161, 43-162, 43-163, 43-164, 43-165, 43-166, 43-167, 43-168, 43-169, 43-170, 43-171, 43-172, 43-173, 43-174, 43-175, 43-176, 43-177, 43-178, 43-179, 43-180, 43-181, 43-182, 43-183, 43-184, 43-185, 43-186, 43-187, 43-188, 43-189, 43-190, 43-191, 43-192, 43-193, 43-194, 43-195, 43-196, 43-197, 43-198, 43-199, and 43-200.

Peptides and Proteins that Begin with Amino Acid 44 of HPV16 L2
44-89, 44-90, 44-91, 44-92, 44-93, 44-94, 44-95, 44-96, 44-97, 44-98, 44-99, 44-100, 44-101, 44-102, 44-103, 44-104, 44-105, 44-106, 44-107, 44-108, 44-109, 44-110, 44-111, 44-112, 44-113, 44-114, 44-115, 44-116, 44-117, 44-118, 44-119, 44-120, 44-121, 44-122, 44-123, 44-124, 44-125, 44-126, 44-127, 44-128, 44-129, 44-130, 44-131, 44-132, 44-133, 44-134, 44-135, 44-136, 44-137, 44-138, 44-139, 44-140, 44-141, 44-142, 44-143, 44-144, 44-145, 44-146, 44-147, 44-148, 44-149, 44-150, 44-151, 44-152, 44-153, 44-154, 44-155, 44-156, 44-157, 44-158, 44-159, 44-160, 44-161, 44-162, 44-163, 44-164, 44-165, 44-166, 44-167, 44-168, 44-169, 44-170, 44-171, 44-172, 44-173, 44-174, 44-175, 44-176, 44-177, 44-178, 44-179, 44-180, 44-181, 44-182, 44-183, 44-184, 44-185, 44-186, 44-187, 44-188, 44-189, 44-190, 44-191, 44-192, 44-193, 44-194, 44-195, 44-196, 44-197, 44-198, 44-199, and 44-200.

Peptides and Proteins that Begin with Amino Acid 45 of HPV16 L2
45-89, 45-90, 45-91, 45-92, 45-93, 45-94, 45-95, 45-96, 45-97, 45-98, 45-99, 45-100, 45-101, 45-102, 45-103, 45-104, 45-105, 45-106, 45-107, 45-108, 45-109, 45-110, 45-111, 45-112, 45-113, 45-114, 45-115, 45-116, 45-117, 45-118, 45-119, 45-120, 45-121, 45-122, 45-123, 45-124, 45-125, 45-126, 45-127, 45-128, 45-129, 45-130, 45-131, 45-132, 45-133, 45-134, 45-135, 45-136, 45-137, 45-138, 45-139, 45-140, 45-141, 45-142, 45-143, 45-144, 45-145, 45-146, 45-147, 45-148, 45-149, 45-150, 45-151, 45-152, 45-153, 45-154, 45-155, 45-156, 45-157, 45-158, 45-159, 45-160, 45-161, 45-162, 45-163, 45-164, 45-165, 45-166, 45-167, 45-168, 45-169, 45-170, 45-171, 45-172, 45-173, 45-174, 45-175, 45-176, 45-177, 45-178, 45-179, 45-180, 45-181, 45-182, 45-183, 45-184, 45-185, 45-186, 45-187, 45-188, 45-189, 45-190, 45-191, 45-192, 45-193, 45-194, 45-195, 45-196, 45-197, 45-198, 45-199, and 45-200.

Peptides and Proteins that Begin with Amino Acid 46 of HPV16 L2

46-89, 46-90, 46-91, 46-92, 46-93, 46-94, 46-95, 46-96, 46-97, 46-98, 46-99, 46-100, 46-101, 46-102, 46-103, 46-104, 46-105, 46-106, 46-107, 46-108, 46-109, 46-110, 46-111, 46-112, 46-113, 46-114, 46-115, 46-116, 46-117, 46-118, 46-119, 46-120, 46-121, 46-122, 46-123, 46-124, 46-125, 46-126, 46-127, 46-128, 46-129, 46-130, 46-131, 46-132, 46-133, 46-134, 46-135, 46-136, 46-137, 46-138, 46-139, 46-140, 46-141, 46-142, 46-143, 46-144, 46-145, 46-146, 46-147, 46-148, 46-149, 46-150, 46-151, 46-152, 46-153, 46-154, 46-155, 46-156, 46-157, 46-158, 46-159, 46-160, 46-161, 46-162, 46-163, 46-164, 46-165, 46-166, 46-167, 46-168, 46-169, 46-170, 46-171, 46-172, 46-173, 46-174, 46-175, 46-176, 46-177, 46-178, 46-179, 46-180, 46-181, 46-182, 46-183, 46-184, 46-185, 46-186, 46-187, 46-188, 46-189, 46-190, 46-191, 46-192, 46-193, 46-194, 46-195, 46-196, 46-197, 46-198, 46-199, and 46-200.

Peptides and Proteins that Begin with Amino Acid 47 of HPV16 L2

47-89, 47-90, 47-91, 47-92, 47-93, 47-94, 47-95, 47-96, 47-97, 47-98, 47-99, 47-100, 47-101, 47-102, 47-103, 47-104, 47-105, 47-106, 47-107, 47-108, 47-109, 47-110, 47-111, 47-112, 47-113, 47-114, 47-115, 47-116, 47-117, 47-118, 47-119, 47-120, 47-121, 47-122, 47-123, 47-124, 47-125, 47-126, 47-127, 47-128, 47-129, 47-130, 47-131, 47-132, 47-133, 47-134, 47-135, 47-136, 47-137, 47-138, 47-139, 47-140, 47-141, 47-142, 47-143, 47-144, 47-145, 47-146, 47-147, 47-148, 47-149, 47-150, 47-151, 47-152, 47-153, 47-154, 47-155, 47-156, 47-157, 47-158, 47-159, 47-160, 47-161, 47-162, 47-163, 47-164, 47-165, 47-166, 47-167, 47-168, 47-169, 47-170, 47-171, 47-172, 47-173, 47-174, 47-175, 47-176, 47-177, 47-178, 47-179, 47-180, 47-181, 47-182, 47-183, 47-184, 47-185, 47-186, 47-187, 47-188, 47-189, 47-190, 47-191, 47-192, 47-193, 47-194, 47-195, 47-196, 47-197, 47-198, 47-199, and 47-200.

Peptides and Proteins that Begin with Amino Acid 48 of HPV16 L2

48-89, 48-90, 48-91, 48-92, 48-93, 48-94, 48-95, 48-96, 48-97, 48-98, 48-99, 48-100, 48-101, 48-102, 48-103, 48-104, 48-105, 48-106, 48-107, 48-108, 48-109, 48-110, 48-111, 48-112, 48-113, 48-114, 48-115, 48-116, 48-117, 48-118, 48-119, 48-120, 48-121, 48-122, 48-123, 48-124, 48-125, 48-126, 48-127, 48-128, 48-129, 48-130, 48-131, 48-132, 48-133, 48-134, 48-135, 48-136, 48-137, 48-138, 48-139, 48-140, 48-141, 48-142, 48-143, 48-144, 48-145, 48-146, 48-147, 48-148, 48-149, 48-150, 48-151, 48-152, 48-153, 48-154, 48-155, 48-156, 48-157, 48-158, 48-159, 48-160, 48-161, 48-162, 48-163, 48-164, 48-165, 48-166, 48-167, 48-168, 48-169, 48-170, 48-171, 48-172, 48-173, 48-174, 48-175, 48-176, 48-177, 48-178, 48-179, 48-180, 48-181, 48-182, 48-183, 48-184, 48-185, 48-186, 48-187, 48-188, 48-189, 48-190, 48-191, 48-192, 48-193, 48-194, 48-195, 48-196, 48-197, 48-198, 48-199, and 48-200.

Peptides and Proteins that Begin with Amino Acid 49 of HPV16 L2

49-89, 49-90, 49-91, 49-92, 49-93, 49-94, 49-95, 49-96, 49-97, 49-98, 49-99, 49-100, 49-101, 49-102, 49-103, 49-104, 49-105, 49-106, 49-107, 49-108, 49-109, 49-110, 49-111, 49-112, 49-113, 49-114, 49-115, 49-116, 49-117, 49-118, 49-119, 49-120, 49-121, 49-122, 49-123, 49-124, 49-125, 49-126, 49-127, 49-128, 49-129, 49-130, 49-131, 49-132, 49-133, 49-134, 49-135, 49-136, 49-137, 49-138, 49-139, 49-140, 49-141, 49-142, 49-143, 49-144, 49-145, 49-146, 49-147, 49-148, 49-149, 49-150, 49-151, 49-152, 49-153, 49-154, 49-155, 49-156, 49-157, 49-158, 49-159, 49-160, 49-161, 49-162, 49-163, 49-164, 49-165, 49-166, 49-167, 49-168, 49-169, 49-170, 49-171, 49-172, 49-173, 49-174, 49-175, 49-176, 49-177, 49-178, 49-179, 49-180, 49-181, 49-182, 49-183, 49-184, 49-185, 49-186, 49-187, 49-188, 49-189, 49-190, 49-191, 49-192, 49-193, 49-194, 49-195, 49-196, 49-197, 49-198, 49-199, and 49-200.

Peptides and Proteins that Begin with Amino Acid 50 of HPV16 L2

50-89, 50-90, 50-91, 50-92, 50-93, 50-94, 50-95, 50-96, 50-97, 50-98, 50-99, 50-100, 50-101, 50-102, 50-103, 50-104, 50-105, 50-106, 50-107, 50-108, 50-109, 50-110, 50-111, 50-112, 50-113, 50-114, 50-115, 50-116, 50-117, 50-118, 50-119, 50-120, 50-121, 50-122, 50-123, 50-124, 50-125, 50-126, 50-127, 50-128, 50-129, 50-130, 50-131, 50-132, 50-133, 50-134, 50-135, 50-136, 50-137, 50-138, 50-139, 50-140, 50-141, 50-142, 50-143, 50-144, 50-145, 50-146, 50-147, 50-148, 50-149, 50-150, 50-151, 50-152, 50-153, 50-154, 50-155, 50-156, 50-157, 50-158, 50-159, 50-160, 50-161, 50-162, 50-163, 50-164, 50-165, 50-166, 50-167, 50-168, 50-169, 50-170, 50-171, 50-172, 50-173, 50-174, 50-175, 50-176, 50-177, 50-178, 50-179, 50-180, 50-181, 50-182, 50-183, 50-184, 50-185, 50-186, 50-187, 50-188, 50-189, 50-190, 50-191, 50-192, 50-193, 50-194, 50-195, 50-196, 50-197, 50-198, 50-199, and 50-200.

Peptides and Proteins that Begin with Amino Acid 51 of HPV16 L2

51-89, 51-90, 51-91, 51-92, 51-93, 51-94, 51-95, 51-96, 51-97, 51-98, 51-99, 51-100, 51-101, 51-102, 51-103, 51-104, 51-105, 51-106, 51-107, 51-108, 51-109, 51-110, 51-111, 51-112, 51-113, 51-114, 51-115, 51-116, 51-117, 51-118, 51-119, 51-120, 51-121, 51-122, 51-123, 51-124, 51-125, 51-126, 51-127, 51-128, 51-129, 51-130, 51-131, 51-132, 51-133, 51-134, 51-135, 51-136, 51-137, 51-138, 51-139, 51-140, 51-141, 51-142, 51-143, 51-144, 51-145, 51-146, 51-147, 51-148, 51-149, 51-150, 51-151, 51-152, 51-153, 51-154, 51-155, 51-156, 51-157, 51-158, 51-159, 51-160, 51-161, 51-162, 51-163, 51-164, 51-165, 51-166, 51-167, 51-168, 51-169, 51-170, 51-171, 51-172, 51-173, 51-174, 51-175, 51-176, 51-177, 51-178, 51-179, 51-180, 51-181, 51-182, 51-183, 51-184, 51-185, 51-186, 51-187, 51-188, 51-189, 51-190, 51-191, 51-192, 51-193, 51-194, 51-195, 51-196, 51-197, 51-198, 51-199, and 51-200.

Peptides and Proteins that Begin with Amino Acid 52 of HPV16 L2

52-89, 52-90, 52-91, 52-92, 52-93, 52-94, 52-95, 52-96, 52-97, 52-98, 52-99, 52-100, 52-101, 52-102, 52-103, 52-104, 52-105, 52-106, 52-107, 52-108, 52-109, 52-110, 52-111, 52-112, 52-113, 52-114, 52-115, 52-116, 52-117, 52-118, 52-119, 52-120, 52-121, 52-122, 52-123, 52-124, 52-125, 52-126, 52-127, 52-128, 52-129, 52-130, 52-131, 52-132, 52-133, 52-134, 52-135, 52-136, 52-137, 52-138, 52-139, 52-140, 52-141, 52-142, 52-143, 52-144, 52-145, 52-146, 52-147, 52-148, 52-149, 52-150, 52-151, 52-152, 52-153, 52-154, 52-155, 52-156, 52-157, 52-158, 52-159, 52-160, 52-161, 52-162, 52-163, 52-164, 52-165, 52-166, 52-167, 52-168, 52-169, 52-170, 52-171, 52-172, 52-173, 52-174, 52-175, 52-176, 52-177, 52-178, 52-179, 52-180, 52-181, 52-182, 52-183, 52-184, 52-185, 52-186, 52-187, 52-188, 52-189, 52-190, 52-191, 52-192, 52-193, 52-194, 52-195, 52-196, 52-197, 52-198, 52-199, and 52-200.

Peptides and Proteins that Begin with Amino Acid 53 of HPV16 L2

53-89, 53-90, 53-91, 53-92, 53-93, 53-94, 53-95, 53-96, 53-97, 53-98, 53-99, 53-100, 53-101, 53-102, 53-103, 53-104, 53-105, 53-106, 53-107, 53-108, 53-109, 53-110, 53-111, 53-112, 53-113, 53-114, 53-115, 53-116, 53-117, 53-118, 53-119, 53-120, 53-121, 53-122, 53-123, 53-124, 53-125, 53-126, 53-127, 53-128, 53-129, 53-130, 53-131, 53-132, 53-133, 53-134, 53-135, 53-136, 53-137, 53-138, 53-139, 53-140, 53-141, 53-142, 53-143, 53-144, 53-145, 53-146, 53-147, 53-148, 53-149, 53-150, 53-151, 53-152, 53-153, 53-154, 53-155, 53-156, 53-157, 53-158, 53-159, 53-160, 53-161, 53-162, 53-163, 53-164, 53-165, 53-166, 53-167, 53-168, 53-169, 53-170, 53-171, 53-172, 53-173, 53-174, 53-175, 53-176, 53-177, 53-178, 53-179, 53-180, 53-181, 53-182, 53-183, 53-184, 53-185, 53-186, 53-187, 53-188, 53-189, 53-190, 53-191, 53-192, 53-193, 53-194, 53-195, 53-196, 53-197, 53-198, 53-199, and 53-200.

Peptides and Proteins that Begin with Amino Acid 54 of HPV16 L2

54-89, 54-90, 54-91, 54-92, 54-93, 54-94, 54-95, 54-96, 54-97, 54-98, 54-99, 54-100, 54-101, 54-102, 54-103, 54-104, 54-105, 54-106, 54-107, 54-108, 54-109, 54-110, 54-111, 54-112, 54-113, 54-114, 54-115, 54-116, 54-117, 54-118, 54-119, 54-120, 54-121, 54-122, 54-123, 54-124, 54-125, 54-126, 54-127, 54-128, 54-129, 54-130, 54-131, 54-132, 54-133, 54-134, 54-135, 54-136, 54-137, 54-138, 54-139, 54-140, 54-141, 54-142, 54-143, 54-144, 54-145, 54-146, 54-147, 54-148, 54-149, 54-150, 54-151, 54-152, 54-153, 54-154, 54-155, 54-156, 54-157, 54-158, 54-159, 54-160, 54-161, 54-162, 54-163, 54-164, 54-165, 54-166, 54-167, 54-168, 54-169, 54-170, 54-171, 54-172, 54-173, 54-174, 54-175, 54-176, 54-177, 54-178, 54-179, 54-180, 54-181, 54-182, 54-183, 54-184, 54-185, 54-186, 54-187, 54-188, 54-189, 54-190, 54-191, 54-192, 54-193, 54-194, 54-195, 54-196, 54-197, 54-198, 54-199, and 54-200.

Peptides and Proteins that Begin with Amino Acid 55 of HPV16 L2

55-89, 55-90, 55-91, 55-92, 55-93, 55-94, 55-95, 55-96, 55-97, 55-98, 55-99, 55-100, 55-101, 55-102, 55-103, 55-104, 55-105, 55-106, 55-107, 55-108, 55-109, 55-110, 55-111, 55-112, 55-113, 55-114, 55-115, 55-116, 55-117, 55-118, 55-119, 55-120, 55-121, 55-122, 55-123, 55-124, 55-125, 55-126, 55-127, 55-128, 55-129, 55-130, 55-131, 55-132, 55-133, 55-134, 55-135, 55-136, 55-137, 55-138, 55-139, 55-140, 55-141, 55-142, 55-143, 55-144, 55-145, 55-146, 55-147, 55-148, 55-149, 55-150, 55-151, 55-152, 55-153, 55-154, 55-155, 55-156, 55-157, 55-158, 55-159, 55-160, 55-161, 55-162, 55-163, 55-164, 55-165, 55-166, 55-167, 55-168, 55-169, 55-170, 55-171, 55-172, 55-173, 55-174, 55-175, 55-176, 55-177, 55-178, 55-179, 55-180, 55-181, 55-182, 55-183, 55-184, 55-185, 55-186, 55-187, 55-188, 55-189, 55-190, 55-191, 55-192, 55-193, 55-194, 55-195, 55-196, 55-197, 55-198, 55-199, and 55-200.

Peptides and Proteins that Begin with Amino Acid 56 of HPV16 L2

56-89, 56-90, 56-91, 56-92, 56-93, 56-94, 56-95, 56-96, 56-97, 56-98, 56-99, 56-100, 56-101, 56-102, 56-103, 56-104, 56-105, 56-106, 56-107, 56-108, 56-109, 56-110, 56-111, 56-112, 56-113, 56-114, 56-115, 56-116, 56-117, 56-118, 56-119, 56-120, 56-121, 56-122, 56-123, 56-124, 56-125, 56-126, 56-127, 56-128, 56-129, 56-130, 56-131, 56-132, 56-133, 56-134, 56-135, 56-136, 56-137, 56-138, 56-139, 56-140, 56-141, 56-142, 56-143, 56-144, 56-145, 56-146, 56-147, 56-148, 56-149, 56-150, 56-151, 56-152, 56-153, 56-154, 56-155, 56-156, 56-157, 56-158, 56-159, 56-160, 56-161, 56-162, 56-163, 56-164, 56-165, 56-166, 56-167, 56-168, 56-169, 56-170, 56-171, 56-172, 56-173, 56-174, 56-175, 56-176, 56-177, 56-178, 56-179, 56-180, 56-181, 56-182, 56-183, 56-184, 56-185, 56-186, 56-187, 56-188, 56-189, 56-190, 56-191, 56-192, 56-193, 56-194, 56-195, 56-196, 56-197, 56-198, 56-199, and 56-200.

Peptides and Proteins that Begin with Amino Acid 57 of HPV16 L2

57-89, 57-90, 57-91, 57-92, 57-93, 57-94, 57-95, 57-96, 57-97, 57-98, 57-99, 57-100, 57-101, 57-102, 57-103, 57-104, 57-105, 57-106, 57-107, 57-108, 57-109, 57-110, 57-111, 57-112, 57-113, 57-114, 57-115, 57-116, 57-117, 57-118, 57-119, 57-120, 57-121, 57-122, 57-123, 57-124, 57-125, 57-126, 57-127, 57-128, 57-129, 57-130, 57-131, 57-132, 57-133, 57-134, 57-135, 57-136, 57-137, 57-138, 57-139, 57-140, 57-141, 57-142, 57-143, 57-144, 57-145, 57-146, 57-147, 57-148, 57-149, 57-150, 57-151, 57-152, 57-153, 57-154, 57-155, 57-156, 57-157, 57-158, 57-159, 57-160, 57-161, 57-162, 57-163, 57-164, 57-165, 57-166, 57-167, 57-168, 57-169, 57-170, 57-171, 57-172, 57-173, 57-174, 57-175, 57-176, 57-177, 57-178, 57-179, 57-180, 57-181, 57-182, 57-183, 57-184, 57-185, 57-186, 57-187, 57-188, 57-189, 57-190, 57-191, 57-192, 57-193, 57-194, 57-195, 57-196, 57-197, 57-198, 57-199, and 57-200.

Peptides and Proteins that Begin with Amino Acid 58 of HPV16 L2

58-89, 58-90, 58-91, 58-92, 58-93, 58-94, 58-95, 58-96, 58-97, 58-98, 58-99, 58-100, 58-101, 58-102, 58-103, 58-104, 58-105, 58-106, 58-107, 58-108, 58-109, 58-110, 58-111, 58-112, 58-113, 58-114, 58-115, 58-116, 58-117, 58-118, 58-119, 58-120, 58-121, 58-122, 58-123, 58-124, 58-125, 58-126, 58-127, 58-128, 58-129, 58-130, 58-131, 58-132, 58-133, 58-134, 58-135, 58-136, 58-137, 58-138, 58-139, 58-140, 58-141, 58-142, 58-143, 58-144, 58-145, 58-146, 58-147, 58-148, 58-149, 58-150, 58-151, 58-152, 58-153, 58-154, 58-155, 58-156, 58-157, 58-158, 58-159, 58-160, 58-161, 58-162, 58-163, 58-164, 58-165, 58-166, 58-167, 58-168, 58-169, 58-170, 58-171, 58-172, 58-173, 58-174, 58-175, 58-176, 58-177, 58-178, 58-179, 58-180, 58-181, 58-182, 58-183, 58-184, 58-185, 58-186, 58-187, 58-188, 58-189, 58-190, 58-191, 58-192, 58-193, 58-194, 58-195, 58-196, 58-197, 58-198, 58-199, and 58-200.

Peptides and Proteins that Begin with Amino Acid 59 of HPV16 L2

59-89, 59-90, 59-91, 59-92, 59-93, 59-94, 59-95, 59-96, 59-97, 59-98, 59-99, 59-100, 59-101, 59-102, 59-103, 59-104, 59-105, 59-106, 59-107, 59-108, 59-109, 59-110, 59-111, 59-112, 59-113, 59-114, 59-115, 59-116, 59-117, 59-118, 59-119, 59-120, 59-121, 59-122, 59-123, 59-124, 59-125, 59-126, 59-127, 59-128, 59-129, 59-130, 59-131, 59-132, 59-133, 59-134, 59-135, 59-136, 59-137, 59-138, 59-139, 59-140, 59-141, 59-142, 59-143, 59-144, 59-145, 59-146, 59-147, 59-148, 59-149, 59-150, 59-151, 59-152, 59-153, 59-154, 59-155, 59-156, 59-157, 59-158, 59-159, 59-160, 59-161, 59-162, 59-163, 59-164, 59-165, 59-166, 59-167, 59-168, 59-169, 59-170, 59-171, 59-172, 59-173, 59-174, 59-175, 59-176, 59-177, 59-178, 59-179, 59-180, 59-181, 59-182, 59-183, 59-184, 59-185, 59-186, 59-187, 59-188, 59-189, 59-190, 59-191, 59-192, 59-193, 59-194, 59-195, 59-196, 59-197, 59-198, 59-199, and 59-200.

Peptides and Proteins that Begin with Amino Acid 60 of HPV16 L2

60-89, 60-90, 60-91, 60-92, 60-93, 60-94, 60-95, 60-96, 60-97, 60-98, 60-99, 60-100, 60-101, 60-102, 60-103, 60-104, 60-105, 60-106, 60-107, 60-108, 60-109, 60-110, 60-111, 60-112, 60-113, 60-114, 60-115, 60-116, 60-117, 60-118, 60-119, 60-120, 60-121, 60-122, 60-123, 60-124, 60-125, 60-126, 60-127, 60-128, 60-129, 60-130, 60-131, 60-132, 60-133, 60-134, 60-135, 60-136, 60-137, 60-138, 60-139, 60-140, 60-141, 60-142, 60-143, 60-144, 60-145, 60-146, 60-147, 60-148, 60-149, 60-150, 60-151, 60-152, 60-153, 60-154, 60-155, 60-156, 60-157, 60-158, 60-159, 60-160, 60-161, 60-162, 60-163, 60-164, 60-165, 60-166, 60-167, 60-168, 60-169, 60-170, 60-171, 60-172, 60-173, 60-174, 60-175, 60-176, 60-177, 60-178, 60-179, 60-180, 60-181, 60-182, 60-183, 60-184, 60-185, 60-186, 60-187, 60-188, 60-189, 60-190, 60-191, 60-192, 60-193, 60-194, 60-195, 60-196, 60-197, 60-198, 60-199, and 60-200.

Peptides and Proteins that Begin with Amino Acid 61 of HPV16 L2

61-89, 61-90, 61-91, 61-92, 61-93, 61-94, 61-95, 61-96, 61-97, 61-98, 61-99, 61-100, 61-101, 61-102, 61-103, 61-104, 61-105, 61-106, 61-107, 61-108, 61-109, 61-110, 61-111, 61-112, 61-113, 61-114, 61-115, 61-116, 61-117, 61-118, 61-119, 61-120, 61-121, 61-122, 61-123, 61-124, 61-125, 61-126, 61-127, 61-128, 61-129, 61-130, 61-131, 61-132, 61-133, 61-134, 61-135, 61-136, 61-137, 61-138, 61-139, 61-140, 61-141, 61-142, 61-143, 61-144, 61-145, 61-146, 61-147, 61-148, 61-149, 61-150, 61-151, 61-152, 61-153, 61-154, 61-155, 61-156, 61-157, 61-158, 61-159, 61-160, 61-161, 61-162, 61-163, 61-164, 61-165, 61-166, 61-167, 61-168, 61-169, 61-170, 61-171, 61-172, 61-173, 61-174, 61-175, 61-176, 61-177, 61-178, 61-179, 61-180, 61-181, 61-182, 61-183, 61-184, 61-185, 61-186, 61-187, 61-188, 61-189, 61-190, 61-191, 61-192, 61-193, 61-194, 61-195, 61-196, 61-197, 61-198, 61-199, and 61-200.

Peptides and Proteins that Begin with Amino Acid 62 of HPV16 L2

62-89, 62-90, 62-91, 62-92, 62-93, 62-94, 62-95, 62-96, 62-97, 62-98, 62-99, 62-100, 62-101, 62-102, 62-103, 62-104, 62-105, 62-106, 62-107, 62-108, 62-109, 62-110, 62-111, 62-112, 62-113, 62-114, 62-115, 62-116, 62-117, 62-118, 62-119, 62-120, 62-121, 62-122, 62-123, 62-124, 62-125, 62-126, 62-127, 62-128, 62-129, 62-130, 62-131, 62-132, 62-133, 62-134, 62-135, 62-136, 62-137, 62-138, 62-139, 62-140, 62-141, 62-142, 62-143, 62-144, 62-145, 62-146, 62-147, 62-148, 62-149, 62-150, 62-151, 62-152, 62-153, 62-154, 62-155, 62-156, 62-157, 62-158, 62-159, 62-160, 62-161, 62-162, 62-163, 62-164, 62-165, 62-166, 62-167, 62-168, 62-169, 62-170, 62-171, 62-172, 62-173, 62-174, 62-175, 62-176, 62-177, 62-178, 62-179, 62-180, 62-181, 62-182, 62-183, 62-184, 62-185, 62-186, 62-187, 62-188, 62-189, 62-190, 62-191, 62-192, 62-193, 62-194, 62-195, 62-196, 62-197, 62-198, 62-199, and 62-200.

Peptides and Proteins that Begin with Amino Acid 63 of HPV16 L2

63-89, 63-90, 63-91, 63-92, 63-93, 63-94, 63-95, 63-96, 63-97, 63-98, 63-99, 63-100, 63-101, 63-102, 63-103, 63-104, 63-105, 63-106, 63-107, 63-108, 63-109, 63-110, 63-111, 63-112, 63-113, 63-114, 63-115, 63-116, 63-117, 63-118, 63-119, 63-120, 63-121, 63-122, 63-123, 63-124, 63-125, 63-126, 63-127, 63-128, 63-129, 63-130, 63-131, 63-132, 63-133, 63-134, 63-135, 63-136, 63-137, 63-138, 63-139, 63-140, 63-141, 63-142, 63-143, 63-144, 63-145, 63-146, 63-147, 63-148, 63-149, 63-150, 63-151, 63-152, 63-153, 63-154, 63-155, 63-156, 63-157, 63-158, 63-159, 63-160, 63-161, 63-162, 63-163, 63-164, 63-165, 63-166, 63-167, 63-168, 63-169, 63-170, 63-171, 63-172, 63-173, 63-174, 63-175, 63-176, 63-177, 63-178, 63-179, 63-180, 63-181, 63-182, 63-183, 63-184, 63-185, 63-186, 63-187, 63-188, 63-189, 63-190, 63-191, 63-192, 63-193, 63-194, 63-195, 63-196, 63-197, 63-198, 63-199, and 63-200.

Peptides and Proteins that Begin with Amino Acid 64 of HPV16 L2

64-89, 64-90, 64-91, 64-92, 64-93, 64-94, 64-95, 64-96, 64-97, 64-98, 64-99, 64-100, 64-101, 64-102, 64-103, 64-104, 64-105, 64-106, 64-107, 64-108, 64-109, 64-110, 64-111, 64-112, 64-113, 64-114, 64-115, 64-116, 64-117, 64-118, 64-119, 64-120, 64-121, 64-122, 64-123, 64-124, 64-125, 64-126, 64-127, 64-128, 64-129, 64-130, 64-131, 64-132, 64-133, 64-134, 64-135, 64-136, 64-137, 64-138, 64-139, 64-140, 64-141, 64-142, 64-143, 64-144, 64-145, 64-146, 64-147, 64-148, 64-149, 64-150, 64-151, 64-152, 64-153, 64-154, 64-155, 64-156, 64-157, 64-158, 64-159, 64-160, 64-161, 64-162, 64-163, 64-164, 64-165, 64-166, 64-167, 64-168, 64-169, 64-170, 64-171, 64-172, 64-173, 64-174, 64-175, 64-176, 64-177, 64-178, 64-179, 64-180, 64-181, 64-182, 64-183, 64-184, 64-185, 64-186, 64-187, 64-188, 64-189, 64-190, 64-191, 64-192, 64-193, 64-194, 64-195, 64-196, 64-197, 64-198, 64-199, and 64-200.

Peptides and Proteins that Begin with Amino Acid 65 of HPV16 L2

65-89, 65-90, 65-91, 65-92, 65-93, 65-94, 65-95, 65-96, 65-97, 65-98, 65-99, 65-100, 65-101, 65-102, 65-103, 65-104, 65-105, 65-106, 65-107, 65-108, 65-109, 65-110, 65-111, 65-112, 65-113, 65-114, 65-115, 65-116, 65-117, 65-118, 65-119, 65-120, 65-121, 65-122, 65-123, 65-124, 65-125, 65-126, 65-127, 65-128, 65-129, 65-130, 65-131, 65-132, 65-133, 65-134, 65-135, 65-136, 65-137, 65-138, 65-139, 65-140, 65-141, 65-142, 65-143, 65-144, 65-145, 65-146, 65-147, 65-148, 65-149, 65-150, 65-151, 65-152, 65-153, 65-154, 65-155, 65-156, 65-157, 65-158, 65-159, 65-160, 65-161, 65-162, 65-163, 65-164, 65-165, 65-166, 65-167, 65-168, 65-169, 65-170, 65-171, 65-172, 65-173, 65-174, 65-175, 65-176, 65-177, 65-178, 65-179, 65-180, 65-181, 65-182, 65-183, 65-184, 65-185, 65-186, 65-187, 65-188, 65-189, 65-190, 65-191, 65-192, 65-193, 65-194, 65-195, 65-196, 65-197, 65-198, 65-199, and 65-200.

Peptides and Proteins that Begin with Amino Acid 66 of HPV16 L2

66-89, 66-90, 66-91, 66-92, 66-93, 66-94, 66-95, 66-96, 66-97, 66-98, 66-99, 66-100, 66-101, 66-102, 66-103, 66-104, 66-105, 66-106, 66-107, 66-108, 66-109, 66-110, 66-111, 66-112, 66-113, 66-114, 66-115, 66-116, 66-117, 66-118, 66-119, 66-120, 66-121, 66-122, 66-123, 66-124, 66-125, 66-126, 66-127, 66-128, 66-129, 66-130, 66-131, 66-132, 66-133, 66-134, 66-135, 66-136, 66-137, 66-138, 66-139, 66-140, 66-141, 66-142, 66-143, 66-144, 66-145, 66-146, 66-147, 66-148, 66-149, 66-150, 66-151, 66-152, 66-153, 66-154, 66-155, 66-156, 66-157, 66-158, 66-159, 66-160, 66-161, 66-162, 66-163, 66-164, 66-165, 66-166, 66-167, 66-168, 66-169, 66-170, 66-171, 66-172, 66-173, 66-174, 66-175, 66-176, 66-177, 66-178, 66-179, 66-180, 66-181, 66-182, 66-183, 66-184, 66-185, 66-186, 66-187, 66-188, 66-189, 66-190, 66-191, 66-192, 66-193, 66-194, 66-195, 66-196, 66-197, 66-198, 66-199, and 66-200.

Peptides and Proteins that Begin with Amino Acid 67 of HPV16 L2

67-89, 67-90, 67-91, 67-92, 67-93, 67-94, 67-95, 67-96, 67-97, 67-98, 67-99, 67-100, 67-101, 67-102, 67-103, 67-104, 67-105, 67-106, 67-107, 67-108, 67-109, 67-110, 67-111, 67-112, 67-113, 67-114, 67-115, 67-116, 67-117, 67-118, 67-119, 67-120, 67-121, 67-122, 67-123, 67-124, 67-125, 67-126, 67-127, 67-128, 67-129, 67-130, 67-131, 67-132, 67-133, 67-134, 67-135, 67-136, 67-137, 67-138, 67-139, 67-140, 67-141, 67-142, 67-143, 67-144, 67-145, 67-146, 67-147, 67-148, 67-149, 67-150, 67-151, 67-152, 67-153, 67-154, 67-155, 67-156, 67-157, 67-158, 67-159, 67-160, 67-161, 67-162, 67-163, 67-164, 67-165, 67-166, 67-167, 67-168, 67-169, 67-170, 67-171, 67-172, 67-173, 67-174, 67-175, 67-176, 67-177, 67-178, 67-179, 67-180, 67-181, 67-182, 67-183, 67-184, 67-185, 67-186, 67-187, 67-188, 67-189, 67-190, 67-191, 67-192, 67-193, 67-194, 67-195, 67-196, 67-197, 67-198, 67-199, and 67-200.

Peptides and Proteins that Begin with Amino Acid 68 of HPV16 L2

68-89, 68-90, 68-91, 68-92, 68-93, 68-94, 68-95, 68-96, 68-97, 68-98, 68-99, 68-100, 68-101, 68-102, 68-103, 68-104, 68-105, 68-106, 68-107, 68-108, 68-109, 68-110, 68-111, 68-112, 68-113, 68-114, 68-115, 68-116, 68-117, 68-118, 68-119, 68-120, 68-121, 68-122, 68-123, 68-124, 68-125, 68-126, 68-127, 68-128, 68-129, 68-130, 68-131, 68-132, 68-133, 68-134, 68-135, 68-136, 68-137, 68-138, 68-139, 68-140, 68-141, 68-142, 68-143, 68-144, 68-145, 68-146, 68-147, 68-148, 68-149, 68-150, 68-151, 68-152, 68-153, 68-154, 68-155, 68-156, 68-157, 68-158, 68-159, 68-160, 68-161, 68-162, 68-163, 68-164, 68-165, 68-166, 68-167, 68-168, 68-169, 68-170, 68-171, 68-172, 68-173, 68-174, 68-175, 68-176, 68-177, 68-178, 68-179, 68-180, 68-181, 68-182, 68-183, 68-184, 68-185, 68-186, 68-187, 68-188, 68-189, 68-190, 68-191, 68-192, 68-193, 68-194, 68-195, 68-196, 68-197, 68-198, 68-199, and 68-200.

Peptides and Proteins that Begin with Amino Acid 69 of HPV16 L2

69-89, 69-90, 69-91, 69-92, 69-93, 69-94, 69-95, 69-96, 69-97, 69-98, 69-99, 69-100, 69-101, 69-102, 69-103, 69-104, 69-105, 69-106, 69-107, 69-108, 69-109, 69-110, 69-111, 69-112, 69-113, 69-114, 69-115, 69-116, 69-117, 69-118, 69-119, 69-120, 69-121, 69-122, 69-123, 69-124, 69-125, 69-126, 69-127, 69-128, 69-129, 69-130, 69-131, 69-132, 69-133, 69-134, 69-135, 69-136, 69-137, 69-138, 69-139, 69-140, 69-141, 69-142, 69-143, 69-144, 69-145, 69-146, 69-147, 69-148, 69-149, 69-150, 69-151, 69-152, 69-153, 69-154, 69-155, 69-156, 69-157, 69-158, 69-159, 69-160, 69-161, 69-162, 69-163, 69-164, 69-165, 69-166, 69-167, 69-168, 69-169, 69-170, 69-171, 69-172, 69-173, 69-174, 69-175, 69-176, 69-177, 69-178, 69-179, 69-180, 69-181, 69-182, 69-183, 69-184, 69-185, 69-186, 69-187, 69-188, 69-189, 69-190, 69-191, 69-192, 69-193, 69-194, 69-195, 69-196, 69-197, 69-198, 69-199, and 69-200.

Peptides and Proteins that Begin with Amino Acid 70 of HPV16 L2

70-89, 70-90, 70-91, 70-92, 70-93, 70-94, 70-95, 70-96, 70-97, 70-98, 70-99, 70-100, 70-101, 70-102, 70-103, 70-104, 70-105, 70-106, 70-107, 70-108, 70-109, 70-110, 70-111, 70-112, 70-113, 70-114, 70-115, 70-116, 70-117, 70-118, 70-119, 70-120, 70-121, 70-122, 70-123, 70-124, 70-125, 70-126, 70-127, 70-128, 70-129, 70-130, 70-131, 70-132, 70-133, 70-134, 70-135, 70-136, 70-137, 70-138, 70-139, 70-140, 70-141, 70-142, 70-143, 70-144, 70-145, 70-146, 70-147, 70-148, 70-149, 70-150, 70-151, 70-152, 70-153, 70-154, 70-155, 70-156, 70-157, 70-158, 70-159, 70-160, 70-161, 70-162, 70-163, 70-164, 70-165, 70-166, 70-167, 70-168, 70-169, 70-170, 70-171, 70-172, 70-173, 70-174, 70-175, 70-176, 70-177, 70-178, 70-179, 70-180, 70-181, 70-182, 70-183, 70-184, 70-185, 70-186, 70-187, 70-188, 70-189, 70-190, 70-191, 70-192, 70-193, 70-194, 70-195, 70-196, 70-197, 70-198, 70-199, and 70-200.

Peptides and Proteins that Begin with Amino Acid 71 of HPV16 L2

71-89, 71-90, 71-91, 71-92, 71-93, 71-94, 71-95, 71-96, 71-97, 71-98, 71-99, 71-100, 71-101, 71-102, 71-103, 71-104, 71-105, 71-106, 71-107, 71-108, 71-109, 71-110, 71-111, 71-112, 71-113, 71-114, 71-115, 71-116, 71-117, 71-118, 71-119, 71-120, 71-121, 71-122, 71-123, 71-124, 71-125, 71-126, 71-127, 71-128, 71-129, 71-130, 71-131, 71-132, 71-133, 71-134, 71-135, 71-136, 71-137, 71-138, 71-139, 71-140, 71-141, 71-142, 71-143, 71-144, 71-145, 71-146, 71-147, 71-148, 71-149, 71-150, 71-151, 71-152, 71-153, 71-154, 71-155, 71-156, 71-157, 71-158, 71-159, 71-160, 71-161, 71-162, 71-163, 71-164, 71-165, 71-166, 71-167, 71-168, 71-169, 71-170, 71-171, 71-172, 71-173, 71-174, 71-175, 71-176, 71-177, 71-178, 71-179, 71-180, 71-181, 71-182, 71-183, 71-184, 71-185, 71-186, 71-187, 71-188, 71-189, 71-190, 71-191, 71-192, 71-193, 71-194, 71-195, 71-196, 71-197, 71-198, 71-199, and 71-200.

Peptides and Proteins that Begin with Amino Acid 72 of HPV16 L2

72-89, 72-90, 72-91, 72-92, 72-93, 72-94, 72-95, 72-96, 72-97, 72-98, 72-99, 72-100, 72-101, 72-102, 72-103, 72-104, 72-105, 72-106, 72-107, 72-108, 72-109, 72-110, 72-111, 72-112, 72-113, 72-114, 72-115, 72-116, 72-117, 72-118, 72-119, 72-120, 72-121, 72-122, 72-123, 72-124, 72-125, 72-126, 72-127, 72-128, 72-129, 72-130, 72-131, 72-132, 72-133, 72-134, 72-135, 72-136, 72-137, 72-138, 72-139, 72-140, 72-141, 72-142, 72-143, 72-144, 72-145, 72-146, 72-147, 72-148, 72-149, 72-150, 72-151, 72-152, 72-153, 72-154, 72-155, 72-156, 72-157, 72-158, 72-159, 72-160, 72-161, 72-162, 72-163, 72-164, 72-165, 72-166, 72-167, 72-168, 72-169, 72-170, 72-171, 72-172, 72-173, 72-174, 72-175, 72-176, 72-177, 72-178, 72-179, 72-180, 72-181, 72-182, 72-183, 72-184, 72-185, 72-186, 72-187, 72-188, 72-189, 72-190, 72-191, 72-192, 72-193, 72-194, 72-195, 72-196, 72-197, 72-198, 72-199, and 72-200.

Peptides and Proteins that Begin with Amino Acid 73 of HPV16 L2

73-89, 73-90, 73-91, 73-92, 73-93, 73-94, 73-95, 73-96, 73-97, 73-98, 73-99, 73-100, 73-101, 73-102, 73-103, 73-104, 73-105, 73-106, 73-107, 73-108, 73-109, 73-110, 73-111, 73-112, 73-113, 73-114, 73-115, 73-116, 73-117, 73-118, 73-119, 73-120, 73-121, 73-122, 73-123, 73-124, 73-125, 73-126, 73-127, 73-128, 73-129, 73-130, 73-131, 73-132, 73-133, 73-134, 73-135, 73-136, 73-137, 73-138, 73-139, 73-140, 73-141, 73-142, 73-143, 73-144, 73-145, 73-146, 73-147, 73-148, 73-149, 73-150, 73-151, 73-152, 73-153, 73-154, 73-155, 73-156, 73-157, 73-158, 73-159, 73-160, 73-161, 73-162, 73-163, 73-164, 73-165, 73-166, 73-167, 73-168, 73-169, 73-170, 73-171, 73-172, 73-173, 73-174, 73-175, 73-176, 73-177, 73-178, 73-179, 73-180, 73-181, 73-182, 73-183, 73-184, 73-185, 73-186, 73-187, 73-188, 73-189, 73-190, 73-191, 73-192, 73-193, 73-194, 73-195, 73-196, 73-197, 73-198, 73-199, and 73-200.

Peptides and Proteins that Begin with Amino Acid 74 of HPV16 L2

74-89, 74-90, 74-91, 74-92, 74-93, 74-94, 74-95, 74-96, 74-97, 74-98, 74-99, 74-100, 74-101, 74-102, 74-103, 74-104, 74-105, 74-106, 74-107, 74-108, 74-109, 74-110, 74-111, 74-112, 74-113, 74-114, 74-115, 74-116, 74-117, 74-118, 74-119, 74-120, 74-121, 74-122, 74-123, 74-124, 74-125, 74-126, 74-127, 74-128, 74-129, 74-130, 74-131, 74-132, 74-133, 74-134, 74-135, 74-136, 74-137, 74-138, 74-139, 74-140, 74-141, 74-142, 74-143, 74-144, 74-145, 74-146, 74-147, 74-148, 74-149, 74-150, 74-151, 74-152, 74-153, 74-154, 74-155, 74-156, 74-157, 74-158, 74-159, 74-160, 74-161, 74-162, 74-163, 74-164, 74-165, 74-166, 74-167, 74-168, 74-169, 74-170, 74-171, 74-172, 74-173, 74-174, 74-175, 74-176, 74-177, 74-178, 74-179, 74-180, 74-181, 74-182, 74-183, 74-184, 74-185, 74-186, 74-187, 74-188, 74-189, 74-190, 74-191, 74-192, 74-193, 74-194, 74-195, 74-196, 74-197, 74-198, 74-199, and 74-200.

Peptides and Proteins that Begin with Amino Acid 75 of HPV16 L2

75-89, 75-90, 75-91, 75-92, 75-93, 75-94, 75-95, 75-96, 75-97, 75-98, 75-99, 75-100, 75-101, 75-102, 75-103, 75-104, 75-105, 75-106, 75-107, 75-108, 75-109, 75-110, 75-111, 75-112, 75-113, 75-114, 75-115, 75-116, 75-117, 75-118, 75-119, 75-120, 75-121, 75-122, 75-123, 75-124, 75-125, 75-126, 75-127, 75-128, 75-129, 75-130, 75-131, 75-132, 75-133, 75-134, 75-135, 75-136, 75-137, 75-138, 75-139, 75-140, 75-141, 75-142, 75-143, 75-144, 75-145, 75-146, 75-147, 75-148, 75-149, 75-150, 75-151, 75-152, 75-153, 75-154, 75-155, 75-156, 75-157, 75-158, 75-159, 75-160, 75-161, 75-162, 75-163, 75-164, 75-165, 75-166, 75-167, 75-168, 75-169, 75-170, 75-171, 75-172, 75-173, 75-174, 75-175, 75-176, 75-177, 75-178, 75-179, 75-180, 75-181, 75-182, 75-183, 75-184, 75-185, 75-186, 75-187, 75-188, 75-189, 75-190, 75-191, 75-192, 75-193, 75-194, 75-195, 75-196, 75-197, 75-198, 75-199, and 75-200.

Peptides and Proteins that Begin with Amino Acid 76 of HPV16 L2

76-89, 76-90, 76-91, 76-92, 76-93, 76-94, 76-95, 76-96, 76-97, 76-98, 76-99, 76-100, 76-101, 76-102, 76-103, 76-104, 76-105, 76-106, 76-107, 76-108, 76-109, 76-110, 76-111, 76-112, 76-113, 76-114, 76-115, 76-116, 76-117, 76-118, 76-119, 76-120, 76-121, 76-122, 76-123, 76-124, 76-125, 76-126, 76-127, 76-128, 76-129, 76-130, 76-131, 76-132, 76-133, 76-134, 76-135, 76-136, 76-137, 76-138, 76-139, 76-140, 76-141, 76-142, 76-143, 76-144, 76-145, 76-146, 76-147, 76-148, 76-149, 76-150, 76-151, 76-152, 76-153, 76-154, 76-155, 76-156, 76-157, 76-158, 76-159, 76-160, 76-161, 76-162, 76-163, 76-164, 76-165, 76-166, 76-167, 76-168, 76-169, 76-170, 76-171, 76-172, 76-173, 76-174, 76-175, 76-176, 76-177, 76-178, 76-179, 76-180, 76-181, 76-182, 76-183, 76-184, 76-185, 76-186, 76-187, 76-188, 76-189, 76-190, 76-191, 76-192, 76-193, 76-194, 76-195, 76-196, 76-197, 76-198, 76-199, and 76-200.

Peptides and Proteins that Begin with Amino Acid 77 of HPV16 L2

77-89, 77-90, 77-91, 77-92, 77-93, 77-94, 77-95, 77-96, 77-97, 77-98, 77-99, 77-100, 77-101, 77-102, 77-103, 77-104, 77-105, 77-106, 77-107, 77-108, 77-109, 77-110, 77-111, 77-112, 77-113, 77-114, 77-115, 77-116, 77-117, 77-118, 77-119, 77-120, 77-121, 77-122, 77-123, 77-124, 77-125, 77-126, 77-127, 77-128, 77-129, 77-130, 77-131, 77-132, 77-133, 77-134, 77-135, 77-136, 77-137, 77-138, 77-139, 77-140, 77-141, 77-142, 77-143, 77-144, 77-145, 77-146, 77-147, 77-148, 77-149, 77-150, 77-151, 77-152, 77-153, 77-154, 77-155, 77-156, 77-157, 77-158, 77-159, 77-160, 77-161, 77-162, 77-163, 77-164, 77-165, 77-166, 77-167, 77-168, 77-169, 77-170, 77-171, 77-172, 77-173, 77-174, 77-175, 77-176, 77-177, 77-178, 77-179, 77-180, 77-181, 77-182, 77-183, 77-184, 77-185, 77-186, 77-187, 77-188, 77-189, 77-190, 77-191, 77-192, 77-193, 77-194, 77-195, 77-196, 77-197, 77-198, 77-199, and 77-200.

Peptides and Proteins that Begin with Amino Acid 78 of HPV16 L2

78-89, 78-90, 78-91, 78-92, 78-93, 78-94, 78-95, 78-96, 78-97, 78-98, 78-99, 78-100, 78-101, 78-102, 78-103, 78-104, 78-105, 78-106, 78-107, 78-108, 78-109, 78-110, 78-111, 78-112, 78-113, 78-114, 78-115, 78-116, 78-117, 78-118, 78-119, 78-120, 78-121, 78-122, 78-123, 78-124, 78-125, 78-126, 78-127, 78-128, 78-129, 78-130, 78-131, 78-132, 78-133, 78-134, 78-135, 78-136, 78-137, 78-138, 78-139, 78-140, 78-141, 78-142, 78-143, 78-144, 78-145, 78-146, 78-147, 78-148, 78-149, 78-150, 78-151, 78-152, 78-153, 78-154, 78-155, 78-156, 78-157, 78-158, 78-159, 78-160, 78-161, 78-162, 78-163, 78-164, 78-165, 78-166, 78-167, 78-168, 78-169, 78-170, 78-171, 78-172, 78-173, 78-174, 78-175, 78-176, 78-177, 78-178, 78-179, 78-180, 78-181, 78-182, 78-183, 78-184, 78-185, 78-186, 78-187, 78-188, 78-189, 78-190, 78-191, 78-192, 78-193, 78-194, 78-195, 78-196, 78-197, 78-198, 78-199, and 78-200.

Peptides and Proteins that Begins with Amino Acid 79 of HPV16 L2

79-89, 79-90, 79-91, 79-92, 79-93, 79-94, 79-95, 79-96, 79-97, 79-98, 79-99, 79-100, 79-101, 79-102, 79-103, 79-104, 79-105, 79-106, 79-107, 79-108, 79-109, 79-110, 79-111, 79-112, 79-113, 79-114, 79-115, 79-116, 79-117, 79-118, 79-119, 79-120, 79-121, 79-122, 79-123, 79-124, 79-125, 79-126, 79-127, 79-128, 79-129, 79-130, 79-131, 79-132, 79-133, 79-134, 79-135, 79-136, 79-137, 79-138, 79-139, 79-140, 79-141, 79-142, 79-143, 79-144, 79-145, 79-146, 79-147, 79-148, 79-149, 79-150, 79-151, 79-152, 79-153, 79-154, 79-155, 79-156, 79-157, 79-158, 79-159, 79-160, 79-161, 79-162, 79-163, 79-164, 79-165, 79-166, 79-167, 79-168, 79-169, 79-170, 79-171, 79-172, 79-173, 79-174, 79-175, 79-176, 79-177, 79-178, 79-179, 79-180, 79-181, 79-182, 79-183, 79-184, 79-185, 79-186, 79-187, 79-188, 79-189, 79-190, 79-191, 79-192, 79-193, 79-194, 79-195, 79-196, 79-197, 79-198, 79-199, and 79-200.

Peptides and Proteins that Begins with Amino Acid 80 of HPV16 L2

80-89, 80-90, 80-91, 80-92, 80-93, 80-94, 80-95, 80-96, 80-97, 80-98, 80-99, 80-100, 80-101, 80-102, 80-103, 80-104, 80-105, 80-106, 80-107, 80-108, 80-109, 80-110, 80-111, 80-112, 80-113, 80-114, 80-115, 80-116, 80-117, 80-118, 80-119, 80-120, 80-121, 80-122, 80-123, 80-124, 80-125, 80-126, 80-127, 80-128, 80-129, 80-130, 80-131, 80-132, 80-133, 80-134, 80-135, 80-136, 80-137, 80-138, 80-139, 80-140, 80-141, 80-142, 80-143, 80-144, 80-145, 80-146, 80-147, 80-148, 80-149, 80-150, 80-151, 80-152, 80-153, 80-154, 80-155, 80-156, 80-157, 80-158, 80-159, 80-160, 80-161, 80-162, 80-163, 80-164, 80-165, 80-166, 80-167, 80-168, 80-169, 80-170, 80-171, 80-172, 80-173, 80-174, 80-175, 80-176, 80-177, 80-178, 80-179, 80-180, 80-181, 80-182, 80-183, 80-184, 80-185, 80-186, 80-187, 80-188, 80-189, 80-190, 80-191, 80-192, 80-193, 80-194, 80-195, 80-196, 80-197, 80-198, 80-199, and 80-200.

Peptides and Proteins that Begins with Amino Acid 81 of HPV16 L2

81-90, 81-91, 81-92, 81-93, 81-94, 81-95, 81-96, 81-97, 81-98, 81-99, 81-100, 81-101, 81-102, 81-103, 81-104, 81-105, 81-106, 81-107, 81-108, 81-109, 81-110, 81-111, 81-112, 81-113, 81-114, 81-115, 81-116, 81-117, 81-118, 81-119, 81-120, 81-121, 81-122, 81-123, 81-124, 81-125, 81-126, 81-127, 81-128, 81-129, 81-130, 81-131, 81-132, 81-133, 81-134, 81-135, 81-136, 81-137, 81-138, 81-139, 81-140, 81-141, 81-142, 81-143, 81-144, 81-145, 81-146, 81-147, 81-148, 81-149, 81-150, 81-151, 81-152, 81-153, 81-154, 81-155, 81-156, 81-157, 81-158, 81-159, 81-160, 81-161, 81-162, 81-163, 81-164, 81-165, 81-166, 81-167, 81-168, 81-169, 81-170, 81-171, 81-172, 81-173, 81-174, 81-175, 81-176, 81-177, 81-178, 81-179, 81-180, 81-181, 81-182, 81-183, 81-184, 81-185, 81-186, 81-187, 81-188, 81-189, 81-190, 81-191, 81-192, 81-193, 81-194, 81-195, 81-196, 81-197, 81-198, 81-199, and 81-200.

Peptides and Proteins that Begins with Amino Acid 82 of HPV16 L2

82-91, 82-92, 82-93, 82-94, 82-95, 82-96, 82-97, 82-98, 82-99, 82-100, 82-101, 82-102, 82-103, 82-104, 82-105, 82-106, 82-107, 82-108, 82-109, 82-110, 82-111, 82-112, 82-113, 82-114, 82-115, 82-116, 82-117, 82-118, 82-119, 82-120, 82-121, 82-122, 82-123, 82-124, 82-125, 82-126, 82-127, 82-128, 82-129, 82-130, 82-131, 82-132, 82-133, 82-134, 82-135, 82-136, 82-137, 82-138, 82-139, 82-140, 82-141, 82-142, 82-143, 82-144, 82-145, 82-146, 82-147, 82-148, 82-149, 82-150, 82-151, 82-152, 82-153, 82-154, 82-155, 82-156, 82-157, 82-158, 82-159, 82-160, 82-161, 82-162, 82-163, 82-164, 82-165, 82-166, 82-167, 82-168, 82-169, 82-170, 82-171, 82-172, 82-173, 82-174, 82-175, 82-176, 82-177, 82-178, 82-179, 82-180, 82-181, 82-182, 82-183, 82-184, 82-185, 82-186, 82-187, 82-188, 82-189, 82-190, 82-191, 82-192, 82-193, 82-194, 82-195, 82-196, 82-197, 82-198, 82-199, and 82-200.

Peptides and Proteins that Begins with Amino Acid 83 of HPV16 L2

83-92, 83-93, 83-94, 83-95, 83-96, 83-97, 83-98, 83-99, 83-100, 83-101, 83-102, 83-103, 83-104, 83-105, 83-106, 83-107, 83-108, 83-109, 83-110, 83-111, 83-112, 83-113, 83-114, 83-115, 83-116, 83-117, 83-118, 83-119, 83-120, 83-121, 83-122, 83-123, 83-124, 83-125, 83-126, 83-127, 83-128, 83-129, 83-130, 83-131, 83-132, 83-133, 83-134, 83-135, 83-136, 83-137, 83-138, 83-139, 83-140, 83-141, 83-142, 83-143, 83-144, 83-145, 83-146, 83-147, 83-148, 83-149, 83-150, 83-151, 83-152, 83-153, 83-154, 83-155, 83-156, 83-157, 83-158, 83-159, 83-160, 83-161, 83-162, 83-163, 83-164, 83-165, 83-166, 83-167, 83-168, 83-169, 83-170, 83-171, 83-172, 83-173, 83-174, 83-175, 83-176, 83-177, 83-178, 83-179, 83-180, 83-181, 83-182, 83-183, 83-184, 83-185, 83-186, 83-187, 83-188, 83-189, 83-190, 83-191, 83-192, 83-193, 83-194, 83-195, 83-196, 83-197, 83-198, 83-199, and 83-200.

Peptides and Proteins that Begins with Amino Acid 84 of HPV16 L2

84-93, 84-94, 84-95, 84-96, 84-97, 84-98, 84-99, 84-100, 84-101, 84-102, 84-103, 84-104, 84-105, 84-106, 84-107, 84-108, 84-109, 84-110, 84-111, 84-112, 84-113, 84-114, 84-115, 84-116, 84-117, 84-118, 84-119, 84-120, 84-121, 84-122, 84-123, 84-124, 84-125, 84-126, 84-127, 84-128, 84-129, 84-130, 84-131, 84-132, 84-133, 84-134, 84-135, 84-136, 84-137, 84-138, 84-139, 84-140, 84-141, 84-142, 84-143, 84-144, 84-145, 84-146, 84-147, 84-148, 84-149, 84-150, 84-151, 84-152, 84-153, 84-154, 84-155, 84-156, 84-157, 84-158, 84-159, 84-160, 84-161, 84-162, 84-163, 84-164, 84-165, 84-166, 84-167, 84-168, 84-169, 84-170, 84-171, 84-172, 84-173, 84-174, 84-175, 84-176, 84-177, 84-178, 84-179, 84-180, 84-181, 84-182, 84-183, 84-184, 84-185, 84-186, 84-187, 84-188, 84-189, 84-190, 84-191, 84-192, 84-193, 84-194, 84-195, 84-196, 84-197, 84-198, 84-199, and 84-200.

Peptides and Proteins that Begins with Amino Acid 85 of HPV16 L2

85-94, 85-95, 85-96, 85-97, 85-98, 85-99, 85-100, 85-101, 85-102, 85-103, 85-104, 85-105, 85-106, 85-107, 85-108, 85-109, 85-110, 85-111, 85-112, 85-113, 85-114, 85-115, 85-116, 85-117, 85-118, 85-119, 85-120, 85-121, 85-122, 85-123, 85-124, 85-125, 85-126, 85-127, 85-128, 85-129, 85-130, 85-131, 85-132, 85-133, 85-134, 85-135, 85-136, 85-137, 85-138, 85-139, 85-140, 85-141, 85-142, 85-143, 85-144, 85-145, 85-146, 85-147, 85-148, 85-149, 85-150, 85-151, 85-152, 85-153, 85-154, 85-155, 85-156, 85-157, 85-158, 85-159, 85-160, 85-161, 85-162, 85-163, 85-164, 85-165, 85-166, 85-167, 85-168, 85-169, 85-170, 85-171, 85-172, 85-173, 85-174, 85-175, 85-176, 85-177, 85-178, 85-179, 85-180, 85-181, 85-182, 85-183, 85-184, 85-185, 85-186, 85-187, 85-188, 85-189, 85-190, 85-191, 85-192, 85-193, 85-194, 85-195, 85-196, 85-197, 85-198, 85-199, and 85-200.

Peptides and Proteins that Begins with Amino Acid 86 of HPV16 L2

86-95, 86-96, 86-97, 86-98, 86-99, 86-100, 86-101, 86-102, 86-103, 86-104, 86-105, 86-106, 86-107, 86-108, 86-109, 86-110, 86-111, 86-112, 86-113, 86-114, 86-115, 86-116, 86-117, 86-118, 86-119, 86-120, 86-121, 86-122, 86-123, 86-124, 86-125, 86-126, 86-127, 86-128, 86-129, 86-130, 86-131, 86-132, 86-133, 86-134, 86-135, 86-136, 86-137, 86-138, 86-139, 86-140, 86-141, 86-142, 86-143, 86-144, 86-145, 86-146, 86-147, 86-148, 86-149, 86-150, 86-151, 86-152, 86-153, 86-154, 86-155, 86-156, 86-157, 86-158, 86-159, 86-160, 86-161, 86-162, 86-163, 86-164, 86-165, 86-166, 86-167, 86-168, 86-169, 86-170, 86-171, 86-172, 86-173, 86-174, 86-175, 86-176, 86-177, 86-178, 86-179, 86-180, 86-181, 86-182, 86-183, 86-184, 86-185, 86-186, 86-187, 86-188, 86-189, 86-190, 86-191, 86-192, 86-193, 86-194, 86-195, 86-196, 86-197, 86-198, 86-199, and 86-200.

Peptides and Proteins that Begins with Amino Acid 87 of HPV16 L2

87-96, 87-97, 87-98, 87-99, 87-100, 87-101, 87-102, 87-103, 87-104, 87-105, 87-106, 87-107, 87-108, 87-109, 87-110, 87-111, 87-112, 87-113, 87-114, 87-115, 87-116, 87-117, 87-118, 87-119, 87-120, 87-121, 87-122, 87-123, 87-124, 87-125, 87-126, 87-127, 87-128, 87-129, 87-130, 87-131, 87-132, 87-133, 87-134, 87-135, 87-136, 87-137, 87-138, 87-139, 87-140, 87-141, 87-142, 87-143, 87-144, 87-145, 87-146, 87-147, 87-148, 87-149, 87-150, 87-151, 87-152, 87-153, 87-154, 87-155, 87-156, 87-157, 87-158, 87-159, 87-160, 87-161, 87-162, 87-163, 87-164, 87-165, 87-166, 87-167, 87-168, 87-169, 87-170, 87-171, 87-172, 87-173, 87-174, 87-175, 87-176, 87-177, 87-178, 87-179, 87-180, 87-181, 87-182, 87-183, 87-184, 87-185, 87-186, 87-187, 87-188, 87-189, 87-190, 87-191, 87-192, 87-193, 87-194, 87-195, 87-196, 87-197, 87-198, 87-199, and 87-200.

Peptides and Proteins that Begins with Amino Acid 88 of HPV16 L2

88-97, 88-98, 88-99, 88-100, 88-101, 88-102, 88-103, 88-104, 88-105, 88-106, 88-107, 88-108, 88-109, 88-110, 88-111, 88-112, 88-113, 88-114, 88-115, 88-116, 88-117, 88-118, 88-119, 88-120, 88-121, 88-122, 88-123, 88-124, 88-125, 88-126, 88-127, 88-128, 88-129, 88-130, 88-131, 88-132, 88-133, 88-134, 88-135, 88-136, 88-137, 88-138, 88-139, 88-140, 88-141, 88-142, 88-143, 88-144, 88-145, 88-146, 88-147, 88-148, 88-149, 88-150, 88-151, 88-152, 88-153, 88-154, 88-155, 88-156, 88-157, 88-158, 88-159, 88-160, 88-161, 88-162, 88-163, 88-164, 88-165, 88-166, 88-167, 88-168, 88-169, 88-170, 88-171, 88-172, 88-173, 88-174, 88-175, 88-176, 88-177, 88-178, 88-179, 88-180, 88-181, 88-182, 88-183, 88-184, 88-185, 88-186, 88-187, 88-188, 88-189, 88-190, 88-191, 88-192, 88-193, 88-194, 88-195, 88-196, 88-197, 88-198, 88-199, and 88-200.

Peptides and Proteins that Begins with Amino Acid 89 of HPV16 L2

89-98, 89-99, 89-100, 89-101, 89-102, 89-103, 89-104, 89-105, 89-106, 89-107, 89-108, 89-109, 89-110, 89-111, 89-112, 89-113, 89-114, 89-115, 89-116, 89-117, 89-118, 89-119, 89-120, 89-121, 89-122, 89-123, 89-124, 89-125, 89-126, 89-127, 89-128, 89-129, 89-130, 89-131, 89-132, 89-133, 89-134, 89-135, 89-136, 89-137, 89-138, 89-139, 89-140, 89-141, 89-142, 89-143, 89-144, 89-145, 89-146, 89-147, 89-148, 89-149, 89-150, 89-151, 89-152, 89-153, 89-154, 89-155, 89-156, 89-157, 89-158, 89-159, 89-160, 89-161, 89-162, 89-163, 89-164, 89-165, 89-166, 89-167, 89-168, 89-169, 89-170, 89-171, 89-172, 89-173, 89-174, 89-175, 89-176, 89-177, 89-178, 89-179, 89-180, 89-181, 89-182, 89-183, 89-184, 89-185, 89-186, 89-187, 89-188, 89-189, 89-190, 89-191, 89-192, 89-193, 89-194, 89-195, 89-196, 89-197, 89-198, 89-199, and 89-200.

Peptides and Proteins that Begins with Amino Acid 90 of HPV16 L2

90-99, 90-100, 90-101, 90-102, 90-103, 90-104, 90-105, 90-106, 90-107, 90-108, 90-109, 90-110, 90-111, 90-112, 90-113, 90-114, 90-115, 90-116, 90-117, 90-118, 90-119, 90-120, 90-121, 90-122, 90-123, 90-124, 90-125, 90-126, 90-127, 90-128, 90-129, 90-130, 90-131, 90-132, 90-133, 90-134, 90-135, 90-136, 90-137, 90-138, 90-139, 90-140, 90-141, 90-142, 90-143, 90-144, 90-145, 90-146, 90-147, 90-148, 90-149, 90-150, 90-151, 90-152, 90-153, 90-154, 90-155, 90-156, 90-157, 90-158, 90-159, 90-160, 90-161, 90-162, 90-163, 90-164, 90-165, 90-166, 90-167, 90-168, 90-169, 90-170, 90-171, 90-172, 90-173, 90-174, 90-175, 90-176, 90-177, 90-178, 90-179, 90-180, 90-181, 90-182, 90-183, 90-184, 90-185, 90-186, 90-187, 90-188, 90-189, 90-190, 90-191, 90-192, 90-193, 90-194, 90-195, 90-196, 90-197, 90-198, 90-199, and 90-200.

Peptides and Proteins that Begins with Amino Acid 91 of HPV16 L2

91-100, 91-101, 91-102, 91-103, 91-104, 91-105, 91-106, 91-107, 91-108, 91-109, 91-110, 91-111, 91-112, 91-113, 91-114, 91-115, 91-116, 91-117, 91-118, 91-119, 91-120, 91-121, 91-122, 91-123, 91-124, 91-125, 91-126, 91-127, 91-128, 91-129, 91-130, 91-131, 91-132, 91-133, 91-134, 91-135, 91-136, 91-137, 91-138, 91-139, 91-140, 91-141, 91-142, 91-143, 91-144, 91-145, 91-146, 91-147, 91-148, 91-149, 91-150, 91-151, 91-152, 91-153, 91-154, 91-155, 91-156, 91-157, 91-158, 91-159, 91-160, 91-161, 91-162, 91-163, 91-164, 91-165, 91-166, 91-167, 91-168, 91-169, 91-170, 91-171, 91-172, 91-173, 91-174, 91-175, 91-176, 91-177, 91-178, 91-179, 91-180, 91-181, 91-182, 91-183, 91-184, 91-185, 91-186, 91-187, 91-188, 91-189, 91-190, 91-191, 91-192, 91-193, 91-194, 91-195, 91-196, 91-197, 91-198, 91-199, and 91-200.

Peptides and Proteins that Begins with Amino Acid 92 of HPV16 L2

92-101, 92-102, 92-103, 92-104, 92-105, 92-106, 92-107, 92-108, 92-109, 92-110, 92-111, 92-112, 92-113, 92-114, 92-115, 92-116, 92-117, 92-118, 92-119, 92-120, 92-121, 92-122, 92-123, 92-124, 92-125; 92-126, 92-127, 92-128, 92-129, 92-130, 92-131, 92-132, 92-133, 92-134, 92-135, 92-136, 92-137, 92-138, 92-139, 92-140, 92-141, 92-142, 92-143, 92-144, 92-145, 92-146, 92-147, 92-148, 92-149, 92-150, 92-151, 92-152, 92-153, 92-154, 92-155, 92-156, 92-157, 92-158, 92-159, 92-160, 92-161, 92-162, 92-163, 92-164, 92-165, 92-166, 92-167, 92-168, 92-169, 92-170, 92-171, 92-172, 92-173, 92-174, 92-175, 92-176, 92-177, 92-178, 92-179, 92-180, 92-181, 92-182, 92-183, 92-184, 92-185, 92-186, 92-187, 92-188, 92-189, 92-190, 92-191, 92-192, 92-193, 92-194, 92-195, 92-196, 92-197, 92-198, 92-199, and 92-200.

Peptides and Proteins that Begins with Amino Acid 93 of HPV16 L2

93-102, 93-103, 93-104, 93-105, 93-106, 93-107, 93-108, 93-109, 93-110, 93-111, 93-112, 93-113, 93-114, 93-115, 93-116, 93-117, 93-118, 93-119, 93-120, 93-121, 93-122, 93-123, 93-124, 93-125, 93-126, 93-127, 93-128, 93-129, 93-130, 93-131, 93-132, 93-133, 93-134, 93-135, 93-136, 93-137, 93-138, 93-139, 93-140, 93-141, 93-142, 93-143, 93-144, 93-145, 93-146, 93-147, 93-148, 93-149, 93-150, 93-151, 93-152, 93-153, 93-154, 93-155, 93-156, 93-157, 93-158, 93-159, 93-160, 93-161, 93-162, 93-163, 93-164, 93-165, 93-166, 93-167, 93-168, 93-169, 93-170, 93-171, 93-172, 93-173, 93-174, 93-175, 93-176, 93-177, 93-178, 93-179, 93-180, 93-181, 93-182, 93-183, 93-184, 93-185, 93-186, 93-187, 93-188, 93-189, 93-190, 93-191, 93-192, 93-193, 93-194, 93-195, 93-196, 93-197, 93-198, 93-199, and 93-200.

Peptides and Proteins that Begins with Amino Acid 94 of HPV16 L2

94-103, 94-104, 94-105, 94-106, 94-107, 94-108, 94-109, 94-110, 94-111, 94-112, 94-113, 94-114, 94-115, 94-116, 94-117, 94-118, 94-119, 94-120, 94-121, 94-122, 94-123, 94-124, 94-125, 94-126, 94-127, 94-128, 94-129, 94-130, 94-131, 94-132, 94-133, 94-134, 94-135, 94-136, 94-137, 94-138, 94-139, 94-140, 94-141, 94-142, 94-143, 94-144, 94-145, 94-146, 94-147, 94-148, 94-149, 94-150, 94-151, 94-152, 94-153, 94-154, 94-155, 94-156, 94-157, 94-158, 94-159, 94-160, 94-161, 94-162, 94-163, 94-164, 94-165, 94-166, 94-167, 94-168, 94-169, 94-170, 94-171, 94-172, 94-173, 94-174, 94-175, 94-176, 94-177, 94-178, 94-179, 94-180, 94-181, 94-182, 94-183, 94-184, 94-185, 94-186, 94-187, 94-188, 94-189, 94-190, 94-191, 94-192, 94-193, 94-194, 94-195, 94-196, 94-197, 94-198, 94-199, and 94-200.

Peptides and Proteins that Begins with Amino Acid 95 of HPV16 L2

95-104, 95-105, 95-106, 95-107, 95-108, 95-109, 95-110, 95-111, 95-112, 95-113, 95-114, 95-115, 95-116, 95-117, 95-118, 95-119, 95-120, 95-121, 95-122, 95-123, 95-124, 95-125, 95-126, 95-127, 95-128, 95-129, 95-130, 95-131, 95-132, 95-133, 95-134, 95-135, 95-136, 95-137, 95-138, 95-139, 95-140, 95-141, 95-142, 95-143, 95-144, 95-145, 95-146, 95-147, 95-148, 95-149, 95-150, 95-151, 95-152, 95-153, 95-154, 95-155, 95-156, 95-157, 95-158, 95-159, 95-160, 95-161, 95-162, 95-163, 95-164, 95-165, 95-166, 95-167, 95-168, 95-169, 95-170, 95-171, 95-172, 95-173, 95-174, 95-175, 95-176, 95-177, 95-178, 95-179, 95-180, 95-181, 95-182, 95-183, 95-184, 95-185, 95-186, 95-187, 95-188, 95-189, 95-190, 95-191, 95-192, 95-193, 95-194, 95-195, 95-196, 95-197, 95-198, 95-199, and 95-200.

Peptides and Proteins that Begins with Amino Acid 96 of HPV16 L2

96-105, 96-106, 96-107, 96-108, 96-109, 96-110, 96-111, 96-112, 96-113, 96-114, 96-115, 96-116, 96-117, 96-118, 96-119, 96-120, 96-121, 96-122, 96-123, 96-124, 96-125, 96-126, 96-127, 96-128, 96-129, 96-130, 96-131, 96-132, 96-133, 96-134, 96-135, 96-136, 96-137, 96-138, 96-139, 96-140, 96-141, 96-142, 96-143, 96-144, 96-145, 96-146, 96-147, 96-148, 96-149, 96-150, 96-151, 96-152, 96-153, 96-154, 96-155, 96-156, 96-157, 96-158, 96-159, 96-160, 96-161, 96-162, 96-163, 96-164, 96-165, 96-166, 96-167, 96-168, 96-169, 96-170, 96-171, 96-172, 96-173, 96-174, 96-175, 96-176, 96-177, 96-178, 96-179, 96-180, 96-181, 96-182, 96-183, 96-184, 96-185, 96-186, 96-187, 96-188, 96-189, 96-190, 96-191, 96-192, 96-193, 96-194, 96-195, 96-196, 96-197, 96-198, 96-199, and 96-200.

Peptides and Proteins that Begins with Amino Acid 97 of HPV16 L2

97-106, 97-107, 97-108, 97-109, 97-110, 97-111, 97-112, 97-113, 97-114, 97-115, 97-116, 97-117, 97-118, 97-119, 97-120, 97-121, 97-122, 97-123, 97-124, 97-125, 97-126, 97-127, 97-128, 97-129, 97-130, 97-131, 97-132, 97-133, 97-134, 97-135, 97-136, 97-137, 97-138, 97-139, 97-140, 97-141, 97-142, 97-143, 97-144, 97-145, 97-146, 97-147, 97-148, 97-149, 97-150, 97-151, 97-152, 97-153, 97-154, 97-155, 97-156, 97-157, 97-158, 97-159, 97-160, 97-161, 97-162, 97-163, 97-164, 97-165, 97-166, 97-167, 97-168, 97-169, 97-170, 97-171, 97-172, 97-173, 97-174, 97-175, 97-176, 97-177, 97-178, 97-179, 97-180, 97-181, 97-182, 97-183, 97-184, 97-185, 97-186, 97-187, 97-188, 97-189, 97-190, 97-191, 97-192, 97-193, 97-194, 97-195, 97-196, 97-197, 97-198, 97-199, and 97-200.

Peptides and Proteins that Begins with Amino Acid 98 of HPV16 L2

98-107, 98-108, 98-109, 98-110, 98-111, 98-112, 98-113, 98-114, 98-115, 98-116, 98-117, 98-118, 98-119, 98-120, 98-121, 98-122, 98-123, 98-124, 98-125, 98-126, 98-127, 98-128, 98-129, 98-130, 98-131, 98-132, 98-133, 98-134, 98-135, 98-136, 98-137, 98-138, 98-139, 98-140, 98-141, 98-142, 98-143, 98-144, 98-145, 98-146, 98-147, 98-148, 98-149, 98-150, 98-151, 98-152, 98-153, 98-154, 98-155, 98-156, 98-157, 98-158, 98-159, 98-160, 98-161, 98-162, 98-163, 98-164, 98-165, 98-166, 98-167, 98-168, 98-169, 98-170, 98-171, 98-172, 98-173, 98-174, 98-175, 98-176, 98-177, 98-178, 98-179, 98-180, 98-181, 98-182, 98-183, 98-184, 98-185, 98-186, 98-187, 98-188, 98-189, 98-190, 98-191, 98-192, 98-193, 98-194, 98-195, 98-196, 98-197, 98-198, 98-199, and 98-200.

Peptides and Proteins that Begins with Amino Acid 99 of HPV16 L2

99-108, 99-109, 99-110, 99-111, 99-112, 99-113, 99-114, 99-115, 99-116, 99-117, 99-118, 99-119, 99-120, 99-121, 99-122, 99-123, 99-124, 99-125, 99-126, 99-127, 99-128, 99-129, 99-130, 99-131, 99-132, 99-133, 99-134, 99-135, 99-136, 99-137, 99-138, 99-139, 99-140, 99-141, 99-142, 99-143, 99-144, 99-145, 99-146, 99-147, 99-148, 99-149, 99-150, 99-151, 99-152, 99-153, 99-154, 99-155, 99-156, 99-157, 99-158, 99-159, 99-160, 99-161, 99-162, 99-163, 99-164, 99-165, 99-166, 99-167, 99-168, 99-169, 99-170, 99-171, 99-172, 99-173, 99-174, 99-175, 99-176, 99-177, 99-178, 99-179, 99-180, 99-181, 99-182, 99-183, 99-184, 99-185, 99-186, 99-187, 99-188, 99-189, 99-190, 99-191, 99-192, 99-193, 99-194, 99-195, 99-196, 99-197, 99-198, 99-199, and 99-200.

Peptides and Proteins that Begins with Amino Acid 100 of HPV16 L2

100-109, 100-110, 100-111, 100-112, 100-113, 100-114, 100-115, 100-116, 100-117, 100-118, 100-119, 100-120, 100-121, 100-122, 100-123, 100-124, 100-125, 100-126, 100-127, 100-128, 100-129, 100-130, 100-131, 100-132, 100-133, 100-134, 100-135, 100-136, 100-137, 100-138, 100-139, 100-140, 100-141, 100-142, 100-143, 100-144, 100-145, 100-146, 100-147, 100-148, 100-149, 100-150, 100-151, 100-152, 100-153, 100-154, 100-155, 100-156, 100-157, 100-158, 100-159, 100-160, 100-161, 100-162, 100-163, 100-164, 100-165, 100-166, 100-167, 100-168, 100-169, 100-170, 100-171, 100-172, 100-173, 100-174, 100-175, 100-176, 100-177, 100-178, 100-179, 100-180, 100-181, 100-182, 100-183, 100-184, 100-185, 100-186, 100-187, 100-188, 100-189, 100-190, 100-191, 100-192, 100-193, 100-194, 100-195, 100-196, 100-197, 100-198, 100-199, and 100-200.

Peptides and Proteins that Begins with Amino Acid 101 of HPV16 L2

101-110, 101-111, 101-112, 101-113, 101-114, 101-115, 101-116, 101-117, 101-118, 101-119, 101-120, 101-121, 101-122, 101-123, 101-124, 101-125, 101-126, 101-127, 101-128, 101-129, 101-130, 101-131, 101-132, 101-133, 101-134, 101-135, 101-136, 101-137, 101-138, 101-139, 101-140, 101-141, 101-142, 101-143, 101-144, 101-145, 101-146, 101-147, 101-148, 101-149, 101-150, 101-151, 101-152, 101-153, 101-154, 101-155, 101-156, 101-157, 101-158, 101-159, 101-160, 101-161, 101-162, 101-163, 101-164, 101-165, 101-166, 101-167, 101-168, 101-169, 101-170, 101-171, 101-172, 101-173, 101-174, 101-175, 101-176, 101-177, 101-178, 101-179, 101-180, 101-181, 101-182, 101-183, 101-184, 101-185, 101-186, 101-187, 101-188, 101-189, 101-190, 101-191, 101-192, 101-193, 101-194, 101-195, 101-196, 101-197, 101-198, 101-199, and 101-200.

Peptides and Proteins that Begins with Amino Acid 102 of HPV16 L2

102-111, 102-112, 102-113, 102-114, 102-115, 102-116, 102-117, 102-118, 102-119, 102-120, 102-121, 102-122, 102-123, 102-124, 102-125, 102-126, 102-127, 102-128, 102-129, 102-130, 102-131, 102-132, 102-133, 102-134, 102-135, 102-136, 102-137, 102-138, 102-139, 102-140, 102-141, 102-142, 102-143, 102-144, 102-145, 102-146, 102-147, 102-148, 102-149, 102-150, 102-151, 102-152, 102-153, 102-154, 102-155, 102-156, 102-157, 102-158, 102-159, 102-160, 102-161, 102-162, 102-163, 102-164, 102-165, 102-166, 102-167, 102-168, 102-169, 102-170, 102-171, 102-172, 102-173, 102-174, 102-175, 102-176, 102-177, 102-178, 102-179, 102-180, 102-181, 102-182, 102-183, 102-184, 102-185, 102-186, 102-187, 102-188, 102-189, 102-190, 102-191, 102-192, 102-193, 102-194, 102-195, 102-196, 102-197, 102-198, 102-199, and 102-200.

Peptides and Proteins that Begins with Amino Acid 103 of HPV16 L2

103-112, 103-113, 103-114, 103-115, 103-116, 103-117, 103-118, 103-119, 103-120, 103-121, 103-122, 103-123, 103-124, 103-125, 103-126, 103-127, 103-128, 103-129, 103-130, 103-131, 103-132, 103-133, 103-134, 103-135, 103-136, 103-137, 103-138, 103-139, 103-140, 103-141, 103-142, 103-143, 103-144, 103-145, 103-146, 103-147, 103-148, 103-149, 103-150, 103-151, 103-152, 103-153, 103-154, 103-155, 103-156, 103-157, 103-158, 103-159, 103-160, 103-161, 103-162, 103-163, 103-164, 103-165, 103-166, 103-167, 103-168, 103-169, 103-170, 103-171, 103-172, 103-173, 103-174, 103-175, 103-176, 103-177, 103-178, 103-179, 103-180, 103-181, 103-182, 103-183, 103-184, 103-185, 103-186, 103-187, 103-188, 103-189, 103-190, 103-191, 103-192, 103-193, 103-194, 103-195, 103-196, 103-197, 103-198, 103-199, and 103-200.

Peptides and Proteins that Begins with Amino Acid 104 of HPV16 L2

104-113, 104-114, 104-115, 104-116, 104-117, 104-118, 104-119, 104-120, 104-121, 104-122, 104-123, 104-124, 104-125, 104-126, 104-127, 104-128, 104-129, 104-130, 104-131, 104-132, 104-133, 104-134, 104-135, 104-136, 104-137, 104-138, 104-139, 104-140, 104-141, 104-142, 104-143, 104-144, 104-145, 104-146, 104-147, 104-148, 104-149, 104-150, 104-151, 104-152, 104-153, 104-154, 104-155, 104-156, 104-157, 104-158, 104-159, 104-160, 104-161, 104-162, 104-163, 104-164, 104-165, 104-166, 104-167, 104-168, 104-169, 104-170, 104-171, 104-172, 104-173, 104-174, 104-175, 104-176, 104-177, 104-178, 104-179, 104-180, 104-181, 104-182, 104-183, 104-184, 104-185, 104-186, 104-187, 104-188, 104-189, 104-190, 104-191, 104-192, 104-193, 104-194, 104-195, 104-196, 104-197, 104-198, 104-199, and 104-200.

Peptides and Proteins that Begins with Amino Acid 105 of HPV16 L2

105-114, 105-115, 105-116, 105-117, 105-118, 105-119, 105-120, 105-121, 105-122, 105-123, 105-124, 105-125, 105-126, 105-127, 105-128, 105-129, 105-130, 105-131, 105-132, 105-133, 105-134, 105-135, 105-136, 105-137, 105-138, 105-139, 105-140, 105-141, 105-142, 105-143, 105-144, 105-145, 105-146, 105-147, 105-148, 105-149, 105-150, 105-151, 105-152, 105-153, 105-154, 105-155, 105-156, 105-157, 105-158, 105-159, 105-160, 105-161, 105-162, 105-163, 105-164, 105-165, 105-166, 105-167, 105-168, 105-169, 105-170, 105-171, 105-172, 105-173, 105-174, 105-175, 105-176, 105-177, 105-178, 105-179, 105-180, 105-181, 105-182, 105-183, 105-184, 105-185, 105-186, 105-187, 105-188, 105-189, 105-190, 105-191, 105-192, 105-193, 105-194, 105-195, 105-196, 105-197, 105-198, 105-199, and 105-200.

Peptides and Proteins that Begins with Amino Acid 106 of HPV16 L2

106-115, 106-116, 106-117, 106-118, 106-119, 106-120, 106-121, 106-122, 106-123, 106-124, 106-125, 106-126, 106-127, 106-128, 106-129, 106-130, 106-131, 106-132, 106-133, 106-134, 106-135, 106-136, 106-137, 106-138, 106-139, 106-140, 106-141, 106-142, 106-143, 106-144, 106-145, 106-146, 106-147, 106-148, 106-149, 106-150, 106-151, 106-152, 106-153, 106-154, 106-155, 106-156, 106-157, 106-158, 106-159, 106-160, 106-161, 106-162, 106-163, 106-164, 106-165, 106-166, 106-167, 106-168, 106-169, 106-170, 106-171, 106-172, 106-173, 106-174, 106-175, 106-176, 106-177, 106-178, 106-179, 106-180, 106-181, 106-182, 106-183, 106-184, 106-185, 106-186, 106-187, 106-188, 106-189, 106-190, 106-191, 106-192, 106-193, 106-194, 106-195, 106-196, 106-197, 106-198, 106-199, and 106-200.

Peptides and Proteins that Begins with Amino Acid 107 of HPV16 L2

107-116, 107-117, 107-118, 107-119, 107-120, 107-121, 107-122, 107-123, 107-124, 107-125, 107-126, 107-127, 107-128, 107-129, 107-130, 107-131, 107-132, 107-133, 107-134, 107-135, 107-136, 107-137, 107-138, 107-139, 107-140, 107-141, 107-142, 107-143, 107-144, 107-145, 107-146, 107-147, 107-148, 107-149, 107-150, 107-151, 107-152, 107-153, 107-154, 107-155, 107-156, 107-157, 107-158, 107-159, 107-160, 107-161, 107-162, 107-163, 107-164, 107-165, 107-166, 107-167, 107-168, 107-169, 107-170, 107-171, 107-172, 107-173, 107-174, 107-175, 107-176, 107-177, 107-178, 107-179, 107-180, 107-181, 107-182, 107-183, 107-184, 107-185, 107-186, 107-187, 107-188, 107-189, 107-190, 107-191, 107-192, 107-193, 107-194, 107-195, 107-196, 107-197, 107-198, 107-199, and 107-200.

Peptides and Proteins that Begins with Amino Acid 108 of HPV16 L2

108-117, 108-118, 108-119, 108-120, 108-121, 108-122, 108-123, 108-124, 108-125, 108-126, 108-127, 108-128, 108-129, 108-130, 108-131, 108-132, 108-133, 108-134, 108-135, 108-136, 108-137, 108-138, 108-139, 108-140, 108-141, 108-142, 108-143, 108-144, 108-145, 108-146, 108-147, 108-148, 108-149, 108-150, 108-151, 108-152, 108-153, 108-154, 108-155, 108-156, 108-157, 108-158, 108-159, 108-160, 108-161, 108-162, 108-163, 108-164, 108-165, 108-166, 108-167, 108-168, 108-169, 108-170, 108-171, 108-172, 108-173, 108-174, 108-175, 108-176, 108-177, 108-178, 108-179, 108-180, 108-181, 108-182, 108-183, 108-184, 108-185, 108-186, 108-187, 108-188, 108-189, 108-190, 108-191, 108-192, 108-193, 108-194, 108-195, 108-196, 108-197, 108-198, 108-199, and 108-200.

Peptides and Proteins that Begins with Amino Acid 109 of HPV16 L2

109-118, 109-119, 109-120, 109-121, 109-122, 109-123, 109-124, 109-125, 109-126, 109-127, 109-128, 109-129, 109-130, 109-131, 109-132, 109-133, 109-134, 109-135, 109-136, 109-137, 109-138, 109-139, 109-140, 109-141, 109-142, 109-143, 109-144, 109-145, 109-146, 109-147, 109-148, 109-149, 109-150, 109-151, 109-152, 109-153, 109-154, 109-155, 109-156, 109-157, 109-158, 109-159, 109-160, 109-161, 109-162, 109-163, 109-164, 109-165, 109-166, 109-167, 109-168, 109-169, 109-170, 109-171, 109-172, 109-173, 109-174, 109-175, 109-176, 109-177, 109-178, 109-179, 109-180, 109-181, 109-182, 109-183, 109-184, 109-185, 109-186, 109-187, 109-188, 109-189, 109-190, 109-191, 109-192, 109-193, 109-194, 109-195, 109-196, 109-197, 109-198, 109-199, and 109-200.

Peptides and Proteins that Begins with Amino Acid 110 of HPV16 L2

110-119, 110-120, 110-121, 110-122, 110-123, 110-124, 110-125, 110-126, 110-127, 110-128, 110-129, 110-130, 110-131, 110-132, 110-133, 110-134, 110-135, 110-136, 110-137, 110-138, 110-139, 110-140, 110-141, 110-142, 110-143, 110-144, 110-145, 110-146, 110-147, 110-148, 110-149, 110-150, 110-151, 110-152, 110-153, 110-154, 110-155, 110-156, 110-157, 110-158, 110-159, 110-160, 110-161, 110-162, 110-163, 110-164, 110-165, 110-166, 110-167, 110-168, 110-169, 110-170, 110-171, 110-172, 110-173, 110-174, 110-175, 110-176, 110-177, 110-178, 110-179, 110-180, 110-181, 110-182, 110-183, 110-184, 110-185, 110-186, 110-187, 110-188, 110-189, 110-190, 110-191, 110-192, 110-193, 110-194, 110-195, 110-196, 110-197, 110-198, 110-199, and 110-200.

Peptides and Proteins that Begins with Amino Acid 111 of HPV16 L2

111-120, 111-121, 111-122, 111-123, 111-124, 111-125, 111-126, 111-127, 111-128, 111-129, 111-130, 111-131, 111-132, 111-133, 111-134, 111-135, 111-136, 111-137, 111-138, 111-139, 111-140, 111-141, 111-142, 111-143, 111-144, 111-145, 111-146, 111-147, 111-148, 111-149, 111-150, 111-151, 111-152, 111-153, 111-154, 111-155, 111-156, 111-157, 111-158, 111-159, 111-160, 111-161, 111-162, 111-163, 111-164, 111-165, 111-166, 111-167, 111-168, 111-169, 111-170, 111-171, 111-172, 111-173, 111-174, 111-175, 111-176, 111-177, 111-178, 111-179, 111-180, 111-181, 111-182, 111-183, 111-184, 111-185, 111-186, 111-187, 111-188, 111-189, 111-190, 111-191, 111-192, 111-193, 111-194, 111-195, 111-196, 111-197, 111-198, 111-199, and 111-200.

Peptides and Proteins that Begins with Amino Acid 112 of HPV16 L2

112-121, 112-122, 112-123, 112-124, 112-125, 112-126, 112-127, 112-128, 112-129, 112-130, 112-131, 112-132, 112-133, 112-134, 112-135, 112-136, 112-137, 112-138, 112-139, 112-140, 112-141, 112-142, 112-143, 112-144, 112-145, 112-146, 112-147, 112-148, 112-149, 112-150, 112-151, 112-152, 112-153, 112-154, 112-155, 112-156, 112-157, 112-158, 112-159, 112-160, 112-161, 112-162, 112-163, 112-164, 112-165, 112-166, 112-167, 112-168, 112-169, 112-170, 112-171, 112-172, 112-173, 112-174, 112-175, 112-176, 112-177, 112-178, 112-179, 112-180, 112-181, 112-182, 112-183, 112-184, 112-185, 112-186, 112-187, 112-188, 112-189, 112-190, 112-191, 112-192, 112-193, 112-194, 112-195, 112-196, 112-197, 112-198, 112-199, and 112-200.

Peptides and Proteins that Begins with Amino Acid 113 of HPV16 L2

113-122, 113-123, 113-124, 113-125, 113-126, 113-127, 113-128, 113-129, 113-130, 113-131, 113-132, 113-133, 113-134, 113-135, 113-136, 113-137, 113-138, 113-139, 113-140, 113-141, 113-142, 113-143, 113-144, 113-145, 113-146, 113-147, 113-148, 113-149, 113-150, 113-151, 113-152, 113-153, 113-154, 113-155, 113-156, 113-157, 113-158, 113-159, 113-160, 113-161, 113-162, 113-163, 113-164, 113-165, 113-166, 113-167, 113-168, 113-169, 113-170, 113-171, 113-172, 113-173, 113-174, 113-175, 113-176, 113-177, 113-178, 113-179, 113-180, 113-181, 113-182, 113-183, 113-184, 113-185, 113-186, 113-187, 113-188, 113-189, 113-190, 113-191, 113-192, 113-193, 113-194, 113-195, 113-196, 113-197, 113-198, 113-199, and 113-200.

Peptides and Proteins that Begins with Amino Acid 114 of HPV16 L2

114-123, 114-124, 114-125, 114-126, 114-127, 114-128, 114-129, 114-130, 114-131, 114-132, 114-133, 114-134, 114-135, 114-136, 114-137, 114-138, 114-139, 114-140, 114-141, 114-142, 114-143, 114-144, 114-145, 114-146, 114-147, 114-148, 114-149, 114-150, 114-151, 114-152, 114-153, 114-154, 114-155, 114-156, 114-157, 114-158, 114-159, 114-160, 114-161, 114-162, 114-163, 114-164, 114-165, 114-166, 114-167, 114-168, 114-169, 114-170, 114-171, 114-172, 114-173, 114-174, 114-175, 114-176, 114-177, 114-178, 114-179, 114-180, 114-181, 114-182, 114-183, 114-184, 114-185, 114-186, 114-187, 114-188, 114-189, 114-190, 114-191, 114-192, 114-193, 114-194, 114-195, 114-196, 114-197, 114-198, 114-199, and 114-200.

Peptides and Proteins that Begins with Amino Acid 115 of HPV16 L2

115-124, 115-125, 115-126, 115-127, 115-128, 115-129, 115-130, 115-131, 115-132, 115-133, 115-134, 115-135, 115-136, 115-137, 115-138, 115-139, 115-140, 115-141, 115-142, 115-143, 115-144, 115-145, 115-146, 115-147, 115-148, 115-149, 115-150, 115-151, 115-152, 115-153, 115-154, 115-155, 115-156, 115-157, 115-158, 115-159, 115-160, 115-161, 115-162, 115-163, 115-164, 115-165, 115-166, 115-167, 115-168, 115-169, 115-170, 115-171, 115-172, 115-173, 115-174, 115-175, 115-176, 115-177, 115-178, 115-179, 115-180, 115-181, 115-182, 115-183, 115-184, 115-185, 115-186, 115-187, 115-188, 115-189, 115-190, 115-191, 115-192, 115-193, 115-194, 115-195, 115-196, 115-197, 115-198, 115-199, and 115-200.

Peptides and Proteins that Begins with Amino Acid 116 of HPV16 L2

116-125, 116-126, 116-127, 116-128, 116-129, 116-130, 116-131, 116-132, 116-133, 116-134, 116-135, 116-136, 116-137, 116-138, 116-139, 116-140, 116-141, 116-142, 116-143, 116-144, 116-145, 116-146, 116-147, 116-148, 116-149, 116-150, 116-151, 116-152, 116-153, 116-154, 116-155, 116-156, 116-157, 116-158, 116-159, 116-160, 116-161, 116-162, 116-163, 116-164, 116-165, 116-166, 116-167, 116-168, 116-169, 116-170, 116-171, 116-172, 116-173, 116-174, 116-175, 116-176, 116-177, 116-178, 116-179, 116-180, 116-181, 116-182, 116-183, 116-184, 116-185, 116-186, 116-187, 116-188, 116-189, 116-190, 116-191, 116-192, 116-193, 116-194, 116-195, 116-196, 116-197, 116-198, 116-199, and 116-200.

Peptides and Proteins that Begins with Amino Acid 117 of HPV16 L2

117-126, 117-127, 117-128, 117-129, 117-130, 117-131, 117-132, 117-133, 117-134, 117-135, 117-136, 117-137, 117-138, 117-139, 117-140, 117-141, 117-142, 117-143, 117-144, 117-145, 117-146, 117-147, 117-148, 117-149, 117-150, 117-151, 117-152, 117-153, 117-154, 117-155, 117-156, 117-157, 117-158, 117-159, 117-160, 117-161, 117-162, 117-163, 117-164, 117-165, 117-166, 117-167, 117-168, 117-169, 117-170, 117-171, 117-172, 117-173, 117-174, 117-175, 117-176, 117-177, 117-178, 117-179, 117-180, 117-181, 117-182, 117-183, 117-184, 117-185, 117-186, 117-187, 117-188, 117-189, 117-190, 117-191, 117-192, 117-193, 117-194, 117-195, 117-196, 117-197, 117-198, 117-199, and 117-200.

Peptides and Proteins that Begins with Amino Acid 118 of HPV16 L2

118-127, 118-128, 118-129, 118-130, 118-131, 118-132, 118-133, 118-134, 118-135, 118-136, 118-137, 118-138, 118-139, 118-140, 118-141, 118-142, 118-143, 118-144, 118-145, 118-146, 118-147, 118-148, 118-149, 118-150, 118-151, 118-152, 118-153, 118-154, 118-155, 118-156, 118-157, 118-158, 118-159, 118-160, 118-161, 118-162, 118-163, 118-164, 118-165, 118-166, 118-167, 118-168, 118-169, 118-170, 118-171, 118-172, 118-173, 118-174, 118-175, 118-176, 118-177, 118-178, 118-179, 118-180, 118-181, 118-182, 118-183, 118-184, 118-185, 118-186, 118-187, 118-188, 118-189, 118-190, 118-191, 118-192, 118-193, 118-194, 118-195, 118-196, 118-197, 118-198, 118-199, and 118-200.

Peptides and Proteins that Begins with Amino Acid 119 of HPV16 L2

119-128, 119-129, 119-130, 119-131, 119-132, 119-133, 119-134, 119-135, 119-136, 119-137, 119-138, 119-139, 119-140, 119-141, 119-142, 119-143, 119-144, 119-145, 119-146, 119-147, 119-148, 119-149, 119-150, 119-151, 119-152, 119-153, 119-154, 119-155, 119-156, 119-157, 119-158, 119-159, 119-160, 119-161, 119-162, 119-163, 119-164, 119-165, 119-166, 119-167, 119-168, 119-169, 119-170, 119-171, 119-172, 119-173, 119-174, 119-175, 119-176, 119-177, 119-178, 119-179, 119-180, 119-181, 119-182, 119-183, 119-184, 119-185, 119-186, 119-187, 119-188, 119-189, 119-190, 119-191, 119-192, 119-193, 119-194, 119-195, 119-196, 119-197, 119-198, 119-199, and 119-200.

Peptides and Proteins that Begins with Amino Acid 120 of HPV16 L2

120-129, 120-130, 120-131, 120-132, 120-133, 120-134, 120-135, 120-136, 120-137, 120-138, 120-139, 120-140, 120-141, 120-142, 120-143, 120-144, 120-145, 120-146, 120-147, 120-148, 120-149, 120-150, 120-151, 120-152, 120-153, 120-154, 120-155, 120-156, 120-157, 120-158, 120-159, 120-160, 120-161, 120-162, 120-163, 120-164, 120-165, 120-166, 120-167, 120-168, 120-169, 120-170, 120-171, 120-172, 120-173, 120-174, 120-175, 120-176, 120-177, 120-178, 120-179, 120-180, 120-181, 120-182, 120-183, 120-184, 120-185, 120-186, 120-187, 120-188, 120-189, 120-190, 120-191, 120-192, 120-193, 120-194, 120-195, 120-196, 120-197, 120-198, 120-199, and 120-200.

Peptides and Proteins that Begins with Amino Acid 121 of HPV16 L2

121-130, 121-131, 121-132, 121-133, 121-134, 121-135, 121-136, 121-137, 121-138, 121-139, 121-140, 121-141, 121-142, 121-143, 121-144, 121-145, 121-146, 121-147, 121-148, 121-149, 121-150, 121-151, 121-152, 121-153, 121-154, 121-155, 121-156, 121-157, 121-158, 121-159, 121-160, 121-161, 121-162, 121-163, 121-164, 121-165, 121-166, 121-167, 121-168, 121-169, 121-170, 121-171, 121-172, 121-173, 121-174, 121-175, 121-176, 121-177, 121-178, 121-179, 121-180, 121-181, 121-182, 121-183, 121-184, 121-185, 121-186, 121-187, 121-188, 121-189, 121-190, 121-191, 121-192, 121-193, 121-194, 121-195, 121-196, 121-197, 121-198, 121-199, and 121-200.

Peptides and Proteins that Begins with Amino Acid 122 of HPV16 L2

122-131, 122-132, 122-133, 122-134, 122-135, 122-136, 122-137, 122-138, 122-139, 122-140, 122-141, 122-142, 122-143, 122-144, 122-145, 122-146, 122-147, 122-148, 122-149, 122-150, 122-151, 122-152, 122-153, 122-154, 122-155, 122-156, 122-157, 122-158, 122-159, 122-160, 122-161, 122-162, 122-163, 122-164, 122-165, 122-166, 122-167, 122-168, 122-169, 122-170, 122-171, 122-172, 122-173, 122-174, 122-175, 122-176, 122-177, 122-178, 122-179, 122-180, 122-181, 122-182, 122-183, 122-184, 122-185, 122-186, 122-187, 122-188, 122-189, 122-190, 122-191, 122-192, 122-193, 122-194, 122-195, 122-196, 122-197, 122-198, 122-199, and 122-200.

Peptides and Proteins that Begins with Amino Acid 123 of HPV16 L2

123-132, 123-133, 123-134, 123-135, 123-136, 123-137, 123-138, 123-139, 123-140, 123-141, 123-142, 123-143, 123-144, 123-145, 123-146, 123-147, 123-148, 123-149, 123-150, 123-151, 123-152, 123-153, 123-154, 123-155, 123-156, 123-157, 123-158, 123-159, 123-160, 123-161, 123-162, 123-163, 123-164, 123-165, 123-166, 123-167, 123-168, 123-169, 123-170, 123-171, 123-172, 123-173, 123-174, 123-175, 123-176, 123-177, 123-178, 123-179, 123-180, 123-181, 123-182, 123-183, 123-184, 123-185, 123-186, 123-187, 123-188, 123-189, 123-190, 123-191, 123-192, 123-193, 123-194, 123-195, 123-196, 123-197, 123-198, 123-199, and 123-200.

Peptides and Proteins that Begins with Amino Acid 124 of HPV16 L2

124-133, 124-134, 124-135, 124-136, 124-137, 124-138, 124-139, 124-140, 124-141, 124-142, 124-143, 124-144, 124-145, 124-146, 124-147, 124-148, 124-149, 124-150, 124-151, 124-152, 124-153, 124-154, 124-155, 124-156, 124-157, 124-158, 124-159, 124-160, 124-161, 124-162, 124-163, 124-164, 124-165, 124-166, 124-167, 124-168, 124-169, 124-170, 124-171, 124-172, 124-173, 124-174, 124-175, 124-176, 124-177, 124-178, 124-179, 124-180, 124-181, 124-182, 124-183, 124-184, 124-185, 124-186, 124-187, 124-188, 124-189, 124-190, 124-191, 124-192, 124-193, 124-194, 124-195, 124-196, 124-197, 124-198, 124-199, and 124-200.

Peptides and Proteins that Begins with Amino Acid 125 of HPV16 L2

125-134, 125-135, 125-136, 125-137, 125-138, 125-139, 125-140, 125-141, 125-142, 125-143, 125-144, 125-145, 125-146, 125-147, 125-148, 125-149, 125-150, 125-151, 125-152, 125-153, 125-154, 125-155, 125-156, 125-157, 125-158, 125-159, 125-160, 125-161, 125-162, 125-163, 125-164, 125-165, 125-166, 125-167, 125-168, 125-169, 125-170, 125-171, 125-172, 125-173, 125-174, 125-175, 125-176, 125-177, 125-178, 125-179, 125-180, 125-181, 125-182, 125-183, 125-184, 125-185, 125-186, 125-187, 125-188, 125-189, 125-190, 125-191, 125-192, 125-193, 125-194, 125-195, 125-196, 125-197, 125-198, 125-199, and 125-200.

Peptides and Proteins that Begins with Amino Acid 126 of HPV16 L2

126-135, 126-136, 126-137, 126-138, 126-139, 126-140, 126-141, 126-142, 126-143, 126-144, 126-145, 126-146, 126-147, 126-148, 126-149, 126-150, 126-151, 126-152, 126-153, 126-154, 126-155, 126-156, 126-157, 126-158, 126-159, 126-160, 126-161, 126-162, 126-163, 126-164, 126-165, 126-166, 126-167, 126-168, 126-169, 126-170, 126-171, 126-172, 126-173, 126-174, 126-175, 126-176, 126-177, 126-178, 126-179, 126-180, 126-181, 126-182, 126-183, 126-184, 126-185, 126-186, 126-187, 126-188, 126-189, 126-190, 126-191, 126-192, 126-193, 126-194, 126-195, 126-196, 126-197, 126-198, 126-199, and 126-200.

Peptides and Proteins that Begins with Amino Acid 127 of HPV16 L2

127-136, 127-137, 127-138, 127-139, 127-140, 127-141, 127-142, 127-143, 127-144, 127-145, 127-146, 127-147, 127-148, 127-149, 127-150, 127-151, 127-152, 127-153, 127-154, 127-155, 127-156, 127-157, 127-158, 127-159, 127-160, 127-161, 127-162, 127-163, 127-164, 127-165, 127-166, 127-167, 127-168, 127-169, 127-170, 127-171, 127-172, 127-173, 127-174, 127-175, 127-176, 127-177, 127-178, 127-179, 127-180, 127-181, 127-182, 127-183, 127-184, 127-185, 127-186, 127-187, 127-188, 127-189, 127-190, 127-191, 127-192, 127-193, 127-194, 127-195, 127-196, 127-197, 127-198, 127-199, and 127-200.

Peptides and Proteins that Begins with Amino Acid 128 of HPV16 L2

128-137, 128-138, 128-139, 128-140, 128-141, 128-142, 128-143, 128-144, 128-145, 128-146, 128-147, 128-148, 128-149, 128-150, 128-151, 128-152, 128-153, 128-154, 128-155, 128-156, 128-157, 128-158, 128-159, 128-160, 128-161, 128-162, 128-163, 128-164, 128-165, 128-166, 128-167, 128-168, 128-169, 128-170, 128-171, 128-172, 128-173, 128-174, 128-175, 128-176, 128-177, 128-178, 128-179, 128-180, 128-181, 128-182, 128-183, 128-184, 128-185, 128-186, 128-187, 128-188, 128-189, 128-190, 128-191, 128-192, 128-193, 128-194, 128-195, 128-196, 128-197, 128-198, 128-199, and 128-200.

Peptides and Proteins that Begins with Amino Acid 129 of HPV16 L2

129-138, 129-139, 129-140, 129-141, 129-142, 129-143, 129-144, 129-145, 129-146, 129-147, 129-148, 129-149, 129-150, 129-151, 129-152, 129-153, 129-154, 129-155, 129-156, 129-157, 129-158, 129-159, 129-160, 129-161, 129-162, 129-163, 129-164, 129-165, 129-166, 129-167, 129-168, 129-169, 129-170, 129-171, 129-172, 129-173, 129-174, 129-175, 129-176, 129-177, 129-178, 129-179, 129-180, 129-181, 129-182, 129-183, 129-184, 129-185, 129-186, 129-187, 129-188, 129-189, 129-190, 129-191, 129-192, 129-193, 129-194, 129-195, 129-196, 129-197, 129-198, 129-199, and 129-200.

Peptides and Proteins that Begins with Amino Acid 130 of HPV16 L2

130-139, 130-140, 130-141, 130-142, 130-143, 130-144, 130-145, 130-146, 130-147, 130-148, 130-149, 130-150, 130-151, 130-152, 130-153, 130-154, 130-155, 130-156, 130-157, 130-158, 130-159, 130-160, 130-161, 130-162, 130-163, 130-164, 130-165, 130-166, 130-167, 130-168, 130-169, 130-170, 130-171, 130-172, 130-173, 130-174, 130-175, 130-176, 130-177, 130-178, 130-179, 130-180, 130-181, 130-182, 130-183, 130-184, 130-185, 130-186, 130-187, 130-188, 130-189, 130-190, 130-191, 130-192, 130-193, 130-194, 130-195, 130-196, 130-197, 130-198, 130-199, and 130-200.

Peptides and Proteins that Begins with Amino Acid 131 of HPV16 L2

131-140, 131-141, 131-142, 131-143, 131-144, 131-145, 131-146, 131-147, 131-148, 131-149, 131-150, 131-151, 131-152, 131-153, 131-154, 131-155, 131-156, 131-157, 131-158, 131-159, 131-160, 131-161, 131-162, 131-163, 131-164, 131-165, 131-166, 131-167, 131-168, 131-169, 131-170, 131-171, 131-172, 131-173, 131-174, 131-175, 131-176, 131-177, 131-178, 131-179, 131-180, 131-181, 131-182, 131-183, 131-184, 131-185, 131-186, 131-187, 131-188, 131-189, 131-190, 131-191, 131-192, 131-193, 131-194, 131-195, 131-196, 131-197, 131-198, 131-199, and 131-200.

Peptides and Proteins that Begins with Amino Acid 132 of HPV16 L2

132-141, 132-142, 132-143, 132-144, 132-145, 132-146, 132-147, 132-148, 132-149, 132-150, 132-151, 132-152, 132-153, 132-154, 132-155, 132-156, 132-157, 132-158, 132-159, 132-160, 132-161, 132-162, 132-163, 132-164, 132-165, 132-166, 132-167, 132-168, 132-169, 132-170, 132-171, 132-172, 132-173, 132-174, 132-175, 132-176, 132-177, 132-178, 132-179, 132-180, 132-181, 132-182, 132-183, 132-184, 132-185, 132-186, 132-187, 132-188, 132-189, 132-190, 132-191, 132-192, 132-193, 132-194, 132-195, 132-196, 132-197, 132-198, 132-199, and 132-200.

Peptides and Proteins that Begins with Amino Acid 133 of HPV16 L2

133-142, 133-143, 133-144, 133-145, 133-146, 133-147, 133-148, 133-149, 133-150, 133-151, 133-152, 133-153, 133-154, 133-155, 133-156, 133-157, 133-158, 133-159, 133-160, 133-161, 133-162, 133-163, 133-164, 133-165, 133-166, 133-167, 133-168, 133-169, 133-170, 133-171, 133-172, 133-173, 133-174, 133-175, 133-176, 133-177, 133-178, 133-179, 133-180, 133-181, 133-182, 133-183, 133-184, 133-185, 133-186, 133-187, 133-188, 133-189, 133-190, 133-191, 133-192, 133-193, 133-194, 133-195, 133-196, 133-197, 133-198, 133-199, and 133-200.

Peptides and Proteins that Begins with Amino Acid 134 of HPV16 L2

134-143, 134-144, 134-145, 134-146, 134-147, 134-148, 134-149, 134-150, 134-151, 134-152, 134-153, 134-154, 134-155, 134-156, 134-157, 134-158, 134-159, 134-160, 134-161, 134-162, 134-163, 134-164, 134-165, 134-166, 134-167, 134-168, 134-169, 134-170, 134-171, 134-172, 134-173, 134-174, 134-175, 134-176, 134-177, 134-178, 134-179, 134-180, 134-181, 134-182, 134-183, 134-184, 134-185, 134-186, 134-187, 134-188, 134-189, 134-190, 134-191, 134-192, 134-193, 134-194, 134-195, 134-196, 134-197, 134-198, 134-199, and 134-200.

Peptides and Proteins that Begins with Amino Acid 135 of HPV16 L2

135-144, 135-145, 135-146, 135-147, 135-148, 135-149, 135-150, 135-151, 135-152, 135-153, 135-154, 135-155, 135-156, 135-157, 135-158, 135-159, 135-160, 135-161, 135-162, 135-163, 135-164, 135-165, 135-166, 135-167, 135-168, 135-169, 135-170, 135-171, 135-172, 135-173, 135-174, 135-175, 135-176, 135-177, 135-178, 135-179, 135-180, 135-181, 135-182, 135-183, 135-184, 135-185, 135-186, 135-187, 135-188, 135-189, 135-190, 135-191, 135-192, 135-193, 135-194, 135-195, 135-196, 135-197, 135-198, 135-199, and 135-200.

Peptides and Proteins that Begins with Amino Acid 136 of HPV16 L2

136-145, 136-146, 136-147, 136-148, 136-149, 136-150, 136-151, 136-152, 136-153, 136-154, 136-155, 136-156, 136-157, 136-158, 136-159, 136-160, 136-161, 136-162, 136-163, 136-164, 136-165, 136-166, 136-167, 136-168, 136-169, 136-170, 136-171, 136-172, 136-173, 136-174, 136-175, 136-176, 136-177, 136-178, 136-179, 136-180, 136-181, 136-182, 136-183, 136-184, 136-185, 136-186, 136-187, 136-188, 136-189, 136-190, 136-191, 136-192, 136-193, 136-194, 136-195, 136-196, 136-197, 136-198, 136-199, and 136-200.

Peptides and Proteins that Begins with Amino Acid 137 of HPV16 L2

137-146, 137-147, 137-148; 137-149, 137-150, 137-151, 137-152, 137-153, 137-154, 137-155, 137-156, 137-157, 137-158, 137-159, 137-160, 137-161, 137-162, 137-163, 137-164, 137-165, 137-166, 137-167, 137-168, 137-169, 137-170, 137-171, 137-172, 137-173, 137-174, 137-175, 137-176, 137-177, 137-178, 137-179, 137-180, 137-181, 137-182, 137-183, 137-184, 137-185, 137-186, 137-187, 137-188, 137-189, 137-190, 137-191, 137-192, 137-193, 137-194, 137-195, 137-196, 137-197, 137-198, 137-199, and 137-200.

Peptides and Proteins that Begins with Amino Acid 138 of HPV16 L2

138-147, 138-148, 138-149, 138-150, 138-151, 138-152, 138-153, 138-154, 138-155, 138-156, 138-157, 138-158, 138-159, 138-160, 138-161, 138-162, 138-163, 138-164, 138-165, 138-166, 138-167, 138-168, 138-169, 138-170, 138-171, 138-172, 138-173, 138-174, 138-175, 138-176, 138-177, 138-178, 138-179, 138-180, 138-181, 138-182, 138-183, 138-184, 138-185, 138-186, 138-187, 138-188, 138-189, 138-190, 138-191, 138-192, 138-193, 138-194, 138-195, 138-196, 138-197, 138-198, 138-199, and 138-200.

Peptides and Proteins that Begins with Amino Acid 139 of HPV16 L2

139-148, 139-149, 139-150, 139-151, 139-152, 139-153, 139-154, 139-155, 139-156, 139-157, 139-158, 139-159, 139-160, 139-161, 139-162, 139-163, 139-164, 139-165, 139-166, 139-167, 139-168, 139-169, 139-170, 139-171, 139-172, 139-173, 139-174, 139-175, 139-176, 139-177, 139-178, 139-179, 139-180, 139-181, 139-182, 139-183, 139-184, 139-185, 139-186, 139-187, 139-188, 139-189, 139-190, 139-191, 139-192, 139-193, 139-194, 139-195, 139-196, 139-197, 139-198, 139-199, and 139-200.

Peptides and Proteins that Begins with Amino Acid 140 of HPV16 L2

140-149, 140-150, 140-151, 140-152, 140-153, 140-154, 140-155, 140-156, 140-157, 140-158, 140-159, 140-160, 140-161, 140-162, 140-163, 140-164, 140-165, 140-166, 140-167, 140-168, 140-169, 140-170, 140-171, 140-172, 140-173, 140-174, 140-175, 140-176, 140-177, 140-178, 140-179, 140-180, 140-181, 140-182, 140-183, 140-184, 140-185, 140-186, 140-187, 140-188, 140-189, 140-190, 140-191, 140-192, 140-193, 140-194, 140-195, 140-196, 140-197, 140-198, 140-199, and 140-200.

Peptides and Proteins that Begins with Amino Acid 141 of HPV16 L2

141-150, 141-151, 141-152, 141-153, 141-154, 141-155, 141-156, 141-157, 141-158, 141-159, 141-160, 141-161, 141-162, 141-163, 141-164, 141-165, 141-166, 141-167, 141-168, 141-169, 141-170, 141-171, 141-172, 141-173, 141-174, 141-175, 141-176, 141-177, 141-178, 141-179, 141-180, 141-181, 141-182, 141-183, 141-184, 141-185, 141-186, 141-187, 141-188, 141-189, 141-190, 141-191, 141-192, 141-193, 141-194, 141-195, 141-196, 141-197, 141-198, 141-199, and 141-200.

Peptides and Proteins that Begins with Amino Acid 142 of HPV16 L2

142-151, 142-152, 142-153, 142-154, 142-155, 142-156, 142-157, 142-158, 142-159, 142-160, 142-161, 142-162, 142-163, 142-164, 142-165, 142-166, 142-167, 142-168, 142-169, 142-170, 142-171, 142-172, 142-173, 142-174, 142-175, 142-176, 142-177, 142-178, 142-179, 142-180, 142-181, 142-182, 142-183, 142-184, 142-185, 142-186, 142-187, 142-188, 142-189, 142-190, 142-191, 142-192, 142-193, 142-194, 142-195, 142-196, 142-197, 142-198, 142-199, and 142-200.

Peptides and Proteins that Begins with Amino Acid 143 of HPV16 L2

143-152, 143-153, 143-154, 143-155, 143-156, 143-157, 143-158, 143-159, 143-160, 143-161, 143-162, 143-163, 143-164, 143-165, 143-166, 143-167, 143-168, 143-169, 143-170, 143-171, 143-172, 143-173, 143-174, 143-175, 143-176, 143-177, 143-178, 143-179, 143-180, 143-181, 143-182, 143-183, 143-184, 143-185, 143-186, 143-187, 143-188, 143-189, 143-190, 143-191, 143-192, 143-193, 143-194, 143-195, 143-196, 143-197, 143-198, 143-199, and 143-200.

Peptides and Proteins that Begins with Amino Acid 144 of HPV16 L2

144-153, 144-154, 144-155, 144-156, 144-157, 144-158, 144-159, 144-160, 144-161, 144-162, 144-163, 144-164, 144-165, 144-166, 144-167, 144-168, 144-169, 144-170, 144-171, 144-172, 144-173, 144-174, 144-175, 144-176, 144-177, 144-178, 144-179, 144-180, 144-181, 144-182, 144-183, 144-184, 144-185, 144-186, 144-187, 144-188, 144-189, 144-190, 144-191, 144-192, 144-193, 144-194, 144-195, 144-196, 144-197, 144-198, 144-199, and 144-200.

Peptides and Proteins that Begins with Amino Acid 145 of HPV16 L2

145-154, 145-155, 145-156, 145-157, 145-158, 145-159, 145-160, 145-161, 145-162, 145-163, 145-164, 145-165, 145-166, 145-167, 145-168, 145-169, 145-170, 145-171, 145-172, 145-173, 145-174, 145-175, 145-176, 145-177, 145-178, 145-179, 145-180, 145-181, 145-182, 145-183, 145-184, 145-185, 145-186, 145-187, 145-188, 145-189, 145-190, 145-191, 145-192, 145-193, 145-194, 145-195, 145-196, 145-197, 145-198, 145-199, and 145-200.

Peptides and Proteins that Begins with Amino Acid 146 of HPV16 L2

146-155, 146-156, 146-157, 146-158, 146-159, 146-160, 146-161, 146-162, 146-163, 146-164, 146-165, 146-166, 146-167, 146-168, 146-169, 146-170, 146-171, 146-172, 146-173, 146-174, 146-175, 146-176, 146-177, 146-178, 146-179, 146-180, 146-181, 146-182, 146-183, 146-184, 146-185, 146-186, 146-187, 146-188, 146-189, 146-190, 146-191, 146-192, 146-193, 146-194, 146-195, 146-196, 146-197, 146-198, 146-199, and 146-200.

Peptides and Proteins that Begins with Amino Acid 147 of HPV16 L2

147-156, 147-157, 147-158, 147-159, 147-160, 147-161, 147-162, 147-163, 147-164, 147-165, 147-166, 147-167, 147-168, 147-169, 147-170, 147-171, 147-172, 147-173, 147-174, 147-175, 147-176, 147-177, 147-178, 147-179, 147-180, 147-181, 147-182, 147-183, 147-184, 147-185, 147-186, 147-187, 147-188, 147-189, 147-190, 147-191, 147-192, 147-193, 147-194, 147-195, 147-196, 147-197, 147-198, 147-199, and 147-200.

Peptides and Proteins that Begins with Amino Acid 148 of HPV16 L2

148-157, 148-158, 148-159, 148-160, 148-161, 148-162, 148-163, 148-164, 148-165, 148-166, 148-167, 148-168, 148-169, 148-170, 148-171, 148-172, 148-173, 148-174, 148-175, 148-176, 148-177, 148-178, 148-179, 148-180, 148-181, 148-182, 148-183, 148-184, 148-185, 148-186, 148-187, 148-188, 148-189, 148-190, 148-191, 148-192, 148-193, 148-194, 148-195, 148-196, 148-197, 148-198, 148-199, and 148-200.

Peptides and Proteins that Begins with Amino Acid 149 of HPV16 L2

149-158, 149-159, 149-160, 149-161, 149-162, 149-163, 149-164, 149-165, 149-166, 149-167, 149-168, 149-169, 149-170, 149-171, 149-172, 149-173, 149-174, 149-175, 149-176, 149-177, 149-178, 149-179, 149-180, 149-181, 149-182, 149-183, 149-184, 149-185, 149-186, 149-187, 149-188, 149-189, 149-190, 149-191, 149-192, 149-193, 149-194, 149-195, 149-196, 149-197, 149-198, 149-199, and 149-200.

Peptides and Proteins that Begins with Amino Acid 150 of HPV16 L2

150-159, 150-160, 150-161, 150-162, 150-163, 150-164, 150-165, 150-166, 150-167, 150-168, 150-169, 150-170, 150-171, 150-172, 150-173, 150-174, 150-175, 150-176, 150-177, 150-178, 150-179, 150-180, 150-181, 150-182, 150-183, 150-184, 150-185, 150-186, 150-187, 150-188, 150-189, 150-190, 150-191, 150-192, 150-193, 150-194, 150-195, 150-196, 150-197, 150-198, 150-199, and 150-200.

Peptides and Proteins that Begins with Amino Acid 151 of HPV16 L2

151-160, 151-161, 151-162, 151-163, 151-164, 151-165, 151-166, 151-167, 151-168, 151-169, 151-170, 151-171, 151-172, 151-173, 151-174, 151-175, 151-176, 151-177, 151-178, 151-179, 151-180, 151-181, 151-182, 151-183, 151-184, 151-185, 151-186, 151-187, 151-188, 151-189, 151-190, 151-191, 151-192, 151-193, 151-194, 151-195, 151-196, 151-197, 151-198, 151-199, and 151-200.

Peptides and Proteins that Begins with Amino Acid 152 of HPV16 L2

152-161, 152-162, 152-163, 152-164, 152-165, 152-166, 152-167, 152-168, 152-169, 152-170, 152-171, 152-172, 152-173, 152-174, 152-175, 152-176, 152-177, 152-178, 152-179, 152-180, 152-181, 152-182, 152-183, 152-184, 152-185, 152-186, 152-187, 152-188, 152-189, 152-190, 152-191, 152-192, 152-193, 152-194, 152-195, 152-196, 152-197, 152-198, 152-199, and 152-200.

Peptides and Proteins that Begins with Amino Acid 153 of HPV16 L2

153-162, 153-163, 153-164, 153-165, 153-166, 153-167, 153-168, 153-169, 153-170, 153-171, 153-172, 153-173, 153-174, 153-175, 153-176, 153-177, 153-178, 153-179, 153-180, 153-181, 153-182, 153-183, 153-184, 153-185, 153-186, 153-187, 153-188, 153-189, 153-190, 153-191, 153-192, 153-193, 153-194, 153-195, 153-196, 153-197, 153-198, 153-199, and 153-200.

Peptides and Proteins that Begins with Amino Acid 154 of HPV16 L2

154-163, 154-164, 154-165, 154-166, 154-167, 154-168, 154-169, 154-170, 154-171, 154-172, 154-173, 154-174, 154-175, 154-176, 154-177, 154-178, 154-179, 154-180, 154-181, 154-182, 154-183, 154-184, 154-185, 154-186, 154-187, 154-188, 154-189, 154-190, 154-191, 154-192, 154-193, 154-194, 154-195, 154-196, 154-197, 154-198, 154-199, and 154-200.

Peptides and Proteins that Begins with Amino Acid 155 of HPV16 L2

155-164, 155-165, 155-166, 155-167, 155-168, 155-169, 155-170, 155-171, 155-172, 155-173, 155-174, 155-175, 155-176, 155-177, 155-178, 155-179, 155-180, 155-181, 155-182, 155-183, 155-184, 155-185, 155-186, 155-187, 155-188, 155-189, 155-190, 155-191, 155-192, 155-193, 155-194, 155-195, 155-196, 155-197, 155-198, 155-199, and 155-200.

Peptides and Proteins that Begins with Amino Acid 156 of HPV16 L2

156-165, 156-166, 156-167, 156-168, 156-169, 156-170, 156-171, 156-172, 156-173, 156-174, 156-175, 156-176, 156-177, 156-178, 156-179, 156-180, 156-181, 156-182, 156-183, 156-184, 156-185, 156-186, 156-187, 156-188, 156-189, 156-190, 156-191, 156-192, 156-193, 156-194, 156-195, 156-196, 156-197, 156-198, 156-199, and 156-200.

Peptides and Proteins that Begins with Amino Acid 157 of HPV16 L2

157-166, 157-167, 157-168, 157-169, 157-170, 157-171, 157-172, 157-173, 157-174, 157-175, 157-176, 157-177, 157-178, 157-179, 157-180, 157-181, 157-182, 157-183, 157-184, 157-185, 157-186, 157-187, 157-188, 157-189, 157-190, 157-191, 157-192, 157-193, 157-194, 157-195, 157-196, 157-197, 157-198, 157-199, and 157-200.

Peptides and Proteins that Begins with Amino Acid 158 of HPV16 L2

158-167, 158-168, 158-169, 158-170, 158-171, 158-172, 158-173, 158-174, 158-175, 158-176, 158-177, 158-178, 158-179, 158-180, 158-181, 158-182, 158-183, 158-184, 158-185, 158-186, 158-187, 158-188, 158-189, 158-190, 158-191, 158-192, 158-193, 158-194, 158-195, 158-196, 158-197, 158-198, 158-199, and 158-200.

Peptides and Proteins that Begins with Amino Acid 159 of HPV16 L2

159-168, 159-169, 159-170, 159-171, 159-172, 159-173, 159-174, 159-175, 159-176, 159-177, 159-178, 159-179, 159-180, 159-181, 159-182, 159-183, 159-184, 159-185, 159-186, 159-187, 159-188, 159-189, 159-190, 159-191, 159-192, 159-193, 159-194, 159-195, 159-196, 159-197, 159-198, 159-199, and 159-200.

Peptides and Proteins that Begins with Amino Acid 160 of HPV16 L2

160-169, 160-170, 160-171, 160-172, 160-173, 160-174, 160-175, 160-176, 160-177, 160-178, 160-179, 160-180, 160-181, 160-182, 160-183, 160-184, 160-185, 160-186, 160-187, 160-188, 160-189, 160-190, 160-191, 160-192, 160-193, 160-194, 160-195, 160-196, 160-197, 160-198, 160-199, and 160-200.

Peptides and Proteins that Begins with Amino Acid 161 of HPV16 L2

161-170, 161-171, 161-172, 161-173, 161-174, 161-175, 161-176, 161-177, 161-178, 161-179, 161-180, 161-181, 161-182, 161-183, 161-184, 161-185, 161-186, 161-187, 161-188, 161-189, 161-190, 161-191, 161-192, 161-193, 161-194, 161-195, 161-196, 161-197, 161-198, 161-199, and 161-200.

Peptides and Proteins that Begins with Amino Acid 162 of HPV16 L2

162-171, 162-172, 162-173, 162-174, 162-175, 162-176, 162-177, 162-178, 162-179, 162-180, 162-181, 162-182, 162-183, 162-184, 162-185, 162-186, 162-187, 162-188, 162-189, 162-190, 162-191, 162-192, 162-193, 162-194, 162-195, 162-196, 162-197, 162-198, 162-199, and 162-200.

Peptides and Proteins that Begins with Amino Acid 163 of HPV16 L2

163-172, 163-173, 163-174, 163-175, 163-176, 163-177, 163-178, 163-179, 163-180, 163-181, 163-182, 163-183, 163-184, 163-185, 163-186, 163-187, 163-188, 163-189, 163-190, 163-191, 163-192, 163-193, 163-194, 163-195, 163-196, 163-197, 163-198, 163-199, and 163-200.

Peptides and Proteins that Begins with Amino Acid 164 of HPV16 L2

164-173, 164-174, 164-175, 164-176, 164-177, 164-178, 164-179, 164-180, 164-181, 164-182, 164-183, 164-184, 164-185, 164-186, 164-187, 164-188, 164-189, 164-190, 164-191, 164-192, 164-193, 164-194, 164-195, 164-196, 164-197, 164-198, 164-199, and 164-200.

Peptides and Proteins that Begins with Amino Acid 165 of HPV16 L2

165-174, 165-175, 165-176, 165-177, 165-178, 165-179, 165-180, 165-181, 165-182, 165-183, 165-184, 165-185, 165-186, 165-187, 165-188, 165-189, 165-190, 165-191, 165-192, 165-193, 165-194, 165-195, 165-196, 165-197, 165-198, 165-199, and 165-200.

Peptides and Proteins that Begins with Amino Acid 166 of HPV16 L2

166-175, 166-176, 166-177, 166-178, 166-179, 166-180, 166-181, 166-182, 166-183, 166-184, 166-185, 166-186, 166-187, 166-188, 166-189, 166-190, 166-191, 166-192, 166-193, 166-194, 166-195, 166-196, 166-197, 166-198, 166-199, and 166-200.

Peptides and Proteins that Begins with Amino Acid 167 of HPV16 L2

167-176, 167-177, 167-178, 167-179, 167-180, 167-181, 167-182, 167-183, 167-184, 167-185, 167-186, 167-187, 167-188, 167-189, 167-190, 167-191, 167-192, 167-193, 167-194, 167-195, 167-196, 167-197, 167-198, 167-199, and 167-200.

Peptides and Proteins that Begins with Amino Acid 168 of HPV16 L2

168-177, 168-178, 168-179, 168-180, 168-181, 168-182, 168-183, 168-184, 168-185, 168-186, 168-187, 168-188, 168-189, 168-190, 168-191, 168-192, 168-193, 168-194, 168-195, 168-196, 168-197, 168-198, 168-199, and 168-200.

Peptides and Proteins that Begins with Amino Acid 169 of HPV16 L2

169-178, 169-179, 169-180, 169-181, 169-182, 169-183, 169-184, 169-185, 169-186, 169-187, 169-188, 169-189, 169-190, 169-191, 169-192, 169-193, 169-194, 169-195, 169-196, 169-197, 169-198, 169-199, and 169-200.

Peptides and Proteins that Begins with Amino Acid 170 of HPV16 L2

170-179, 170-180, 170-181, 170-182, 170-183, 170-184, 170-185, 170-186, 170-187, 170-188, 170-189, 170-190, 170-191, 170-192, 170-193, 170-194, 170-195, 170-196, 170-197, 170-198, 170-199, and 170-200.

Peptides and Proteins that Begins with Amino Acid 171 of HPV16 L2

171-180, 171-181, 171-182, 171-183, 171-184, 171-185, 171-186, 171-187, 171-188, 171-189, 171-190, 171-191, 171-192, 171-193, 171-194, 171-195, 171-196, 171-197, 171-198, 171-199, and 171-200.

Peptides and Proteins that Begins with Amino Acid 172 of HPV16 L2

172-181, 172-182, 172-183, 172-184, 172-185, 172-186, 172-187, 172-188, 172-189, 172-190, 172-191, 172-192, 172-193, 172-194, 172-195, 172-196, 172-197, 172-198, 172-199, and 172-200.

Peptides and Proteins that Begins with Amino Acid 173 of HPV16 L2

173-182, 173-183, 173-184, 173-185, 173-186, 173-187, 173-188, 173-189, 173-190, 173-191, 173-192, 173-193, 173-194, 173-195, 173-196, 173-197, 173-198, 173-199, and 173-200.

Peptides and Proteins that Begins with Amino Acid 174 of HPV16 L2

174-183, 174-184, 174-185, 174-186, 174-187, 174-188, 174-189, 174-190, 174-191, 174-192, 174-193, 174-194, 174-195, 174-196, 174-197, 174-198, 174-199, and 174-200.

Peptides and Proteins that Begins with Amino Acid 175 of HPV16 L2

175-184, 175-185, 175-186, 175-187, 175-188, 175-189, 175-190, 175-191, 175-192, 175-193, 175-194, 175-195, 175-196, 175-197, 175-198, 175-199, and 175-200.

Peptides and Proteins that Begins with Amino Acid 176 of HPV16 L2

176-185, 176-186, 176-187, 176-188, 176-189, 176-190, 176-191, 176-192, 176-193, 176-194, 176-195, 176-196, 176-197, 176-198, 176-199, and 176-200.

Peptides and Proteins that Begins with Amino Acid 177 of HPV16 L2
177-186, 177-187, 177-188, 177-189, 177-190, 177-191, 177-192, 177-193±177-194, 177-195, 177-196, 177-197, 177-198, 177-199, and 177-200.
Peptides and Proteins that Begins with Amino Acid 178 of HPV16 L2
178-187, 178-188, 178-189, 178-190, 178-191, 178-192, 178-193, 178-194, 178-195, 178-196, 178-197, 178-198, 178-199, and 178-200.
Peptides and Proteins that Begins with Amino Acid 179 of HPV16 L2
179-188, 179-189, 179-190, 179-191, 179-192, 179-193, 179-194, 179-195, 179-196, 179-197, 179-198, 179-199, and 179-200.
Peptides and Proteins that Begins with Amino Acid 180 of HPV16 L2
180-189, 180-190, 180-191, 180-192, 180-193, 180-194, 180-195, 180-196, 180-197, 180-198, 180-199, and 180-200.
Peptides and Proteins that Begins with Amino Acid 181 of HPV16 L2
181-190, 181-191, 181-192, 181-193, 181-194, 181-195, 181-196, 181-197, 181-198, 181-199, and 181-200.
Peptides and Proteins that Begins with Amino Acid 182 of HPV16 L2
182-191, 182-192, 182-193, 182-194, 182-195, 182-196, 182-197, 182-198, 182-199, and 182-200.
Peptides and Proteins that Begins with Amino Acid 183 of HPV16 L2
183-192, 183-193, 183-194, 183-195, 183-196, 183-197, 183-198, 183-199, and 183-200.
Peptides and Proteins that Begins with Amino Acid 184 of HPV16 L2
184-193, 184-194, 184-195, 184-196, 184-197, 184-198, 184-199, and 184-200.
Peptides and Proteins that Begins with Amino Acid 185 of HPV16 L2
185-194, 185-195, 185-196, 185-197, 185-198, 185-199, and 185-200.
Peptides and Proteins that Begins with Amino Acid 186 of HPV16 L2
186-195, 186-196, 186-197, 186-198, 186-199, and 186-200.
Peptides and Proteins that Begins with Amino Acid 187 of HPV16 L2
187-196, 187-197, 187-198, 187-199, and 187-200.
Peptides and Proteins that Begins with Amino Acid 188 of HPV16 L2
188-197, 188-198, 188-199, and 188-200.
Peptides and Proteins that Begins with Amino Acid 189 of HPV16 L2
189-198, 189-199, and 189-200.
Peptides and Proteins that Begins with Amino Acid 190 of HPV16 L2
190-199, and 190-200.
Peptides and Proteins that Begins with Amino Acid 191 of HPV16 L2
191-200.

In other embodiments, peptides and proteins come from the N-terminal region of the L2 protein of other human papillomaviruses: HPV1, HPV2, HPV3, HPV4, HPV5, HPV6, HPV7, HPV8, HPV9, HPV10, HPV11, HPV12, HPV13, HPV14, HPV15, HPV17, HPV18, HPV19, HPV20, HPV21, HPV22, HPV23, HPV24, HPV25, HPV26, HPV27, HPV28, HPV29, HPV30, HPV31, HPV32, HPV33, HPV34, HPV35, HPV36, HPV37, HPV38, HPV39, HPV40, HPV41, HPV42, HPV43, HPV44, HPV45, HPV46, HPV47, HPV48, HPV49, HPV50, HPV51, HPV52, HPV53, HPV54, HPV55, HPV56, HPV57, HPV58, HPV59, HPV60, HPV61, HPV62, HPV63, HPV64, HPV65, HPV66, HPV67, HPV68, HPV69, HPV70; and animal papillomaviruses: bovine papillomavirus type 1 (BPV1), bovine papillomavirus type 2 (BPV2), bovine papillomavirus type 4 (BPV4), cottontail rabbit papillomavirus (CRPV), deer papillomavirus (DPV), European elk papillomavirus (EEPV), and canine oral papillomavirus (COPV), Rhesus monkey papillomavirus (RhPV) and rabbit oral papillomavirus (ROPV)

The Human Papillomaviruses Compendium On Line compiles and publishes relevant molecular data concerning the human papillomaviruses (HPV) and related animal papillomaviruses. The scope of the compendium and database comprises: (I) HPV and animal PV Nucleotide Sequences; (II) Amino Acid and Nucleotide Sequence Alignments; (III) Analyses; (IV) Related Host Sequences; and (V) Database Communications. The compendium is accessed on the internet at (hpv-web.1an1.gov/stdgen/virus/hpv/compendium/ht-docs/HTML_FILES/HPVcompintro4.html)

One or more of the polypeptides are useful as a vaccine composition when combined with a pharmaceutical carrier for the prophylaxis, treatment, or prevention of papillomavirus infection. The vaccine composition is administered to an individual prior to papillomavirus exposure to minimize or prevent papillomavirus infection or is administered after a patient has been infected to reduce the severity of infection and retard or halt progression of the disease.

Definitions

Unless defined otherwise, technical and scientific terms used herein have the same meaning as commonly understood by one of ordinary skill in the art to which this invention belongs. See, e.g., Singleton P and Sainsbury D., Dictionary of Microbiology and Molecular Biology 3rd ed., J. Wiley & Sons, Chichester, N.Y., 2001, and Fields Virology 4th ed., Knipe D. M. and Howley P. M. eds, Lippincott Williams & Wilkins, Philadelphia 2001.

The terms "a", "an" and "the" as used herein are defined to mean "one or more" and include the plural unless the context is inappropriate.

By "'isolated" is meant peptide or protein free from at least some of the components with which it naturally occurs.

"Peptides", "polypeptides", and "proteins" are used interchangeably and are defined herein as chains of amino acids (typically L-amino acids) in which the carbonyl group of one amino acid is linked to the amino group of a second amino acid by an amide linkage. The terminal amino acid at one end of the chain (i.e., the amino terminal) has a free amino group, while the terminal amino acid at the other end of the chain (i.e., the carboxy terminal) has a free carboxyl group.

The term "polynucleotide" refers to any polymer of mononucleotides (e.g., ribonucleotides, deoxyribonucleotides).

Typically, the amino acids making up a peptide are numbered in order, starting at the amino terminal and increasing in the direction of the carboxy terminal of the peptide. Thus, when one amino acid is said to "follow" another, that amino acid is positioned closer to the carboxy terminal of the peptide than the "preceding" amino acid.

The term "residue" is used herein to refer to an amino acid (D or L) or an amino acid mimetic that is incorporated into a peptide by an amide bond or an amide bond mimetic. As such, the amino acid may be a naturally occurring amino acid or, unless otherwise limited, may encompass known analogs of natural amino acids that function in a manner similar to the naturally occurring amino acids (i.e. amino acid mimetics). Moreover, an amide bond mimetic includes peptide backbone modifications well known to those skilled in the art.

"Antigen" refers to a molecule which can induce an immune response in an animal. It induces the formation of an antibody. The term includes immunogens.

"Epitope" or "determinant" refers to the antibody binding site on an antigen.

"Antibody" refers to a molecule produced by animals in response to antigen which has the particular property of combining specifically with the antigen which induced its formation.

"Neutralizing antibody" refers to an antibody that blocks viral infection of a cell.

"Neutralizing antigenic epitope" or "neutralizing epitope" refers to an epitope that elicits a neutralizing antibody.

The phrases "specifically binds to a peptide" or "specifically immunoreactive with", when referring to an antibody, refers to a binding reaction which is determinative of the presence of the peptide, or an antibody to the peptide, in the presence of a heterogeneous population of proteins and other biologics. Thus, under designated immunoassay conditions, the specified antibodies bind preferentially to a particular peptide and do not bind in a significant amount to other proteins present in the sample. Specific binding to a peptide under such conditions requires an antibody that is selected for its specificity for a particular protein. A variety of immunoassay formats may be used to select antibodies specifically immunoreactive with a particular protein. For example, solid phase ELISA immunoassays are routinely used to select monoclonal antibodies specifically immunoreactive with a protein. See, Harlow and Lane (1988) Antibodies, A Laboratory Manual, Cold Spring Harbor Publications, New York, for a description of immunoassay formats and conditions that can be used to determine specific immunoreactivity.

"Conservative variations" or "conservative modified variations" of a particular sequence refers to amino acids encoded by nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given peptide. Such nucleic acid variations are silent variations, which are one species of conservatively modified variations. One of skill will recognize that each codon in a nucleic acid (except AUG, which is ordinarily the only codon for methionine) can be modified to yield a functionally identical molecule by standard techniques. Accordingly, each silent variation of a nucleic acid which encodes a peptide is implicit in any described amino acid sequence. Furthermore, one of skill will recognize that individual substitutions, deletions or additions which alter, add or delete a single amino acid or a small percentage of amino acids in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Two polypeptides are said to be "identical" if the sequence of amino acid residues in the two sequences is the same when aligned for maximum correspondence. Optimal alignment of sequences for comparison may be conducted by the local homology algorithm of Smith and Waterman 1981 *Adv Appl Math* 2:482-489, by the homology alignment algorithm of Needleman and Wunsch 1970 *J Mol Biol* 48:443-453, by the search for similarity method of Pearson and Lipman 1988 *Proc Natl Acad Sci USA* 85:2444-2448, by computerized implementations of these algorithms (GAP, BESTFIT, FASTA, and TFASTA in the Wisconsin Genetics Software Package, Genetics Computer Group, 575 Science Dr., Madison, Wis.), or by inspection. When using BESTFIT or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The term "substantial identity" means that a polypeptide comprises a sequence that has at least 55%, 60%, 65%, 70%, 75%, 80%, or 85% sequence identity, preferably 90%, more preferably 95% or more, compared to a reference sequence. Another indication that polypeptide sequences are substantially identical is if one peptide is immunologically reactive with antibodies raised against the disclosed peptide. Thus, the peptides of the invention include peptides immunologically reactive with antibodies raised against the disclosed immunogenic peptides.

The term "neutralization" refers to the process by which antibody alone or antibody plus complement neutralizes the infectivity of a virus.

The term "cross-neutralization" refers to a process where an antibody raised against one type of virus is capable of neutralizing a heterologous type.

The term "heterologous type" pertains to a virus type that is not the one that elicited the production of an antibody.

The term "homologous type" refers to the virus type that elicited the production of an antibody.

The term "mucosal" refers to having an affinity for a mucous membrane. The term "cutaneous" refers to having an affinity for non-mucosal, skin epithelial cells.

Of the 118 papillomavirus types, many are listed in Tables A-1 and A-2 along with their affinity.

TABLE A-1

Human Papillomaviruses

| Human | Type |
|---|---|
| HPV1 | Cutaneous |
| HPV2 | Cutaneous |
| HPV3 | Cutaneous |
| HPV4 | Cutaneous |
| HPV5 | Cutaneous |
| HPV6 | Mucosal |
| HPV7 | Cutaneous |
| HPV8 | Cutaneous |
| HPV9 | Cutaneous |
| HPV10 | Cutaneous |
| HPV11 | Mucosal |
| HPV12 | Cutaneous |
| HPV13 | Mucosal |
| HPV14 | Cutaneous |
| HPV15 | Cutaneous |
| HPV16 | Mucosal |
| HPV17 | Cutaneous |
| HPV18 | Mucosal |
| HPV19 | Cutaneous |
| HPV20 | Cutaneous |
| HPV21 | Cutaneous |

TABLE A-1-continued

Human Papillomaviruses

| Human | Type |
|---|---|
| HPV22 | Cutaneous |
| HPV23 | Cutaneous |
| HPV24 | Cutaneous |
| HPV25 | Cutaneous |
| HPV26 | Cutaneous |
| HPV27 | Cutaneous |
| HPV28 | Cutaneous |
| HPV29 | Cutaneous |
| HPV30 | Mucosal |
| HPV31 | Mucosal |
| HPV32 | Mucosal |
| HPV33 | Mucosal |
| HPV34 | Mucosal and Cutaneous |
| HPV35 | Mucosal |
| HPV36 | Cutaneous |
| HPV37 | Cutaneous |
| HPV38 | Cutaneous |
| HPV39 | Mucosal |
| HPV40 | Mucosal |
| HPV41 | Cutaneous |
| HPV42 | Mucosal |
| HPV43 | Mucosal |
| HPV44 | Mucosal |
| HPV45 | Mucosal |
| HPV46 | Cutaneous |
| HPV47 | Cutaneous |
| HPV48 | Cutaneous |
| HPV49 | Cutaneous |
| HPV50 | Cutaneous |
| HPV51 | Mucosal |
| HPV52 | Mucosal |
| HPV53 | Mucosal |
| HPV54 | Mucosal |
| HPV55 | Mucosal |
| HPV56 | Mucosal |
| HPV57 | Cutaneous and mucosal |
| HPV58 | Mucosal |
| HPV59 | Mucosal |
| HPV60 | Cutaneous |
| HPV61 | Mucosal |
| HPV62 | Mucosal |
| HPV63 | Cutaneous |
| HPV64 | Mucosal |
| HPV65 | Cutaneous mucosal |
| HPV66 | Mucosal |
| HPV67 | Mucosal |
| HPV68 | Mucosal |
| HPV69 | Mucosal |
| HPV70 | Mucosal |
| HPV71 | Mucosal |
| HPV72 | Mucosal |
| HPV73 | Mucosal |

TABLE A-2

Animal Papillomaviruses

| Animal | Type |
|---|---|
| BPV1 | Cutaneous |
| BPV2 | Cutaneous |
| BPV4 | Cutaneous |
| CRPV | Cutaneous |
| DPV | Cutaneous |
| EEPV | Cutaneous |
| COPV | Mucosal |
| RhPV | Mucosal |
| RoPV | Mucosal |

Synthetic Polypeptides

The polypeptides described herein generally contain from about 10 to about 200 amino acid residues. The polypeptides can be prepared using any of a number of chemical peptide synthesis techniques well known to those of ordinary skill in the art including both solution methods and solid phase methods, with solid phase synthesis being presently preferred.

In particular, solid phase synthesis in which the C-terminal amino acid of the polypeptide sequence is attached to an insoluble support followed by sequential addition of the remaining amino acids in the sequence is a preferred synthetic method for preparing the polypeptides. Techniques for solid phase synthesis are described by Merrifield, et al, 1963 *J Am Chem Soc* 85:2149-2154. Many automated systems for performing solid phase peptide synthesis are commercially available.

Solid phase synthesis is started from the carboxy-terminal end (i.e., the C-terminus) of the polypeptide by coupling a protected amino acid via its carboxyl group to a suitable solid support. The solid support used is not a critical feature provided that it is capable of binding to the carboxyl group while remaining substantially inert to the reagents utilized in the peptide synthesis procedure. For example, a starting material can be prepared by attaching an amino-protected amino acid via a benzyl ester linkage to a chloromethylated resin or a hydroxymethyl resin or via an amide bond to a benzhydrylamine (BHA) resin or p-methylbenzhydrylamine (MBHA) resin. Materials suitable for use as solid supports are well known to those of skill in the art and include, but are not limited to, the following: halomethyl resins, such as chloromethyl resin or bromomethyl resin; hydroxymethyl resins; phenol resins, such as 4-(a-[2,4-dimethoxyphenyl]-Fmoc-aminomethyl)phenoxy resin; tert-alkyloxycarbonyl-hydrazidated resins; and the like. Such resins are commercially available and their methods of preparation are known to those of ordinary skill in the art.

The acid form of the peptides may be prepared by the solid phase peptide synthesis procedure using a benzyl ester resin as a solid support. The corresponding amides may be produced by using benzhydrylamine or methylbenzhydrylamine resin as the solid support. Those skilled in the art will recognize that when the BHA or MBHA resin is used treatment with anhydrous hydrofluoric acid to cleave the peptide from the solid support produces a peptide having a terminal amide group.

The α-amino group of each amino acid used in the synthesis should be protected during the coupling reaction to prevent side reactions involving the reactive α-amino function. Certain amino acids also contain reactive side-chain functional groups (e.g. sulfhydryl, amino, carboxyl, hydroxyl, etc.) which must also be protected with appropriate protecting groups to prevent chemical reactions from occurring at those sites during the peptide synthesis. Protecting groups are well known to those of skill in the art. See, for example, The Peptides: Analysis, Synthesis, Biology, Vol. 3: Protection of Functional Groups in Peptide Synthesis (Gross and Meienhofer (eds.), Academic Press, N.Y. (1981)).

A properly selected α-amino protecting group will render the α-amino function inert during the coupling reaction, will be readily removable after coupling under conditions that will not remove side chain protecting groups, will not alter the structure of the peptide fragment, and will prevent racemization upon activation immediately prior to coupling. Similarly, side chain protecting groups must be chosen to render the side chain functional group inert during the synthesis, must be stable under the conditions used to remove the α-amino protecting group, and must be removable after completion of the peptide synthesis under conditions that will not alter the structure of the peptide.

Coupling of the amino acids may be accomplished by a variety of techniques known to those of skill in the art. Typical approaches involve either the conversion of the amino acid to a derivative that will render the carboxyl group more susceptible to reaction with the free N-terminal amino group of the peptide fragment, or use of a suitable coupling agent such as, for example, N,N'-dicyclohexylcarbodiimide (DCC) or N,N'-diisopropylcarbodiimide (DIPCDI). Frequently, hydroxybenzotriazole (HOBt) is employed as a catalyst in these coupling reactions.

Generally, synthesis of the peptide is commenced by first coupling the C-terminal amino acid, which is protected at the N-amino position by a protecting group such as fluorenylmethyloxycarbonyl (Fmoc), to a solid support. Prior to coupling of an Fmoc-amino acid, the Fmoc residue has to be removed from the polymer. Fmoc-amino acid can, for example, be coupled to the 4-(α-[2,4-dimethoxyphenyl]-Fmoc-amino-methyl)phenoxy resin using N,N'-dicyclohexylcarbodiimide (DCC) and hydroxybenzotriazole (HOBt) at about 25° C. for about two hours with stirring. Following the coupling of the Fmoc protected amino acid to the resin support, the α-amino protecting group is removed using 20% piperidine in DMF at room temperature.

After removal of the α-amino protecting group, the remaining Fmoc-protected amino acids are coupled stepwise in the desired order. Appropriately protected amino acids are commercially available from a number of suppliers (e.g., Novartis (Switzerland) or Bachem (California)). As an alternative to the stepwise addition of individual amino acids, appropriately protected peptide fragments consisting of more than one amino acid may also be coupled to the "growing" peptide. Selection of an appropriate coupling reagent, as explained above, is well known to those of skill in the art.

Each protected amino acid or amino acid sequence is introduced into the solid phase reactor in excess and the coupling is carried out in a medium of dimethylformamide (DMF), methylene chloride ($CH_2Cl_2$), or mixtures thereof. If coupling is incomplete, the coupling reaction may be repeated before deprotection of the N-amino group and addition of the next amino acid. Coupling efficiency may be monitored by a number of means well known to those of skill in the art. A preferred method of monitoring coupling efficiency is by the ninhydrin reaction. Peptide synthesis reactions may be performed automatically using a number of commercially available peptide synthesizers such as the Applied Biosystems ABI 433A peptide synthesizer (Foster City, Calif.).

The peptide can be cleaved and the protecting groups removed by stirring the insoluble carrier or solid support in anhydrous, liquid hydrogen fluoride (HF) in the presence of anisole and dimethylsulfide at about 0° C. for about 20 to 90 minutes, preferably 60 minutes; by bubbling hydrogen bromide (HBr) continuously through a 1 mg/10 ml suspension of the resin in trifluoroacetic acid (TFA) for 60 to 360 minutes at about room temperature, depending on the protecting groups selected; or by incubating the solid support inside the reaction column used for the solid phase synthesis with 90% trifluoroacetic acid, 5% water and 5% triethylsilane for about 30 to 60 minutes. Other deprotection methods well known to those of skill in the art may also be used.

The peptides can be isolated and purified from the reaction mixture by means of peptide purification well known to those of skill in the art. For example, the peptides may be purified using known chromatographic procedures such as reverse phase HPLC, gel permeation, ion exchange, size exclusion, affinity, partition, or countercurrent distribution.

Recombinant Polypeptides

It will be understood by those of ordinary skill in the art that the polypeptides can also be prepared by other means including, for example, recombinant techniques. Examples of appropriate cloning and sequencing techniques, and instructions sufficient to direct persons of skill through many cloning exercises are found in Sambrook et al. 1989 Molecular Cloning—A Laboratory, Manual (2nd ed.) Vol. 1-3, Cold Spring Harbor Laboratory, Cold Spring Harbor Press, NY, (Sambrook). Product information from manufacturers of biological reagents and experimental equipment, such as the SIGMA Chemical Company (Saint Louis, Mo.), also provide information useful in known biological methods.

The polypeptides described herein are derived from papillomavirus L2 protein. The nucleotide sequence of the nucleic acid that encodes L2 is known. Accordingly, the known nucleic acid sequence can be used to make the polypeptides recombinantly or a nucleic acid encoding the desired polypeptide can be derived from the amino acid sequence.

Generally, this involves creating a nucleic acid sequence that encodes the polypeptide, placing the nucleic acid in an expression cassette under the control of a particular promoter, expressing the polypeptide in a host, isolating the expressed polypeptide and, if required, renaturing the polypeptide. Techniques sufficient to guide one of skill through such procedures are found in Sambrook, supra.

Provided with the polypeptide sequences described herein, one of skill will recognize a variety of equivalent nucleic acids that encode the polypeptide. This is because the genetic code requires that each amino acid residue in a peptide is specified by at least one triplet of nucleotides in a nucleic acid which encodes the peptide. Due to the degeneracy of the genetic code, many amino acids are equivalently coded by more than one triplet of nucleotides. For instance, the triplets CGU, CGC, CGA, CGG, AGA, and AGG all encode the amino acid arginine. Thus, at every position where an arginine is to be encoded by a nucleic acid triplet, the nucleic acid has any of the triplets which encode arginine. One of skill is thoroughly familiar with the genetic code and its use. An introduction to the subject is found in, for example, chapter 15 of Watson, et al. 1987 Molecular Biology, of the Gene (Fourth Edition, The Benjamin/Cummings Company, Inc., Menlo Park, Calif.), and the references cited therein.

Although any nucleic acid triplet or codon which encodes an amino acid can be used to specify the position of the amino acid in a peptide, certain codons are preferred. It is desirable to select codons for elevated expression of an encoded peptide, for example, when the peptide is purified for use as an immunogenic reagent. Codons are selected by reference to species codon bias tables, which show which codons are most typically used by the organism in which the peptide is to be expressed. The codons used frequently by an organism are translated by the more abundant t-RNAs in the cells of the organism. Because the t-RNAs are abundant, translation of the nucleic acid into a peptide by the cellular translation machinery is facilitated. Codon bias tables are available for most organisms. For an introduction to codon bias tables, see, e.g. Watson et al., supra.

Conservative Substitutions

In addition, it will be readily apparent to those of ordinary skill in the art that the polypeptides described herein and the nucleic acid molecules encoding such immunogenic polypeptides can be subject to various changes, such as insertions, deletions, and substitutions, either conservative or non conservative, where such changes might provide for certain advantages in their use, e.g., to increase biological activity.

One of skill will appreciate that many conservative variations of nucleic acid constructs yield a functionally identical construct. For example, due to the degeneracy of the genetic code, silent substitutions (i.e., substitutions of a nucleic acid sequence which do not result in an alteration in an encoded peptide) are an acceptable feature of every nucleic acid sequence which encodes an amino acid. In addition, one of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See Sambrook, supra.

Modifications to nucleic acids are evaluated by routine screening techniques in suitable assays for the desired characteristic. For instance, changes in the immunological character of encoded peptides can be detected by an appropriate immunological assay. Modifications of other properties such as nucleic acid hybridization to a complementary nucleic acid, redox or thermal stability of encoded proteins, hydrophobicity, susceptibility to proteolysis, or the tendency to aggregate are all assayed according to standard techniques.

Similarly, conservative amino acid substitutions, in one or a few amino acids in an amino acid sequence of a protein are substituted with different amino acids with highly similar properties (see the definitions section, supra), are also readily identified as being highly similar to a disclosed construct.

Immunogenic Conjugates

Immunogenic conjugates containing one or more of the synthetic or recombinant polypeptides described above, covalently attached to a carrier protein, are also provided. Suitable carrier proteins include, but are not limited to, the following: thyroglobulin, albumins such as human serum albumin, tetanus toxoid, polyamino acids such as poly(D-lysine:D-glutamic acid), lambda virus gpD, influenza, hepatitis B virus core protein, hepatitis B virus recombinant vaccine, and the like.

When the polypeptide and carrier protein are relatively short in length, they can be synthesized using standard chemical peptide synthesis techniques. When both molecules are relatively short, a chimeric molecule is optionally synthesized as a single contiguous polypeptide. Alternatively, the peptide and the carrier molecule can be synthesized separately and then fused chemically. Alternatively, the polypeptide and carrier can be produced individually recombinantly and then fused chemically. Most preferably, the polypeptide and carrier are produced recombinantly as a single polypeptide.

Generally, this involves creating a nucleic acid sequence that encodes the polypeptide-carrier protein immunogenic conjugate, placing the nucleic acid in an expression cassette under the control of a particular promoter, expressing the protein in a host, isolating the expressed protein and, if required, renaturing the protein. Techniques sufficient to guide one of skill through such procedures are found in Sambrook, supra.

While the polypeptide and carrier molecule are often joined directly together, one of skill will appreciate that the molecules may be separated by a spacer molecule (e.g., a peptide) consisting of one or more amino acids. Generally, the spacer will have no specific biological activity other than to join the immunogenic peptide to the carrier protein, or to preserve some minimum distance or other spatial relationship between them. However, the constituent amino acids of the spacer may be selected to influence some property of the molecule such as the folding, net charge, or hydrophobicity.

Once expressed, recombinant immunogenic conjugates can be purified according to standard procedures, including ammonium sulfate precipitation, affinity columns, column chromatography, gel electrophoresis and the like. Substantially pure compositions of about 50 to 95% homogeneity are preferred, and 80 to 95% or greater homogeneity are most preferred for use as therapeutic agents.

One of skill in the art will recognize that after chemical synthesis, or recombinant expression, the immunogenic conjugates of the present invention may possess a conformation substantially different from the native conformations of the constituent polypeptides. In this case, it is often necessary to denature and reduce the polypeptide and then to cause the polypeptide to re-fold into the preferred conformation. Methods of reducing and denaturing proteins and inducing re-folding are well known to those of skill in the art.

Multiepitope Polypeptides

In an alternative embodiment, the immunogenic polypeptides described herein are combined into multiepitope, or polyepitope, polypeptides or proteins. Typically, two or more of the immunogenic polypeptides are fused into a single polypeptide by recombinant or synthetic techniques.

In recombinant procedures, multiepitope proteins are made by ligating synthetic or recombinant nucleic acids which encode immunogenic peptides. These nucleic acids are ligated enzymatically (e.g., using a DNA ligase enzyme) or synthetically. Alternatively, a single nucleic acid molecule is synthesized which encodes multiple immunogenic peptides. In either case, the resulting nucleic acid encodes multiple immunogenic peptides, all in the same reading frame. Thus, the translated polypeptide contains two or more immunogenic peptide domains.

When the multiepitope polypeptides are produced by automated chemical synthetic procedures, concatamers of peptides are coupled directly. This is performed chemically by joining peptides using standard chemical methods. Alternatively, a polypeptide is synthetically produced that encodes multiple immunogenic peptides.

Chemical or recombinant linker regions are optionally included between immunogenic polypeptide domains to facilitate presentation of the domains to antibodies which bind the domains. In preferred embodiments, 10 to 50 amino acids are inserted between immunogenic domains. Essentially any amino acid or chemical moiety which forms amide and carboxyl linkages can be used as a linker.

Multiepitope Particles

Preferably the fusion protein should be one that self-assembles into particles, such as described in PCT/US01/25625, in which the immunogenic malaria epitope is expressed on the surface of the particles.

Alternatively, the antigen is attached to self-assembled particles, such as described in PCT/IB99/01925 or PCT/US99/24548 (e.g., papillomavirus VLPs).

Antibody Production

Antibodies that bind with specificity to the polypeptides described above are also provided. The antibodies include individual, allelic, strain, or species variants, and fragments thereof, both in their naturally occurring (full-length) forms and in recombinant forms. Additionally, antibodies are raised to these polypeptides in either their native configurations or in non-native configurations. Anti-idiotypic antibodies can also be generated. Many methods of making antibodies are known to persons of skill. The antibodies are useful as research tools for the isolation of additional quantities of the antigenic polypeptides and for studying the pathogenesis of papillomavirus in general. The antibodies may also be useful therapeutically for passive immunization of an HPV-infected patient.

The antibodies include neutralization antibodies. Methods for screening antibodies for neutralization are known in the art. A specific in vitro neutralization assay is described in Dvoretsky et al. 1980 *Virology* 103:369-375; Roden et al. 1996 *J Virol* 70:5875-5883; and Pastrana et al. 2004 *Virology* 321:205-216.

The following discussion is presented as a general overview of the techniques available for the production of antibodies; however, one of skill will recognize that many variations upon the following methods are known.

A number of immunogens are used to produce antibodies specifically reactive with polypeptides. Recombinant or synthetic polypeptides of at least 10 amino acids in length, or greater, selected from the polypeptides disclosed herein are the preferred polypeptide immunogens for the production of monoclonal or polyclonal antibodies. In one class of preferred embodiments, an immunogenic polypeptide conjugate is also included as an immunogen. The polypeptides are used either in pure, partially pure or impure form.

Recombinant polypeptides are expressed in eukaryotic or prokaryotic cells and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

Methods of producing polyclonal antibodies are known to those of skill in the art. In brief, an immunogen, preferably a purified peptide, a peptide coupled to an appropriate carrier (e.g., GST, keyhole limpet hemanocyanin, etc.), or a peptide incorporated into an immunization vector such as a recombinant vaccinia virus is mixed with an adjuvant and animals are immunized with the mixture. The animal's immune response to the immunogen preparation is monitored by taking test bleeds and determining the titer of reactivity to the peptide of interest. When appropriately high titers of antibody to the immunogen are obtained, blood is collected from the animal and antisera are prepared. Further fractionation of the antisera to enrich for antibodies reactive to the peptide is performed where desired.

Antibodies, including binding fragments and single chain recombinant versions thereof, against the polypeptides are raised by immunizing animals, e.g., using immunogenic conjugates comprising a polypeptide covalently attached (conjugated) to a carrier protein as described above. Typically, the immunogen of interest is a polypeptide of at least about 10 amino acids, in another embodiment the polypeptide is 20 amino acids in length, and in another embodiment, the fragment is about 30 amino acids in length and comprises amino acids acid residues 1 through 200 from the N-terminal of the papillomavirus L2 protein. The immunogenic conjugates are typically prepared by coupling the polypeptide to a carrier protein (e.g., as a fusion protein) or, alternatively, they are recombinantly expressed in an immunization vector.

Monoclonal antibodies are prepared from cells secreting the desired antibody. These antibodies are screened for binding to normal or modified peptides, or screened for agonistic or antagonistic activity. Specific monoclonal and polyclonal antibodies will usually bind with a $K_D$ of at least about 0.1 mM, more usually at least about 50 mM, and most preferably at least about 1 mM or better. Often, specific monoclonal antibodies bind with a $K_D$ of 0.1 mM or better.

In some instances, it is desirable to prepare monoclonal antibodies from various mammalian hosts, such as mice, rodents, primates, humans, etc. Description of techniques for preparing such monoclonal antibodies are found in Kohler and Milstein 1975 *Nature* 256:495-497. Summarized briefly, this method proceeds by injecting an animal with an immunogen, e.g., an immunogenic peptide of the present invention either alone or optionally linked to a carrier protein. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The polypeptides and antibodies of the present invention are used with or without modification, and include chimeric antibodies such as humanized murine antibodies. Other suitable techniques involve selection of libraries of recombinant antibodies in phage or similar vectors. See, Huse et al. 1989 *Science* 246:1275-1281; and Ward et al. 1989 *Nature* 341:544-546.

Frequently, the polypeptide or antibody will be labeled by joining, either covalently or noncovalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

As mentioned above, the antibodies provided herein can be used in affinity chromatography for isolating additional amounts of the polypeptides identified herein. Columns are prepared, e.g., with the antibodies linked to a solid support, e.g. particles, such as agarose, Sephadex, or the like, where a cell lysate is passed through the column, washed, and treated with increasing concentrations of a mild denaturant, whereby purified polypeptides are released. In addition, the antibodies can be used to screen expression libraries for particular expression products, for example, papillomavirus proteins. Usually, the antibodies in such a procedure are labeled with a moiety allowing easy detection of presence of antigen by antibody binding. Moreover, antibodies raised against the immunogenic polypeptides described herein can also be used to raise anti-idiotypic antibodies. Such antibodies are useful for detecting or diagnosing various pathological or resistance conditions related to the presence of the respective antigens.

Immunoassays

Both the polypeptides described herein and the antibodies that bind with specificity to the polypeptides are useful as reagents, as capture agents or labeling agents, in assays to detect a target peptide or antibody. In general, the target molecule can be quantified by a variety of immunoassay methods. Moreover, the immunoassays can be performed in any of several configurations.

Immunoassays often utilize a labeling agent to specifically bind to and label the binding complex formed by the capture agent and the analyte. The labeling agent may itself be one of the moieties comprising the antibody/analyte complex. Thus, the labeling agent may be a labeled peptide or a labeled anti-peptide antibody. Alternatively, the labeling agent may be a third moiety, such as another antibody, that specifically binds to the antibody/peptide complex, or to a modified capture group (e.g., biotin) which is covalently linked to the peptide or anti-peptide antibody.

Alternatively, the labeling agent can be a streptavidin molecule which has a fluorescent dye on it and onto which are captured the peptides complexed with MHC (HLA) molecules. These reagents can be used to count single T cells specific for the peptides using commonly used equipment such as flow cytometers, thus providing precise quantitation and phenotype information on the immune response as described by Altman, J. D. et al. 1996 *Science* 274:94-96.

In a preferred embodiment, the labeling agent is an antibody that specifically binds to the capture agent. Such agents are well known to those of skill in the art, and most typically comprise labeled antibodies that specifically bind antibodies of the particular animal species from which the capture agent is derived, such as an anti-idiotypic antibody, or antibodies against a peptide when the peptide is the capture agent. Thus, for example, where the capture agent is a mouse derived anti-peptide antibody, the label agent may be a goat anti-mouse IgG, e.g., an antibody specific to the constant region of the mouse antibody.

Other proteins capable of specifically binding immunoglobulin constant regions, such as streptococcal protein A or protein G are also used as the labeling agent. These proteins are normal constituents of the cell walls of streptococcal bacteria. They exhibit a strong nonimmunogenic reactivity with immunoglobulin constant regions from a variety of species.

Throughout the assays, incubation and/or washing steps may be required after each combination of reagents. Incubation steps can vary from about five seconds to several hours, preferably from about five minutes to about 24 hours. However, the incubation time will depend upon the assay format, analyte, volume of solution, concentrations, and the like. Usually, the assays are carried out at ambient temperature, although they can be conducted over a range of temperatures, such as 5° C. to 45° C.

Non competitive assay formats such as "sandwich" assays, where the captured analyte (e.g., anti-peptide antibody) is directly measured may be used. In competitive assays, the amount of analyte (e.g. immunogenic peptide or antibody to an immunogenic peptide) present in the sample is measured indirectly by measuring the amount of added (exogenous) analyte displaced (or competed away) from a capture agent (e.g., an antibody or peptide) by the analyte present in the sample. Other assay formats such as Western blot analysis may also be utilized. Depending on the assay, various components, including the immunogenic polypeptide or anti-peptide antibody may be bound to a solid surface ("solid phase" assay).

Broad Cross-Neutralizing Responses against Cutaneous and Genital Types, or in Another Embodiment Against Heterologous Types We have discovered that epitopes at the N-terminus of L2 shared by cutaneous and mucosal types and by types that infect divergent species are broadly cross-neutralizing. BPV1 L2 was exceptionally effective at inducing cross-neutralizing antibodies to these shared epitopes. To map which polypeptide of the BPV1 L2 was responsible for the cross-neutralization, sera raised against different regions of BPV1 L2 were tested for their anti-BPV1 and HPV16 activity. There is 67.4% identity between HPV16 and HPV18 within the first 88 amino acids of these proteins. The high homology in this region and its importance in infectivity raised the possibility that an immunogen based on a peptide from this region might induce cross-neutralizing antibodies against divergent HPV types. The present invention is based on the finding that BPV1 L2 amino acids 1-88, or equivalent thereof, constitutes an immunogen capable of generating broad cross-neutralizing responses against both cutaneous and genital types of human papillomaviruses, or in another embodiment against heterologous types.

Pharmaceutical Compositions

Vaccine and other pharmaceutical compositions containing one or more of the polypeptides or antibodies described herein in a pharmaceutically acceptable carrier are provided. The compositions are useful in therapeutic and prophylactic methods for the treatment, prevention, or reduction of papillomavirus infection in mammals, preferably in humans. Such compositions are suitable for use in a variety of drug delivery systems. Suitable formulations are found in Remington's Pharmaceutical Sciences, Mack Publishing Company, Easton, Pa., 18th ed. (1990). A brief review of methods for drug delivery is provided by Langer 1990 *Science* 249:1527-1533.

The compositions are suitable for single administrations or a series of administrations. When given as a series, inoculations subsequent to the initial administration are given to boost the immune response and are typically referred to as booster inoculations.

The pharmaceutical compositions are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration that comprise a solution of the agents described above dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10% to 95% of active ingredient and more preferably at a concentration of 25% to 75% of active ingredient.

For aerosol administration, the polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, such as the inclusion of lecithin for intranasal delivery.

The amount administered to the patient will vary depending upon what is being administered, the state of the patient and the manner of administration. In therapeutic applications, compositions are administered to a patient already infected with the papillomavirus in an amount sufficient to inhibit spread of the virus, or at least partially arrest the symptoms of the disease and its complications. An amount adequate to accomplish this is defined as "therapeutically effective dose." Amounts effective for this use will depend on the severity of the disease, the particular composition, and the weight and general state of the patient. Generally, the dose will be in the range of about 100 µg to about 3000 µg per day, preferably about 1500 µg per day, for a 70 kg patient.

More preferably, the polypeptide is used prophylactically as a vaccine. All of the immunogenic polypeptides disclosed herein can be used as vaccines, either alone or in combination, as in a multiepitope or polyepitope vaccine. The immune response may include the generation of antibodies, activation of cytotoxic T lymphocytes (CTL) against cells presenting the immunogenic polypeptides, or another mechanism well known in the art. Preferably, the immune response includes the generation of neutralizing antibodies. The preferred dose will be in the range of 100 µg to about 3000 µg per day, preferably about 1500 µg per day, administered in one to six doses.

Adjuvants

The vaccines can also contain an adjuvant. Adjuvants such as incomplete Freund's adjuvant, aluminum phosphate and aluminum hydroxide are materials well known in the art. Other adjuvants useful with the present invention include QS-21, Detox-PC, MPL-SE, MoGM-CSF, TiterMax-G, CRL-I005, GERBU, TERamide, PSC97B, Adjumer, PG-026, GSK-1, GcMAF, B-alethine, MPC-026, Adjuvax, CpG ODN, Betafectin, Alum, AS04 and MF59 (see Kim et al. *Vaccine* 1999 18:597-603 and references therein).

Polynucleotide Vaccines

In addition, DNA or RNA encoding the immunogenic polypeptides of the present invention may be introduced into patients to obtain an immune response to the immunogenic polypeptides which the nucleic acid encodes. See Wolff, et al. 1990 *Science* 247:1465-1468 which describes the use of nucleic acids to produce expression of the immunogenic polypeptides which the nucleic acids encode. Vaccines composed of DNA or RNA encoding immunogenic polypeptides are commonly referred to in the art as polynucleotide vaccines.

Vaccine compositions containing the immunogenic polypeptides and nucleic acids of the invention are administered to a patient to elicit a protective immune response against the polypeptide. A "protective immune response" is one which prevents or inhibits the spread of papillomavirus and, thus, at least partially prevents the symptoms of the disease and its complications. An amount sufficient to accomplish this is defined as an "immunogenically effective dose." Amounts effective for this use will depend on the composition, the manner of administration, the weight and general state of health of the patient, and the judgment of the prescribing physician. For peptide compositions, the general range for the initial immunization (that is for therapeutic or prophylactic administration) is from about 100 µg to about 3000 µg per day, preferably about 1500 µg per day, followed by boosting dosages of the peptide pursuant to a boosting regimen over weeks to months depending upon the patient's response and condition, e.g., by measuring levels of papillomavirus in the patient's blood. For nucleic acids, the same range of doses is preferred.

Cutaneous and Mucosal Warts

Common, contagious, epithelial tumors are caused by over 100 types of human papillomavirus. Warts may appear at any age but are most frequent in older children and uncommon in the elderly. Warts may be single or multiple and may develop by autoinoculation. Appearance and size depend on the location and on the degree of irritation and trauma. The course may be variable. Complete regression after many months is usual, but warts may persist for years and may recur at the same or different sites. Some warts can become malignant (See Table B).

TABLE B

Types of Wart Virus and Clinical Correlations

| Clinical Form | Human Papillomavirus Type | Clinical correlations |
| --- | --- | --- |
| Common: (palmar, plantar and periungual) | 1, 2, 4, 7, 27, 57, 63 and 65. | Benign (see Hagiwara K. et al. 2005 J Med Virol 77: 107-112). |
| Flat | 3, 10 | Benign |
| Genital (also found in the mouth, perianal area, bladder and lung) | 6,11 | Of women, 28% have associated cervical dysplasia with koilocytic cells |
| | 16, 18, 31, 33, 35, 39, 45, 51, 52, 56, 58, 59, 66, 68 and 73. | These are the 15 types thought to cause cervical cancer (see Munoz N. et al. 2004 Int J Cancer 111: 278-285). |
| | 6a, b, c, d, e | Bushke-Löewenstein giant condyloma often malignant; also in cervical dyslasia and laryngeal tumors. |
| Butcher's (meat handler's) | 7, 10 | Common warts, usually benign. |
| Malignant epidermodysplasia verruciformis | 5a, b; 8 | Often malignant; sunlight and x-ray therapy are cofactors, especially with type 5. |
| Epidermodysplasia verruciformis | 1, 2, 3, 4, 7, 9, 10, 12, 14, 17, 18, 19, 20, 23, 24, 25 | Most seem benign, except possibly 14, 17 and 20. |
| Cutaneous warts in immunosuppressed transplantation patients | 8 or others | Often malignant; sunlight a cofactor. |

TABLE B-continued

Types of Wart Virus and Clinical Correlations

| Clinical Form | Human Papillomavirus Type | Clinical correlations |
|---|---|---|
| Laryngeal papillomas | 6, 11, 16, 30 | May become malignant; may occur in infants on passage through the vaginal canal and in adults as a consequence of oral genital sex. May spread to lungs as cancer. |
| Oral papillomas (Heck's Disease) | 13 | Benign |

Common warts (verrucae vulgaris) are almost universal in the population. They are sharply demarcated, rough-surfaced, round or irregular, firm, and light gray, yellow, brown, or gray-black nodules 2 to 10 mm in diameter. They appear most often on sites subject to trauma (e.g., fingers, elbows, knees, face) but may spread elsewhere. Periungual warts (around the nail plate) are common, as are plantar warts (on the sole of the foot), which are flattened by pressure and surrounded by cornified epithelium. They may be exquisitely tender and can be distinguished from corns and calluses by their tendency to pinpoint bleeding when the surface is pared away. Mosaic warts are plaques formed by the coalescence of myriad smaller, closely set plantar warts. Filiform warts are long, narrow, frondlike growths usually on the eyelids, face, neck, or lips. This morphologically distinctive variant of the common wart is benign and easy to treat. Flat warts (smooth, flat-topped, yellow-brown papules) are more common in children and young adults, most often on the face and along scratch marks, and develop by autoinoculation. Variants of the common wart that are of unusual shape (e.g., pedunculated, or resembling a cauliflower) are most frequent on the head and neck, especially on the scalp and bearded region.

Anogenital warts caused by HPV types 6, 11, 16, 18, 31, 33, and 35 are transmitted sexually and have an incubation period of 1 to 6 months. Cervical wart infections caused by types 16 or 18 have been implicated as a cause of cervical intraepithelial neoplasia and cervical cancer. Types 16 and 18 HPV generally do not cause external genital warts, which are usually caused by types 6 and 11. The 15 types thought to cause cervical cancer are HPV16, HPV18, HPV31, HPV33, HPV35, HPV39, HPV45, HPV51, HPV52, HPV56, HPV58, HPV59, HPV66, HPV68 and HPV73 (see Munoz. et al. 2004 Int J Cancer 111: 278-285).

Genital warts usually appear as soft, moist, minute pink or gray polyps that enlarge, may become pedunculated, and are usually found in clusters. The surfaces resemble the surface of a cauliflower. In men, they occur most commonly on warm, moist surfaces in the subpreputial area, on the coronal sulcus, within the urethral meatus, and on the penile shaft. In women, the vulva, the vaginal wall, the cervix, and the perineum may become involved. They are particularly common in the perianal region and rectum in homosexual men and may be more severe and difficult to treat in immunosuppressed patients. Growth rates vary, but pregnancy, immunosuppression, or maceration of the skin may accelerate both the growth of individual lesions and their spread.

Genital warts usually can be identified by their appearance but must be differentiated from the flat-topped condyloma lata of secondary syphilis. Biopsies of atypical or persistent warts may be necessary to exclude carcinoma. Cervical warts can be detected only at colposcopy and should not be treated until Papanicolaou smear results are available.

Cytologic and Histologic Analyses

In one embodiment, cervical samples for Papanicolaou testing are deposited in sectioning compound that can be hardened for thin sectioning. Thin-layer slides are prepared according to the manufacturer's specifications, screened by cytotechnologists, and reviewed by pathologists at designated cytology laboratories. The results are classified as unsatisfactory if more than 60 percent of the target area of the slide has no epithelial cells. Cellular changes are classified according to the Bethesda system (Kurman, R. J. et al. 1991 Obset Gynecol 77:779-782). Cervical-biopsy specimens are fixed in 10 percent formalin and embedded in paraffin. Slides are stained with hematoxylin and eosin and reviewed first by a laboratory pathologist for purposes of clinical care, and second by an independent pathologist who has no knowledge of the women's other clinical or laboratory data. Diagnoses are assigned according to the Bethesda and cervical intraepithelial neoplasia systems (Kurman, R. J. et al. 1991 Obset Gynecol 77:779-782).

Detection of HPV DNA by Hybridization Assays

A variety of hybridization assays have been employed for detection of HPVs. Nick-translated or random-primed DNA probes and in vitro-transcribed RNA probes are prepared from reference DNA clones. The probes can be labeled with radioactive or nonradioactive compounds. Southern hybridization of DNAs extracted from fresh or fresh-frozen tissues serves well. Dot-blot and slot-blot hybridization techniques are another example. Reverse-blot hybridization also serves for HPV detection. In tissue in situ hybridization tests, cells or tissue sections on slides are hybridized using radioactive or nonradioactive probes. This is another example for HPV detection.

Detection of HPV DNA by PCR

Another method to detect HPV DNA utilizes polymerase chain reaction (PCR). Cutaneous or genital specimens are prepared for PCR according to standard methods. DNA is amplified with the use of HPV type-specific primers based on HPV L1, or alternatively E6, and E7 genes. PCR products are identified by hybridization with the use of HPV type- and gene-specific oligonucleotides. A positive result is defined as any signal that exceeds the background level associated with an HPV negative sample of human DNA. Appropriate negative and positive controls are included in each assay. Any sample that tests positive for at least two genes is considered positive. Any sample that tests positive for only one gene is considered positive if, on retesting, it is positive for two or three genes or the same single gene.

HPV Serologic Assay

Serological assays are used to quantify serum HPV antibodies using immunoassays such as those described hereinbefore. HPV polypeptides are used as capture agents to detect a target antibody. A serological assay based on virus like particles (VLPs) is the most extensively used and validated method for type-specific serodiagnosis of HPV infection (Kirnbauer et al., 1994 *J Natl Cancer Inst* 86: 494-499). Serum antibodies directed against an HPV of interest can be quantified by a variety of immunoassay methods and the immunoassays can be performed in any of several configurations.

Cross-Neutralization of Cutaneous and Mucosal Papillomavirus Types with Anti-Sera to the Amino Terminus of L2

Cross-Neutralization of BPV1, HPV16, and HPV18 Pseudoviruses with Anti-Full-Length L2 Serum Neutralization of different papilloma pseudoviruses with sera from rabbits immunized with L2 (full-length or peptides) was performed. As positive and type-specificity controls, and for inter-assay normalization of the different papillomavirus neutralization assays, L1 VLP antiserum or monoclonal antibodies were used; H16.V5 monoclonal for HPV16 (Christensen, N. D. et al. 1996 *Virology* 223:174-184), 5B6 monoclonal for BPV1 (Roden, R. B. S. et al. 1994 *J Virol* 68:7570-7574), or sera from rabbits immunized with VLPs from the homologous type for the remaining pseudoviruses. As described previously (Roden, R. B. et al. 2000 *Virology* 270: 254-257), none of the sera raised against L1 or L1/L2 VLP immunogens derived from HPV6, HPV16, HPV18, BPV1 or CRPV induced cross-neutralizing antibodies in the pseudovirus infectivity assays tested. This is consistent with the presence of immuno-dominant neutralizing epitopes in L1 and the sub-dominance of L2 in the context of the capsid (Roden, R. B. et al. 2000 *Virology* 270:254-257).

Analysis of anti-full-length L2 sera was initially performed with BPV1, HPV16 and HPV18 pseudoviruses. The sera showed neutralization of the homologous types with reciprocal titers that were 600 for BPV1; 2100 for HPV16; and 1350 for HPV18 (Table 1A). Unlike L1 VLP antiserum, anti-HPV18 and HPV16 full-length L2 sera showed reciprocal cross-neutralization. These two types had been shown to share neutralizing L2 epitope(s) (Roden, R. B. et al. 2000 *Virology* 270:254-257), and their L2 proteins share 53.4% amino acid identity (FIG. 3). Anti-sera raised against recombinant full-length HPV16, and HPV18 L2 protein were also able to neutralize BPV1 pseudoviruses in this assay, albeit with lower titers (Table 1A). In a previous study, neutralizing activity against BPV1 pseudoviruses was not detected in the sera of sheep immunized with these proteins (Roden, R. B. et al. 2000 *Virology* 270:254-257); however, the lack of neutralization might be attributable to the less sensitive neutralization method used in that study. Unexpectedly, a serum raised against full-length BPV1 L2 neutralized HPV16 and HPV18 pseudovirions as effectively as it neutralized BPV1 pseudovirions. HPV16 and HPV18 L2 proteins only share 38.4% or 35.7% amino acid identity, respectively, with BPV1 L2 (FIG. 3). Another unexpected result was the relative lack of cross-neutralization of HPV types that are more closely related. For example, serum against HPV31 L2, which shares 69% identity with HPV16 and 54.3% with HPV18 (FIG. 3), only neutralized HPV16 at a titer of 110 and did not neutralize HPV18 at the highest concentration tested (1:50). The anti-HPV6 L2 serum cross-neutralized HPV16 and HPV18, but not BPV1. CRPV L2 shares 34-39% identity with BPV1, HPV16 and HPV18 L2, and although it also unexpectedly cross-neutralized HPV16 with relatively high titers (1350) (Table 1A), it failed to neutralize BPV1 and HPV18.

TABLE 1A

Cross-neutralization of divergent human and animal papillomaviral pseudoviruses by polyclonal antisera to full length L2 from diverse papillomaviruses

| Anti-Serum | Neutralization Titer* | | | | | |
|---|---|---|---|---|---|---|
| | BPV1 | HPV16 | HPV18 | HPV31 | HPV6 | CRPV |
| Preimmune full length BPVL2 | <50 (2) | <50 (2) | <50 (2) | <50 (2) | <50 (2) | <50 (2) |
| Full-length BPV L2-His | 600 (4) | 780 (4) | 1780 (4) | <50 (2) | <50 (2) | <50 (2) |
| Full-length HPV16 L2-GST | <50 (2) | 12,150 (4) | 1350 (2) | 2340 (2) | 260 (2) | 450 (3) |
| Full-length HPV16 L2-His | 90 (8) | 2100 (10) | 650 (6) | 260 (2) | 110 (4) | 90 (2) |
| Full-length HPV18 L2-His | 150 (2) | 4050 (2) | 1350 (2) | 450 (2) | 70 (3) | 70 (3) |
| Full-length HPV31 L2-His | <50 (2) | 110 (4) | <50 (2) | 450 (2) | <50 (3) | <50 (3) |
| Full-length HPV6 L2-His | <50 (2) | 90 (2) | 150 (2) | <50 (2) | 4050 (3) | <50 (3) |
| Full-length CRPV L2-His | <50 (2) | 1350 (4) | <50 (2) | 780 (2) | 260 (2) | 10,120 (6) |

*The bolded and underlined titers in this table represent the geometric mean neutralization titer against the homologous virus. The number in parenthesis indicates the number of times the assay was performed.

TABLE 1B

Cross-neutralization of divergent human and animal papillomaviral pseudovirus types by polyclonal antisera to BPV1 or HPV16 amino-terminal L2 peptides

| Anti-Serum | Neutralization titer[a] | | | | | |
|---|---|---|---|---|---|---|
| | BPV1 | HPV16 | HPV18 | HPV31 | HPV6 | CRPV |
| BPV1 L2 a.a. 1-88 | 3460 (7) | 4740 (7) | 7020 (5) | 220 (3) | 340 (4) | 780 (3) |
| HPV16 L2 a.a. 1-88#1 | <50 (4) | 3080 (4) | 150 (2) | 260 (2) | <50 (4) | 260 (2) |
| HPV16 L2 a.a. 1-88#2 | 50 (4) | 1350 (4) | 150 (2) | 260 (2) | <50 (4) | <50 (2) |
| HPV16 L2 a.a. 1-88#3 | 50 (4) | 1780 (4) | 150 (2) | 90 (2) | 90 (4) | 260 (2) |
| HPV16 L2 a.a. 1-88#4 | <50 (4) | 780 (4) | 90 (2) | 150 (2) | 60 (4) | 90 (2) |

[a]Titers are given as geometric means. The number in parenthesis indicates the number of times the assay was performed These data together indicated that BPV1 L2 has epitope(s) that are either more immunogenic or more efficiently displayed/folded and allows for generation of reactive, broadly cross-neutralizing anti-L2 sera. The apparent broad cross-neutralizing activity obtained with the full-length BPV1 L2 serum, although promising, also generated some concerns because it was obtained from a single animal. Immunization of another animal with the same recombinant preparation showed similar homologous and heterologous (HPV16) neutralization results (Table 2). Furthermore, similar results were obtained with GST and 6-His tagged HPV16 L2 antiserum (Table 1A), indicating that the tag plays no role in generating neutralizing antibodies.

TABLE 2

Neutralization of BPV1 and HPV16 pseudoviruses by polyclonal antisera to BPVL2 polypeptides

| Antiserum | Neutralization titer | |
|---|---|---|
| | BPV1 | HPV16 |
| Pre-immune full length BPV1 L2 | <50 (2) | <50 (2) |
| Full-length BPV1 L2#1 | 600 (4) | 780 (4) |
| Full-length BPV1 L2#2 | 780 (2) | 780 (2) |
| BPV1 L2 a.a. 1-88#1 | 2600 (5) | 1780 (4) |
| BPV1 L2 a.a. 1-88#2 | 3460 (7) | 4740 (7) |
| BPV1 L2 a.a. 45-173 | 90 (4) | <50 (4) |
| BPV1 L2 a.a. 130-257 | <50 (4) | <50 (4) |
| BPV1 L2 a.a. 216-340 | <50 (2) | <50 (2) |
| BPV1 L2 a.a. 300-425 | <50 (2) | <50 (2) |
| BPV1 L2 a.a. 384-469 | <50 (2) | <50 (2) |

Titers are given as geometric means. The number in parenthesis indicates the number of times the assay was performed.

Cross-Neutralization of BPV1, HPV16, and HPV18 Pseudoviruses with Anti-L2 a.a. 1-88 Serum To map which polypeptide of the BPV1 L2 was responsible for the cross-neutralization, sera raised against different regions BPV1 L2 were tested for their anti-BPV1 and HPV16 activity. The only defined cross-neutralizing epitope described so far is for residues 108-120 of HPV16 L2 (Kawana, K. et al. 1999 *J Virol* 73:6188-6190). This peptide is a conserved region in L2 with 46% identity between HPV16 and HPV18. However, there is little homology with BPV1 L2 in this region (15% identity). In contrast, the amino termini of L2 proteins of different PV types exhibit considerably higher percent identities, even for distantly related papillomaviruses. There is 67.4% identity between HPV16 and HPV18 within the first 88 amino acids of these proteins, and both HPV16 and HPV18 share roughly 55% identity with BPV1 L2 (FIG. 3), indicating a conserved structure and perhaps also function. Of note, BPV1 L2 amino acids 1-88 encompass a region that can bind to the surface of a variety of cell lines, interfere with BPV1 infection, and may be involved in transport of particles across the cytoplasm (Yang, R. et al. 2003 *J Virol* 77:3531-3541). Furthermore, a portion of the region appears to be displayed on BPV1 virion surfaces (a.a. 61-123) (Liu, W. J. et al. 1997 *Virology* 227:474-483). In addition, Kawana et al. (Kawana, K. et al. 1999 *J Virol* 73:6188-6190) showed that the epitope of an HPV16 monoclonal antibody that neutralizes HPV16 but not HPV6 also maps to residues 69-81. The only two cysteines of L2 and a region very rich in glycines (FIG. 3), both with unknown function, are in this 1-88 region. Highly conserved lysines and arginines involved in DNA binding (Zhou, J. et al. 1994 *J Virol* 68:619-625) and infection (Roden, R. B. et al. 2001 *J Virol* 75:10493-10497) are also in this region. The high homology in this region and its importance in infectivity raised the possibility that an immunogen based on a peptide from this region might induce cross-neutralizing antibodies against divergent HPV types.

Anti-BPV1 L2 1-88 sera from two rabbits were able to neutralize HPV16 and BPV1 pseudovirions with approximately the same titers (Table 2), attesting to the reproducibility and to the ability of sera raised against the N-terminal portion of BPV1 L2 to have good neutralizing activity against HPV16. Anti-BPV1 L2 1-88 sera had neutralizing titers ranging between 1780 and 4740 (Table 2), confirming what had been seen with full-length BPV1 L2 immunization. Furthermore, serum from a third rabbit, immunized with a different preparation of the BPV1 L2 1-88 recombinant protein, had similar activity.

Cross-Neutralization of Native HPV11 Virions by L2 a.a. 1-88 Antiserum

Figure 4:
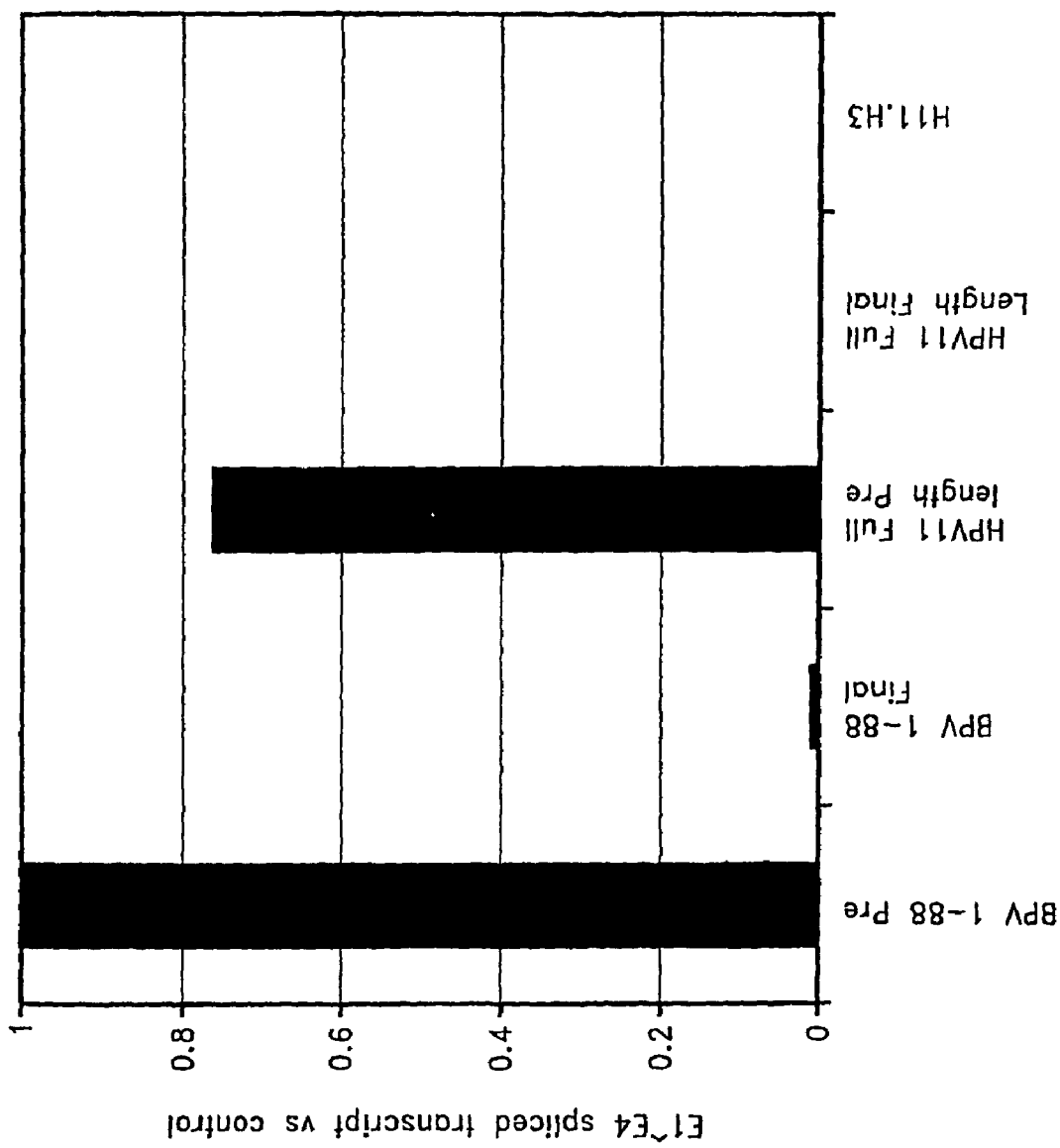
FIG. 4. Neutralization of native HPV11 virions by BPV1 L2 1-88 antiserum.

Although BPV1 L2 1-88 antisera neutralizes BPV1 virions in the focal transformation assay (Roden, R. B. S. et al. 1994 *J Virol* 68:7570-7574), it was possible that the observed cross-neutralization was an artifact of the pseudovirion system. To address this issue and extend evidence of cross-neutralization to another HPV type, we tested the ability of BPV1 L2 1-88 antisera to neutralize native HPV11 in vitro (FIG. 4). Both neutralizing monoclonal antibody H11.H3 and rabbit antiserum to full-length HPV11 L2 (1:50) completely neutralized HPV11 infection. Furthermore, a 1:50 dilution of BPV1 L2 1-88 antiserum, but not the pre-immune serum, also neutralized native HPV11 virions. In addition to showing that BPV1 L2 1-88 can also neutralize HPV11, this result supports the conclusion that the neutralization data obtained with pseudovirus assay are biologically relevant.

We sought to further define the nature of the cross-neutralizing epitopes. An anti-BPV1 L2 45-172 serum that had previously been shown to neutralize BPV1 (Roden, R. B. S. et al. 1994 *J Virol* 68:7570-7574) failed to neutralize HPV16, although it did neutralize BPV1 in our assay at low titers. Sera raised against peptides 130-257, 216-340, 300425 and 384-469 failed to neutralize either BPV1 or HPV16 pseudovirus detectably (Table 2). Analysis for all experiments in Tables 1A and 1B and 2 shows that rabbits vaccinated with the L2 1-88 peptide (n=7) do not generate significantly higher titers against homologous type virus than rabbits (n=8) vaccinated with the full-length L2 protein (P=0.28). Our data are consistent with the localization of the major cross-neutralizing epitopes at the N-terminus of L2. The high titer cross-neutralizing response obtained when immunizing with the amino terminus of BPV1 L2 indicates that vaccination strategies should focus on this highly conserved region.

Figure 5:
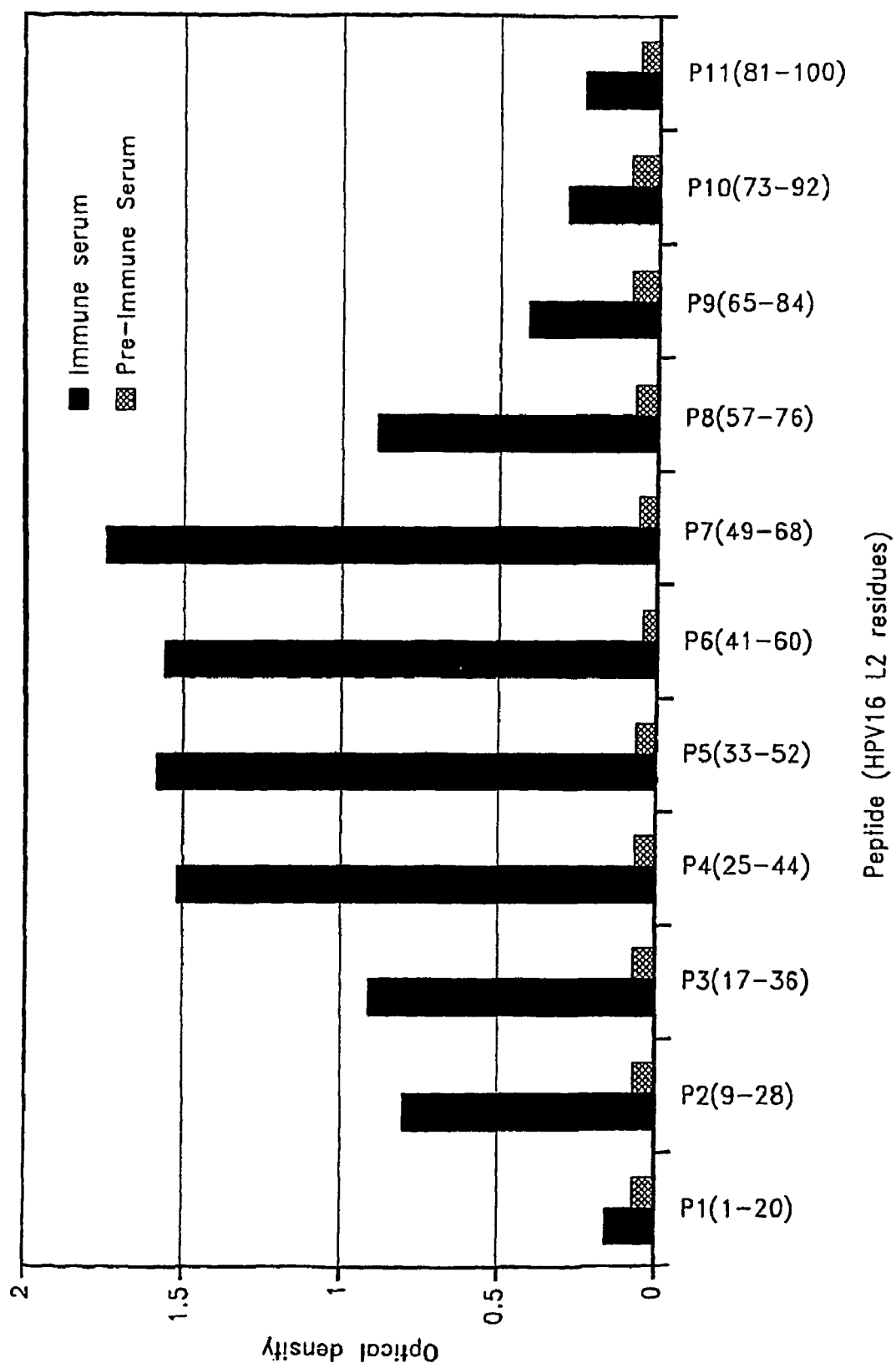
FIG. 5. Reactivity of BPV1 L2 1-88 antiserum with an HPV16 L2 peptide array.

To further define the nature of the cross-neutralizing epitopes in HPV16 L2 recognized by BPV1 L2 1-88 antiserum, we tested its reactivity with a peptide array comprising 20-mer peptides of the first hundred amino acids of HPV16 L2 that overlapped by 12 residues. While no single epitope was dominant, reactivity mapped predominantly to the central region of this peptide (FIG. 5).

We also examined sera from amino acids 1-88 of HPV16 L2 for cross-neutralizing activity. Sera from all four immunized rabbits had relatively high homologous neutralization titers (Table 1B) that ranged from 780 to 3080 and differed by less than 4-fold. All of the anti-HPV16 L2 1-88 sera were able to cross neutralize HPV18, but with lower titers than those observed with the anti BPV1 L2 1-88 sera. Only two of the four anti-HPV16 L2 1-88 sera tested were able to neutralize BPV1 pseudoviruses at 1:50. Although the mean titer of the anti BPV1 L2 1-88 serum appears to be higher against the heterologous HPV16 and HPV18 pseudovirions than against the homologous type, in each case, the median neutralization titers are 4050, whether it is against BPV1, HPV16 or HPV18 pseudovirus, and they do not differ more than 3-fold from the median for each type. However, subtle effects of differing particle to infectivity ratios between pseudovirions preparations are also possible. The neutralizing titer against homologous type pseudovirus generated by vaccination with residues 1-88 from BPV1 (3 rabbits) and HPV16 (4 rabbits) were not significantly different (P=0.67). By contrast, the neutralizing titer of antiserum to BPV1 peptide 1-88 neutralized HPV16 pseudovirus with a higher titer than antiserum to HPV16 peptide 1-88 against BPV1 pseudovirus (P=0.02). These results again pointed to BPV1 L2 1-88 being a better immunogen than HPV16 L2 for eliciting cross-neutralizing HPVs.

It is possible that neutralization titers against homologous type virus versus heterologous type virus might vary after repeated immunization. Therefore, we measured the BPV1 and HPV16 pseudovirion neutralizing titers of L2 1-88 antisera of BPV1 and HPV16 from sera obtained 74 days (P1), 88 days (P2) and 102 days (Final) after the initial immunization from animals that had received 3 or 4 boosts (Table 3). Both sera demonstrated a consistent neutralization titer against homologous type and heterologous type virus. Thus, we find no evidence of narrowing of BPV1 L2 1-88 antiserum specificity over this time window and with repeated boosts.

TABLE 3

Stability of neutralization titers with repeated immunization

| Serum | Bleed | Boosts | Day | Anti HPV16 titer | Anti BPV1 titer |
|---|---|---|---|---|---|
| Rabbit S844-2 anti HPV16 L2 1-88 | Prebleed | 0 | 0 | <50 | <50 |
| | P1 | 3 | 74 | 4050 | 50 |
| | P2 | 4 | 88 | 4050 | 150 |
| | Final | 4 | 102 | 4050 | 50 |

TABLE 3-continued

Stability of neutralization titers with repeated immunization

| Serum | Bleed | Boosts | Day | Anti HPV16 titer | Anti BPV1 titer |
|---|---|---|---|---|---|
| Rabbit 5315#2 anti-BPV1 L2 1-88 | Prebleed | 0 | 0 | <50 | <50 |
| | P1 | 3 | 74 | 12,150 | 12,150 |
| | P2 | 4 | 88 | 12,150 | 12,150 |
| | Final | 4 | 102 | 12,150 | 12,150 |

Cross Neutralization of HPV31, HPV6, and CRPV Pseudoviruses with Anti-Full-Length L2 Serum Sera raised against full-length L2s were also tested against additional pseudoviruses. The BPV1 full-length L2 sera, which had cross-neutralized HPV16 and 18 pseudoviruses, was unexpectedly negative against HPV31, CRPV and HPV6 (Table 1A). HPV16 L2 shares about 69.1% identity with HPV31, but only 53.6% and 39.4% with HPV6 and CRPV, respectively. However, anti-HPV16 L2 sera cross-neutralized HPV31, HPV6 and CRPV, and the titers differed by no more than 3-fold (Table 1A). HPV31 L2 shares 38.7% identity with CRPV, an identity similar to that between HPV16 and CRPV, but anti-HPV31 L2 was unable to neutralize CRPV pseudoviruses. It is tempting to attribute the lack of cross-reactivity to the relatively low homologous titer of that serum (450); however, the homologous BPV1 L2 titer was comparable (600), and as noted above this serum was able to cross-neutralize HPV16 and HPV18 with similar titers (Table 1A). Anti-HPV31 full-length L2 serum also failed to neutralize CRPV and HPV6 pseudovirions. In addition to its HPV16 cross-neutralizing capabilities, the anti-CRPV L2 serum was also cross-neutralizing for HPV31 and HPV6, but not for HPV18 or BPV1, despite a similar degree of homology with these proteins.

Cross-Neutralization of HPV31, HPV6, and CRPV Pseudoviruses with Anti-L2 a.a. 1-88 serum We tested anti-BPV1 L2 a.a. 1-88 serum. Despite the failure of anti-full-length BPV1 L2 serum to neutralize HPV31, we found that the anti-BPV1 L2 1-88 peptide serum was able to cross-neutralize HPV31, with titers similar to those obtained with anti-HPV16 L2 peptide 1-88 (Table 1B). Identities in this region of L2 between HPV16 and HPV31 are 77% (FIG. 3), and 58% between BPV1 and HPV31. The anti-BPV1 L2 serum was also able to neutralize HPV6 with a titer of 340 and CRPV with a titer of 780. Of note is the fact that the 1-88 a.a. region of BPV1 L2 has about the same amount of homology (56-58%) with HPV16, HPV18, HPV31 and HPV6; and only slightly lower (47.6%) with CRPV (FIG. 3).

Serum IgG is Responsible for the Cross-Neutralizing Activity

To determine whether immune IgG was responsible for the cross-neutralization, the following two experiments were conducted. In the first experiment, sera depleted of IgG using protein G Sepharose was tested in HPV16 and BPV1 neutralization assays. Neither pre- nor post-immune IgG depleted sera were able to neutralize either HPV16 or BPV1 pseudovirus (Table 4). In the second experiment, IgG from pre- and post-immune samples were purified using protein G columns (Pierce). Purified IgG from pre-immune sera was unable to neutralize either pseudovirus (Table 4) at the highest concentration tested, 1:30 (28 ng/µl), while purified IgG from anti-BPV1 L2 1-88 serum neutralized both BPV1 and HPV16 at a dilution of 6400 (0.2 ng/µl). Purified IgG from rabbits immunized with HPV16 L2 1-88 neutralized both HPV16 and BPV1, but the titers were higher against HPV16 compared to BPV1, as had been observed with whole serum (Table 4).

TABLE 4

Cross-neutralization of BPV1 and HPV16 pseudoviruses is IgG-dependent

| | Neutralization titer | | | | | |
|---|---|---|---|---|---|---|
| | BPV1 | | | HPV16 | | |
| Anti-Serum | Un-treated | IgG depleted | Purified IgG | Un-treated | IgG depleted | Purified IgG |
| Pre-immune serum #1 | <50 | <50 | <30 (28 ng/μl) | <50 | <50 | <30 (28 ng/μl) |
| Pre-immune serum #3 | <50 | <50 | <30 (28 ng/μl) | <50 | 50 | <30 (28 ng/μl) |
| BPV L2 a.a. 1-88 | | <50 | 6400 (0.2 ng/μl) | 4050 | <50 | 6400 (0.2 ng/μl) |
| HPV16 L2 a.a. 1-88#1 | <50 | <50 | 80 (10.4 ng/μl) | 4050 | <50 | 6400 (0.1 ng/μl) |
| HPV16 L2 a.a. 1-88#2 | 50 | <50 | 240 (4.3 ng/μl) | 1350 | <50 | 2130 (0.5 ng/μl) |
| HPV16 L2 a.a. 1-88#3 | 50 | <50 | 80 (11.2 ng/μl) | 1350 | <50 | 2130 (0.4 ng/μl) |
| HPV16 L2 a.a. 1-88#4 | <50 | <50 | 80 (14.1 ng/μl) | 1350 | <50 | 710 (1.6 ng/μl) |

Titers are given as geometric means.

Immune responses to L2 are suboptimal, since the anti-L2 neutralizing titers are significantly lower than anti-L1 neutralizing titers raised against L1 only VLPs; yet studies in rabbits and cattle have consistently shown that L2 immunization can be sufficient to provide protection, probably via neutralizing antibodies, from experimental challenge with homologous virus (Campo, M. S. 1997 *Virology* 234:261-266; Embers, M. E. et al. 2002 *J Virol* 76:9798-9805). Furthermore, vaccination of both humans and mice with full-length HPV16 L2 peptides elicits cross-neutralizing antibodies, suggesting that this phenomenon is not restricted by species (Kawana, K. et al. 2001 *Vaccine* 19:1496-1502; Kawana, K. et al. 2003 *Vaccine* 21:4256-4260).

Taken together, the data indicate that BPV1 L2 a.a. 1-88 constitutes an immunogen capable of generating broad cross-neutralizing responses against both cutaneous and genital types, including all pseudoviruses tested to date. Since the corresponding peptide from HPV16 failed to yield similar results, it indicates that the BPV1 L2 immunogen in particular may have sequences that foster re-folding of the peptide such that a relevant cross-neutralizing epitope is efficiently displayed. Alternatively, BPV1 L2 1-88 may less efficiently display non-neutralizing epitopes, which inhibit induction of antibodies to the cross-neutralizing epitope(s). Further mapping of this region using monoclonal antibodies would be informative as to which residues comprise the neutralizing epitope(s) that are envisioned as forming the basis of a broadly protective HPV L2 peptide vaccine. Although directed solely against mucosal types, vaccination of patients with the HPV16 L2 108-120 peptide generated antibody that neutralized both HPV16 and HPV52 (Kawana, K. et al. 2003 *Vaccine* 21:4256-4260).

EXAMPLE 1

For generation of N-terminally 6-histidine tagged L2 fusion proteins, the open reading frames for L2 genes were cloned into the pQE-12 (Qiagen) or pPro-EXHt (Invitrogen) vectors. Full-length L2 genes included those for BPV1, HPV16, HPV18, HPV31, HPV6 and CRPV. BPV1 His-fusion peptides spanning the length of BPV1 L2: peptide A (a.a. 1-88), peptide B (a.a. 45-173), peptide C (a.a. 130-257), peptide D (a.a. 216-340), peptide E (a.a. 300-425) and peptide F (a.a. 384-469) and full-length BPV1 L2 (a.a. 1-469) were those described previously (Roden, R. B. S. et al. 1994 *J Virol* 68:7570-7574). A similar histidine fusion peptide spanning amino acids 1-88 of HPV16 was also constructed, expressed and purified as for the BPV1 peptides. The proteins were expressed in *E. coli* by induction with IPTG, purified after being solubilized in 6M guanidine HCl on a Nickel agarose column (NTA from Qiagen) and eluted at low pH (4.5) in 8M urea. The preparations were dialyzed overnight against PBS and stored at −80° C. The HPV16 L2-GST fusion protein that was described by Roden et al. (Roden, R. B. et al. 2000 *Virology* 270:254-257), was gel-purified after induction in *E. coli*. Immunization of New Zealand white rabbits with these fusion proteins was also previously described (Roden, R. B. S. et al. 1994 *J Virol* 68:7570-7574). Briefly, rabbits were primed with aggregates of L2 protein (300 μg) resuspended in complete Freunds adjuvant on day 1, and boosted on days 28, 42, 60 and 76 with incomplete Freunds adjuvant. A test bleed was taken on 56 and additional bleeds taken on 74 and 88 before exsanguination on day 102 (Proteintech).

Maps of plasmids used for generation of high-titer pseudoviruses are available at the website (ccr.cancer.gov/Staff/links.asp?profileid=5637). Generation of pseudoviruses using the codon-modified L1 and L2 genes of BPV1 (plasmid pSheLL) (Buck, C. B. et al. 2004 *J Virol* 78:751-757; Zhou, J. et al. 1999 *J Virol* 73:4972-4982), HPV16 (plasmids p16L1h and p16L2h) (Leder, C. et al. 2001. *J Virol* 75:9201-9209), and HPV18 (plasmids peL1fB and peL2bhb) (Pastrana, D. V. et al. 2004 *Virology* 321:205-216) has been described previously. HPV6 and CRPV pseudoviruses were produced using expression plasmids carrying L1 and L2 genes that were entirely codon-modified using a previously described strategy (Buck, C. B. et al. 2004 *J Virol* 78:751-757). For HPV31, it was possible to express limited amounts of L1 and L2 using minimally codon modified genes in the context of an expression plasmid carrying the woodchuck hepatitis virus post-transcriptional regulatory element (WRPE) (Donello, J. E. et al. 1998 *J Virol* 72:5085-5092).

Pseudovirions were produced as previously described (Buck, C. B. et al. 2004 *J Virol* 78:751-757; Pastrana, D. V. et al. 2004 *Virology* 321:205-216) with minor modifications. Briefly, plasmids encoding L1 and L2 genes were cotransfected into 293TT cells along with a reporter plasmid encoding secreted alkaline phosphatase (pYSEAP) (Pastrana, D. V. et al. 2004 *Virology* 321:205-216). After 48 h, cells were lysed with 0.2% Brij-58, 9.5 mM $MgCl_2$, 0.1-0.2% Benzonase (Sigma) and 0.1% plasmid safe (Epicentre) and incubated at 37° C. for 15 min. The resulting pseudovirions were then matured by overnight incubation of the lysates at 25° C. (BPV1, HPV16 and HPV18) or 37° C. (HPV31, CRPV, and HPV6) overnight (Buck, C. B. et al. 2005 *Virol* 79:2839-2846). The mature pseudovirions were solubilized by addition of 0.17 volumes of 5M NaCl, then clarified by low speed (1500×g) centrifugation. Pseudoviruses were purified on a pre-formed 27, 33, 39% Optiprep (Sigma) step gradient. Optiprep fractions containing SEAP-transducing activity were pooled and frozen.

Serum from individual rabbits was diluted 3-fold, with 1:50 being the highest concentration of serum tested. Diluted sera were incubated with pseudoviruses at 4° C. for 1 h and the combination was then used to infect 293TT cells. The supernatants were analyzed for SEAP activity after 72 h with the GreatEscape Chemiluminescent substrate (BD Clontech Biosciences) on a luminometer (Dynex Technologies). The geometric mean of the inverse neutralizing titer of 2-10 experiments is reported.

Neutralization assays using native HPV11 virions were performed using Q-PCR as described in (Culp, T. D. and Christensen, N. D. 2003 *J Virol Methods* 111:135-144; Culp, T. D. and Christensen, N. D. 2004 *Virology* 319:152-161). Briefly, sera were maintained at 1:50 during a 1-h pre-incubation with virions and during the entire first 48 h of infection of HaCaT cells. At 48 h, the spent medium was removed, monolayers were rinsed with DMEM-10 and cells were fed fresh DMEM-10 containing H11.H3 to neutralize any virions possibly remaining at the cell surface. RNA was harvested at 72 h p.i. The relative expression of spliced E1^4 message was determined by reverse transcription and Q-PCR (Culp, T. D. and Christensen, N. D. 2003 *J Virol Methods* 111:135-144).

For IgG depletion, 68 µl of packed Protein G sepharose beads (Pierce) were used to absorb 60 µl of serum, and 180 µl of PBS were added to ensure proper mixing of the sample. The samples were rocked at 4° C. for 5 h. After a brief centrifugation, the supernatant was transferred to a fresh tube with an additional 68 µl of beads and rocked at 4° C. overnight. The samples were centrifuged and the supernatants used in neutralization assays.

For IgG purification, samples were purified with the Pierce's Nab Protein G spin purification kit, according to the manufacturer's recommendation.

Multiple sequence alignments were performed using the T-Coffee computer program Notredame, C. et al. 2000 *J Mol Biol* 302:205-217).

EXAMPLE 2

A Highly Conserved and Broadly Neutralizing Epitope of L2 Critical to Human Papillomavirus Infection We generated a monoclonal antibody (Mab) that bound to highly conserved L2 residues 17-36 and neutralized human papillomavirus (HPV) 16 and HPV18. Residues 17-36 of L2 are necessary for infection and HPV16 L2 17-36 peptide antiserum neutralized pseudoviruses of HPV5, HPV6, HPV16, HPV18, HPV 45, BPV1 and HPV11 native virions. Depletion of HPV16 L2 17-36-reactive antibodies from broadly cross-neutralizing rabbit and human L2-specific sera abolished cross-neutralization and drastically reduced neutralization of the cognate type. This cross-neutralization of common HPV types associated with cervical cancer, genital warts and Epidermodysplasia verruciformis, confirms the notion of a broadly protective, peptide-based vaccine.

Introduction

A possible alternative to highly multivalent L1 VLP vaccines is to identify a single cross-protective antigen. Vaccination with L2 protein as full-length protein, partial polypeptides or synthetic peptides protects rabbits and cattle against homologous type viral challenges at both cutaneous and mucosal sites (Campo, M. S. 1997 *Clin Dermatol* 15:275-283; Chandrachud, L. M. et al. 1995 *Virology* 211:204-208; Christensen, N. D. et al. 1991 Virology 181:572-529; Embers, M. E. et al. 2002 *J Virol* 76:9798-9805; Lin, Y. L. et al. 1992 *Virology* 187:612-619). L2-dependent immunity is likely mediated by neutralizing antibodies (Embers, M. E. et al. 2004 *Vaccine* 22:670-680; Gaukroger, J. M. et al. 1996 *J Gen Virol* 77:1577-1583). L2 of genital HPV types contains broadly cross-neutralizing epitopes that are subdominant in the context of L1/L2 VLPs (Roden, R. B. 2000 *Virology* 270:254-257). Surprisingly, antisera to BPV1 residues 1-88 produced in *E. coli* cross neutralizes cutaneous as well as mucosal papillomavirus types as described hereinbefore. This suggests that neutralizing epitopes at the N-terminus of L2 may be conserved across HPV types and clades due to some critical viral function (Longworth, M. S. and Laimins, L. A. 2004 *Microbiol Mol Biol Rev* 68:362-372). Furthermore, it confirms the notion that a single L2-based vaccine simply generated in *E. coli* or by direct chemical synthesis provides comprehensive protection against the HPV types of genital cancer and genital warts, and even those associated with cutaneous warts, and *Epidermodyplasia vemmciformis* (EDV).

Identification of Neutralizing Epitopes within HPV16 L2

Rational design of a broadly protective L2-based preventive vaccine requires knowledge of the relevant neutralizing epitopes. To identify the neutralizing epitopes in L2, we took two approaches. First, we utilized 31 guinea pig antisera raised to overlapping peptides that together cover the entire HPV16 L2 sequence (Heino, P. B. et al. 1995 *J Gen Virol* 76:1141-1153). While nine of the peptide antisera failed to recognize HPV16 L2 by ELISA, the remainder were tested for reactivity by ELISA and for in vitro neutralization activity against HPV16 pseudovirions. The epitopes reactive on the surface of HPV16 pseudovirions were generally consistent to those previously described on HPV16 L1/L2 VLPs (Heino, P. B. et al. 1995 *J Gen Virol* 76:1141-1153). Only antiserum to HPV16 L2 residues 62-81 neutralized HPV16 (1:800). This serum failed to neutralize HPV18 pseudovirions, suggesting that this epitope induces type-specific neutralization, as previously described by Kawana et al (Kawana, K. et al. 1998 *Virology* 245:353-359; Kawana, K. et al. 1999 *J Virol* 73:6188-6190).

Since we did not identify a cross-neutralizing epitope and a number of the guinea pig antisera failed to react with L2, we initiated a second approach. Mice were vaccinated with full length 6His-tagged HPV16 L2 protein and hybridomas generated using standard procedures for the development of Mabs. In total 1000 hybridoma culture supernatants were screened by both L2 ELISA and HPV16 L1/L2 VLP ELISA. Of the 100 clones that were positive by L2 ELISA, only 45 of them reacted with HPV16 L1/L2 pseudovirions. All of the L2-reactive hybridoma supernatants were tested for their ability to neutralize HPV16 pseudovirus. Only one hybridoma culture supernatant neutralized HPV16 pseudovirus with a titer of 40 or greater; clone RG-1 exhibited a neutralizing titer of 1:1280 and also reacted with HPV16 L1/L2 VLPs by ELISA. Hybridomas producing the neutralizing Mab along with 4 other L1/L2 VLP reactive non-neutralizing Mabs (that had highest titers by ELISA) were subcloned by limiting dilution (Table 5). The 5 monoclonal antibodies were all IgG2a isotype with a κ light chain and each reacted with HPV16 L2 protein by Western blot (Table 5).

TABLE 5

Capsid surface reactivity and neutralizing activity of HPV16 L2 Mabs.

| Hybridoma | RG-1 | 10 | B1 | C9 | 11 |
|---|---|---|---|---|---|
| $OD_{405}$ L2 ELISA | 1.3 | 1.3 | 1.2 | 1.14 | 1.25 |
| $OD_{405}$ L1/L2 ELISA | 0.9 | 0.6 | 0.5 | 0.7 | 0.7 |
| L2 Western blot | Yes | Yes | Yes | Yes | Yes |
| HPV16 neutralization | 1:1280 | <50 | <50 | <50 | <50 |
| Isotype | IgG2aκ | IgG2aκ | IgG2aκ | IgG2aκ | IgG2aκ |
| Epitope | 17-36 | 89-100 | 89-100 | 73-84 | 33-52 |

Undiluted hybridoma supernatants from 5 clones were tested by L2 protein ELISA, by L1/L2 VLP ELISA (presented at optical density at 405nm after background subtraction), for L2 reactivity by Western blot (shown as yes/no on table), for antibody isotype and for their ability to neutralize HPV16 pseudovirus. The epitopes recognized by each monoclonal antibody were defined by peptide ELISA using 56 20mer peptides derived from HPV16 L2 each overlapping by 12 amino acids. Where adjacent peptides reacted, the full sequences given.

Each Mab was screened for reactivity with 56 20mer peptides of HPV16 L2 that overlapped each other by 12 amino acids (Table 5). The neutralizing Mab RG-1 reacted with a peptide comprising residues 17-36 of HPV16 L2. Two of the 4 other non-neutralizing, surface reactive Mabs recognized HPV16 L2 residues 89-100, one recognized 73-84 and one bound residues 33-52 (Table 5). Notably, these epitopes all reside at the N-terminus of L2, consistent with prior studies indicating that this region is exposed on the capsid surface (Heino, P. et al. 1995 *Virology* 214:349-359; Kawana, K. et al. 1998 *Virology* 245:353-359; Kawana, K. et al. 1999 *J Virol* 73:6188-6190).

RG-1 ascites exhibited a titer of 1:1,024,000 in an HPV16 L1/L2 VLP ELISA and neutralized both HPV16 and HPV18 pseudovirions with titers of 1:204,800 and 1:25,600 respectively. However, RG-1 ascites failed to neutralize HPV5, HPV6, HPV45 or BPV1 pseudovirions at a 1:40 dilution. RG-1 may recognize KTCKQAGTCP (residues 20-29 of SEQ ID NO: 23), which is highly conserved between HPV16 and 18 and was different among the types not neutralized. Notably, while all are of the IgG2a isotype, only one of 5 Mabs binding surface-accessible epitopes in the N-terminus of HPV16 L2 is neutralizing. This suggests that RG-1 may block some critical interaction between L2 and a cellular factor (Bossis, I. et al. 2005 *J Virol* 79:6723-6731; Yang, R. et al. 2003 *J Virol* 77:3531-3541 Yang, R. et al. 2003 *J Biol Chem* 278:12546-12553).

Role of the L2 17-36 Region in Viral Infection

Figure 6D:
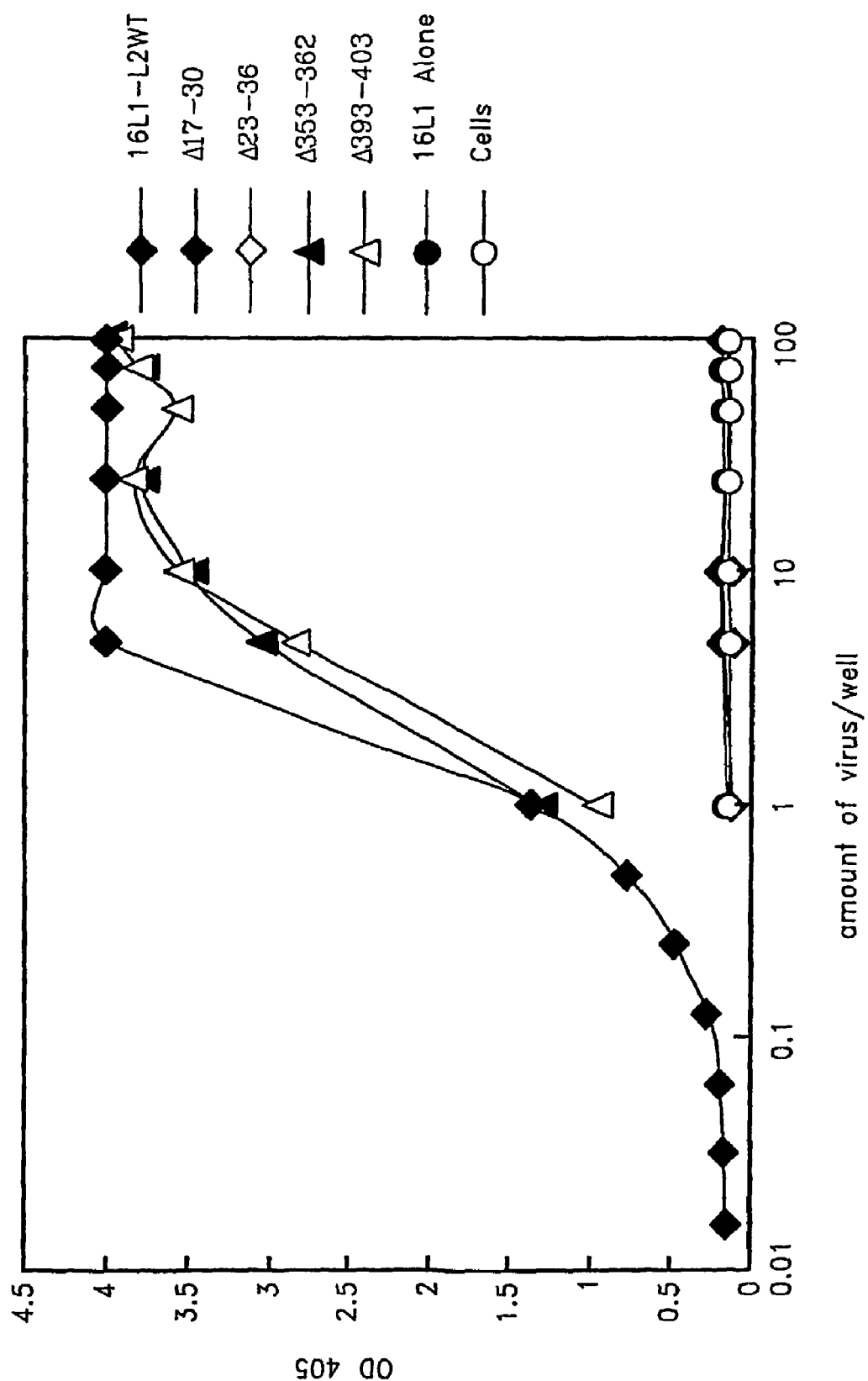

L2 plays an important, but poorly defined role in papillomavirus infection and binds to a number of cellular proteins (Bossis, I. et al. 2005 *J Virol* 79:6723-6731; Yang, R. et al. 2003 *J Virol* 77:3531-3541 Yang, R. et al. 2003 *J Biol Chem* 278:12546-12553). To address the importance of the 17-36 region to virion biology, HPV16 pseudoviruses were prepared using L2 deletion mutants lacking residues within the 17-36aa region (L2Δ17-30 and L2Δ23-36), or as a control in the C-terminal region (L2Δ353-362 and L2Δ393-403) and their properties compared to those containing wild type L2 (FIG. 6A-D). These pseudovirus preparations were purified on Optiprep gradients, and all of the collected fractions were tested for infectivity. Both deletions within the L2 17-36 region Tendered the mutant pseudovirus at least 1000-fold less infectious as compared to wild type L2, whereas the deletions at the C-terminus of L2 had no effect on pseudoviral infectivity (FIG. 6D). This suggests that the location rather than the size of the deletion in L2 is responsible for the reduction in infectivity. One possible explanation for the failure of L2Δ17-30 and L2Δ23-36 to generate infectious virus is that these deletions prevent binding of L2 to L1 and its incorporation within the capsid. However, Western blot analysis of the gradient purified HPV pseudovirions containing L2Δ17-30 and L2Δ23-36 reveal similar yields and ratios of L1 and L2 as for wild type and L2Δ353-362 and L2Δ393-403 (FIGS. 6A and B). In addition, these deletions did not prevent DNA encapsidation (FIG. 6C). Thus the L2Δ17-30 and L2Δ23-36 deletion mutants support L1 binding and assembly into full virions but not the infectious process. By contrast, L2 mutants with similar size deletions at the C-terminus (L2Δ353-362 and L2Δ393-403) behave as wild type.

Figure 6E:
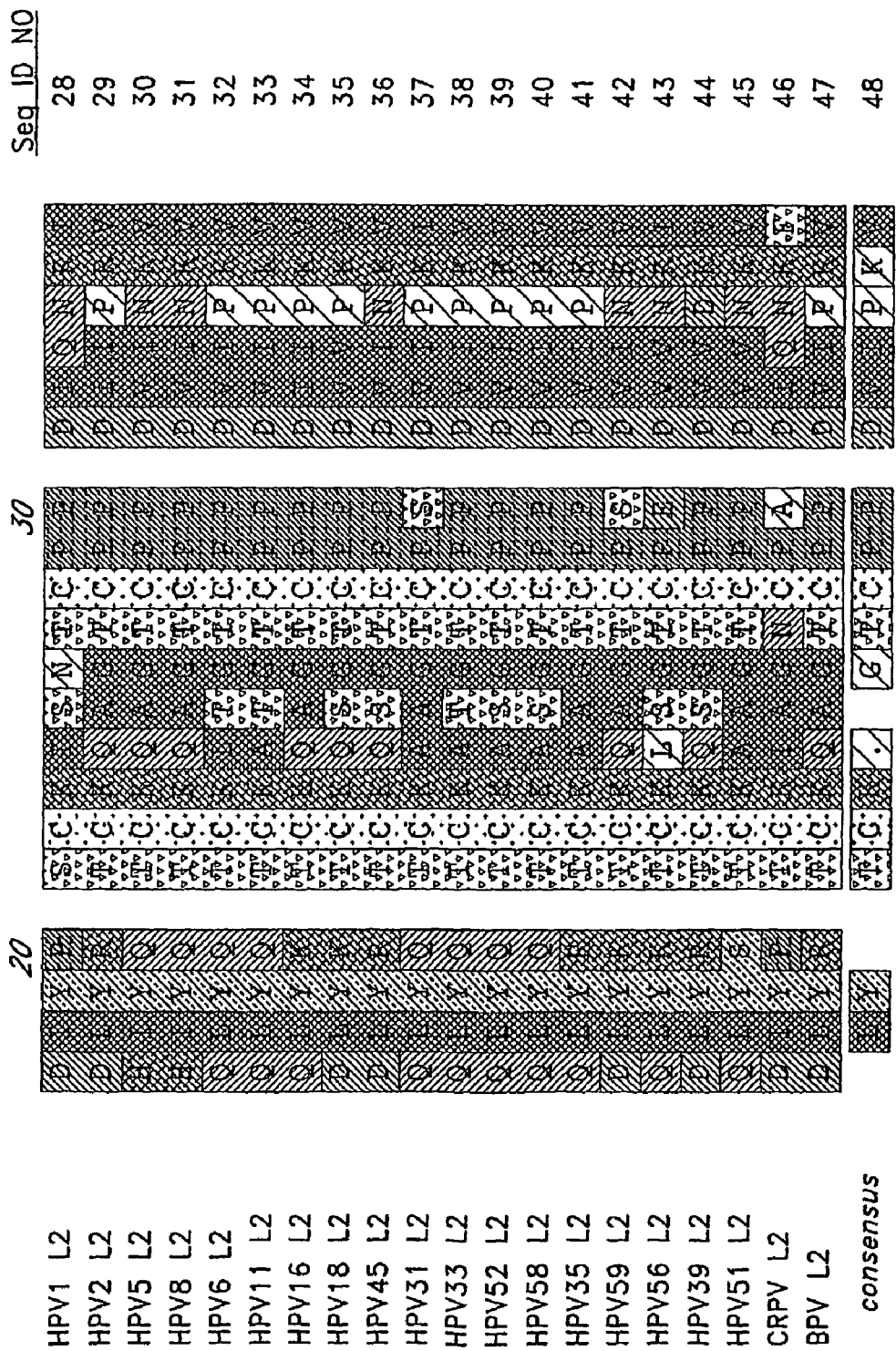
Figure 6F:
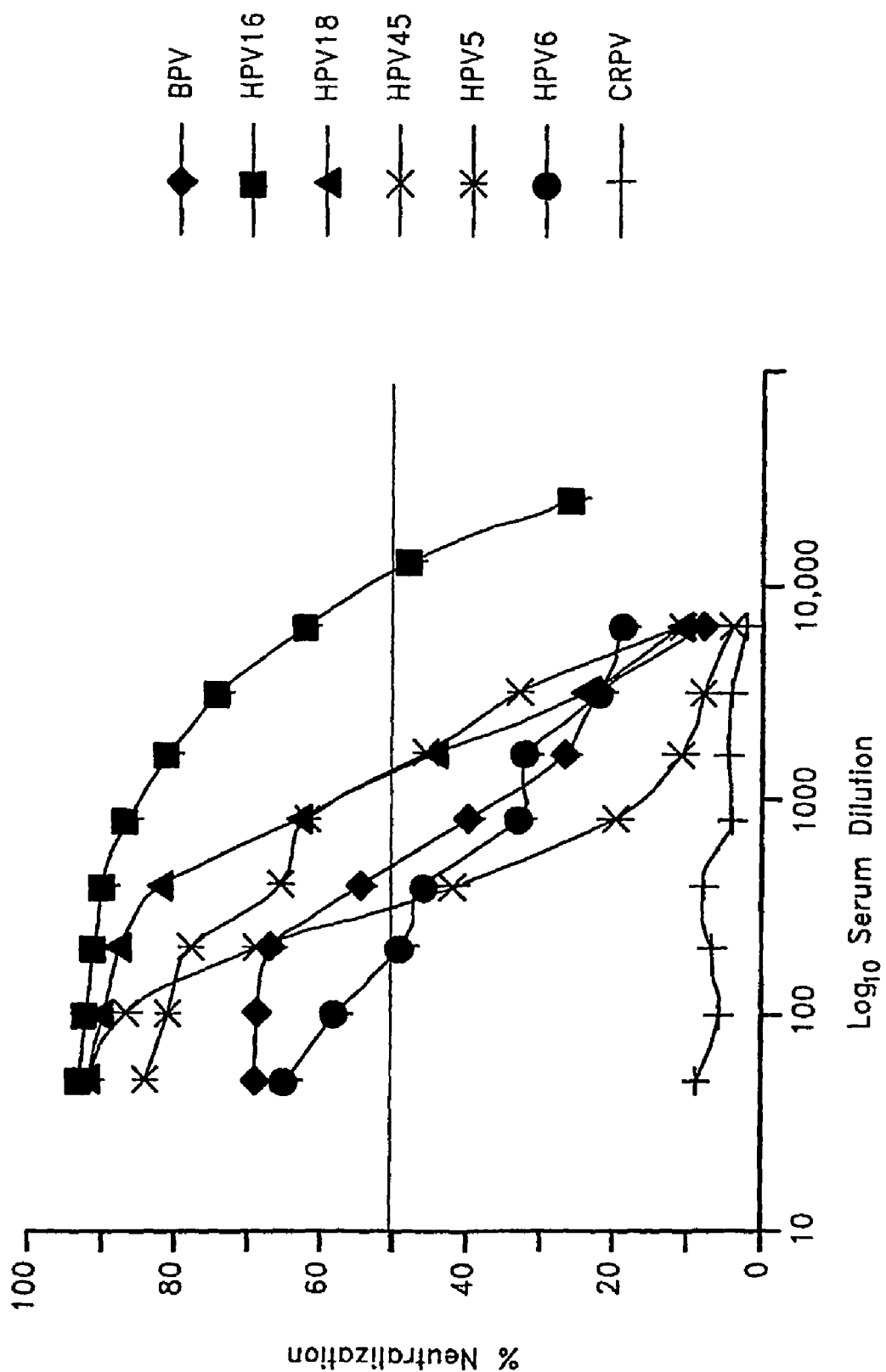
Figure 8:
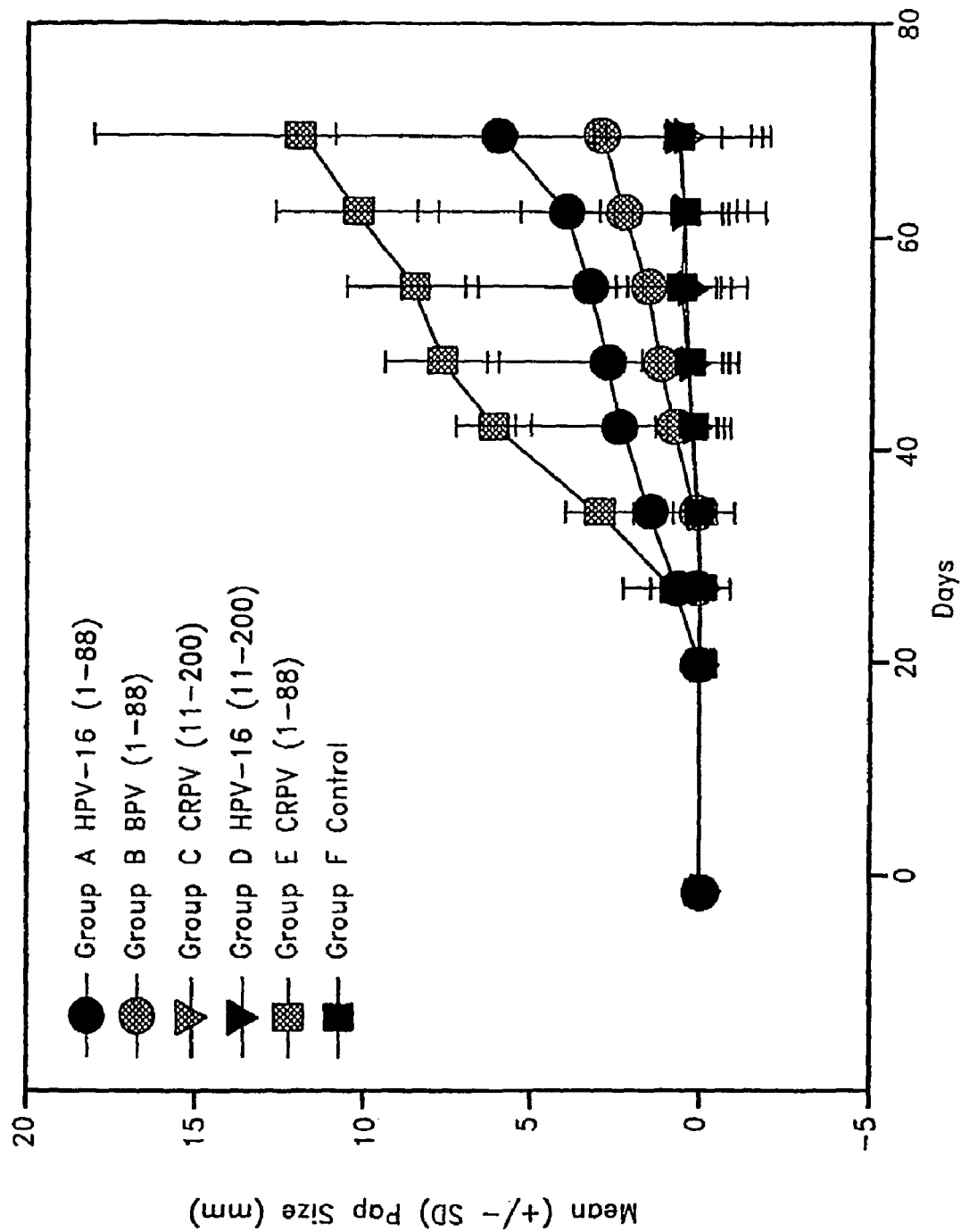
FIG. 8. Growth of papillomas in L2-vaccinated rabbits after cutaneous challenge at four sites with CRPV crude virion stock. Mean size+/−standard deviation in mm versus days post challenge.
Figure 9:
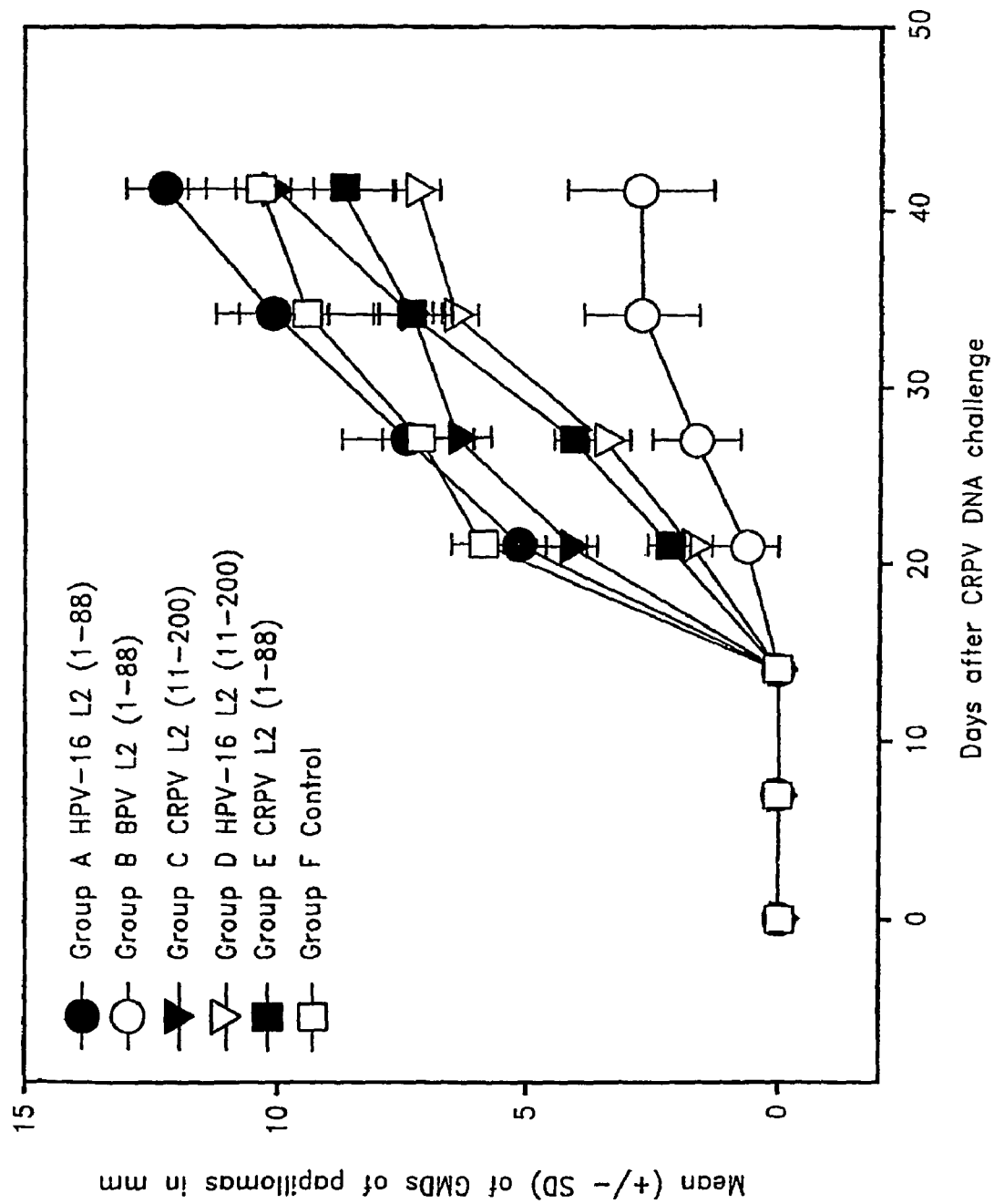
FIG. 9. Size of cutaneous papillomas in L2 vaccinated rabbits after challenge with CRPV DNA (both CRPV wild type and L2 deficient DNA-induced papillomas are grouped together).

Pseudovirus and Native HPV11 Virus-Based Neutralization with HPV16 L2 17-36aa Peptide Antiserum Since our aim was to identify a broadly neutralizing epitope and the HPV16 L2 17-36 peptide was well conserved among different HPVs (FIG. 6E), we immunized a rabbit with HPV16 L2 17-36 peptide coupled to KLH. The rabbit antiserum was analyzed by 6His HPV16 L2 protein ELISA as well as HPV16 L1/L2 VLP ELISA. The final bleed had an ELISA titer of 1:128,000 against L2 protein and 1:16,000 to L1/L2 VLP. Similar results were obtained with earlier bleeds and the prebleed serum had minimal background reactivity on both the protein as well as VLP ELISAs. The final bleed serum was used in carrying out further neutralization experiments. The HPV16 L2 17-36 peptide antiserum, but not the pre-immunization serum, neutralized not only HPV16 pseudovirions (1:12,800) but also cross-neutralized pseudovirions of other oncogenic types (HPV18 at 1:1600 and HPV45 at 1:400), the benign mucosal type HPV6 (1:200), and the cutaneous EDV type HPV5 (1:1600). The HPV16 L2 17-36 peptide antiserum neutralized the evolutionarily divergent BPV1 (1:800), but not CRPV, indicating specificity (FIG. 6F). To extend our observation of cross-neutralization to an additional HPV type and to eliminate the possibility that the neutralization was an artifact of the pseudovirus system, the peptide antiserum was tested at 1:50 for neutralization activity against native HPV11 virus derived from a human xenograft as described hereinbefore. As a measure of infection, E1^E4 early spliced transcripts were observed in cells exposed to HPV11 treated with the pre-immunization serum whereas the final bleed 17-36aa antiserum completely neutralized the viral infection. Thus, L2 17-36 peptide antiserum neutralized HPV11 native virus as well as very divergent pseudoviruses derived from cutaneous and mucosal HPV types associated with EDV, condylomata accuminata and genital cancers.

Depletion of 17-36α-Specific Antibodies Eliminates Cross Neutralization

In order to study the contribution of the 17-36aa epitope relative to others in both homologous type neutralization and cross-neutralization of heterologous PV types, antibodies specific to this region of L2 were depleted from L2 immune sera using an L2 17-36 peptide column. As described herein, we have demonstrated that rabbit sera raised against L2 residues 1-88 of BPV1 exhibits very broad cross-neutralizing activity. Depletion of HPV16 L2 17-36-reactive antibodies from BPV1 L2 1-88 antiserum reduced the homologous BPV1 neutralization titers from 1:20,480 to 1:40 (FIG. 7A). After factoring for the dilution that occurs upon elution of the peptide column, we recovered 25% of the BPV1 neutralizing activity. More markedly depletion of HPV16 L2 17-36-reactive antibodies from BPV1 L2 1-88 antiserum eliminated detectable (<1:20) cross-neutralization of HPV16 and HPV18 (both at 1:5120). Again, cross-neutralizing activity was recovered from the HPV16 L2 17-36 peptide column (FIGS. 7B and C).

Chandrachud et al. demonstrated that vaccination with BPV4 L2 11-200, but not a C-terminal polypeptide, protects cattle from experimental BPV4 challenge (Chandrachud, L. M. et al. 1995 *Virology* 211:204-208), and this group first described protective epitopes outside of the first 88 amino acids of L2 (Campo, M. S. et al. 1997 *Virology* 234:261-266). To address the relative contribution of L2 17-36 and these other neutralizing epitopes, we performed similar depletion experiments in serum of a rabbit vaccinated with HPV16 L2 11-200. The HPV16 neutralizing titer of antiserum to HPV16 L2 11-200 drops upon depletion of HPV16 L2 17-36-reactive antibodies from 1:20,480 to 1:80. Again, after correcting for the dilution that occurs upon elution of the peptide column, we recovered 25% of the homologous type HPV16 neutralizing activity. Lack of complete elimination of neutralization titer against the homologous virus is consistent with previous descriptions of other neutralizing epitopes outside of the L2 17-36 region. However, depletion of the HPV16 L2 11-200 antiserum with an HPV16 L2 17-36 peptide column removed detectable cross-neutralizing activity against HPV18 (1:2, 560 to >1:20), suggesting that the neutralizing epitopes outside this 17-36 region are likely type-specific. Again, 25% of the neutralizing activity was recovered upon elution of the column (after correction for dilution), supporting the epitope specificity of the depletion.

Finally, we wished to determine whether L2 17-36 represents a neutralizing B cell epitope in humans. We obtained sera from a group of 24 HPV16+ anogenital intraepithelial neoplasia (AGIN) patients vaccinated three times at monthly intervals with 500 µg of HPV16 L2E7E6 fusion protein (TA-CIN) without adjuvant and bled one month later at week 12 (Smyth, L. J. et al. 2004 Clin Cancer Res 10:2954-2961). Vaccination induced L2-specific antibodies in five patients (Table 6). Only one patient, code number 201, had no detectable HPV16 neutralizing antibodies at week 0, whereas the serum after vaccination exhibited an HPV16 neutralizing titer of 1600 (Table 6). These neutralizing antibodies correlated with reactivity to HPV16 L2 by ELISA (Table 6), and neither pre-immunization nor post-immunization serum from patient 201 exhibited antibodies to HPV16 L1 above background (Smyth, L. J. et al. 2004 Clin Cancer Res 10:2954-2961). The week 12 serum from patient 201 also neutralized HPV18 with a titer of 100, whereas the week 0 serum did not (Table 6). Depletion of this serum with an HPV16 L2 17-36 peptide column removed detectable neutralizing activity against HPV16 (FIG. 7F), and 40% of this neutralizing activity was recovered upon elution of the column. This suggests that, although HPV16 L2 108-120 peptide can induce cross-neutralizing antibodies in mice and patients (Kawana, K. et al. 2001 Vaccine 19:1496-1502; Kawana, K. et al. 2003 Vaccine 21:4256-4260), this region may not contain optimal cross-neutralizing epitopes (Kawana, K. et al. 1999 J Virol 73:6188-6190). Since the patient was vaccinated with full length HPV16 L2 fusion protein, this finding supports the importance of the L2 17-36 region as a neutralizing epitope in this patient. The sera of the five AGIN patients vaccinated with HPV16 L2E7E6 that reacted to full length HPV16 L2 also reacted to HPV16 L2 17-36 peptide (Table 6), suggesting that L2 17-36 is a B cell epitope recognized by multiple patients.

tion suggests immunity is mediated by neutralizing antibody (Embers, M. E. et al. 2002 J Virol 76:9798-9805). Immunization of calves with BPV4 L2 11-200 yielded ELISA titers of 1:100 (and neutralization at a dilution of 1:5 (Gaukroger, J. M. et al. 1996 J Gen Virol 77:1577-1583)) yet the calves were completely protected against BPV4 challenge (Chandrachud, L. M. et al. 1995 Virology 211:204-208). Vaccination with three BPV4 L2 peptides (101-120, 131-151 and 151-170 combined, but not separately) also protected calves from experimental challenge, but generated ELISA titers of only 1:30 (Campo, M. S. et al. 1997 Virology 234:261-266). Similarly, vaccination with L2 polypeptide induces both protection and low neutralization titers (Christensen, N. D. et al. 1991 Virology 181:572-529; Lin, Y. L. et al. 1992 Virology 187:612-619). Thus earlier studies suggest that even low titers of L2-specific neutralizing antibodies in serum are likely to confer protection.

FIG. 6

Pseudoviruses were generated by transfecting 293TT cells with HPV16 L1, along with the indicated L2 deletion mutants and pY-SEAP DNAs. The cell lysates were benzonase treated to remove free DNA and the viruses purified on an Optiprep gradient. A) pseudoviruses were subject to 4-15% SDS-PAGE and were Western blotted with HPV16 L1-reactive Mab or B) HPV16 L2-reactive antiserum. C) encapsidated DNA was extracted from the nuclease-treated and Optiprep gradient-purified HPV16 pseudovirion preparations and visualized after agarose gel electrophoresis. D) The Optiprep gradient-purified viruses were titrated and incubated with 293TT cells. Infection was detected by measuring SEAP released into the supernatant after 72 hrs. E) CLUSTAL W homology comparison between residues 17-36 of HPV16 L2 peptide and L2 sequences from different papillomavirus types. The L2 17-36 amino acid sequence is highly conserved among different types ranging from benign skin types like HPV1 and 2, EDV related types like HPV5 and HPV8, benign mucosal types like HPV6 and HPV11, as well as malignant mucosal types including the four most prevalent types HPV16, 18, 31 and 45. Surprisingly this sequence was even conserved in BPV1, which is evolutionarily distant from high

TABLE 6

In vitro HPV neutralization titers in sera of AGIN patients who were vaccinated with TA-CIN and mounted an HPV16 L2-specific antibody response

| Patient | HPV16 L2 full length ELISA | | HPV16 L2 17-36 peptide ELISA | | HPV16 neutralization | | HPV18 neutralization | |
|---|---|---|---|---|---|---|---|---|
| | Week 0 | Week 12 | Week 0 | Week 12 | Week 0 | Week 12 | Week 0 | Week 12 |
| 201 | <50 | 1:1600 | <50 | 1:1600 | <50 | 1:1600 | <50 | 1:100 |
| 303 | <50 | 1:400 | <50 | 1:400 | 1:200 | 1:1600 | <50 | 1:50 |
| 307 | <50 | 1:100 | <50 | 1:100 | 1:400 | 1:1600 | <50 | 1:400 |
| 309 | <50 | 1:200 | <50 | 1:200 | 1:3200 | 1:3200 | <50 | <50 |
| 311 | <50 | 1:1600 | <50 | 1:1600 | 1:6400 | 1:12800 | 1:200 | 1:200 |

Sera were obtained from HPV16+ AGIN patients either before or one month after three monthly vaccinations with 500ug of HPV16 L2E7E6 fusion protein (TA-CIN) without adjuvant. The sera were tested for ELISA reactivity with either full length HPV16 L2 protein or HPV16 L2 17-36 peptide arid for their ability to neutralize either HPV16 or HPV18 in vitro. Note that in vitro neutralization titers at week 0 represents LI-specific neutralizing antibody, and reflects pre-existing HPV infection.

Will the low cross-neutralization titers compared to those obtained with L1 VLP against the homologous type be sufficient to provide protection? Vaccination with residues 94-112 or 107-122 of CRPV induced neutralization titers ranging from 1:5 to 1:10 but protected rabbits from experimental viral infection by CRPV, but not ROPV (Embers, M. E. et al. 2002 J Virol 76:9798-9805). Protection from CRPV challenge but not CRPV DNA-induced papillomas by L2 peptide vaccinarisk HPV. The HPV16 L2 17-36aa region exhibits 78% identity with HPV2, HPV5, and HPV45 L2; 80% identity with HPV6 and HPV11 L2; and 84% identity with HPV18. In contrast, L2 as a whole exhibits only ~25% conservation among these types. F) In vitro neutralization of the 17-36aa anti peptide rabbit serum for pseudovirions derived from HPV5, HPV6, HPV16, HPV18, HPV45, BPV1 but not CRPV.

FIG. 7

BPV1 L2 1-88 antiserum (A-C) and HPV16 L2 11-200 (D and E) antiserum both raised in rabbits, and serum of an HPV16+AGIN patient who had been vaccinated with HPV16 L2E7E6 L2 (F) were depleted of HPV16 L2 17-36 specific antibodies using a peptide column. Antibodies bound to the column were recovered by elution at low pH and brought back to neutral pH. The sera, both before and after depletion, as well as the recovered antibodies were tested for neutralizing titer for BPV1, HPV16 or HPV18 pseudovirions, as indicated. The serum dilutions for the antibody recovered from the column are not corrected for the dilution that occurs during their elution and return to neutral pH. A) Neutralization of BPV1 pseudovirions by BPV1 L2 1-88 antiserum, B) Neutralization of HPV16 pseudovirions by BPV1 L2 1-88 antiserum, C) Neutralization of HPV18 pseudovirions by BPV1 L2 1-88 antiserum, D) Neutralization of HPV16 pseudovirions by HPV16 L2 11-200 antiserum, E) Neutralization of HPV18 pseudovirions by HPV16 L2 11-200 antiserum, F) Neutralization of HPV16 pseudovirions by immune serum from a patient vaccinated with HPV16 L2E7E6.

EXAMPLE 3

The rabbit model system provides the opportunity to study protective immunity to both cutaneous and mucosotropic papillomaviruses types, namely CRPV and ROPV respectively (Embers et al. 2002 *J Virol.* 76:9798-805). To examine the in vivo protective and cross-protective potential of polypeptides as vaccine antigens, we constructed and expressed in *E. coli* hexahistidine-tagged recombinant polypeptides from the L2 region 1-88 of CRPV, HPV16 and BPV1 as well as L2 region 11-200 of CRPV. The recombinant L2 polypeptides were affinity purified under denaturing conditions and dialyzed into PBS.

Thirty six New Zealand White rabbits were divided into six groups of six rabbits per group, each receiving three immunizations as indicated. Immunizations consisted of ~300 μg of L2 polypeptide in RIBI adjuvant delivered subcutaneously at 3-4 week intervals.

Each experimental animal was challenged with both ROPV and CRPV 4 to 12 weeks after the last immunization. For CRPV infection, rabbits received doses of crude viral stock (CRPV Hershey strain). Virus was applied, under anesthesia, to scarified skin at four sites. For ROPV infection, crude stock (Hershey isolate) was applied to 9 needle puncture sites on the underside of tongues. Cutaneous and oral papilloma growth was monitored.

TABLE 7

Results at 35 days post ROPV challenge.

| Group | Immunogen | Papillomas on each animal | Total papillomas | Approximate papilloma size |
|---|---|---|---|---|
| A | HPV16 L2 1-88 | 1, 0, 2, 1, 2, 0 | 6 | all very small |
| B | BPV1 L2 1-88 | 1, 2, 1, 2, 0, 0 | 6 | all very small |
| C | CRPV L2 11-200 | 1, 0, 1, 1, 0, 0 | 3 | all very small |
| D | HPV16 L2 11-200 | 0, 1, 1, 0, 0, 1 | 3 | all very small |
| E | CRPV L2 1-88 | 0, 1, 1, 4, 0, 0 | 6 | very small, to small |
| F | Control (none) | 1, 2, 5, 7, 1, 3 | 19 | all large |

Each animal received 9 tongue punctures but not all sites became papillomas. Numbers of papillomas per animal and approximate size are presented. Two animals died in the control group but ROPV data were obtained. Papillomas on each animal were compared between groups by ANOVA. The following were the only significant differences between groups: A, F p = 0.0077; B, F p = 0.0077; C, F p = 0.0014; D, F p = 0.0014; E, F p = 0.0077.

TABLE 8

Results at 35 days post CRPV challenge.

| Group | Immunogen | Papillomas/site | Rabbits with any papillomas | Approximate papilloma size |
|---|---|---|---|---|
| A | HPV16 L2 1-88 | 7/20 | 3/5 (one animal lost) | 1-4 mm |
| B | BPV1 L2 1-88 | 3/24 | 2/6 | about 1 mm |
| C | CRPV L2 11-200 | 1/24 | 1/6 | 3 mm |
| D | HPV16 L2 11-200 | 2/24 | 1/6 | 1 mm |
| E | CRPV L2 1-88 | 1/24 | 1/6 | 1 mm |
| F | Control (none) | 15/16 | 4/4 (two animals lost) | 3-8 mm |

4 cutaneous sites per rabbit were infected with CRPV virions.

TABLE 9

Summary of cutaneous papillomas 10 weeks post challenge is presented for each vaccine group.

| Group | Papillomas/site infected | Rabbits with papillomas/ rabbits per group |
|---|---|---|
| A | 10/20 | 4/5 |
| B | 13/24 | 4/6 |
| C | 1/24 | 1/6 |
| D | 2/24 | 1/6 |
| E | 2/24 | 2/6 |
| F | 14/16 (2 late regressions on one rabbit) | 4/4 |

To determine if the protection was mediated by the antibody response to the L2 protein, the L2 vaccinated experimental rabbits that failed to develop papillomas after CRPV challenge plus three additional naïve rabbits were challenged with infectious CRPV DNA. CRPV genomic DNA was applied to scarified skin at two sites and CRPV genomic DNA deficient for L2 expression (ATG mutant) was applied in two other sites. Papilloma growth was monitored (Embers et al. 2002 *J Virol.* 76:9798-805).

TABLE 10

Summary of papilloma growth after CRPV DNA challenge of L2-vaccinated rabbits.

| Group | Immunogen | Number of rabbits in group | Sites with papillomas/ total sites inoculated |
|---|---|---|---|
| A | HPV16 L2 1-88 | 1 | 4/4 |
| B | BPV1 L2 1-88 | 2 | 4/8 (one rabbit had 0/4 papillomas) |
| C | CRPV L2 11-200 | 5 | 20/20 |
| D | HPV16 L2 11-200 | 5 | 20/20 |
| E | CRPV L2 1-88 | 4 | 16/16 |
| F | Naïve control | 3 | 11/12 |

Both CRPV wild type and L2 deficient DNA-induced papillomas are grouped together.

The failure of the L2 vaccination to protect against viral DNA challenge (despite protecting against challenge with CRPV virions) and the similarity of growth rates for papillomas amongst vaccination groups provides evidence that protection upon vaccination with L2 polypeptides is mediated by cross-neutralizing antibodies.

\* \* \*

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. A method for inducing broadly cross-neutralizing antibodies against cutaneous and mucosal papillomavirus types comprising:
   administering to a human in need thereof an immunogenic peptide or protein of at least 10 and up to 88 amino acid residues in length, said peptide or protein having a sequence corresponding to a sequence of corresponding length from the N terminal amino acids 1-88 of a papillomavirus L2 protein,
   wherein administration of said immunogenic peptide or protein thereby induces the production of broadly cross-neutralizing antibodies against cutaneous and mucosal papillomavirus types in said human.

2. The method of claim 1, wherein said peptide or protein has a sequence corresponding to a sequence from the N-terminal amino acids 1-88 of HPV16 L2 protein.

3. The method of claim 1, wherein said peptide or protein comprises a sequence corresponding to a sequence from the N-terminal amino acids 17-36 of HPV16 L2.

4. The method of claim 1, wherein said immunogenic peptide or protein is conjugated or fused to an amino acid, protein, or peptide other than a papilloma virus L2 protein or peptide.

* * * * *

UNITED STATES PATENT AND TRADEMARK OFFICE
CERTIFICATE OF CORRECTION

PATENT NO. : 8,404,244 B2  
APPLICATION NO. : 11/883495  
DATED : March 26, 2013  
INVENTOR(S) : Schiller et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1191 days.

Signed and Sealed this
First Day of September, 2015

Michelle K. Lee
*Director of the United States Patent and Trademark Office*

SEQUENCE LISTING

<160> NUMBER OF SEQ ID NOS: 48

<210> SEQ ID NO 1
<211> LENGTH: 85
<212> TYPE: PRT
<213> ORGANISM: Human papillomavirus 1 (HPV1)

<400> SEQUENCE: 1

```
Met Tyr Arg Leu Arg Arg Lys Arg Ala Ala Pro Lys Asp Ile Tyr Pro
 1               5                  10                  15
Ser Cys Lys Ile Ser Asn Thr Cys Pro Pro Asp Ile Gln Asn Lys Ile
                20                  25                  30
Glu His Thr Thr Ile Ala Asp Lys Ile Leu Gln Tyr Gly Ser Leu Gly
            35                  40                  45
Val Phe Leu Gly Gly Leu Gly Ile Gly Thr Ala Arg Gly Ser Gly Gly
        50                  55                  60
Arg Ile Gly Tyr Thr Pro Leu Gly Glu Gly Gly Val Arg Val Ala
 65                  70                  75                  80
Thr Arg Pro Thr Pro
                85
```

<210> SEQ ID NO 2
<211> LENGTH: 87
<212> TYPE: PRT
<213> ORGANISM: Human papillomavirus 2 (HPV2)

<400> SEQUENCE: 2

```
Met Ser Ile Arg Ala Lys Arg Lys Arg Ala Ser Pro Thr Asp Leu
 1               5                  10                  15
Tyr Arg Thr Cys Lys Gln Ala Gly Thr Cys Pro Pro Asp Ile Ile Pro
                20                  25                  30
Arg Val Glu Gln Asn Thr Leu Ala Asp Lys Ile Leu Lys Trp Gly Ser
            35                  40                  45
Leu Gly Val Phe Phe Gly Gly Leu Gly Ile Gly Thr Gly Ser Gly Thr
        50                  55                  60
Gly Gly Arg Thr Gly Tyr Ile Pro Val Gly Ser Arg Pro Thr Thr Val
 65                  70                  75                  80
Val Asp Ile Gly Pro Thr Pro
                85
```

<210> SEQ ID NO 3
<211> LENGTH: 86
<212> TYPE: PRT
<213> ORGANISM: Human papillomavirus 5 (HPV5)

<400> SEQUENCE: 3

```
Met Ala Arg Ala Lys Thr Val Lys Arg Asp Ser Val Thr His Ile Tyr
 1               5                  10                  15
Gln Thr Cys Lys Gln Ala Gly Thr Cys Pro Pro Asp Val Ile Asn Lys
                20                  25                  30
Val Glu Gln Thr Thr Val Ala Asp Asn Ile Leu Lys Tyr Gly Ser Ala
            35                  40                  45
Gly Val Phe Phe Gly Gly Leu Gly Ile Ser Thr Gly Arg Gly Thr Gly
        50                  55                  60
Gly Ala Thr Gly Tyr Val Pro Leu Gly Glu Gly Pro Gly Val Arg Val
```

```
                       65                  70                  75                  80

Gly Gly Thr Pro Thr Val
                 85

<210> SEQ ID NO 4
<211> LENGTH: 86
<212> TYPE: PRT
<213> ORGANISM: Human papillomavirus 8 (HPV8)

<400> SEQUENCE: 4

Met Ala Arg Ala Arg Val Lys Arg Asp Ser Val Thr His Ile Tyr
1               5                   10                  15

Gln Thr Cys Lys Gln Ala Gly Thr Cys Pro Pro Asp Val Ile Asn Lys
                20                  25                  30

Val Glu Gln Thr Thr Val Ala Asp Asn Ile Leu Lys Tyr Gly Ser Ala
            35                  40                  45

Gly Val Phe Phe Gly Gly Leu Gly Ile Gly Thr Gly Arg Gly Thr Gly
        50                  55                  60

Gly Val Thr Gly Tyr Thr Pro Leu Ser Glu Gly Pro Gly Ile Arg Val
65                  70                  75                  80

Gly Asn Thr Pro Thr Val
                 85

<210> SEQ ID NO 5
<211> LENGTH: 88
<212> TYPE: PRT
<213> ORGANISM: Human papillomavirus 6 (HPV6)

<400> SEQUENCE: 5

Met Ala His Ser Arg Ala Arg Arg Arg Lys Arg Ala Ser Ala Thr Gln
1               5                   10                  15

Leu Tyr Gln Thr Cys Lys Leu Thr Gly Thr Cys Pro Pro Asp Val Ile
                20                  25                  30

Pro Lys Val Glu His Asn Thr Ile Ala Asp Gln Ile Leu Lys Trp Gly
            35                  40                  45

Ser Leu Gly Val Phe Phe Gly Gly Leu Gly Ile Gly Thr Gly Ser Gly
        50                  55                  60

Thr Gly Gly Arg Thr Gly Tyr Val Pro Leu Gly Thr Ser Ala Lys Pro
65                  70                  75                  80

Ser Ile Thr Ser Gly Pro Met Ala
                 85

<210> SEQ ID NO 6
<211> LENGTH: 87
<212> TYPE: PRT
<213> ORGANISM: Human papillomavirus 11 (HPV11)

<400> SEQUENCE: 6

Met Lys Pro Arg Ala Arg Arg Arg Lys Arg Ala Ser Ala Thr Gln Leu
1               5                   10                  15

Tyr Gln Thr Cys Lys Ala Thr Gly Thr Cys Pro Pro Asp Val Ile Pro
                20                  25                  30

Lys Val Glu His Thr Thr Ile Ala Asp Gln Ile Leu Lys Trp Gly Ser
            35                  40                  45

Leu Gly Val Phe Phe Gly Gly Leu Gly Ile Gly Thr Gly Ala Gly Ser
        50                  55                  60

Gly Gly Arg Ala Gly Tyr Ile Pro Leu Gly Ser Ser Pro Lys Pro Ala
65                  70                  75                  80
```

```
Ile Thr Gly Gly Pro Ala Ala
                85

<210> SEQ ID NO 7
<211> LENGTH: 89
<212> TYPE: PRT
<213> ORGANISM: Human papillomavirus 16 (HPV16)

<400> SEQUENCE: 7

Met Arg His Lys Arg Ser Ala Lys Arg Thr Lys Arg Ala Ser Ala Thr
 1               5                  10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Glu Gln Ile Leu Gln Tyr
        35                  40                  45

Gly Ser Met Gly Val Phe Phe Gly Gly Leu Gly Ile Gly Thr Gly Ser
    50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val
                85

<210> SEQ ID NO 8
<211> LENGTH: 88
<212> TYPE: PRT
<213> ORGANISM: Human papillomavirus 18 (HPV18)

<400> SEQUENCE: 8

Met Val Ser His Arg Ala Ala Arg Arg Lys Arg Ala Ser Val Thr Asp
 1               5                  10                  15

Leu Tyr Lys Thr Cys Lys Gln Ser Gly Thr Cys Pro Pro Asp Val Val
            20                  25                  30

Pro Lys Val Glu Gly Thr Thr Leu Ala Asp Lys Ile Leu Gln Trp Ser
        35                  40                  45

Ser Leu Gly Ile Phe Leu Gly Gly Leu Gly Ile Gly Thr Gly Ser Gly
    50                  55                  60

Thr Gly Gly Arg Thr Gly Tyr Ile Pro Leu Gly Gly Arg Ser Asn Thr
65                  70                  75                  80

Val Val Asp Val Gly Pro Thr Arg
                85

<210> SEQ ID NO 9
<211> LENGTH: 88
<212> TYPE: PRT
<213> ORGANISM: Human papillomavirus 45 (HPV45)

<400> SEQUENCE: 9

Met Val Ser His Arg Ala Ala Arg Arg Lys Arg Ala Ser Ala Thr Asp
 1               5                  10                  15

Leu Tyr Arg Thr Cys Lys Gln Ser Gly Thr Cys Pro Pro Asp Val Ile
            20                  25                  30

Asn Lys Val Glu Gly Thr Thr Leu Ala Asp Lys Ile Leu Gln Trp Ser
        35                  40                  45

Ser Leu Gly Ile Phe Leu Gly Gly Leu Gly Ile Gly Thr Gly Ser Gly
    50                  55                  60

Ser Gly Gly Arg Thr Gly Tyr Val Pro Leu Gly Gly Arg Ser Asn Thr
65                  70                  75                  80

Val Val Asp Val Gly Pro Thr Arg
                85
```

<210> SEQ ID NO 10
<211> LENGTH: 89
<212> TYPE: PRT
<213> ORGANISM: Human papillomavirus 31 (HPV31)

<400> SEQUENCE: 10

Met Arg Ser Lys Arg Ser Thr Lys Arg Ala Ser Ala Thr
1               5                   10                  15

Gln Leu Tyr Gln Thr Cys Lys Ala Ala Gly Thr Cys Pro Ser Asp Val
            20                  25                  30

Ile Pro Lys Ile Glu His Thr Thr Ile Ala Asp Gln Ile Leu Arg Tyr
        35                  40                  45

Gly Ser Met Gly Val Phe Phe Gly Gly Leu Gly Ile Gly Ser Gly Ser
    50                  55                  60

Gly Thr Gly Gly Arg Thr Gly Tyr Val Pro Leu Ser Thr Arg Pro Ser
65                  70                  75                  80

Thr Val Ser Glu Ala Ser Ile Pro Ile
                85

<210> SEQ ID NO 11
<211> LENGTH: 88
<212> TYPE: PRT
<213> ORGANISM: Human papillomavirus 33 (HPV33)

<400> SEQUENCE: 11

Met Arg His Lys Arg Ser Thr Arg Arg Lys Arg Ala Ser Ala Thr Gln
1               5                   10                  15

Leu Tyr Gln Thr Cys Lys Ala Thr Gly Thr Cys Pro Pro Asp Val Ile
            20                  25                  30

Pro Lys Val Glu Gly Ser Thr Ile Ala Asp Gln Ile Leu Lys Tyr Gly
        35                  40                  45

Ser Leu Gly Val Phe Phe Gly Gly Leu Gly Ile Gly Thr Gly Ser Gly
    50                  55                  60

Ser Gly Gly Arg Thr Gly Tyr Val Pro Ile Gly Thr Asp Pro Pro Thr
65                  70                  75                  80

Ala Ala Ile Pro Leu Gln Pro Ile
                85

<210> SEQ ID NO 12
<211> LENGTH: 88
<212> TYPE: PRT
<213> ORGANISM: Human papillomavirus 52 (HPV52)

<400> SEQUENCE: 12

Met Arg Tyr Arg Arg Ser Thr Arg His Lys Arg Ala Ser Ala Thr Gln
1               5                   10                  15

Leu Tyr Gln Thr Cys Lys Ala Ser Gly Thr Cys Pro Pro Asp Val Ile
            20                  25                  30

Pro Lys Val Glu Gly Thr Thr Ile Ala Asp Gln Leu Leu Lys Tyr Gly
        35                  40                  45

Ser Leu Gly Val Phe Phe Gly Gly Leu Gly Ile Gly Thr Gly Ala Gly
    50                  55                  60

Ser Gly Gly Arg Ala Gly Tyr Val Pro Leu Ser Thr Arg Pro Pro Thr
65                  70                  75                  80

Ser Ser Ile Thr Thr Ser Thr Ile
                85

<210> SEQ ID NO 13
<211> LENGTH: 88
<212> TYPE: PRT
<213> ORGANISM: Human papillomavirus 58 (HPV58)

<400> SEQUENCE: 13

Met Arg His Lys Arg Ser Thr Arg Arg Lys Arg Ala Ser Ala Thr Gln
1               5                   10                  15

Leu Tyr Gln Thr Cys Lys Ala Ser Gly Thr Cys Pro Pro Asp Val Ile
            20                  25                  30

Pro Lys Val Glu Gly Thr Thr Ile Ala Asp Gln Ile Leu Arg Tyr Gly
        35                  40                  45

Ser Leu Gly Val Phe Phe Gly Gly Leu Gly Ile Gly Thr Gly Ser Gly
    50                  55                  60

Thr Gly Gly Arg Thr Gly Tyr Val Pro Leu Gly Ser Thr Pro Pro Ser
65                  70                  75                  80

Glu Ala Ile Pro Leu Gln Pro Ile
                85

<210> SEQ ID NO 14
<211> LENGTH: 88
<212> TYPE: PRT
<213> ORGANISM: Human papillomavirus 35 (HPV35)

<400> SEQUENCE: 14

Met Arg His Lys Arg Ser Thr Lys Arg Val Lys Arg Ala Ser Ala Thr
1               5                   10                  15

Gln Leu Tyr Arg Thr Cys Lys Ala Ala Gly Thr Cys Pro Pro Asp Val
            20                  25                  30

Ile Pro Lys Val Glu Gly Asn Thr Val Ala Asp Gln Ile Leu Lys Tyr
        35                  40                  45

Gly Ser Met Ala Val Phe Phe Gly Gly Leu Gly Ile Gly Ser Gly Ser
    50                  55                  60

Gly Thr Gly Gly Arg Ser Gly Tyr Val Pro Leu Gly Thr Thr Pro Pro
65                  70                  75                  80

Thr Ala Ala Thr Asn Ile Pro Ile
                85

<210> SEQ ID NO 15
<211> LENGTH: 88
<212> TYPE: PRT
<213> ORGANISM: Human papillomavirus 59 (HPV59)

<400> SEQUENCE: 15

Met Val Ser His Arg Ala Ala Arg Arg Lys Arg Ala Ser Ala Thr Asp
1               5                   10                  15

Leu Tyr Lys Thr Cys Lys Gln Ala Gly Thr Cys Pro Ser Asp Val Ile
            20                  25                  30

Asn Lys Val Glu Gly Thr Thr Leu Ala Asp Lys Ile Leu Gln Trp Thr
        35                  40                  45

Ser Leu Gly Ile Phe Leu Gly Gly Leu Gly Ile Gly Thr Gly Ser Gly
    50                  55                  60

Thr Gly Gly Arg Thr Gly Tyr Ile Pro Leu Gly Gly Arg Thr Asn Thr
65                  70                  75                  80

Ile Val Asp Val Ser Pro Ala Lys
                85

<210> SEQ ID NO 16
<211> LENGTH: 88

```
<212> TYPE: PRT
<213> ORGANISM: Human papillomavirus 56 (HPV56)

<400> SEQUENCE: 16

Met Val Ala His Arg Ala Thr Arg Arg Lys Arg Ala Ser Ala Thr Gln
1               5                   10                  15

Leu Tyr Lys Thr Cys Lys Leu Ser Gly Thr Cys Pro Glu Asp Val Val
            20                  25                  30

Asn Lys Ile Glu Gln Lys Thr Trp Ala Asp Lys Ile Leu Gln Trp Gly
        35                  40                  45

Ser Leu Phe Thr Tyr Phe Gly Gly Leu Gly Ile Gly Thr Gly Thr Gly
    50                  55                  60

Ser Gly Gly Arg Ala Gly Tyr Val Pro Leu Gly Ser Arg Pro Ser Thr
65                  70                  75                  80

Ile Val Asp Val Thr Pro Ala Arg
                85

<210> SEQ ID NO 17
<211> LENGTH: 88
<212> TYPE: PRT
<213> ORGANISM: Human papillomavirus 39 (HPV39)

<400> SEQUENCE: 17

Met Val Ser His Arg Ala Ala Arg Arg Lys Arg Ala Ser Ala Thr Asp
1               5                   10                  15

Leu Tyr Arg Thr Cys Lys Gln Ser Gly Thr Cys Pro Pro Asp Val Val
            20                  25                  30

Asp Lys Val Glu Gly Thr Thr Leu Ala Asp Lys Ile Leu Gln Trp Thr
        35                  40                  45

Ser Leu Gly Ile Phe Leu Gly Gly Leu Gly Ile Gly Thr Gly Thr Gly
    50                  55                  60

Thr Gly Gly Arg Thr Gly Tyr Ile Pro Leu Gly Gly Arg Pro Asn Thr
65                  70                  75                  80

Val Val Asp Val Ser Pro Ala Arg
                85

<210> SEQ ID NO 18
<211> LENGTH: 89
<212> TYPE: PRT
<213> ORGANISM: Human papillomavirus 51 (HPV51)

<400> SEQUENCE: 18

Met Val Ala Thr Arg Ala Arg Arg Arg Lys Arg Ala Ser Val Thr Gln
1               5                   10                  15

Leu Tyr Ser Thr Cys Lys Ala Ala Gly Thr Cys Pro Pro Asp Val Val
            20                  25                  30

Asn Lys Val Glu Gly Thr Thr Leu Ala Asp Lys Ile Leu Gln Trp Ser
        35                  40                  45

Gly Leu Gly Ile Phe Leu Gly Gly Leu Gly Ile Gly Thr Gly Ser Gly
    50                  55                  60

Ser Gly Gly Arg Thr Gly Tyr Ile Pro Leu Gly Gly Gly Arg Pro
65                  70                  75                  80

Gly Val Val Asp Ile Ala Pro Ala Arg
                85

<210> SEQ ID NO 19
<211> LENGTH: 85
<212> TYPE: PRT
<213> ORGANISM: Cottontail Rabbit Papillomavirus (CRPV)
```

-continued

<400> SEQUENCE: 19

Met Val Ala Arg Ser Arg Lys Arg Arg Ala Ala Pro Gln Asp Ile Tyr
1               5                   10                  15

Pro Thr Cys Lys Ile Ala Gly Asn Cys Pro Ala Asp Ile Gln Asn Lys
            20                  25                  30

Phe Glu Asn Lys Thr Ile Ala Asp Lys Ile Leu Gln Tyr Gly Ser Leu
        35                  40                  45

Gly Val Phe Phe Gly Gly Leu Gly Ile Ser Ser Ala Gly Gly Ser Gly
    50                  55                  60

Gly Arg Leu Gly Tyr Thr Pro Leu Ser Gly Gly Gly Arg Val Ile
65                  70                  75                  80

Ala Ala Ala Pro Val
                85

<210> SEQ ID NO 20
<211> LENGTH: 89
<212> TYPE: PRT
<213> ORGANISM: Bovine papillomavirus

<400> SEQUENCE: 20

Met Ser Ala Arg Lys Arg Val Lys Arg Ala Ser Ala Tyr Asp Leu Tyr
1               5                   10                  15

Arg Thr Cys Lys Gln Ala Gly Thr Cys Pro Pro Asp Val Ile Pro Lys
            20                  25                  30

Val Glu Gly Asp Thr Ile Ala Asp Lys Ile Leu Lys Phe Gly Gly Leu
        35                  40                  45

Ala Ile Tyr Leu Gly Gly Leu Gly Ile Gly Thr Trp Ser Thr Gly Arg
    50                  55                  60

Val Ala Ala Gly Gly Ser Pro Arg Tyr Thr Pro Leu Arg Thr Ala Gly
65                  70                  75                  80

Ser Thr Ser Ser Leu Ala Ser Ile Gly
                85

<210> SEQ ID NO 21
<211> LENGTH: 95
<212> TYPE: PRT
<213> ORGANISM: Artificial Sequence
<220> FEATURE:
<221> NAME/KEY: VARIANT
<222> LOCATION: 2
<223> OTHER INFORMATION: Xaa = Met, Ala, Arg, or Val
<220> FEATURE:
<221> NAME/KEY: VARIANT
<222> LOCATION: 3
<223> OTHER INFORMATION: Xaa = Met, Ser, Arg, His, Lys, Tyr, Ala or Val
<220> FEATURE:
<221> NAME/KEY: VARIANT
<222> LOCATION: 4
<223> OTHER INFORMATION: Xaa = Tyr, Ile, Ala, Ser, Pro, Lys, His, Arg,
      Thr or Met
<220> FEATURE:
<221> NAME/KEY: VARIANT
<222> LOCATION: 6
<223> OTHER INFORMATION: Xaa = Leu, Thr, Arg, Ala or Ser
<220> FEATURE:
<221> NAME/KEY: VARIANT
<222> LOCATION: 7
<223> OTHER INFORMATION: Xaa = Arg, Lys, Val, Ala or Thr
<220> FEATURE:
<221> NAME/KEY: VARIANT
<222> LOCATION: 10
<223> OTHER INFORMATION: Xaa = Thr or Val
<220> FEATURE:
<221> NAME/KEY: VARIANT
<222> LOCATION: (17)...(0)

-continued

```
<223> OTHER INFORMATION: Xaa = Asp, His or Gln
<220> FEATURE:
<221> NAME/KEY: VARIANT
<222> LOCATION: (20)...(0)
<223> OTHER INFORMATION: Xaa = Pro, Arg, Gln, Lys or Ser
<220> FEATURE:
<221> NAME/KEY: VARIANT
<222> LOCATION: (24)...(0)
<223> OTHER INFORMATION: Xaa = Ile, Gln, Leu or Ala
<220> FEATURE:
<221> NAME/KEY: VARIANT
<222> LOCATION: (25)...(0)
<223> OTHER INFORMATION: Xaa = Ser, Ala or Thr
<220> FEATURE:
<221> NAME/KEY: VARIANT
<222> LOCATION: (41)...(0)
<223> OTHER INFORMATION: Xaa = Ile, Leu, Val or Trp
<220> FEATURE:
<221> NAME/KEY: VARIANT
<222> LOCATION: (44)...(0)
<223> OTHER INFORMATION: Xaa = Lys, Asn or Gln
<220> FEATURE:
<221> NAME/KEY: VARIANT
<222> LOCATION: (47)...(0)
<223> OTHER INFORMATION: Xaa = Gln, Lys or Arg
<220> FEATURE:
<221> NAME/KEY: VARIANT
<222> LOCATION: (48)...(0)
<223> OTHER INFORMATION: Xaa = Tyr, Trp, Phe
<220> FEATURE:
<221> NAME/KEY: VARIANT
<222> LOCATION: (77)...(0)
<223> OTHER INFORMATION: Xaa = Thr, Ile or Val
<220> FEATURE:
<221> NAME/KEY: VARIANT
<222> LOCATION: (81)...(0)
<223> OTHER INFORMATION: Xaa = Glu, Ser, Thr or Gly
<220> FEATURE:
<221> NAME/KEY: VARIANT
<222> LOCATION: (86)...(0)
<223> OTHER INFORMATION: Xaa = Gly, Thr, Lys, Pro, Asn or Ser
<220> FEATURE:
<221> NAME/KEY: VARIANT
<222> LOCATION: (88)...(0)
<223> OTHER INFORMATION: Xaa = Arg, Val, Ser, Ala, Glu, Ile or Thr
<220> FEATURE:
<221> NAME/KEY: VARIANT
<222> LOCATION: (90)...(0)
<223> OTHER INFORMATION: Xaa = Ala, Asp, Gly, Thr, Glu, Ile or Ser
<220> FEATURE:
<221> NAME/KEY: VARIANT
<222> LOCATION: (91)...(0)
<223> OTHER INFORMATION: Xaa = Thr, Ile, Gly, Asn, Ser, Val, Ala, Pro or
      Leu
<220> FEATURE:
<221> NAME/KEY: VARIANT
<222> LOCATION: (92)...(0)
<223> OTHER INFORMATION: Xaa = Arg, Gly, Thr, Leu, Ser or Ala
<220> FEATURE:
<221> NAME/KEY: VARIANT
<222> LOCATION: (94)...(0)
<223> OTHER INFORMATION: Xaa = Thr, Met, Ala, Pro or Ile
<220> FEATURE:
<221> NAME/KEY: VARIANT
<222> LOCATION: (95)...(0)
<223> OTHER INFORMATION: Xaa = Pro, Val, Ala, Arg, Ile, Lys or Gly
<220> FEATURE:
<223> OTHER INFORMATION: consensus sequence

<400> SEQUENCE: 21

Met Xaa Xaa Xaa Arg Xaa Xaa Arg Arg Xaa Lys Arg Ala Ser Ala Thr
 1               5                  10                  15

Xaa Leu Tyr Xaa Thr Cys Lys Xaa Xaa Gly Thr Cys Pro Pro Asp Val
                20                  25                  30

Ile Pro Lys Val Glu Gly Thr Thr Xaa Ala Asp Xaa Ile Leu Xaa Xaa
                35                  40                  45
```

```
Gly Ser Leu Gly Val Phe Phe Gly Gly Leu Gly Ile Gly Thr Gly Ser
        50                  55                  60

Gly Gly Arg Val Ala Thr Gly Gly Arg Thr Gly Tyr Xaa Pro Leu Gly
65                  70                  75                  80

Xaa Gly Gly Arg Pro Xaa Thr Xaa Val Xaa Xaa Pro Xaa Xaa
                85                  90                  95

<210> SEQ ID NO 22
<211> LENGTH: 88
<212> TYPE: PRT
<213> ORGANISM: Bovine Papillomavirus (BPV)

<400> SEQUENCE: 22

Met Ser Ala Arg Lys Arg Val Lys Arg Ala Ser Ala Tyr Asp Leu Tyr
1               5                   10                  15

Arg Thr Cys Lys Gln Ala Gly Thr Cys Pro Pro Asp Val Ile Pro Lys
                20                  25                  30

Val Glu Gly Asp Thr Ile Ala Asp Lys Ile Leu Lys Phe Gly Gly Leu
            35                  40                  45

Ala Ile Tyr Leu Gly Gly Leu Gly Ile Gly Thr Trp Ser Thr Gly Arg
        50                  55                  60

Val Ala Ala Gly Gly Ser Pro Arg Tyr Thr Pro Leu Arg Thr Ala Gly
65                  70                  75                  80

Ser Thr Ser Ser Leu Ala Ser Ile
                85

<210> SEQ ID NO 23
<211> LENGTH: 87
<212> TYPE: PRT
<213> ORGANISM: Human papillomavirus 16 (HPV16)

<400> SEQUENCE: 23

Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
                20                  25                  30

Ile Pro Lys Val Glu Gly Lys Thr Ile Ala Asp Gln Ile Leu Gln Tyr
            35                  40                  45

Gly Ser Met Gly Val Phe Phe Gly Gly Leu Gly Ile Gly Thr Gly Ser
        50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala
                85

<210> SEQ ID NO 24
<211> LENGTH: 86
<212> TYPE: PRT
<213> ORGANISM: Human papillomavirus 18 (HPV18)

<400> SEQUENCE: 24

Met Val Ser His Arg Ala Ala Arg Arg Lys Arg Ala Ser Val Thr Asp
1               5                   10                  15

Leu Tyr Lys Thr Cys Lys Gln Ser Gly Thr Cys Pro Pro Asp Val Val
                20                  25                  30

Pro Lys Val Glu Gly Thr Thr Leu Ala Asp Lys Ile Leu Gln Trp Ser
            35                  40                  45

Ser Leu Gly Ile Phe Leu Gly Gly Leu Gly Ile Gly Thr Gly Ser Gly
        50                  55                  60
```

```
Thr Gly Gly Arg Thr Gly Tyr Ile Pro Leu Gly Gly Arg Ser Asn Thr
 65                  70                  75                  80

Val Val Asp Val Gly Pro
                85
```

<210> SEQ ID NO 25
<211> LENGTH: 87
<212> TYPE: PRT
<213> ORGANISM: Human papillomavirus 31 (HPV31)

<400> SEQUENCE: 25

```
Met Arg Ser Lys Arg Ser Thr Lys Arg Ala Ser Ala Thr
 1               5                  10                  15

Gln Leu Tyr Gln Thr Cys Lys Ala Ala Gly Thr Cys Pro Ser Asp Val
                20                  25                  30

Ile Pro Lys Ile Glu His Thr Thr Ile Ala Asp Gln Ile Leu Arg Tyr
                35                  40                  45

Gly Ser Met Gly Val Phe Phe Gly Gly Leu Gly Ile Gly Ser Gly Ser
             50                  55                  60

Gly Thr Gly Gly Arg Thr Gly Tyr Val Pro Leu Ser Thr Arg Pro Ser
 65                  70                  75                  80

Thr Val Ser Glu Ala Ser Ile
                85
```

<210> SEQ ID NO 26
<211> LENGTH: 86
<212> TYPE: PRT
<213> ORGANISM: Human papillomavirus 6b (HPV6b)

<400> SEQUENCE: 26

```
Met Ala His Ser Arg Ala Arg Arg Arg Lys Arg Ala Ser Ala Thr Gln
 1               5                  10                  15

Leu Tyr Gln Thr Cys Lys Leu Thr Gly Thr Cys Pro Pro Asp Val Ile
                20                  25                  30

Pro Lys Val Glu His Asn Thr Ile Ala Asp Gln Ile Leu Lys Trp Gly
                35                  40                  45

Ser Leu Gly Val Phe Phe Gly Gly Leu Gly Ile Gly Thr Gly Ser Gly
             50                  55                  60

Thr Gly Gly Arg Thr Gly Tyr Val Pro Leu Gln Thr Ser Ala Lys Pro
 65                  70                  75                  80

Ser Ile Thr Ser Gly Pro
                85
```

<210> SEQ ID NO 27
<211> LENGTH: 84
<212> TYPE: PRT
<213> ORGANISM: Cottontail Rabbit Papillomavirus (CRPV)

<400> SEQUENCE: 27

```
Met Val Ala Arg Ser Arg Lys Arg Arg Ala Ala Pro Gln Asp Ile Tyr
 1               5                  10                  15

Pro Thr Cys Lys Ile Ala Gly Asn Cys Pro Ala Asp Ile Gln Asn Lys
                20                  25                  30

Phe Glu Asn Lys Thr Ile Ala Asp Lys Ile Leu Gln Tyr Gly Ser Leu
                35                  40                  45

Gly Val Phe Phe Gly Gly Leu Gly Ile Ser Ser Ala Gly Gly Ser Gly
             50                  55                  60

Gly Arg Leu Gly Tyr Thr Pro Leu Ser Gly Gly Gly Arg Val Ile
```

-continued

```
                65                  70                  75                  80

Ala Ala Ala Pro

<210> SEQ ID NO 28
<211> LENGTH: 20
<212> TYPE: PRT
<213> ORGANISM: Human papillomavirus 1 (HPV1)

<400> SEQUENCE: 28

Asp Ile Tyr Pro Ser Cys Lys Ile Ser Asn Thr Cys Pro Pro Asp Ile
1               5                   10                  15

Gln Asn Lys Ile
            20

<210> SEQ ID NO 29
<211> LENGTH: 20
<212> TYPE: PRT
<213> ORGANISM: Human papillomavirus 2 (HPV2)

<400> SEQUENCE: 29

Asp Leu Tyr Arg Thr Cys Lys Gln Ala Gly Thr Cys Pro Pro Asp Ile
1               5                   10                  15

Ile Pro Arg Val
            20

<210> SEQ ID NO 30
<211> LENGTH: 20
<212> TYPE: PRT
<213> ORGANISM: Human papillomavirus 5 (HPV5)

<400> SEQUENCE: 30

His Ile Tyr Gln Thr Cys Lys Gln Ala Gly Thr Cys Pro Pro Asp Val
1               5                   10                  15

Ile Asn Lys Val
            20

<210> SEQ ID NO 31
<211> LENGTH: 20
<212> TYPE: PRT
<213> ORGANISM: Human papillomavirus 8 (HPV8)

<400> SEQUENCE: 31

His Ile Tyr Gln Thr Cys Lys Gln Ala Gly Thr Cys Pro Pro Asp Val
1               5                   10                  15

Ile Asn Lys Val
            20

<210> SEQ ID NO 32
<211> LENGTH: 20
<212> TYPE: PRT
<213> ORGANISM: Human papillomavirus 6 (HPV6)

<400> SEQUENCE: 32

Gln Leu Tyr Gln Thr Cys Lys Leu Thr Gly Thr Cys Pro Pro Asp Val
1               5                   10                  15

Ile Pro Lys Val
            20

<210> SEQ ID NO 33
<211> LENGTH: 20
<212> TYPE: PRT
<213> ORGANISM: Human papillomavirus 11 (HPV11)
```

```
<400> SEQUENCE: 33

Gln Leu Tyr Gln Thr Cys Lys Ala Thr Gly Thr Cys Pro Pro Asp Val
1               5                   10                  15

Ile Pro Lys Val
            20

<210> SEQ ID NO 34
<211> LENGTH: 20
<212> TYPE: PRT
<213> ORGANISM: Human papillomavirus 16 (HPV16)

<400> SEQUENCE: 34

Gln Leu Tyr Lys Thr Cys Lys Gln Ala Gly Thr Cys Pro Pro Asp Ile
1               5                   10                  15

Ile Pro Lys Val
            20

<210> SEQ ID NO 35
<211> LENGTH: 20
<212> TYPE: PRT
<213> ORGANISM: Human papillomavirus 18 (HPV18)

<400> SEQUENCE: 35

Asp Leu Tyr Lys Thr Cys Lys Gln Ser Gly Thr Cys Pro Pro Asp Val
1               5                   10                  15

Val Pro Lys Val
            20

<210> SEQ ID NO 36
<211> LENGTH: 20
<212> TYPE: PRT
<213> ORGANISM: Human papillomavirus 45 (HPV45)

<400> SEQUENCE: 36

Asp Leu Tyr Arg Thr Cys Lys Gln Ser Gly Thr Cys Pro Pro Asp Val
1               5                   10                  15

Ile Asn Lys Val
            20

<210> SEQ ID NO 37
<211> LENGTH: 20
<212> TYPE: PRT
<213> ORGANISM: Human papillomavirus 31 (HPV31)

<400> SEQUENCE: 37

Gln Leu Tyr Gln Thr Cys Lys Ala Ala Gly Thr Cys Pro Ser Asp Val
1               5                   10                  15

Ile Pro Lys Ile
            20

<210> SEQ ID NO 38
<211> LENGTH: 20
<212> TYPE: PRT
<213> ORGANISM: Human papillomavirus 33 (HPV33)

<400> SEQUENCE: 38

Gln Leu Tyr Gln Thr Cys Lys Ala Thr Gly Thr Cys Pro Pro Asp Val
1               5                   10                  15

Ile Pro Lys Val
            20

<210> SEQ ID NO 39
```

```
<211> LENGTH: 20
<212> TYPE: PRT
<213> ORGANISM: Human papillomavirus 52 (HPV52)

<400> SEQUENCE: 39

Gln Leu Tyr Gln Thr Cys Lys Ala Ser Gly Thr Cys Pro Pro Asp Val
1               5                   10                  15

Ile Pro Lys Val
            20

<210> SEQ ID NO 40
<211> LENGTH: 20
<212> TYPE: PRT
<213> ORGANISM: Human papillomavirus 58 (HPV58)

<400> SEQUENCE: 40

Gln Leu Tyr Gln Thr Cys Lys Ala Ser Gly Thr Cys Pro Pro Asp Val
1               5                   10                  15

Ile Pro Lys Val
            20

<210> SEQ ID NO 41
<211> LENGTH: 20
<212> TYPE: PRT
<213> ORGANISM: Human papillomavirus 35 (HPV35)

<400> SEQUENCE: 41

Gln Leu Tyr Arg Thr Cys Lys Ala Ala Gly Thr Cys Pro Pro Asp Val
1               5                   10                  15

Ile Pro Lys Val
            20

<210> SEQ ID NO 42
<211> LENGTH: 20
<212> TYPE: PRT
<213> ORGANISM: Human papillomavirus 59 (HPV59)

<400> SEQUENCE: 42

Asp Leu Tyr Lys Thr Cys Lys Gln Ala Gly Thr Cys Pro Ser Asp Val
1               5                   10                  15

Ile Asn Lys Val
            20

<210> SEQ ID NO 43
<211> LENGTH: 20
<212> TYPE: PRT
<213> ORGANISM: Human papillomavirus 56 (HPV56)

<400> SEQUENCE: 43

Gln Leu Tyr Lys Thr Cys Lys Leu Ser Gly Thr Cys Pro Glu Asp Val
1               5                   10                  15

Val Asn Lys Ile
            20

<210> SEQ ID NO 44
<211> LENGTH: 20
<212> TYPE: PRT
<213> ORGANISM: Human papillomavirus 39 (HPV39)

<400> SEQUENCE: 44

Asp Leu Tyr Arg Thr Cys Lys Gln Ser Gly Thr Cys Pro Pro Asp Val
1               5                   10                  15

Val Asp Lys Val
```

<210> SEQ ID NO 45
<211> LENGTH: 20
<212> TYPE: PRT
<213> ORGANISM: Human papillomavirus 51 (HPV51)

<400> SEQUENCE: 45

Gln Leu Tyr Ser Thr Cys Lys Ala Ala Gly Thr Cys Pro Pro Asp Val
1               5                   10                  15

Val Asn Lys Val
            20

<210> SEQ ID NO 46
<211> LENGTH: 20
<212> TYPE: PRT
<213> ORGANISM: Cottontail Rabbit Papillomavirus (CRPV)

<400> SEQUENCE: 46

Asp Ile Tyr Pro Thr Cys Lys Ile Ala Gly Asn Cys Pro Ala Asp Ile
1               5                   10                  15

Gln Asn Lys Phe
            20

<210> SEQ ID NO 47
<211> LENGTH: 20
<212> TYPE: PRT
<213> ORGANISM: Bovine Papillomavirus (BPV)

<400> SEQUENCE: 47

Asp Leu Tyr Arg Thr Cys Lys Gln Ala Gly Thr Cys Pro Pro Asp Val
1               5                   10                  15

Ile Pro Lys Val
            20

<210> SEQ ID NO 48
<211> LENGTH: 20
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = Asp, His or Gln
<220> FEATURE:
<221> NAME/KEY: VARIANT
<222> LOCATION: 4
<223> OTHER INFORMATION: Xaa = Pro, Arg, Gln, Lys, Arg or Ser
<220> FEATURE:
<221> NAME/KEY: VARIANT
<222> LOCATION: 8
<223> OTHER INFORMATION: Xaa = Ile, Gln, Leu or Ala,
<220> FEATURE:
<221> NAME/KEY: VARIANT
<222> LOCATION: 9
<223> OTHER INFORMATION: Xaa = Ser, Ala or Thr
<220> FEATURE:
<223> OTHER INFORMATION: consensus sequence

<400> SEQUENCE: 48

Xaa Leu Tyr Xaa Thr Cys Lys Xaa Xaa Gly Thr Cys Pro Pro Asp Val
1               5                   10                  15

Ile Pro Lys Val
            20